(12) United States Patent
Busser et al.

(10) Patent No.: US 11,873,511 B2
(45) Date of Patent: Jan. 16, 2024

(54) TARGETED GENE INSERTION FOR IMPROVED IMMUNE CELLS THERAPY

(71) Applicant: CELLECTIS, Paris (FR)

(72) Inventors: Brian Busser, New York, NY (US); Philippe Duchateau, Draveil (FR); Alexandre Juillerat, New York, NY (US); Laurent Poirot, Paris (FR); Julien Valton, New York, NY (US)

(73) Assignee: CELLECTIS, Paris (FR)

( * ) Notice: Subject to any disclaimer, the term of this patent is extended or adjusted under 35 U.S.C. 154(b) by 682 days.

(21) Appl. No.: 16/340,222

(22) PCT Filed: Oct. 19, 2017

(86) PCT No.: PCT/EP2017/076798
§ 371 (c)(1),
(2) Date: Apr. 8, 2019

(87) PCT Pub. No.: WO2018/073391
PCT Pub. Date: Apr. 26, 2018

(65) Prior Publication Data
US 2020/0224163 A1 Jul. 16, 2020

Related U.S. Application Data

(60) Provisional application No. 62/410,187, filed on Oct. 19, 2016.

(30) Foreign Application Priority Data

Oct. 27, 2016 (DK) .............................. PA201670840

(51) Int. Cl.
| | |
|---|---|
| *C12N 5/078* | (2010.01) |
| *A61K 35/17* | (2015.01) |
| *C12N 15/90* | (2006.01) |
| *C12N 9/22* | (2006.01) |
| *C12N 5/0783* | (2010.01) |

(52) U.S. Cl.
CPC ............ *C12N 5/0638* (2013.01); *A61K 35/17* (2013.01); *C12N 9/22* (2013.01); *C12N 15/907* (2013.01); *C12N 2510/00* (2013.01); *C12N 2750/14143* (2013.01); *C12N 2830/008* (2013.01)

(58) Field of Classification Search
CPC ...... C12N 5/0638; C12N 9/22; C12N 15/907; C12N 2510/00; C12N 2750/14143; C12N 2830/008; C12N 5/0636; C12N 5/0634; A61K 35/17; A61K 2039/5156; A61K 2039/5158; A61K 39/0011; C07K 14/7051; C07K 2319/03
See application file for complete search history.

(56) References Cited

U.S. PATENT DOCUMENTS

| | | | |
|---|---|---|---|
| 10,166,255 B2 * | 1/2019 | Moriarity | ................. C12N 9/96 |
| 2013/0315884 A1 * | 11/2013 | Galetto | ................... A61P 35/02 |
| | | | 435/375 |
| 2016/0272999 A1 | 9/2016 | Duchateau et al. | |
| 2016/0361359 A1 | 12/2016 | Valton et al. | |
| 2017/0065636 A1 * | 3/2017 | Moriarity | ........... C07K 14/7158 |

FOREIGN PATENT DOCUMENTS

| | | | | |
|---|---|---|---|---|
| WO | 2014191128 A1 | 12/2014 | | |
| WO | WO-2014191128 A1 * | 12/2014 | ............. | A61K 35/17 |
| WO | 2015075195 A1 | 5/2015 | | |
| WO | 2016124765 A1 | 8/2016 | | |
| WO | WO-2017023803 A1 * | 2/2017 | ............. | A61K 35/00 |

OTHER PUBLICATIONS

Rongvaux A, Willinger T, Takizawa H, Rathinam C, Auerbach W, Murphy AJ, Valenzuela DM, Yancopoulos GD, Eynon EE, Stevens S, Manz MG. Human thrombopoietin knockin mice efficiently support human hematopoiesis in vivo. Proceedings of the National Academy of Sciences. Feb. 8, 2011;108(6):2378-83. (Year: 2011).*
Willinger T, Rongvaux A, Takizawa H,et al, Flavell RA. Human IL-3/GM-CSF knock-in mice support human alveolar macrophage development and human immune responses in the lung. Proceedings of the National Academy of Sciences. Feb. 8, 2011;108(6):2390-5. (Year: 2011).*
Willinger T, Rongvaux A, Strowig T, Manz MG, Flavell RA. Improving human hemato-lymphoid-system mice by cytokine knock-in gene replacement. Trends in immunology. Jul. 1, 2011;32(7):321-7. (Year: 2011).*
Chmielewski M, Kopecky C, Hombach AA, Abken H. IL-12 release by engineered T cells expressing chimeric antigen receptors can effectively muster an antigen-independent macrophage response on tumor cells that have shut down tumor antigen expression. Cancer Res. (2011) 71:5697-706. (Year: 2011).*
Fesnak AD, June CH, Levine BL. Engineered T cells: the promise and challenges of cancer immunotherapy. Nature reviews cancer. Sep. 2016;16(9):566-81. (Year: 2016).*
(Pegram HJ, Lee JC, Hayman EG, Imperato GH, Tedder TF, Sadelain M, Brentjens RJ. Tumor-targeted T cells modified to secrete IL-12 eradicate systemic tumors without need for prior conditioning. Blood, The Journal of the American Society of Hematology. May 3, 2012;119(18):4133-41) (Year: 2012).*

(Continued)

*Primary Examiner* — James D Schultz
*Assistant Examiner* — Masudur Rahman
(74) *Attorney, Agent, or Firm* — Arrigo, Lee, Guttman & Mouta-Bellum LLP

(57) ABSTRACT

The invention pertains to the field of adaptive cell immunotherapy. It provides with the genetic insertion of exogenous coding sequence(s) that help the immune cells to direct their immune response against infected or malignant cells. These exogenous coding sequences are more particularly inserted under the transcriptional control of endogenous gene promoters that are sensitive to immune cells activation. Such method allows the production of safer immune primary cells of higher therapeutic potential.

Figure 1:
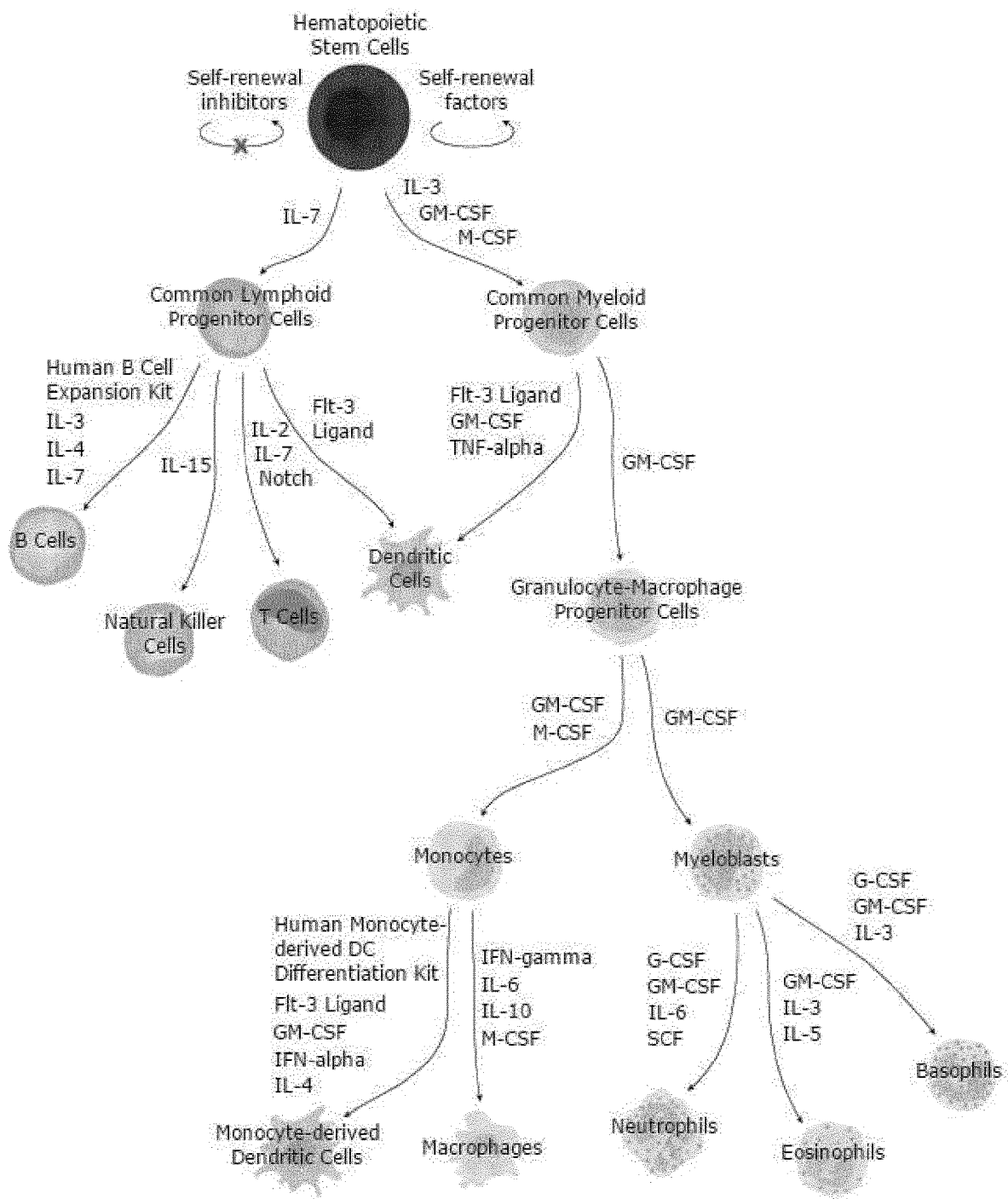

19 Claims, 16 Drawing Sheets
Specification includes a Sequence Listing.

(56) References Cited

OTHER PUBLICATIONS

Austin JW, Lu P, Majumder P, Ahmed R, Boss JM. STAT3, STAT4, NFATc1, and CTCF regulate PD-1 through multiple novel regulatory regions in murine T cells. The Journal of Immunology. May 15, 2014;192(10):4876-86 (Year: 2014).*

Bally AP, Austin JW, Boss JM. Genetic and epigenetic regulation of PD-1 expression. The Journal of Immunology. Mar. 15, 2016;196(6):2431-7 (Year: 2016).*

Tsai AK, Davila E. Producer T cells: Using genetically engineered T cells as vehicles to generate and deliver therapeutics to tumors. Oncoimmunology. May 3, 2016;5(5):e1122158 (Year: 2016).*

Chu et al., Efficient CRISPR-mediated mutagenesis in primary immune cells using CrispRGold and a C57BL/6 Cas9 transgenic mouse line, PNAS, Nov. 1, 2016, vol. 113, No. 44, 12514-12519.

Sather et al., Efficient modification of CCR5 in primary human hematopoietic cells using a megaTAL nuclease and AAV donor template, Sci Transl Med. Sep. 30, 2015; 7(307):1-29.

Wang et al., Homology-driven genome editing in hematopoietic stem and progenitor cells using zinc finger nuclease MRNA and AAV6 donors, Nat Biotechnol. Dec. 2015; 33(12): 1256-1263.

* cited by examiner

A

B

TARGETED GENE INSERTION FOR IMPROVED IMMUNE CELLS THERAPY

CROSS-REFERENCE TO RELATED APPLICATIONS

This application is a U.S. Natl. Stage of International Application PCT/EP2017/076798 filed Oct. 19, 2017, which claims the benefit of U.S. provisional application 62/410,187 filed Oct. 19, 2016.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Apr. 6, 2022, is named 16340222_2_seq_l-st.txt and is 225,583 bytes in size.

FIELD OF THE INVENTION

The invention pertains to the field of adaptive cell immunotherapy. It aims to enhance the functionality of primary immune cells against pathologies that develop immune resistance, such as tumors, thereby improving the therapeutic potential of these immune cells. The method of the invention provides with the genetic insertion of exogenous coding sequence(s) that help the immune cells to direct their immune response against infected or malignant cells. These exogenous coding sequences are more particularly inserted under the transcriptional control of endogenous gene promoters that are up or downregulated upon immune cells activation, upon tumor microenvironment or life threatening inflammatory conditions or promoters that are insensitive to immune cells activation. The invention also provides with sequence-specific endonuclease reagents and donor DNA vectors, such as AAV vectors, to perform such targeted insertions at said particular loci. The method of the invention contributes to improving the therapeutic potential and safety of engineered primary immune cells for their efficient use in cell therapy

BACKGROUND OF THE INVENTION

Effective clinical application of primary immune cell populations including hematopoietic cell lineages has been established by a number of clinical trials over a decade against a range of pathologies, in particular HIV infection and Leukemia (Tristen S. J. et al. (2011) Treating cancer with genetically engineered T cells. *Trends in Biotechnology*. 29(11):550-557).

However, most of these clinical trials have used immune cells, mainly NK and T-cells, obtained from the patients themselves or from compatible donors, bringing some limitations with respect to the number of available immune cells, their fitness, and their efficiency to overcome diseases that have already developed strategies to get around or reduce patient's immune system.

As a primary advance into the procurement of allogeneic immune cells, universal immune cells, available as "off-the-shelf" therapeutic products, have been produced by gene editing (Poirot et al. (2015) Multiplex Genome-Edited T-cell Manufacturing Platform for "Off-the-Shelf" Adoptive T-cell Immunotherapies *Cancer Res.* 75: 3853-64). These universal immune cells are obtainable by expressing specific rare-cutting endonuclease into immune cells originating from donors, with the effect of disrupting, by double strand-break, their self-recognition genetic determinants.

Since the emergence of the first programmable sequence-specific reagents by the turn of the century, initially referred to as Meganucleases (Smith et al. (2006) A combinatorial approach to create artificial homing endonucleases cleaving chosen sequences. *Nucl. Acids Res.* 34 (22):e149), different types of sequence-specific endonucleases reagents have been developed offering improved specificity, safety and reliability.

TALE-nucleases (WO2011072246), which are fusions of a TALE binding domain with a cleavage catalytic domain have been successfully applied to primary immune cells, in particular T-cells from peripheral blood mononuclear cell (PBMC). Such TALE-nucleases, marketed under the name TALEN®, are those currently used to simultaneously inactivate gene sequences in T-cells originating from donors, in particular to produce allogeneic therapeutic T-Cells in which the genes encoding TCR (T-cell receptor) and CD52 are disrupted. These cells can be endowed with chimeric antigen receptors (CAR) for treating cancer patients (US2013/0315884). TALE-nucleases are very specific reagents because they need to bind DNA by pairs under obligatory heterodimeric form to obtain dimerization of the cleavage domain Fok-1. Left and right heterodimer members each recognizes a different nucleic sequences of about 14 to 20 bp, together spanning target sequences of 30 to 50 bp overall specificity.

Other endonucleases reagents have been developed based on the components of the type II prokaryotic CRISPR (Clustered Regularly Interspaced Short palindromic Repeats) adaptive immune system of the bacteria *S. pyogenes*. This multi-component system referred to as RNA-guided nuclease system (Gasiunas, Barrangou et al. 2012; Jinek, Chylinski et al. 2012), involves members of Cas9 or Cpf1 endonuclease families coupled with a guide RNA molecules that have the ability to drive said nuclease to some specific genome sequences (Zetsche et al. (2015). Cpf1 is a single RNA-guided endonuclease that provides immunity in bacteria and can be adapted for genome editing in mammalian cells. *Cell* 163:759-771). Such programmable RNA-guided endonucleases are easy to produce because the cleavage specificity is determined by the sequence of the RNA guide, which can be easily designed and cheaply produced. The specificity of CRISPR/Cas9 although stands on shorter sequences than TAL-nucleases of about 10 pb, which must be located near a particular motif (PAM) in the targeted genetic sequence. Similar systems have been described using a DNA single strand oligonucleotide (DNA guide) in combination with Argonaute proteins (Gao, F. et al. DNA-guided genome editing using the *Natronobacterium gregoryi* Argonaute (2016) doi:10.1038/nbt.3547). Other endonuclease systems derived from homing endonucleases (ex: I-Onul, or I-Crel), combined or not with TAL-nuclease (ex: MegaTAL) or zing-finger nucleases have also proven specificity, but to a lesser extend so far.

In parallel, novel specificities can be conferred to immune cells through the genetic transfer of transgenic T-cell receptors or so-called chimeric antigen receptors (CARs) (Jena et al. (2010) Redirecting T-cell specificity by introducing a tumor-specific chimeric antigen receptor. *Blood.* 116:1035-1044). CARs are recombinant receptors comprising a targeting moiety that is associated with one or more signaling domains in a single fusion molecule. In general, the binding moiety of a CAR consists of an antigen-binding domain of a single-chain antibody (scFv), comprising the light and heavy variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), ICOS and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors.

Recently engineered T-cells disrupted in their T-cell receptor (TCR) using TALE-nucleases, endowed with chimeric antigen receptor (CAR) targeting CD19 malignant antigen, referred to as "UCART19" product, have shown therapeutic potential in at least two infants who had refractory leukemia (Leukaemia success heralds wave of gene-editing therapies (2015) *Nature* 527:146-147). To obtain such UCART19 cells, the TALE-nuclease was transiently expressed into the cells upon electroporation of capped mRNA to operate TCR gene disruption, whereas a cassette encoding the chimeric antigen receptor (CAR CD19) was introduced randomly into the genome using a retroviral vector.

In this later approach, the steps of gene inactivation and of expressing the chimeric antigen receptor are independently performed after inducing activation of the T-Cell "ex-vivo".

However, engineering primary immune cells is not without any consequences on the growth/physiology of such cells. In particular one major challenge is to ovoid cells exhaustion/anergy that significantly reduces their immune reaction and life span. This is more likely to happen when the cells are artificially activated ahead of their infusion into the patient. It is also the case when a cell is endowed with a CAR that is too reactive.

To avoid these pitfalls, the inventors have thought about taking advantage of the transcriptional regulation of some key genes during T-cell activation to express exogenous genetic sequences increasing the therapeutic potential of the immune cells. The exogenous genetic sequences to be expressed or co-expressed upon immune cell activation are introduced by gene targeted insertion using sequence-specific endonuclease reagents, so that their coding sequences are transcribed under the control of the endogenous promoters present at said loci. Alternatively, loci that are not expressed during immune cell activation can be used as "safe-harbor loci" for the integration of expression cassettes without any adverse consequences on the genome.

These cell engineering strategies, as per the present invention, tend to reinforce the therapeutic potential of primary immune cells in general, in particular by increasing their life span, persistence and immune activity, as well as by limiting cell exhaustion. The invention may be carried out on primary cells originating from patients as part of autologous treatment strategies, as well as from donors, as part of allogeneic treatment strategies.

SUMMARY OF THE INVENTION

Non-homologous end-joining (NHEJ) and homology-directed repair (HDR) are the two major pathways used to repair in vivo DNA breaks. The latter pathway repairs the break in a template-dependent manner (HDR naturally utilizes the sister chromatid as a DNA repair template). Homologous recombination has been used for decades to precisely edit genomes with targeted DNA modifications using exogenously supplied donor template. The artificial generation of a double strand break (DSB) at the target location using rare-cutting endonucleases considerably enhances the efficiency of homologous recombination (e.g. U.S. Pat. No. 8,921,332). Also the co-delivery of a rare-cutting endonuclease along with a donor template containing DNA sequences homologous to the break site enables HDR-based gene editing such as gene correction or gene insertion. However, such techniques have not been widely used in primary immune cells, especially CAR T-cells, due to several technical limitations: difficulty of transfecting DNA into such types of cells leading to apoptosis, immune cells have a limited life span and number of generations, homologous recombination occurs at a low frequency in general.

So far, sequence specific endonuclease reagents have been mainly used in primary immune cells for gene inactivation (e.g. WO2013176915) using the NHEJ pathway.

In a general aspect, the present invention relies on performing site directed gene editing, in particular gene insertion (or multi gene insertions) in a target cell in order to have the integrated gene transcription be under the control of an endogenous promoter.

In a general aspect the invention relies on performing gene editing in primary immune cells to have integrated genes transcription be under the control of an endogenous promoter while maintaining the expression of the native gene through the use of cis-regulatory elements (e.g. 2A cis-acting hydrolase elements) or of internal ribosome entry site (IRES) in the donor template.

In a general aspect the invention relies, as non-limiting examples, on controlling the expression, in primary T-cells, of chimeric antigen receptors (CAR), of critical cytokines to drive an anti-tumor response, of stimulatory cytokines to increase proliferative potential, of chemokine receptors to encourage trafficking to the tumor, or of different protective or inhibitory genes to block the immune inhibition provided by the tumor. Indeed, one major advantage of the present invention is to place such exogenous sequences under control of endogenous promoters, which transcriptional activity is not reduced by the effects of the immune cells activation.

By contrast to previous method for engineering therapeutic immune cells, where for instance an exogenous coding sequence was integrated and expressed at the TCR locus for constitutive gene expression, the inventors have integrated coding sequence at loci, which are specifically transcribed during T-cells activation, preferably on a CAR dependent fashion.

In one aspect, the invention relies on expressing a chimeric antigen receptor (CAR) at selected gene loci that are upregulated upon immune cells activation. The exogenous sequence(s) encoding the CAR and the endogenous gene coding sequence (s) may be co-transcribed, for instance by being separated by cis-regulatory elements (e.g. 2A cis-acting hydrolase elements) or by an internal ribosome entry site (IRES), which are also introduced. For instance, the exogenous sequences encoding a CAR can be placed under transcriptional control of the promoter of endogenous genes that are activated by the tumor microenvironment, such as HIF1a, transcription factor hypoxia-inducible factor, or the aryl hydrocarbon receptor (AhR), which are gene sensors respectively induced by hypoxia and xenobiotics in the close environment of tumors.

The present invention is thus useful to improve the therapeutic outcome of CAR T-cell therapies by integrating exogenous genetic attributes/circuits under the control of endogenous T-cell promoters influenced by tumor microenvironment (TME). TME features, including as non-limiting examples, arginine, cysteine, tryptophan and oxygen deprivation as well as extracellular acidosis (lactate build up), are known to upregulate specific endogenous genes. Pursuant to the invention, upregulation of endogenous genes can be "hijacked" to re-express relevant exogenous coding sequences to improve the antitumor activity of CAR T-cells in certain tumor microenvironment.

In preferred embodiments, the method of the invention comprises the step of generating a double-strand break at a locus highly transcribed under tumor microenvironment, by expressing sequence-specific nuclease reagents, such as TALEN, ZFN or RNA-guided endonucleases as non-limiting examples, in the presence of a DNA repair matrix preferably set into an AAV6 based vector. This DNA donor template generally includes two homology arms embedding unique or multiple Open Reading Frames and regulatory genetic elements (stop codon and polyA sequences) referred to herein as exogenous coding sequences.

In another aspect, said exogenous sequence is introduced into the genome by deleting or modifying the endogenous coding sequence(s) present at said locus (knock-out by knock-in), so that a gene inactivation is combined with transgenesis.

Depending on the locus targeted and its involvement in immune cells activity, the targeted endogenous gene may be inactivated or maintained in its original function. Should the targeted gene be essential for immune cells activity, this insertion procedure can generate a single knock-in (KI) without gene inactivation. In the opposite, if the targeted gene is deemed involved in immune cells inhibition/exhaustion, the insertion procedure is designed to prevent expression of the endogenous gene, preferably by knocking-out the endogenous sequence, while enabling expression of the introduced exogenous coding sequence(s).

In more specific aspects, the invention relies on up-regulating, with various kinetics, the target gene expression upon activation of the CAR signalling pathway by targeted integration (with or without the native gene disruption) at the specific loci such as, as non-limiting example, PD1, PDL1, CTLA-4, TIM3, LAG3, TNFa or IFNg.

In an even more specific aspect, it is herein described engineered immune cells, and preferably primary immune cells for infusion into patients, comprising exogenous sequences encoding IL-15 or IL-12 polypeptide(s), which are integrated at the PD1, CD25 or CD69 endogenous locus for their expression under the control of the endogenous promoters present at these loci.

The immune cells according to the present invention can be [CAR]$^{positive}$, [CAR]$^{negative}$, [TCR]$^{positive}$, or [TCR]$^{negative}$, depending on the therapeutic indications and recipient patients. In one preferred aspect, the immune cells are further made [TCR]$^{negative}$ for allogeneic transplantation. This can be achieved especially by genetic disruption of at least one endogenous sequence encoding at least one component of TCR, such as TRAC (locus encoding TCRalpha), preferably by integration of an exogenous sequence encoding a chimeric antigen receptor (CAR) or a recombinant TCR, or component(s) thereof.

According to a further aspect of the invention, the immune cells are transfected with an exogenous sequence coding for a polypeptide which can associate and preferably interfere with a cytokine receptor of the IL-6 receptor family, such as a mutated GP130, In particular, the invention provides immune cells, preferably T-cells, which secrete soluble mutated GP130, aiming at reducing cytokine release syndrome (CRS) by interfering, and ideally block, interleukine-6 (IL-6) signal transduction. CRS is a well-known complication of cell immunotherapy leading to auto immunity that appears when the transduced immune cells start to be active in-vivo. Following binding of IL-6 to its receptor IL-6R, the complex associate with the GP130 subunit, initiating signal transduction and a cascade of inflammatory responses. According to a particular aspect, a dimeric protein comprising the extracellular domain of GP130 fused to the Fc portion of an IgG1 antibody (sgp130Fc) is expressed in the engineered immune cells to bind specifically soluble IL-R/IL-6 complex to achieve partial or complete blockade of IL-6 trans signaling. The present invention thus refers to a method for limiting CRS in immunotherapy, wherein immune cells are genetically modified to express a soluble polypeptide which can associate and preferably interfere with a cytokine receptor of the IL-6 receptor family, such as sgp130Fc. According to a preferred aspect, this sequence encoding said soluble polypeptide which can associate and preferably interfere with a cytokine receptor of the IL-6 receptor family, is integrated under control of an endogenous promoter, preferably at one locus responsive to T-cells activation, such as one selected from Tables 6, 8 or 9, more especially PD1, CD25 or CD69. Polynucleotide sequences of the vectors, donor templates comprising the exogenous coding sequences and/or sequences homologous to the endogenous loci, the sequences pertaining to the resulting engineered cells, as well as those permitting the detection of said engineered cells are all part of the present disclosure.

In a general aspect the invention relies, as non-limiting examples, on controlling the expression of components of biological "logic gates" ("AND" or "OR" or "NOT" or any combination of these) by targeted integration of genes. Similar to the electronic logic gates, cellular components expressed at different loci can exchange negative and positive signals that rule, for instance, the conditions of activation of an immune cell. Such component encompasses as non-limiting examples positive and negative chimeric antigen receptors that may be used to control T-cell activation and the resulting cytotoxicity of the engineered T-cells in which they are expressed.

According to a preferred embodiment, the invention relies on introducing the sequence specific endonuclease reagent and/or the donor template containing the gene of interest and sequences homologous to the target gene by transfecting ssDNA (oligonucleotides as non-limiting example), dsDNA (plasmid DNA as non-limiting example), and more particularly adeno-associated virus (AAV) as non-limiting example.

The invention also relates to the vectors, donor templates, reagents and resulting engineered cells pertaining to the above methods, as well as their use in therapy.

BRIEF DESCRIPTION OF THE FIGURES AND TABLES

FIG. 1: Strategies for engineering hematopoietic stem cells (HSCs) by introducing exogenous sequences at specific loci under transcriptional control of endogenous promoters specifically activated in specific immune cell types. The figure lists examples of specific endogenous genes, at which loci the exogenous coding sequence(s) can be inserted for expression in the desired hematopoietic lineages as per the present invention. The goal is to produce ex-vivo engineered HSCs to be engrafted into patients, in order for them to produce immune cells in-vivo, which will express selected transgenes while they get differentiated into a desired lineage.

Figure 2:
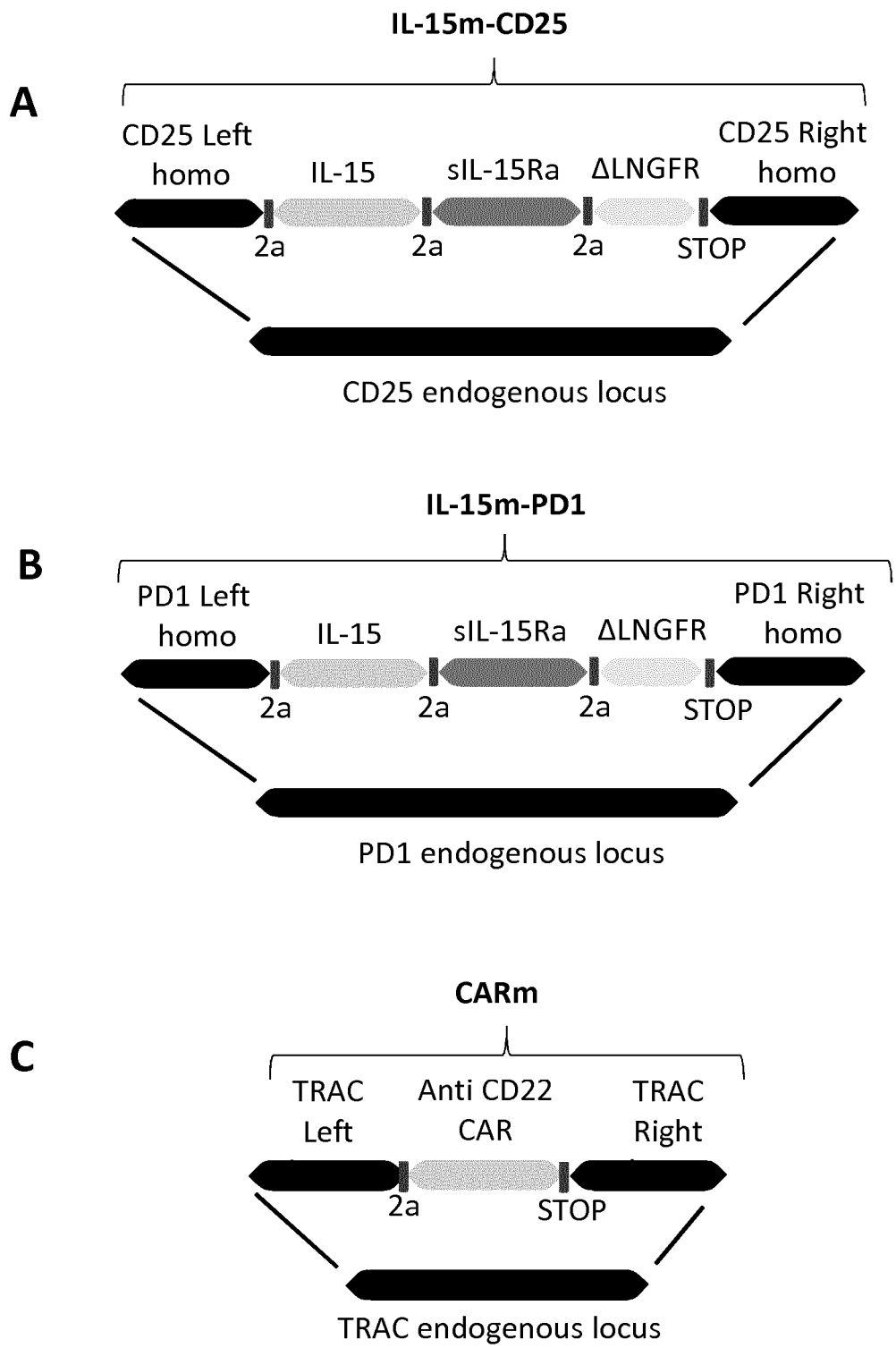

FIG. 2: Schematic representation of the donor sequences used in the experimental section to insert IL-15 exogenous coding sequence at the CD25 and PD1 loci and also the anti-CD22 CAR exogenous coding sequence at the TRAC locus. A: donor template (designated IL-15m-CD25) designed for site directed insertion of IL-15 at the CD25 locus for obtaining co-transcription of CD25 and IL-15 polypeptides by the immune cell. Sequences are detailed in the examples. B: donor template (designated IL-15m-PD1) designed for site directed insertion of IL-15 at the PD1 locus for obtaining transcription of IL-15 under the transcriptional activity of the promoter of PD1 endogenous gene. The PD1 right and Left border sequences can be selected so as to keep the PD1 endogenous coding sequence intact or disrupted. In this later case, PD1 is knocked-out while IL-15 is Knocked-in and transcribed. C: donor template designed for site directed insertion of a chimeric antigen receptor (ex: anti-CD22 CAR) into the TCR locus (ex: TRAC). In general, the left and right borders are chosen so as to disrupt the TCR in order to obtain [TCR]$^{neg}$[CAR]$^{pos}$ engineered immune cells suitable for allogeneic transplant into patients.

Figure 3:
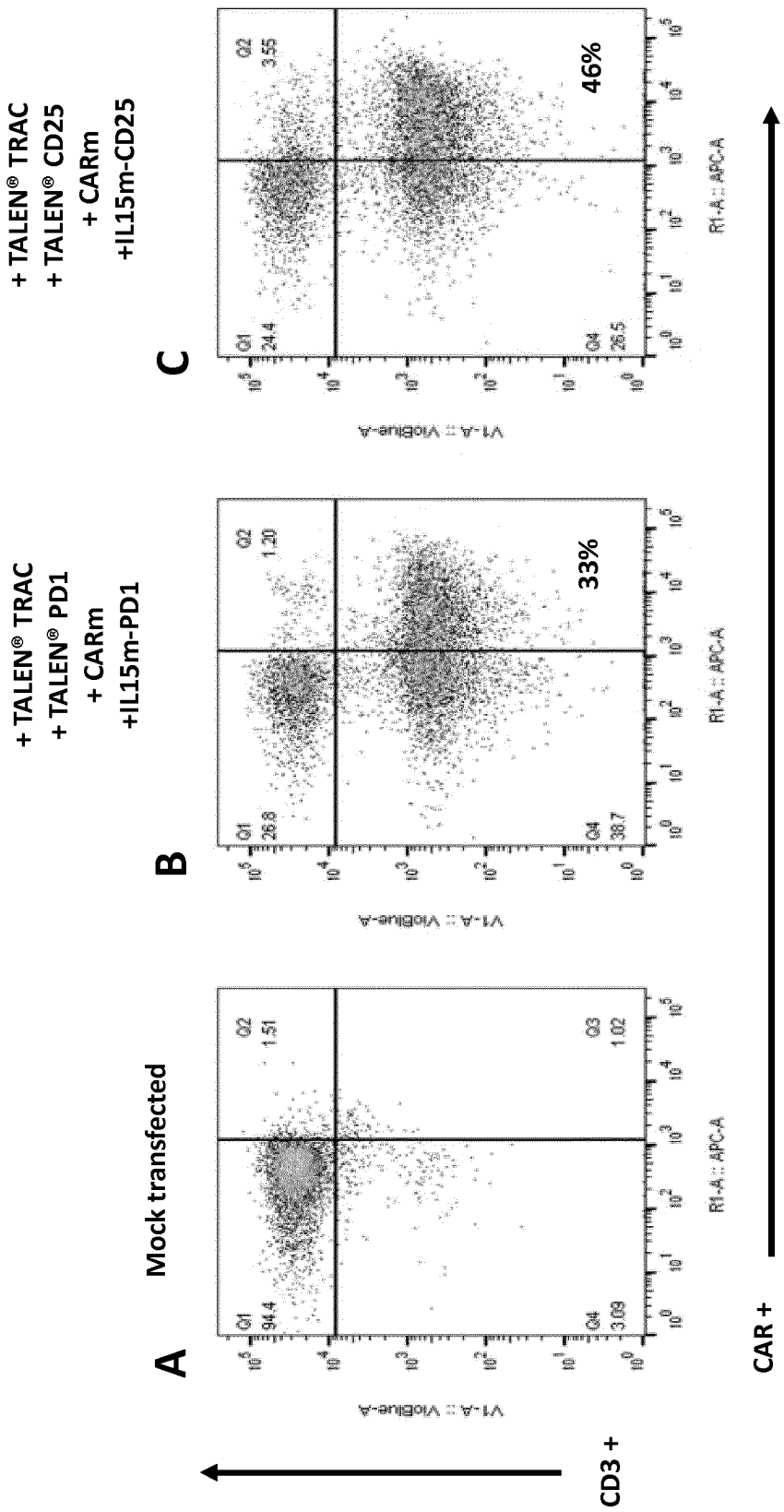

FIG. 3: Flow cytometry measures of the frequency of targeted integration of IL-15m at either the PD1 or CD25 locus by using respectively PD1 or CD25 TALEN®, in a context where an anti-CD22 CAR is also integrated at the TRAC locus using TRAC TALEN®. These results show efficient targeted integration of both the CAR anti-CD22 at the TRAC locus together and the IL-15 coding sequence at the PD1 or CD25 loci. A: mock transfected primary T-cells. B: primary T-cells transfected with the donor sequences described in FIG. 1 (B and C) and specific TALEN® for the double integration at the TCR and PDI loci. C: primary T-cells transfected with the donor sequences described in FIG. 1 (A and C) and specific TALEN® for the double integration at the TCR and CD25 loci.

Figure 4:
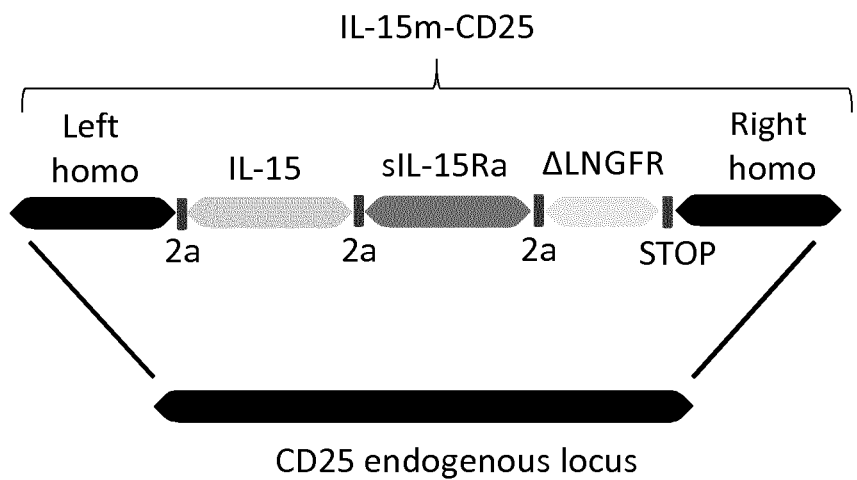
Figure 4:
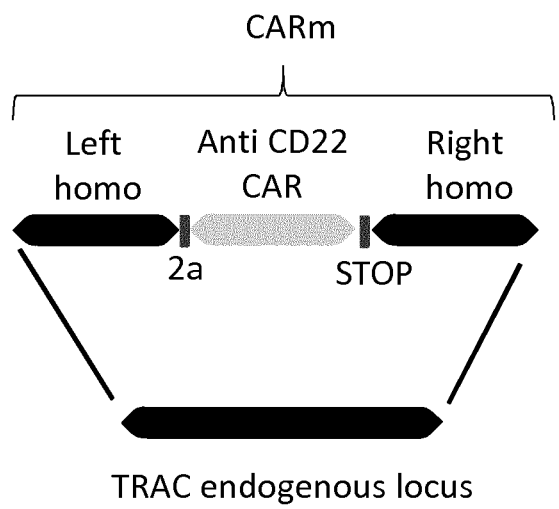

FIG. 4: Schematic representation of the exogenous sequences used in the experimental section to transfect the primary immune cells to obtain the results shown in FIGS. 5 and 6.

Figure 5:
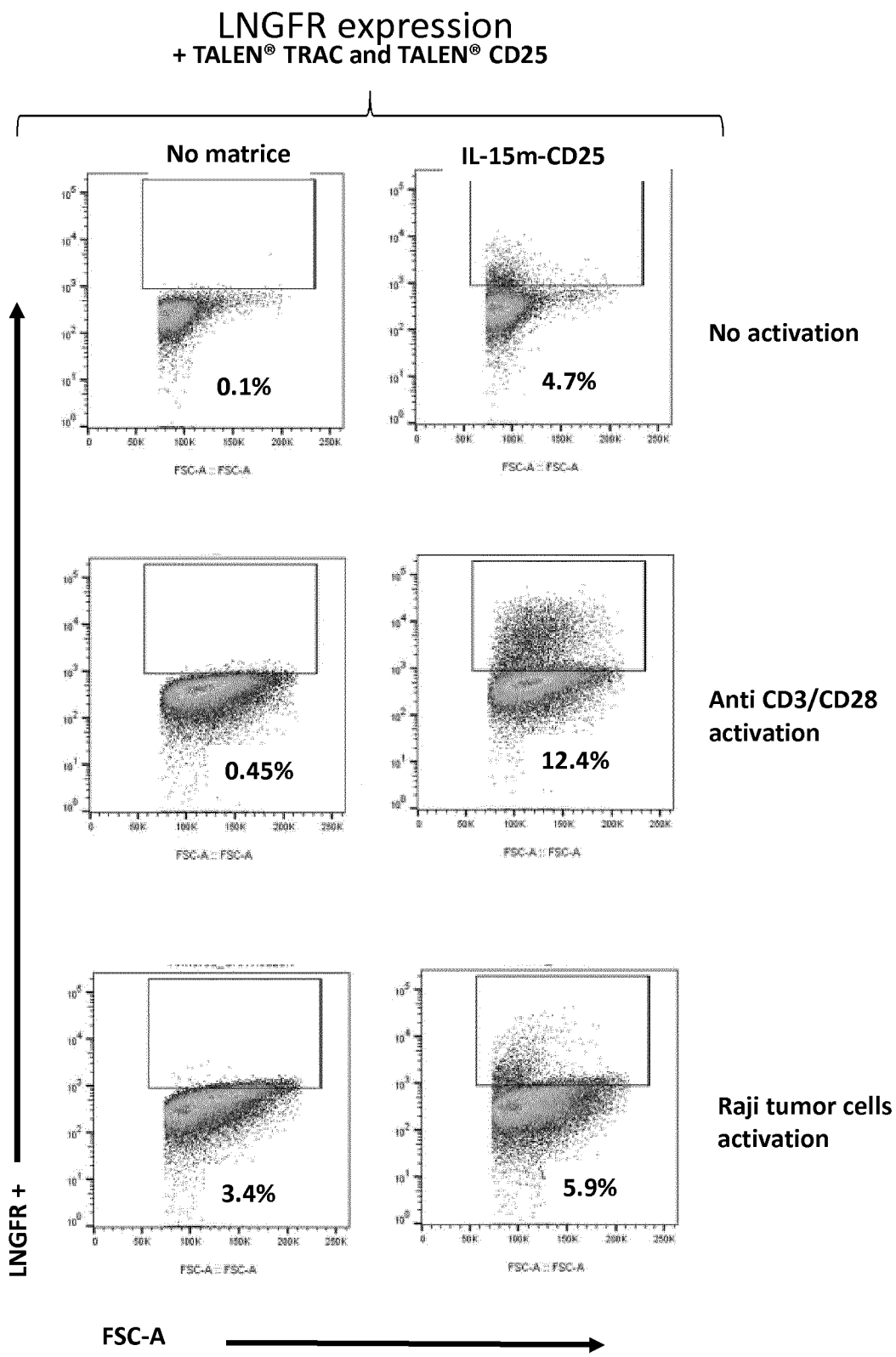
Figure 6:
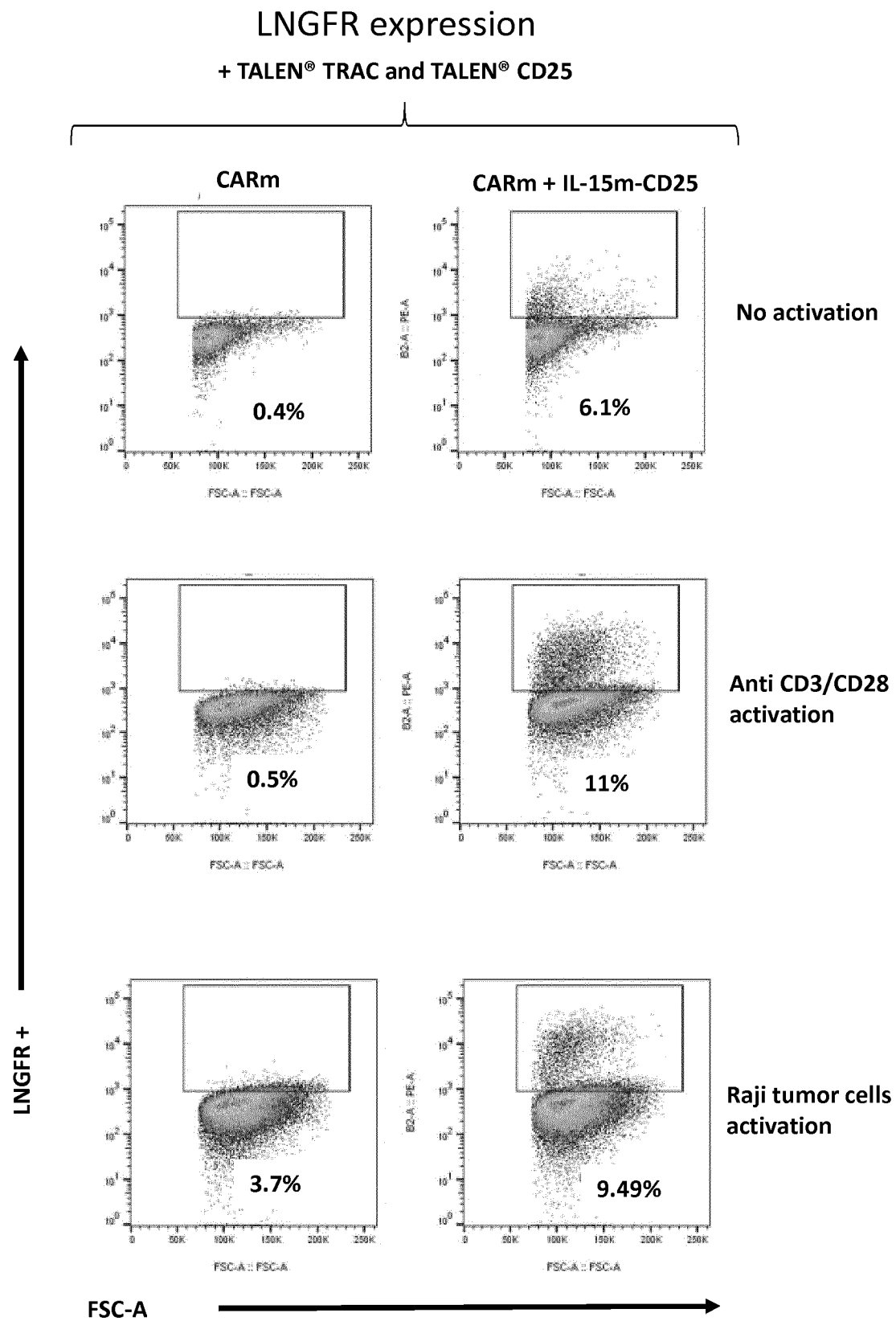

FIGS. 5 and 6: Flow cytometry measures for LNGFR expression among viable T-cells transfected with donor templates of FIG. 4 and specific TALEN® (TCR and CD25), upon antiCD3/CD28 non-specific activation (Dynabeads®) and upon CAR dependent tumor cell activation (raji tumor cells). As shown in FIG. 6, LNGFR expression was specifically induced in [CAR anti-CD22]$^{positive}$ cells upon CAR/tumor engagement.

Figure 7:
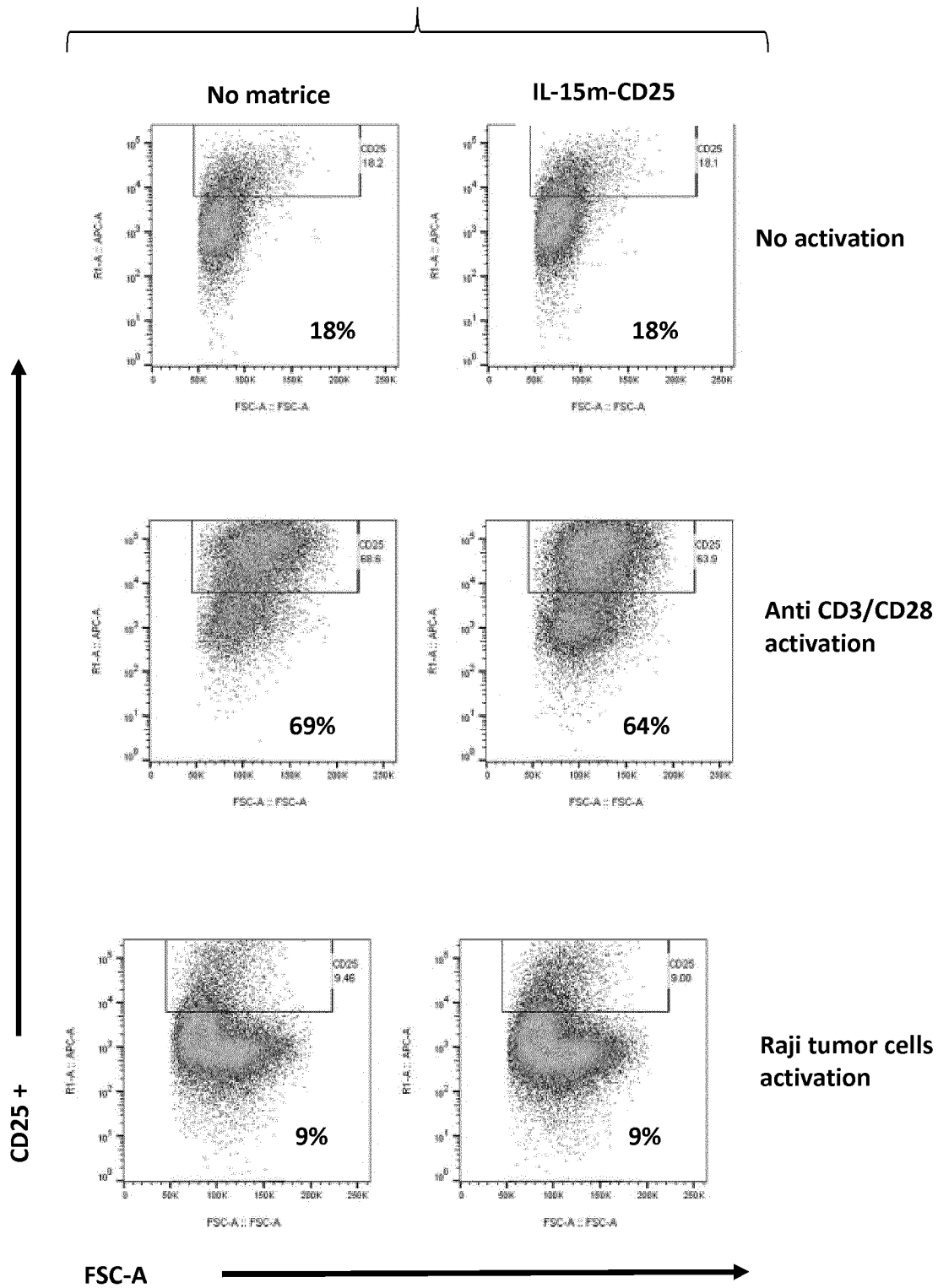
Figure 8:
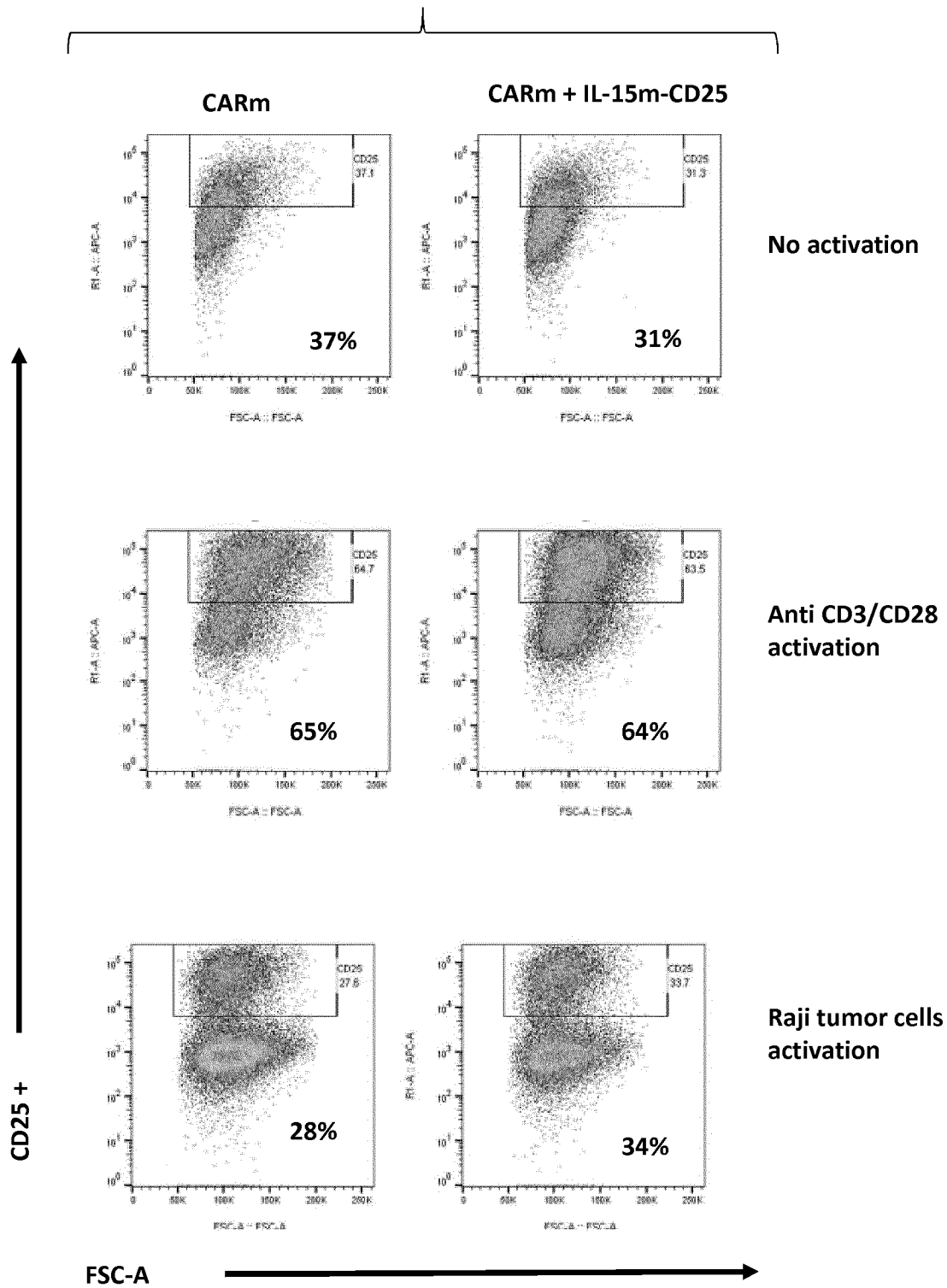

FIGS. 7 and 8: Flow cytometry measures for CD25 expression among viable T-cells transfected with donor templates of FIG. 4 and specific TALEN® (TCR and CD25) upon antiCD3/CD28 non-specific activation (Dynabeads®*) and Tumor cell activation (raji tumor cells). As shown in FIG. 8, CD25 expression was specifically induced in [CAR anti-CD22]$^{positive}$ cells upon CAR/tumor engagement.

Figure 9:
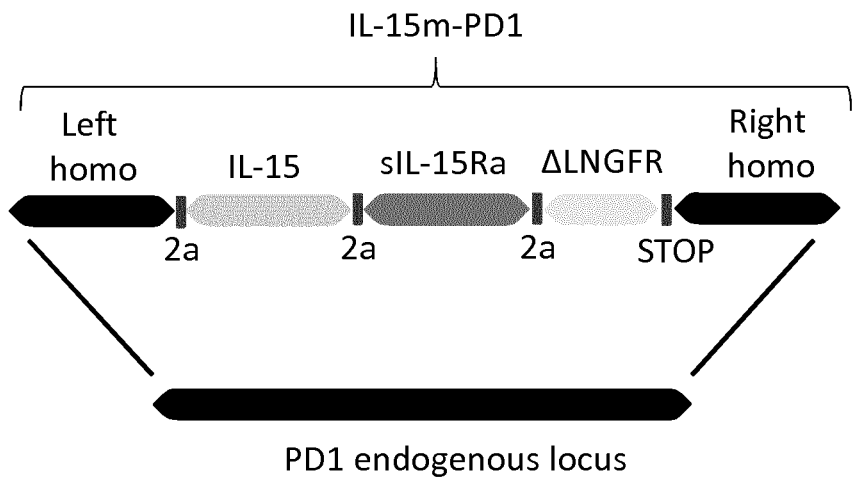
Figure 9:
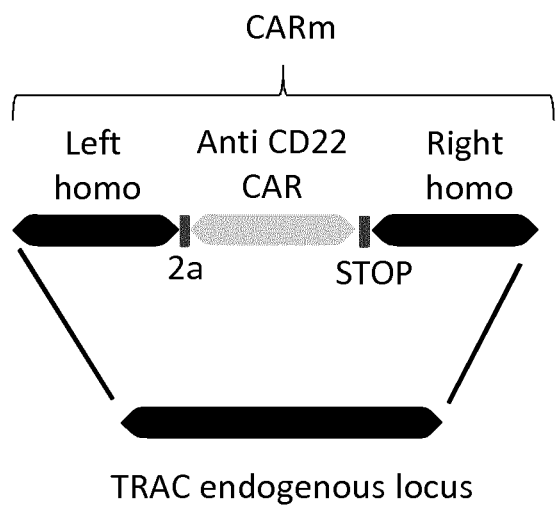

FIG. 9: Schematic representation of the exogenous sequences used in the experimental section to transfect the primary immune cells to obtain the results shown in FIGS. 11 and 12.

Figure 10:
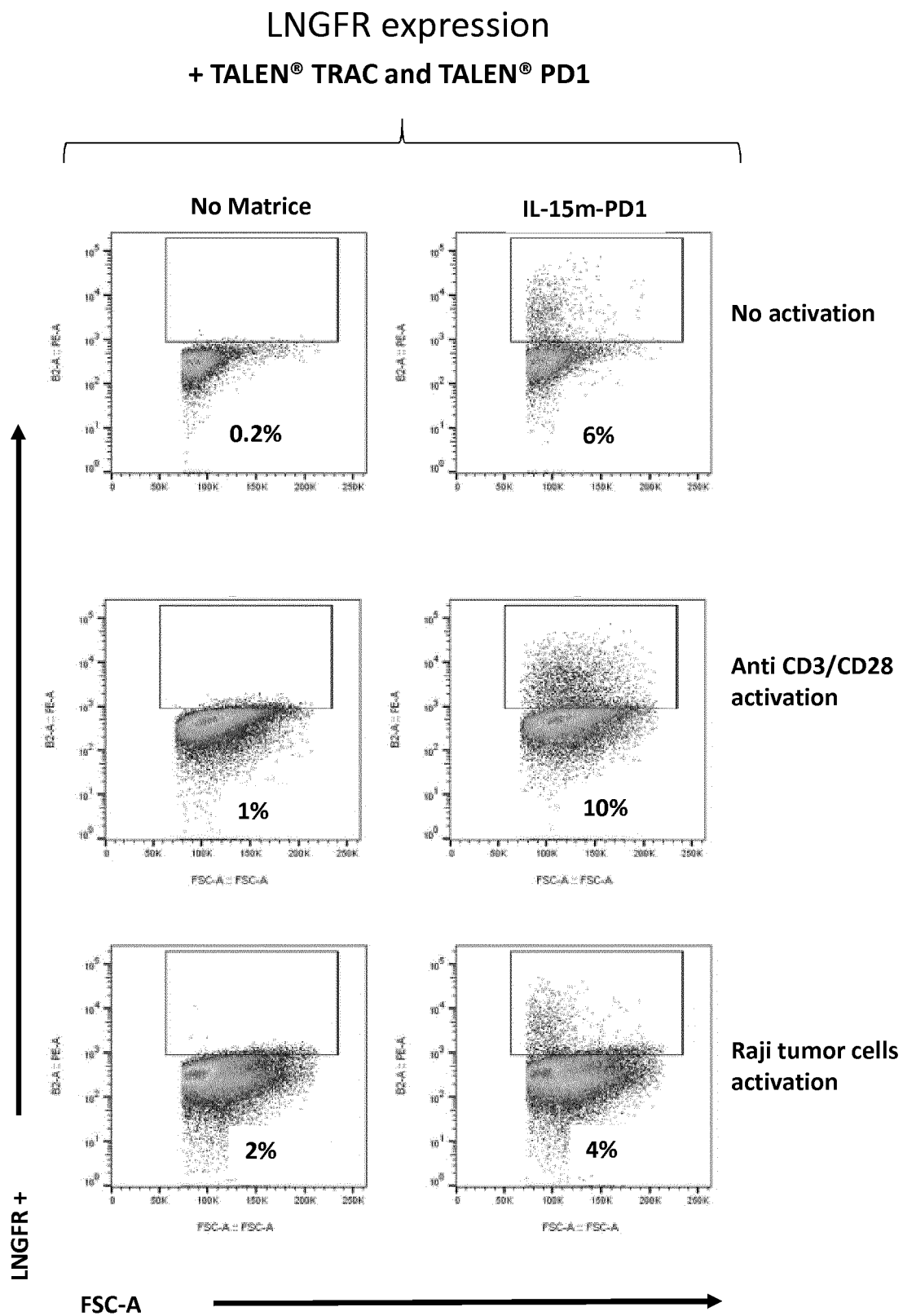
Figure 11:
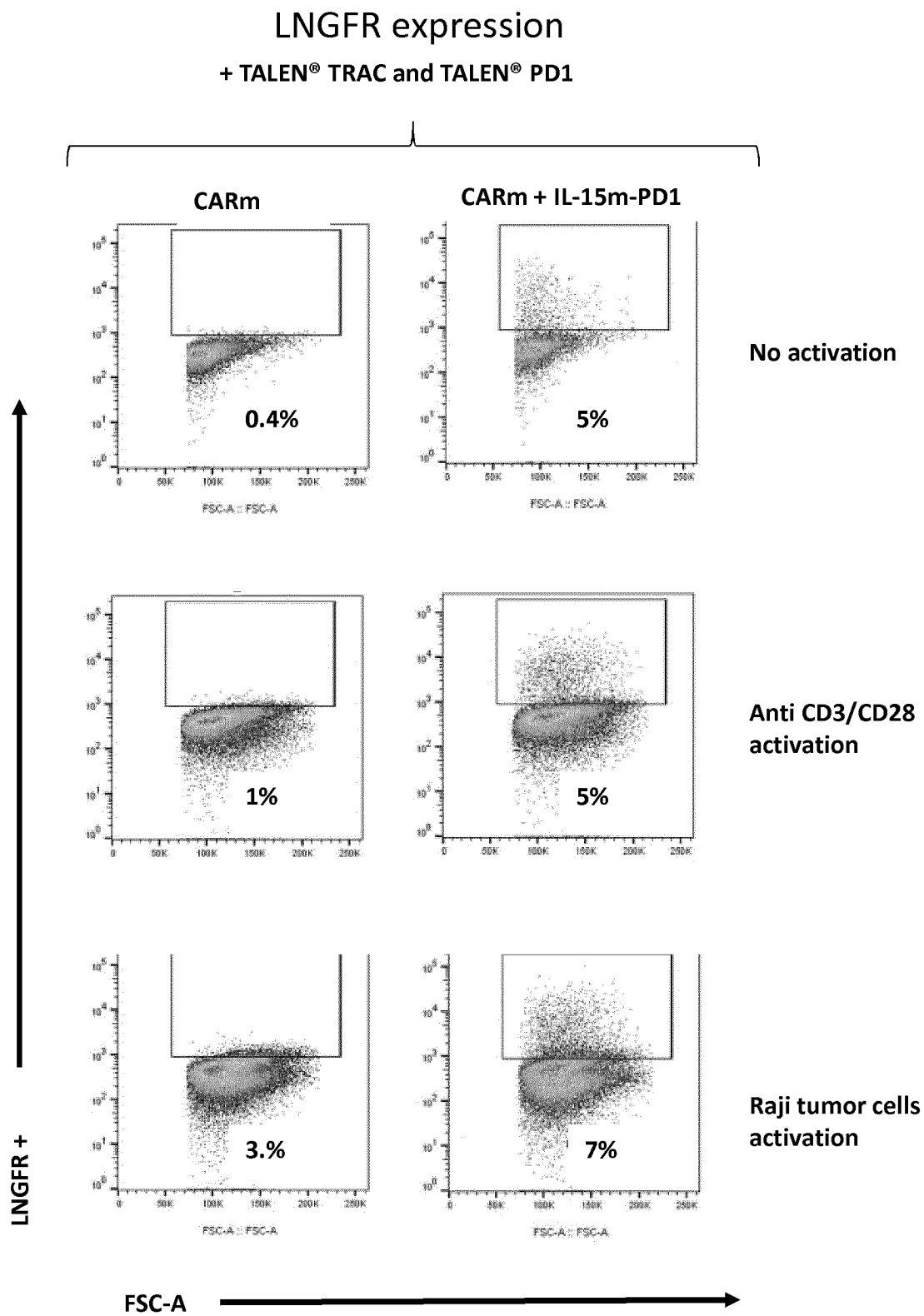

FIGS. 10 and 11: Flow cytometry measures for LNGFR expression among viable T-cells transfected with donor templates of FIG. 9 and specific TALEN® (TCR and PD1) upon antiCD3/CD28 non-specific activation (Dynabeads©) and Tumor cell activation (raji tumor cells). As shown in FIG. 11, LNGFR expression was specifically induced in [CAR anti-CD22]$^{positive}$ cells upon CAR/tumor engagement.

Figure 12:
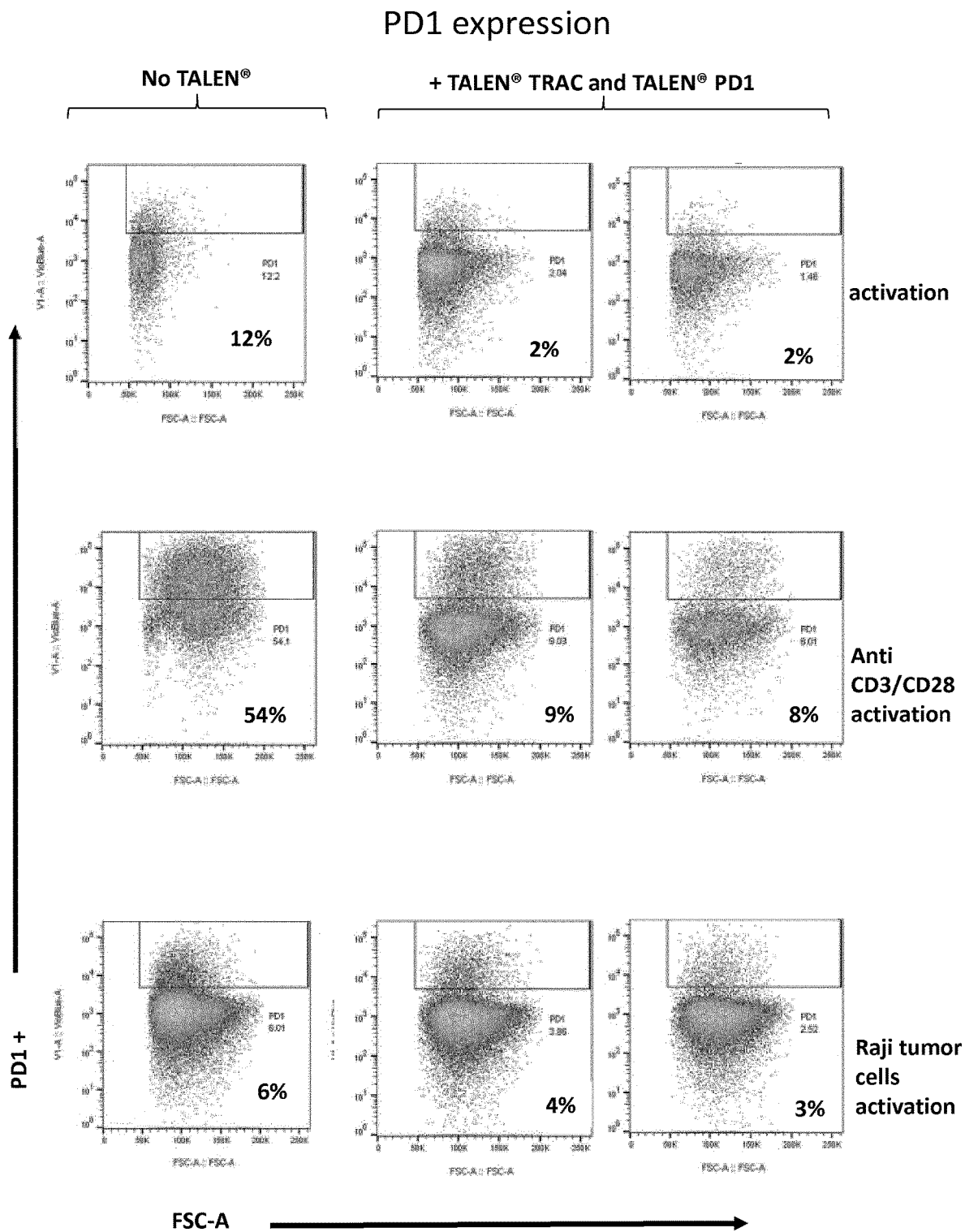

FIG. 12: Flow cytometry measures for endogenous PD1 expression among viable T-cells transfected with donor templates of FIG. 9 upon antiCD3/CD28 non-specific activation (Dynabeads®) and Tumor cell activation (raji tumor cells) with and without using TALEN® (TCR and PD1). PD1 was efficiently Knocked-out by TALEN treatment (8% remaining expression of PD1 out of 54%).

Figure 13:
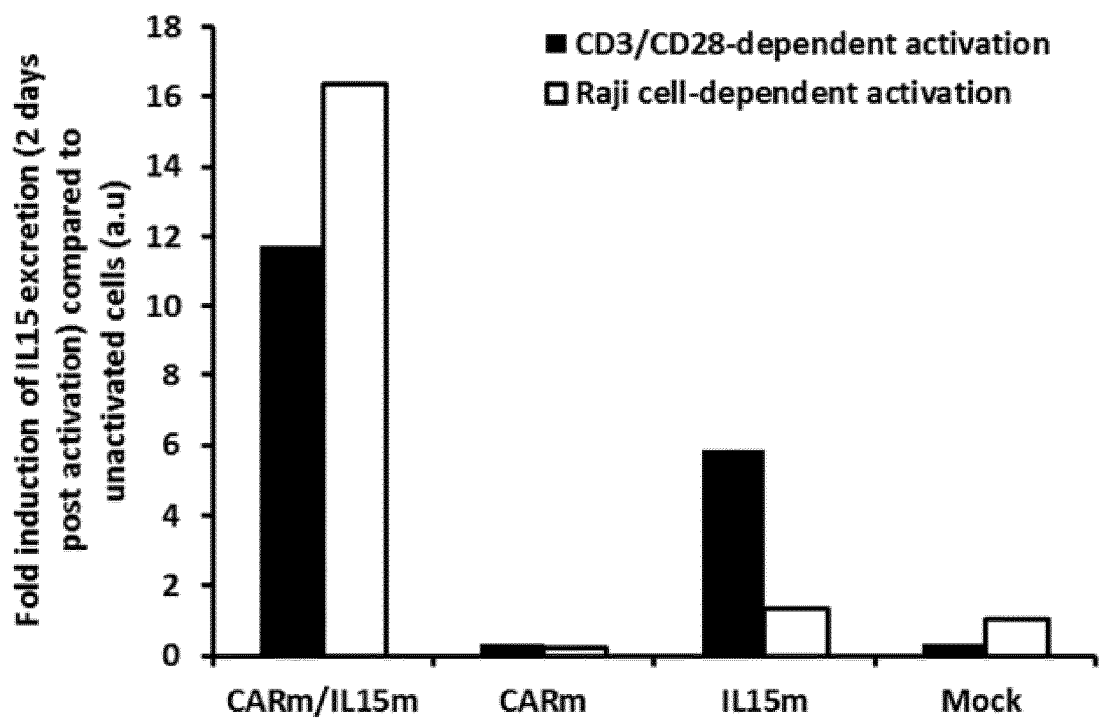

FIG. 13: Diagram showing IL-15 production in [CAR]$^{positive}$ (CARm) and [CAR]$^{negative}$ engineered immune cells according to the invention transfected with the donor template described in FIG. 2 (B) and TALEN® for insertion of IL-15 exogenous coding sequences into the PD1 locus. IL15, which transcription was under control of endogenous PD1 promoter, was efficiently induced upon antiCD3/CD28 non-specific activation (Dynabeads®) and Tumor cell activation (raji tumor cells) and secreted in the culture media.

Figure 14:
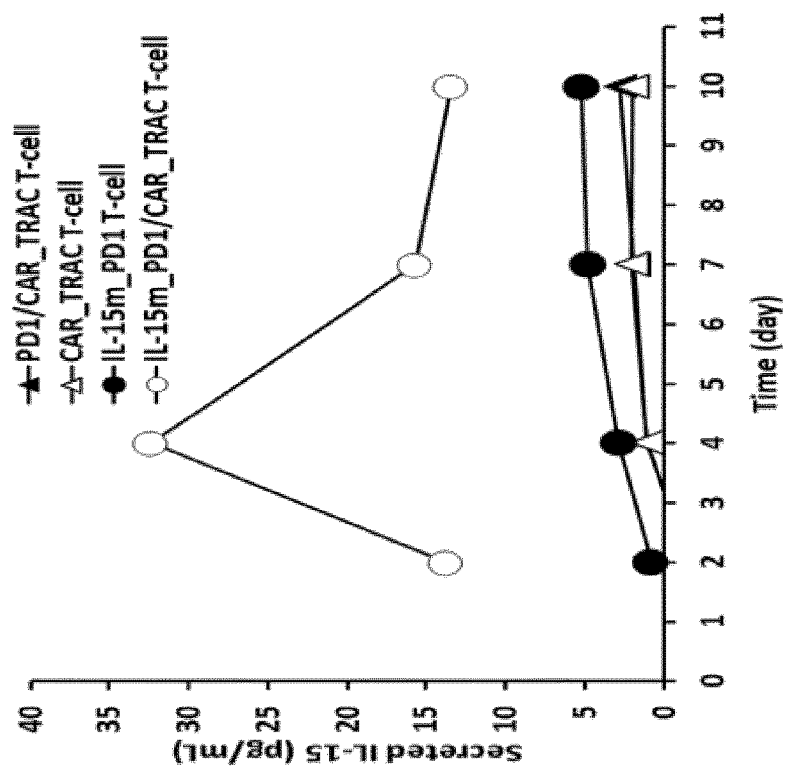
Figure 14:
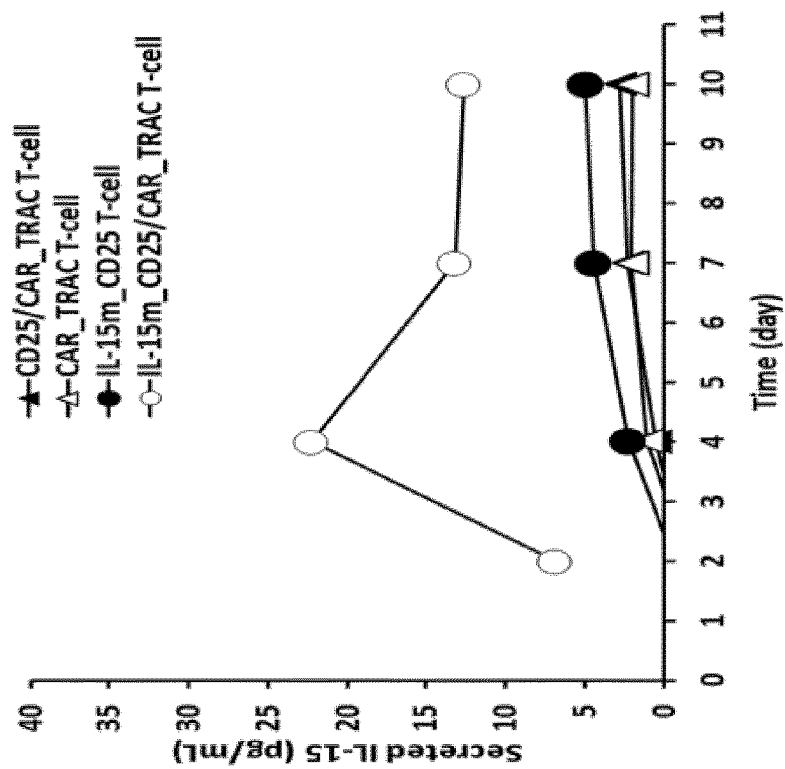

FIG. 14: Graph showing the amount of IL-15 secreted over time (days) post activation by the immune cells engineered according to the invention. A: Cells engineered by integration of the IL-15 coding sequence at the CD25 locus using the DNA donor templates described in FIG. 2A (IL-15m_CD25) and/or 2C (CARm). B: Cells engineered by integration of the IL-15 coding sequence at the PD1 locus using the DNA donor templates described in FIG. 2B (IL-15m_PD1) and/or 2C (CARm). Integrations at both loci show similar IL-15 secretion profiles. Secretion of IL-15 is significant increased by tumor specific activation of CAR.

Figure 15:
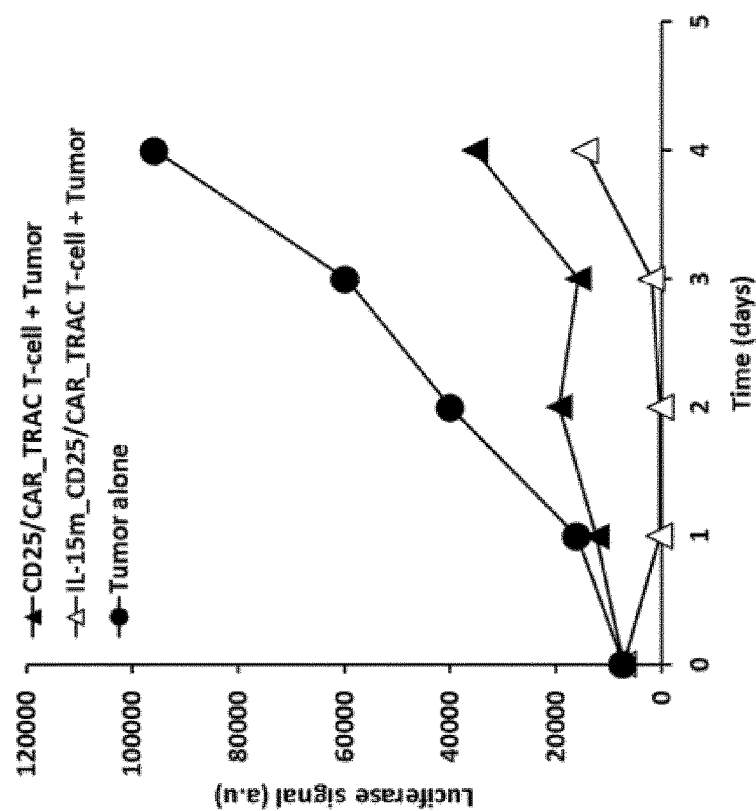
Figure 15:
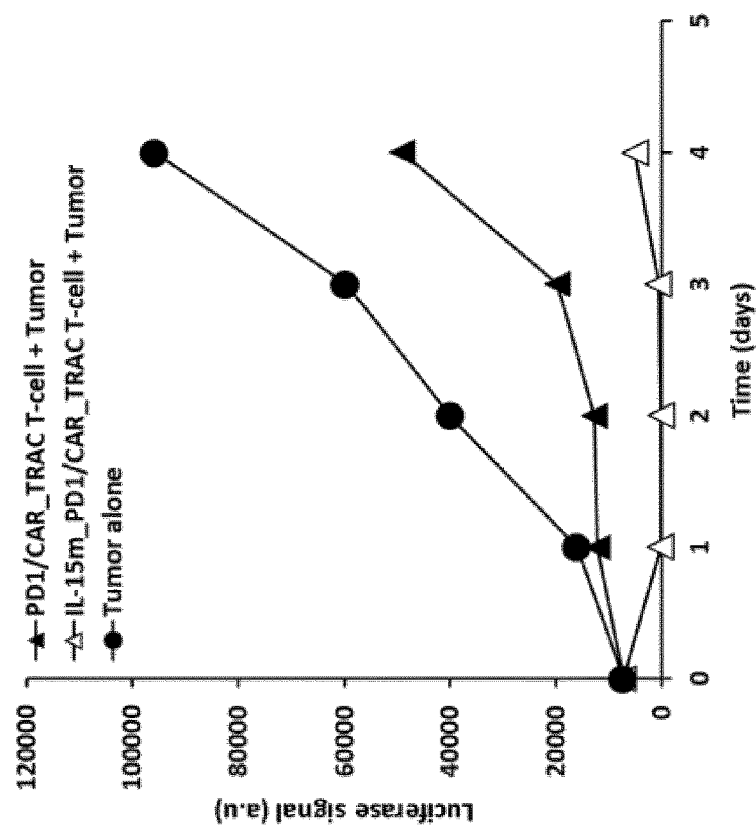

FIG. 15: Graph reporting number of Raji-Luc tumor cells expressing CD22 antigen (luciferase signal) overtime in a survival assay (serial killing assay) as described in Example 2. The immune cells (PBMCs) have been engineered to integrate IL-15 coding sequences at the PD1 (A) or CD25 locus (B) and to express anti-CD22-CAR at the TCR locus (thereby disrupting TCR expression). In this assay, tumor cells are regularly added to the culture medium, while being partially or totally eliminated by the CAR positive cells. The re-expression of IL-15 at either PD1 or CD25 cells dramatically helps the elimination of the tumor cells by the CAR positive cells.

Figure 16:
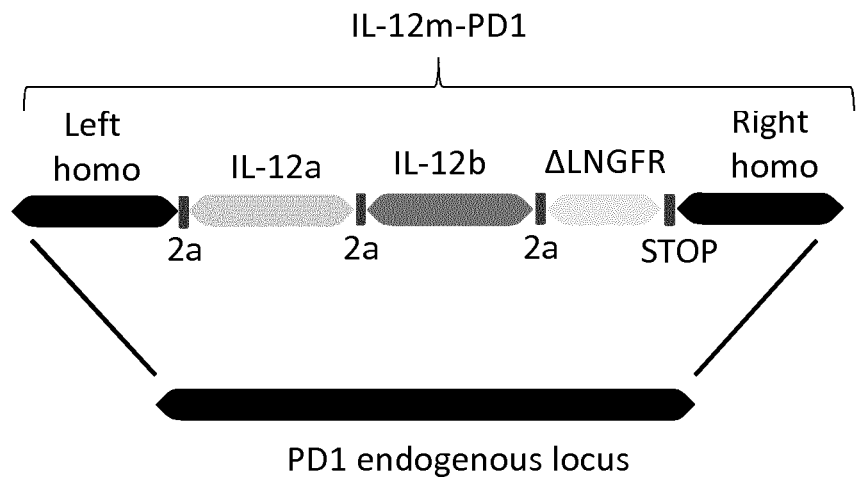
Figure 16:
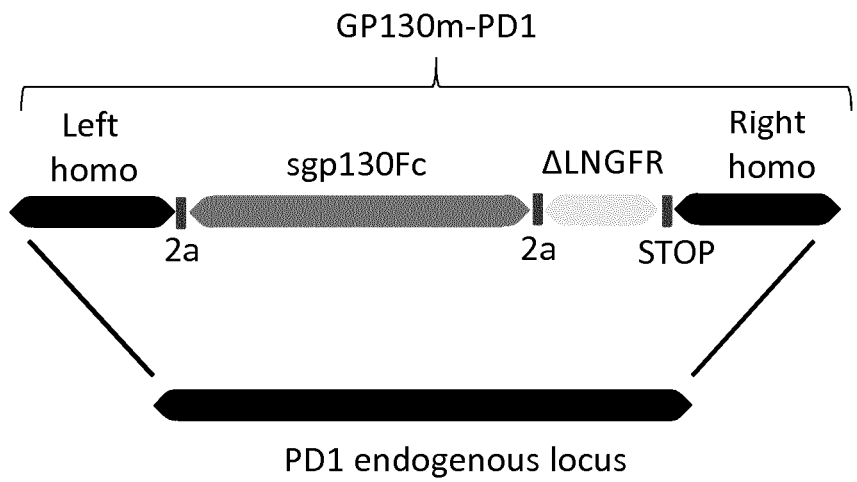

FIG. 16: Schematic representation of the donor sequences used in the experimental section to insert at the PD1 locus the exogenous sequences encoding IL-12 and gp130Fc. A: donor template (designated IL-12m-PD1) designed for site directed insertion of IL-12a and IL-12b coding sequences (SEQ ID NO:47 and 48) at the PD1 locus for obtaining co-transcription of IL-12a and IL-12b, while disrupting PD1 endogenous coding sequence. The right and left border sequences homologous to the PD1 locus sequences are at least 100 pb long, preferably at least 200 pb long, and more preferably at least 300 pb long and comprising SEQ ID NO:45 and 46. Sequences are detailed in Table 5. B: donor template (designated gp130Fcm-PD1) designed for site directed insertion of gp130Fc coding sequences (SEQ ID NO:51) for obtaining transcription at the PD1 locus under PD1 promoter, while disrupting PD1 endogenous coding sequence. The right and left border sequences homologous to the PD1 locus sequences are at least 100 pb long, preferably at least 200 pb long, and more preferably at least 300 pb long and comprising SEQ ID NO:45 and 46. Sequences are detailed in Table 5.

Table 1: ISU domain variants from diverse viruses.

Table 2: Aminoacid sequences of FP polypeptide from natural and artificial origins.

Table 3: List of genes involved into immune cells inhibitory pathways, which can be advantageously modified or inactivated by inserting exogenous coding sequence according to the invention.

Table 4: sequences referred to in example 1.

Table 5: sequences referred to in example 2.

Table 6: List of human genes that are up-regulated upon T-cell activation (CAR activation sensitive promoters), in which gene targeted insertion is sought according to the present invention to improve immune cells therapeutic potential.

Table 7: Selection of genes that are steadily transcribed during immune cell activation (dependent or independent from T-cell activation).

Table 8: Selection of genes that are transiently upregulated upon T-cell activation.

Table 9: Selection of genes that are upregulated over more than 24 hours upon T-cell activation.

Table 10: Selection of genes that are down-regulated upon immune cell activation.

Table 11: Selection of genes that are silent upon T-cell activation (safe harbor gene targeted integration loci).

Table 12: List of gene loci upregulated in tumor exhausted infiltrating lymphocytes (compiled from multiple tumors) useful for gene integration of exogenous coding sequences as per the present invention.

Table 13: List of gene loci upregulated in hypoxic tumor conditions useful for gene integration of exogenous coding sequences as per the present invention.

DETAILED DESCRIPTION OF THE INVENTION

Unless specifically defined herein, all technical and scientific terms used herein have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

The present invention is drawn to a general method of preparing primary immune cells for cell immunotherapy involving gene targeted integration of an exogenous coding sequence into the chromosomal DNA of said immune cells. According to some aspects, this integration is performed in such a way that said coding sequence is placed under the transcriptional control of at least one promoter endogenous to said cells, said endogenous promoter being preferably not a constitutive promoter, such as the one transcribing T-cell receptor alpha constant (TRAC—NCBI Gene ID #28755) A constitutive promoter as per the present invention is for instance a promoter that is active independently from CAR activation—ex: when T-cells are not yet activated.

Improving the Therapeutic Potential of Immune Cells by Gene Targeted Integration Gene editing techniques using polynucleotide sequence-specific reagents, such as rare-cutting endonucleases, have become the state of the art for the introduction of genetic modifications into primary cells. However, they have not been used so far in immune cells to introduce exogenous coding sequences under the transcriptional control of endogenous promoters.

The present invention aims to improve the therapeutic potential of immune cells through gene editing techniques, especially by gene targeted integration.

By "gene targeting integration" is meant any known site-specific methods allowing to insert, replace or correct a genomic sequence into a living cell. According to a preferred aspect of the present invention, said gene targeted integration involves homologous gene recombination at the locus of the targeted gene to result the insertion or replacement of at least one exogenous nucleotide, preferably a sequence of several nucleotides (i.e. polynucleotide), and more preferably a coding sequence.

By "sequence-specific reagent" is meant any active molecule that has the ability to specifically recognize a selected polynucleotide sequence at a genomic locus, preferably of at least 9 bp, more preferably of at least 10 bp and even more preferably of at least 12 pb in length, in view of modifying said genomic locus. According to a preferred aspect of the invention, said sequence-specific reagent is preferably a sequence-specific nuclease reagent.

By "immune cell" is meant a cell of hematopoietic origin functionally involved in the initiation and/or execution of innate and/or adaptative immune response, such as typically CD3 or CD4 positive cells. The immune cell according to the present invention can be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and from tumors, such as tumor infiltrating lymphocytes. In some embodiments, said immune cell can be derived from a healthy donor, from a patient diagnosed with cancer or from a patient diagnosed with an infection. In another embodiment, said cell is part of a mixed population of immune cells which present different phenotypic characteristics, such as comprising CD4, CD8 and CD56 positive cells.

By "primary cell" or "primary cells" are intended cells taken directly from living tissue (e.g. biopsy material) and established for growth in vitro for a limited amount of time, meaning that they can undergo a limited number of population doublings. Primary cells are opposed to continuous tumorigenic or artificially immortalized cell lines. Non-limiting examples of such cell lines are CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells. Primary cells are generally used in cell therapy as they are deemed more functional and less tumorigenic.

In general, primary immune cells are provided from donors or patients through a variety of methods known in the art, as for instance by leukapheresis techniques as reviewed by Schwartz J. et al. (Guidelines on the use of therapeutic apheresis in clinical practice-evidence-based approach from the Writing Committee of the American Society for Apheresis: the sixth special issue (2013) *J Clin Apher.* 28(3):145-284).

The primary immune cells according to the present invention can also be differentiated from stem cells, such as cord blood stem cells, progenitor cells, bone marrow stem cells, hematopoietic stem cells (HSC) and induced pluripotent stem cells (iPS).

By "nuclease reagent" is meant a nucleic acid molecule that contributes to an nuclease catalytic reaction in the target cell, preferably an endonuclease reaction, by itself or as a subunit of a complex such as a guide RNA/Cas9, preferably leading to the cleavage of a nucleic acid sequence target.

The nuclease reagents of the invention are generally "sequence-specific reagents", meaning that they can induce DNA cleavage in the cells at predetermined loci, referred to by extension as "targeted gene". The nucleic acid sequence which is recognized by the sequence specific reagents is referred to as "target sequence". Said target sequence is usually selected to be rare or unique in the cell's genome, and more extensively in the human genome, as can be determined using software and data available from human genome databases, such as ensembl. org/index. html.

"Rare-cutting endonucleases" are sequence-specific endonuclease reagents of choice, insofar as their recognition sequences generally range from 10 to 50 successive base pairs, preferably from 12 to 30 bp, and more preferably from 14 to 20 bp.

According to a preferred aspect of the invention, said endonuclease reagent is a nucleic acid encoding an "engineered" or "programmable" rare-cutting endonuclease, such as a homing endonuclease as described for instance by Arnould S., et al. (WO2004067736), a zing finger nuclease (ZFN) as described, for instance, by Urnov F., et al. (Highly efficient endogenous human gene correction using designed zinc-finger nucleases (2005) *Nature* 435:646-651), a TALE-Nuclease as described, for instance, by Mussolino et al. (A novel TALE nuclease scaffold enables high genome editing activity in combination with low toxicity (2011) *Nucl. Acids Res.* 39(21):9283-9293), or a MegaTAL nuclease as described, for instance by Boissel et al. (MegaTALs: a rare-cleaving nuclease architecture for therapeutic genome engineering (2013) Nucleic Acids Research 42 (4):2591-2601).

According to another embodiment, the endonuclease reagent is a RNA-guide to be used in conjunction with a RNA guided endonuclease, such as Cas9 or Cpf1, as per, inter alia, the teaching by Doudna, J., and Chapentier, E., (The new frontier of genome engineering with CRISPR-Cas9 (2014) *Science* 346 (6213):1077), which is incorporated herein by reference.

According to a preferred aspect of the invention, the endonuclease reagent is transiently expressed into the cells, meaning that said reagent is not supposed to integrate into the genome or persist over a long period of time, such as be the case of RNA, more particularly mRNA, proteins or complexes mixing proteins and nucleic acids (eg: Ribonucleoproteins).

In general, 80% the endonuclease reagent is degraded by 30 hours, preferably by 24, more preferably by 20 hours after transfection.

An endonuclease under mRNA form is preferably synthetized with a cap to enhance its stability according to techniques well known in the art, as described, for instance, by Kore A. L., et al. (Locked nucleic acid (LNA)-modified dinucleotide mRNA cap analogue: synthesis, enzymatic incorporation, and utilization (2009) *J Am Chem Soc.* 131 (18):6364-5).

In general, electroporation steps that are used to transfect immune cells are typically performed in closed chambers comprising parallel plate electrodes producing a pulse electric field between said parallel plate electrodes greater than 100 volts/cm and less than 5,000 volts/cm, substantially uniform throughout the treatment volume such as described in WO/2004/083379, which is incorporated by reference, especially from page 23, line 25 to page 29, line 11. One such electroporation chamber preferably has a geometric factor (cm-1) defined by the quotient of the electrode gap squared (cm2) divided by the chamber volume (cm$^3$), wherein the geometric factor is less than or equal to 0.1 cm$^{-1}$, wherein the suspension of the cells and the sequence-specific reagent is in a medium which is adjusted such that the medium has conductivity in a range spanning 0.01 to 1.0 milliSiemens. In general, the suspension of cells undergoes one or more pulsed electric fields. With the method, the treatment volume of the suspension is scalable, and the time of treatment of the cells in the chamber is substantially uniform.

Due to their higher specificity, TALE-nuclease have proven to be particularly appropriate sequence specific nuclease reagents for therapeutic applications, especially under heterodimeric forms—i.e. working by pairs with a "right" monomer (also referred to as "5'" or "forward") and 'left" monomer (also referred to as "3'" or "reverse") as reported for instance by Mussolino et al. (TALEN® facilitate targeted genome editing in human cells with high specificity and low cytotoxicity (2014) *Nucl. Acids Res.* 42(10): 6762-6773).

As previously stated, the sequence specific reagent is preferably under the form of nucleic acids, such as under DNA or RNA form encoding a rare cutting endonuclease a subunit thereof, but they can also be part of conjugates involving polynucleotide(s) and polypeptide(s) such as so-called "ribonucleoproteins". Such conjugates can be formed with reagents as Cas9 or Cpf1 (RNA-guided endonucleases) or Argonaute (DNA-guided endonucleases) as recently respectively described by Zetsche, B. et al. (Cpf1 Is a Single RNA-Guided Endonuclease of a Class 2 CRISPR-Cas System (2015) Cell 163(3): 759-771) and by Gao F. et al. (DNA-guided genome editing using the *Natronobacterium*

*gregoryi* Argonaute (2016) *Nature Biotech*), which involve RNA or DNA guides that can be complexed with their respective nucleases.

"Exogenous sequence" refers to any nucleotide or nucleic acid sequence that was not initially present at the selected locus. This sequence may be homologous to, or a copy of, a genomic sequence, or be a foreign sequence introduced into the cell. By opposition "endogenous sequence" means a cell genomic sequence initially present at a locus. The exogenous sequence preferably codes for a polypeptide which expression confers a therapeutic advantage over sister cells that have not integrated this exogenous sequence at the locus. A endogenous sequence that is gene edited by the insertion of a nucleotide or polynucleotide as per the method of the present invention, in order to express a different polypeptide is broadly referred to as an exogenous coding sequence The method of the present invention can be associated with other methods involving physical of genetic transformations, such as a viral transduction or transfection using nanoparticles, and also may be combined with other gene inactivation and/or transgene insertions.

According to one aspect, the method according to the invention comprises the steps of:
providing a population of primary immune cells;
introducing into a proportion of said primary immune cells:
i) At least one nucleic acid comprising an exogenous nucleotide or polynucleotide sequence to be integrated at a selected endogenous locus to encode at least one molecule improving the therapeutic potential of said immune cells population;
ii) At least one sequence-specific reagent that specifically targets said selected endogenous locus,
wherein said exogenous nucleotide or polynucleotide sequence is inserted by targeted gene integration into said endogenous locus, so that said exogenous nucleotide or polynucleotide sequence forms an exogenous coding sequence under transcriptional control of an endogenous promoter present at said locus.

According to one aspect of the method, the sequence specific reagent is a nuclease and the targeted gene integration is operated by homologous recombination or NHEJ into said immune cells.

According to a further aspect of the invention, said endogenous promoter is selected to be active during immune cell activation and preferably up-regulated. More specifically, the invention is drawn to a method for preparing engineered primary immune cells for cell immunotherapy, said method comprising:
providing a population of primary immune cells;
introducing into a proportion of said primary immune cells:
i) At least one exogenous nucleic acid comprising an exogenous coding sequence encoding at least one molecule improving the therapeutic potential of said immune cells population;
ii) At least one sequence-specific nuclease reagent that specifically targets a gene which is under control of an endogenous promoter active during immune cell activation;
wherein said coding sequence is introduced into the primary immune cells genome by targeted homologous recombination, so that said coding sequence is placed under the transcriptional control of at least one endogenous promoter of said gene.

By "improving therapeutic potential" is meant that the engineered immune cells gain at least one advantageous property for their use in cell therapy by comparison to their sister non-engineered immune cells. The therapeutic properties sought by the invention may be any measurable one as referred to in the relevant scientific literature.

Improved therapeutic potential can be more particularly reflected by a resistance of the immune cells to a drug, an increase in their persistence in-vitro or in-vivo, or a safer/more convenient handling during manufacturing of therapeutic compositions and treatments.

In general said molecule improving the therapeutic potential is a polypeptide, but it can also be a nucleic acid able to direct or repress expression of other genes, such as interference RNAs or guide-RNAs. The polypeptides may act directly or indirectly, such as signal transducers or transcriptional regulators.

According to one embodiment of the present method, the exogenous sequence is introduced into the endogenous chromosomal DNA by targeted homologous recombination. Accordingly, the exogenous nucleic acid introduced into the immune cell comprises at least one coding sequence(s), along with sequences that can hybridize endogenous chromosomal sequences under physiological conditions. In general, such homologous sequences show at least 70%, preferably 80% and more preferably 90% sequence identity with the endogenous gene sequences located at the insertion locus. These homologous sequences may flank the coding sequence to improve the precision of recombination as already taught for instance in U.S. Pat. No. 6,528,313. Using available software and on-line genome databases, it is possible to design vectors that includes said coding sequence (s), in such a way that said sequence(s) is (are) introduced at a precise locus, under transcriptional control of at least one endogenous promoter, which is a promoter of an endogenous gene. The exogenous coding sequence(s) is (are) then preferably inserted "in frame" with said endogenous gene. The sequences resulting from the integration of the exogenous polynucleotide sequence(s) can encode many different types of proteins, including fusion proteins, tagged protein or mutated proteins. Fusion proteins allow adding new functional domains to the proteins expressed in the cell, such as a dimerization domain that can be used to switch-on or switch-off the activity of said protein, such as caspase-9 switch. Tagged proteins can be advantageous for the detection of the engineered immune cells and the follow-up of the patients treated with said cells. Introducing mutation into proteins can confer resistance to drugs or immune depletion agents as further described below.

Conferring Resistance to Drugs or Immune Depletion Agents

According to one aspect of the present method, the exogenous sequence that is integrated into the immune cells genomic locus encodes a molecule that confers resistance of said immune cells to a drug.

Examples of preferred exogenous sequences are variants of dihydrofolate reductase (DHFR) conferring resistance to folate analogs such as methotrexate, variants of inosine monophosphate dehydrogenase 2 (IMPDH2) conferring resistance to IMPDH inhibitors such as mycophenolic acid (MPA) or its prodrug mycophenolate mofetil (MMF), variants of calcineurin or methylguanine transferase (MGMT) conferring resistance to calcineurin inhibitor such as FK506 and/or CsA, variants of mTOR such as mTORmut conferring resistance to rapamycin) and variants of Lck, such as Lckmut conferring resistance to Imatinib and Gleevec.

The term "drug" is used herein as referring to a compound or a derivative thereof, preferably a standard chemotherapy agent that is generally used for interacting with a cancer cell, thereby reducing the proliferative or living status of the cell. Examples of chemotherapeutic agents include, but are not limited to, alkylating agents (e.g., cyclophosphamide, ifosamide), metabolic antagonists (e.g., purine nucleoside antimetabolite such as clofarabine, fludarabine or 2'-deoxyadenosine, methotrexate (MTX), 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, and the like. Such agents may further include, but are not limited to, the anti-cancer agents TRIMETHOTRIXATE™ (TMTX), TEMOZOLOMIDE™, RALTRITREXED™ S-(4-Nitrobenzyl)-6-thioinosine (NBMPR), 6-benzyguanidine (6-BG), bis-chloronitrosourea (BCNU) and CAMPTOTHECIN™, or a therapeutic derivative of any thereof.

As used herein, an immune cell is made "resistant or tolerant" to a drug when said cell, or population of cells is modified so that it can proliferate, at least in-vitro, in a culture medium containing half maximal inhibitory concentration (IC50) of said drug (said IC50 being determined with respect to an unmodified cell(s) or population of cells).

In a particular embodiment, said drug resistance can be conferred to the immune cells by the expression of at least one "drug resistance coding sequence". Said drug resistance coding sequence refers to a nucleic acid sequence that confers "resistance" to an agent, such as one of the chemotherapeutic agents referred to above. A drug resistance coding sequence of the invention can encode resistance to anti-metabolite, methotrexate, vinblastine, cisplatin, alkylating agents, anthracyclines, cytotoxic antibiotics, anti-immunophilins, their analogs or derivatives, and the like (Takebe, N., S. C. Zhao, et al. (2001) "Generation of dual resistance to 4-hydroperoxycyclophosphamide and methotrexate by retroviral transfer of the human aldehyde dehydrogenase class 1 gene and a mutated dihydrofolate reductase gene". Mol. Ther. 3(1): 88-96), (Zielske, S. P., J. S. Reese, et al. (2003) "In vivo selection of MGMT (P140K) lentivirus-transduced human NOD/SCID repopulating cells without pretransplant irradiation conditioning." J. Clin. Invest. 112 (10): 1561-70) (Nivens, M. C., T. Felder, et al. (2004) "Engineered resistance to camptothecin and antifolates by retroviral coexpression of tyrosyl DNA phosphodiesterase-I and thymidylate synthase" Cancer Chemother Pharmacol 53(2): 107-15), (Bardenheuer, W., K. Lehmberg, et al. (2005). "Resistance to cytarabine and gemcitabine and in vitro selection of transduced cells after retroviral expression of cytidine deaminase in human hematopoietic progenitor cells". Leukemia 19(12): 2281-8), (Kushman, M. E., S. L. Kabler, et al. (2007) "Expression of human glutathione S-transferase P1 confers resistance to benzo[a]pyrene or benzo[a]pyrene-7,8-dihydrodiol mutagenesis, macromolecular alkylation and formation of stable N2-Gua-BPDE adducts in stably transfected V79MZ cells co-expressing hCYP1A1" Carcinogenesis 28(1): 207-14).

The expression of such drug resistance exogenous sequences in the immune cells as per the present invention more particularly allows the use of said immune cells in cell therapy treatment schemes where cell therapy is combined with chemotherapy or into patients previously treated with these drugs.

Several drug resistance coding sequences have been identified that can potentially be used to confer drug resistance according to the invention. One example of drug resistance coding sequence can be for instance a mutant or modified form of Dihydrofolate reductase (DHFR). DHFR is an enzyme involved in regulating the amount of tetrahydrofolate in the cell and is essential to DNA synthesis. Folate analogs such as methotrexate (MTX) inhibit DHFR and are thus used as anti-neoplastic agents in clinic. Different mutant forms of DHFR which have increased resistance to inhibition by anti-folates used in therapy have been described. In a particular embodiment, the drug resistance coding sequence according to the present invention can be a nucleic acid sequence encoding a mutant form of human wild type DHFR (GenBank: AAH71996.1), which comprises at least one mutation conferring resistance to an anti-folate treatment, such as methotrexate. In particular embodiment, mutant form of DHFR comprises at least one mutated amino acid at position G15, L22, F31 or F34, preferably at positions L22 or F31 (Schweitzer et al. (1990) "Dihydrofolate reductase as a therapeutic target" Faseb J 4(8): 2441-52; International application WO94/24277; and U.S. Pat. No. 6,642,043). In a particular embodiment, said DHFR mutant form comprises two mutated amino acids at position L22 and F31. Correspondence of amino acid positions described herein is frequently expressed in terms of the positions of the amino acids of the form of wild-type DHFR polypeptide. In a particular embodiment, the serine residue at position 15 is preferably replaced with a tryptophan residue. In another particular embodiment, the leucine residue at position 22 is preferably replaced with an amino acid which will disrupt binding of the mutant DHFR to antifolates, preferably with uncharged amino acid residues such as phenylalanine or tyrosine. In another particular embodiment, the phenylalanine residue at positions 31 or 34 is preferably replaced with a small hydrophilic amino acid such as alanine, serine or glycine.

Another example of drug resistance coding sequence can also be a mutant or modified form of ionisine-5'-monophosphate dehydrogenase II (IMPDH2), a rate-limiting enzyme in the de novo synthesis of guanosine nucleotides. The mutant or modified form of IMPDH2 is a IMPDH inhibitor resistance gene. IMPDH inhibitors can be mycophenolic acid (MPA) or its prodrug mycophenolate mofetil (MMF). The mutant IMPDH2 can comprises at least one, preferably two mutations in the MAP binding site of the wild type human IMPDH2 (Genebank: NP_000875.2) leading to a significantly increased resistance to IMPDH inhibitor. Mutations in these variants are preferably at positions T333 and/or S351 (Yam, P., M. Jensen, et al. (2006) "Ex vivo selection and expansion of cells based on expression of a mutated inosine monophosphate dehydrogenase 2 after HIV vector transduction: effects on lymphocytes, monocytes, and CD34+ stem cells" Mol. Ther. 14(2): 236-44)(Jonnalagadda, M., et al. (2013) "Engineering human T cells for resistance to methotrexate and mycophenolate mofetil as an in vivo cell selection strategy." PLoS One 8(6): e65519).

Another drug resistance coding sequence is the mutant form of calcineurin. Calcineurin (PP2B—NCBI: ACX34092.1) is an ubiquitously expressed serine/threonine protein phosphatase that is involved in many biological processes and which is central to T-cell activation. Calcineurin is a heterodimer composed of a catalytic subunit (CnA; three isoforms) and a regulatory subunit (CnB; two isoforms). After engagement of the T-cell receptor, calcineurin dephosphorylates the transcription factor NFAT, allowing it to translocate to the nucleus and active key target gene such as IL2. FK506 in complex with FKBP12, or cyclosporine A (CsA) in complex with CyPA block NFAT access to calcineurin's active site, preventing its dephosphorylation and thereby inhibiting T-cell activation (Brewin et al. (2009)

"Generation of EBV-specific cytotoxic T cells that are resistant to calcineurin inhibitors for the treatment of post-transplantation lymphoproliferative disease" *Blood* 114(23): 4792-803). In a particular embodiment, said mutant form can comprise at least one mutated amino acid of the wild type calcineurin heterodimer a at positions: V314, Y341, M347, T351, W352, L354, K360, preferably double mutations at positions T351 and L354 or V314 and Y341. In a particular embodiment, the valine residue at position 341 can be replaced with a lysine or an arginine residue, the tyrosine residue at position 341 can be replaced with a phenylalanine residue; the methionine at position 347 can be replaced with the glutamic acid, arginine or tryptophane residue; the threonine at position 351 can be replaced with the glutamic acid residue; the tryptophane residue at position 352 can be replaced with a cysteine, glutamic acid or alanine residue, the serine at position 353 can be replaced with the histidine or asparagines residue, the leucine at position 354 can be replaced with an alanine residue; the lysine at position 360 can be replaced with an alanine or phenylalanine residue. In another particular embodiment, said mutant form can comprise at least one mutated amino acid of the wild type calcineurin heterodimer b at positions: V120, N123, L124 or K125, preferably double mutations at positions L124 and K125. In a particular embodiment, the valine at position 120 can be replaced with a serine, an aspartic acid, phenylalanine or leucine residue; the asparagines at position 123 can be replaced with a tryptophan, lysine, phenylalanine, arginine, histidine or serine; the leucine at position 124 can be replaced with a threonine residue; the lysine at position 125 can be replaced with an alanine, a glutamic acid, tryptophan, or two residues such as leucine-arginine or isoleucine-glutamic acid can be added after the lysine at position 125 in the amino acid sequence. Correspondence of amino acid positions described herein is frequently expressed in terms of the positions of the amino acids of the form of wild-type human calcineurin heterodimer b polypeptide (NCBI: ACX34095.1).

Another drug resistance coding sequence is 0(6)-methylguanine methyltransferase (MGMT—UniProtKB: P16455) encoding human alkyl guanine transferase (hAGT). AGT is a DNA repair protein that confers resistance to the cytotoxic effects of alkylating agents, such as nitrosoureas and temozolomide (TMZ). 6-benzylguanine (6-BG) is an inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-BG, but retain their ability to repair DNA damage (Maze, R. et al. (1999) "Retroviral-mediated expression of the P140A, but not P140A/G156A, mutant form of O6-methylguanine DNA methyltransferase protects hematopoietic cells against O6-benzylguanine sensitization to chloroethylnitrosourea treatment" *J. Pharmacol. Exp. Ther.* 290(3): 1467-74). In a particular embodiment, AGT mutant form can comprise a mutated amino acid of the wild type AGT position P140. In a preferred embodiment, said proline at position 140 is replaced with a lysine residue.

Another drug resistance coding sequence can be multi-drug resistance protein (MDR1) gene. This gene encodes a membrane glycoprotein, known as P-glycoprotein (P-GP) involved in the transport of metabolic byproducts across the cell membrane. The P-Gp protein displays broad specificity towards several structurally unrelated chemotherapy agents. Thus, drug resistance can be conferred to cells by the expression of nucleic acid sequence that encodes MDR-1 (Genebank NP_000918).

Another drug resistance coding sequence can contribute to the production of cytotoxic antibiotics, such as those from ble or mcrA genes. Ectopic expression of ble gene or mcrA in an immune cell gives a selective advantage when exposed to the respective chemotherapeutic agents bleomycine and mitomycin C (Belcourt, M. F. (1999) "Mitomycin resistance in mammalian cells expressing the bacterial mitomycin C resistance protein MCRA". *PNAS.* 96(18):10489-94).

Another drug resistance coding sequence can come from genes encoded mutated version of drug targets, such as mutated variants of mTOR (mTOR mut) conferring resistance to rapamycin such as described by Lorenz M. C. et al. (1995) "TOR Mutations Confer Rapamycin Resistance by Preventing Interaction with FKBP12-Rapamycin" *The Journal of Biological Chemistry* 270, 27531-27537, or certain mutated variants of Lck (Lckmut) conferring resistance to Gleevec as described by Lee K. C. et al. (2010) "Lck is a key target of imatinib and dasatinib in T-cell activation", *Leukemia,* 24: 896-900.

As described above, the genetic modification step of the method can comprise a step of introduction into cells of an exogeneous nucleic acid comprising at least a sequence encoding the drug resistance coding sequence and a portion of an endogenous gene such that homologous recombination occurs between the endogenous gene and the exogeneous nucleic acid. In a particular embodiment, said endogenous gene can be the wild type "drug resistance" gene, such that after homologous recombination, the wild type gene is replaced by the mutant form of the gene which confers resistance to the drug.

Enhancing Persistence of the Immune Cells In-Vivo

According to one aspect of the present method, the exogenous sequence that is integrated into the immune cells genomic locus encodes a molecule that enhances persistence of the immune cells, especially in-vivo persistence in a tumor environment.

By "enhancing persistence" is meant extending the survival of the immune cells in terms of life span, especially once the engineered immune cells are injected into the patient. For instance, persistence is enhanced, if the mean survival of the modified cells is significantly longer than that of non-modified cells, by at least 10%, preferably 20%, more preferably 30%, even more preferably 50%.

This especially relevant when the immune cells are allogeneic. This may be done by creating a local immune protection by introducing coding sequences that ectopically express and/or secrete immunosuppressive polypeptides at, or through, the cell membrane. A various panel of such polypeptides in particular antagonists of immune checkpoints, immunosuppressive peptides derived from viral envelope or NKG2D ligand can enhance persistence and/or an engraftment of allogeneic immune cells into patients.

According to one embodiment, the immunosuppressive polypeptide to be encoded by said exogenous coding sequence is a ligand of Cytotoxic T-Lymphocyte Antigen 4 (CTLA-4 also known as CD152, GenBank accession number AF414120.1). Said ligand polypeptide is preferably an anti-CTLA-4 immunoglobulin, such as CTLA-4a Ig and CTLA-4b Ig or a functional variant thereof.

According to one embodiment, the immunosuppressive polypeptide to be encoded by said exogenous coding sequence is an antagonist of PD1, such as PD-L1 (other names: CD274, Programmed cell death 1 ligand; ref. UniProt for the human polypeptide sequence Q9NZQ7), which encodes a type I transmembrane protein of 290 amino acids consisting of a Ig V-like domain, a Ig C-like domain, a hydrophobic transmembrane domain and a cytoplasmic tail of 30 amino acids. Such membrane-bound form of PD-L1 ligand is meant in the present invention under a native form (wild-type) or under a truncated form such as, for instance, by removing the intracellular domain, or with one or more mutation(s) (Wang S et al., 2003, *J Exp Med.* 2003; 197(9): 1083-1091). Of note, PD1 is not considered as being a membrane-bound form of PD-L1 ligand according to the present invention. According to another embodiment, said immunosuppressive polypeptide is under a secreted form. Such recombinant secreted PD-L1 (or soluble PD-L1) may be generated by fusing the extracellular domain of PD-L1 to the Fc portion of an immunoglobulin (Haile S T et al., 2014, *Cancer Immunol. Res.* 2(7): 610-615; Song M Y et al., 2015, Gut. 64(2):260-71). This recombinant PD-L1 can neutralize PD-1 and abrogate PD-1-mediated T-cell inhibition. PD-L1 ligand may be co-expressed with CTLA4 Ig for an even enhanced persistence of both.

According to another embodiment, the exogenous sequence encodes a polypeptide comprising a viral env immusuppressive domain (ISU), which is derived for instance from HIV-1, HIV-2, SIV, MoMuLV, HTLV-I, -II, MPMV, SRV-1, Syncitin 1 or 2, HERV-K or FELV.

The following Table 1 shows variants of ISU domain from diverse virus which can be expressed within the present invention.

globulin/CD3ζ polypeptides expressed in T cells convert MHC class I peptide ligands into T cell activation receptors: a potential tool for specific targeting of pathogenic CD8+ T cells" *Int. Immunol.* 15 (11): 1379-1387.

According to one embodiment, the exogenous sequence encodes NKG2D ligand. Some viruses such as cytomegaloviruses have acquired mechanisms to avoid NK cell mediate immune surveillance and interfere with the NKG2D pathway by secreting a protein able to bind NKG2D ligands and prevent their surface expression (Welte, S. A et al. (2003) "Selective intracellular retention of virally induced NKG2D ligands by the human cytomegalovirus UL16 glycoprotein". *Eur. J. Immunol.*, 33, 194-203). In tumors cells, some mechanisms have evolved to evade NKG2D response by secreting NKG2D ligands such as ULBP2, MICB or MICA (Salih H R, Antropius H, Gieseke F, Lutz S Z, Kanz L, et al. (2003) Functional expression and release of ligands for the activating immunoreceptor NKG2D in leukemia. *Blood* 102: 1389-1396)

According to one embodiment, the exogenous sequence encodes a cytokine receptor, such as an IL-12 receptor. IL-12 is a well known activator of immune cells activation (Curtis J. H. (2008) "IL-12 Produced by Dendritic Cells Augments CD8+ T Cell Activation through the Production

TABLE 1

ISU domain variants from diverse viruses
ISU Amino acids sequences

| Amino acid positions | | | | | | | | | | | | | | Virus origin | |
|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | Origin | SEQ ID NO |
| L | Q | A | R | I/V | L | A | V | E | R | Y | L | K/R/Q | D | HIV-1 | SEQ ID NO: 68 |
| L | Q | A | R | V | T | A | I | E | K | Y | L | K/A/Q | D/H | HIV-2 | SEQ ID NO: 69 |
| L | Q | A | R | L | L | A | V | E | R | Y | L | K | D | SIV | SEQ ID NO: 70 |
| L | Q | N | R | R | G | L | D | L | L | F | L | K | E | MoMuLV | SEQ ID NO: 71 |
| A | Q | N | R | R | G | L | D | L | L | F | W | E | Q | HTLV-I, -II | SEQ ID NO: 72 |
| L | Q | N | R | R | G | L | D | L | L | T | A | E | Q | MPMV, SRV-1 | SEQ ID NO: 73 |
| L | Q | N | R | R | A | L | D | L | L | T | A | E | R | Syncitin 1 | SEQ ID NO: 74 |
| L | Q | N | R | R | G | L | D | M | L | T | A | A | Q | Syncitin 2 | SEQ ID NO: 75 |
| L | A | N | Q | I | N | D | L | R | Q | T | V | I | W | HERV-K | SEQ ID NO: 76 |
| L | Q | N | R | R | G | L | D | I | L | F | L | Q | E | FELV | SEQ ID NO: 77 |

According to another embodiment, the exogenous sequence encodes a FP polypeptide such as gp41. The following Table 2 represents several FP polypeptide from natural and artificial origins.

TABLE 2

Amino acid sequences of FP polypeptide from
natural and artificial origins
FP Amino acids sequences

| Amino acid positions | | | | | | | | | | SEQ |
|---|---|---|---|---|---|---|---|---|---|---|
| 1 | 2 | 3 | 4 | 5 | 6 | 7 | 8 | 9 | Origin | ID NO |
| G | A | L | F | L | G | F | L | G | HIV-1 gp41 | SEQ ID NO: 78 |
| A | G | F | G | L | L | L | G | F | Synthetic | SEQ ID NO: 79 |
| A | G | L | F | L | G | F | L | G | Synthetic | SEQ ID NO: 80 |

According to another embodiment, the exogenous sequence encodes a non-human MHC homolog, especially a viral MHC homolog, or a chimeric β2m polypeptide such as described by Margalit A. et al. (2003) "Chimeric β2 microof the Chemokines CCL1 and CCL171". *The Journal of Immunology.* 181 (12): 8576-8584.

According to one embodiment the exogenous sequence encodes an antibody that is directed against inhibitory peptides or proteins. Said antibody is preferably be secreted under soluble form by the immune cells. Nanobodies from shark and camels are advantageous in this respect, as they are structured as single chain antibodies (Muyldermans S. (2013) "Nanobodies: Natural Single-Domain Antibodies" *Annual Review of Biochemistry* 82: 775-797). Same are also deemed more easily to fuse with secretion signal polypeptides and with soluble hydrophilic domains.

The different aspects developed above to enhance persistence of the cells are particularly preferred, when the exogenous coding sequence is introduced by disrupting an endogenous gene encoding β2m or another MHC component, as detailed further on.

Enhancing the Therapeutic Activity of Immune Cells

According to one aspect of the present method, the exogenous sequence that is integrated into the immune cells genomic locus encodes a molecule that enhances the therapeutic activity of the immune cells.

By "enhancing the therapeutic activity" is meant that the immune cells, or population of cells, engineered according to the present invention, become more aggressive than non-engineered cells or population of cells with respect to a selected type of target cells. Said target cells generally belong to a defined type of cells, or population of cells, preferably characterized by common surface marker(s). In the present specification, "therapeutic potential" reflects the therapeutic activity, as measured through in-vitro experiments. In general sensitive cancer cell lines, such as Daudi cells, are used to assess whether the immune cells are more or less active towards said cells by performing cell lysis or growth reduction measurements. This can also be assessed by measuring levels of degranulation of immune cells or chemokines and cytokines production. Experiments can also be performed in mice with injection of tumor cells, and by monitoring the resulting tumor expansion. Enhancement of activity is deemed significant when the number of developing cells in these experiments is reduced by the immune cells by more than 10%, preferably more than 20%, more preferably more than 30%, even more preferably by more than 50%.

According to one aspect of the invention, said exogenous sequence encodes a chemokine or a cytokine, such as IL-12. It is particularly advantageous to express IL-12 as this cytokine is extensively referred to in the literature as promoting immune cell activation (Colombo M. P. et al. (2002) "Interleukin-12 in anti-tumor immunity and immunotherapy" *Cytokine Growth Factor Rev.* 13(2):155-68).

According to a preferred aspect of the invention the exogenous coding sequence encodes or promote secreted factors that act on other populations of immune cells, such as T-regulatory cells, to alleviate their inhibitory effect on said immune cells.

According to one aspect of the invention, said exogenous sequence encodes an inhibitor of regulatory T-cell activity is a polypeptide inhibitor of forkhead/winged helix transcription factor 3 (FoxP3), and more preferably is a cell-penetrating peptide inhibitor of FoxP3, such as that referred as P60 (Casares N. et al. (2010) "A peptide inhibitor of FoxP3 impairs regulatory T cell activity and improves vaccine efficacy in mice." *J Immunol* 185(9):5150-9).

By "inhibitor of regulatory T-cells activity" is meant a molecule or precursor of said molecule secreted by the T-cells and which allow T-cells to escape the down regulation activity exercised by the regulatory T-cells thereon. In general, such inhibitor of regulatory T-cell activity has the effect of reducing FoxP3 transcriptional activity in said cells.

According to one aspect of the invention, said exogenous sequence encodes a secreted inhibitor of Tumor Associated Macrophages (TAM), such as a CCR2/CCL2 neutralization agent. Tumor-associated macrophages (TAMs) are critical modulators of the tumor microenvironment. Clinicopathological studies have suggested that TAM accumulation in tumors correlates with a poor clinical outcome. Consistent with that evidence, experimental and animal studies have supported the notion that TAMs can provide a favorable microenvironment to promote tumor development and progression. (Theerawut C. et al. (2014) "Tumor-Associated Macrophages as Major Players in the Tumor Microenvironment" *Cancers (Basel)* 6(3): 1670-1690). Chemokine ligand 2 (CCL2), also called monocyte chemoattractant protein 1 (MCP1—NCBI NP_002973.1), is a small cytokine that belongs to the CC chemokine family, secreted by macrophages, that produces chemoattraction on monocytes, lymphocytes and basophils. CCR2 (C-C chemokine receptor type 2—NCBI NP_001116513.2), is the receptor of CCL2. Enhancing Specificity and Safety of Immune Cells Expressing chimeric antigen receptors (CAR) have become the state of the art to direct or improve the specificity of primary immune cells, such as T-Cells and NK-cells for treating tumors or infected cells. CARs expressed by these immune cells specifically target antigen markers at the surface of the pathological cells, which further help said immune cells to destroy these cells in-vivo (Sadelain M. et al. "The basic principles of chimeric antigen receptor design" (2013) *Cancer Discov.* 3(4):388-98). CARs are usually designed to comprise activation domains that stimulate immune cells in response to binding to a specific antigen (so-called positive CAR), but they may also comprise an inhibitory domain with the opposite effect (so-called negative CAR)(Fedorov, V. D. (2014) "Novel Approaches to Enhance the Specificity and Safety of Engineered T Cells" *Cancer Journal* 20 (2):160-165. Positive and negative CARs may be combined or co-expressed to finely tune the cells immune specificity depending of the various antigens present at the surface of the target cells.

The genetic sequences encoding CARs are generally introduced into the cells genome using retroviral vectors that have elevated transduction efficiency but integrate at random locations. Here, according to the present invention, components of chimeric antigen receptor (CAR) car be introduced at selected loci, more particularly under control of endogenous promoters by targeted gene recombination.

According to one aspect, while a positive CAR is introduced into the immune cell by a viral vector, a negative CAR can be introduced by targeted gene insertion and vice-versa, and be active preferably only during immune cells activation. Accordingly, the inhibitory (i.e. negative) CAR contributes to an improved specificity by preventing the immune cells to attack a given cell type that needs to be preserved. Still according to this aspect, said negative CAR can be an apoptosis CAR, meaning that said CAR comprise an apoptosis domain, such as FasL (CD95—NCBI: NP_000034.1) or a functional variant thereof, that transduces a signal inducing cell death (Eberstadt M; et al. "NMR structure and mutagenesis of the FADD (Mort1) death-effector domain" (1998) *Nature.* 392 (6679): 941-5).

Accordingly, the exogenous coding sequence inserted according to the invention can encode a factor that has the capability to induce cell death, directly, in combination with, or by activating other compound(s).

As another way to enhance the safety of us of the primary immune cells, the exogenous coding sequence can encodes molecules that confer sensitivity of the immune cells to drugs or other exogenous substrates. Such molecules can be cytochrome(s), such as from the P450 family (Preissner S et al. (2010) "SuperCYP: a comprehensive database on Cytochrome P450 enzymes including a tool for analysis of CYP-drug interactions". *Nucleic Acids Res* 38 (Database issue): D237-43), such as CYP2D6-1 (NCBI—NP_000097.3), CYP2D6-2 (NCBI—NP_001020332.2), CYP2C9( ), CYP3A4 (NCBI—NP_000762.2), CYP2C19 (NCBI—NP_000760.1) or CYP1A2 (NCBI—NP_000752.2), conferring hypersensitivity of the immune cells to a drug, such as cyclophosphamide and/or isophosphamide.

According to a further aspect of the invention, an exogenous sequence is introduced in the immune cells for its expression, especially in vivo, to reduce IL-6 or IL-8 trans signalling in view of controlling potential Cyokine Release Syndrome (CRS).

Such an exogenous sequence can encode for instance antibodies directed against IL-6 or IL-8 or against their receptors IL-6R or IL-8R.

According to a preferred aspect said exogenous sequence can encode soluble extracellular domain of GP130, such as one showing at least 80% identity with SEQ ID NO:61.

Such soluble extracellular domain of GP130 is described for instance by Rose-John S. [The Soluble Interleukine Receptor: Advanced Therapeutic Options in Inflammation (2017) *Clinical Pharmacology & Therapeutics,* 102(4):591-598] can be fused with fragments of immunoglobulins, such as sgp130Fc (SEQ ID NO:62). As stated before, said exogenous sequence can be stably integrated into the genome by site directed mutagenesis (i.e. using sequence specific nuclease reagents) and be placed under the transcriptional activity of an endogenous promoter at a locus which is active during immune cell activation, such as one listed in Tables 6, 8 or 9, and preferably up-regulated upon CAR activation or being CAR dependent.

According to a more preferred embodiment, the exogenous sequence is introduced into a CAR positive immune cell, such as one expressing an anti-CD22 CAR T-cell polynucleotide sequence such as SEQ ID NO:31. According to some more specific embodiments, said exogenous sequence coding for a polypeptide which can associate, and preferably interfere, with a cytokine receptor of the IL-6 receptor family, such as said soluble extracellular domain of GP130, is integrated at a PD1, CD25 or CD69 locus. As per the present invention, the endogenous sequence encoding PD1 locus is preferably disrupted by said exogenous sequence.

The invention thus provides with a method for treating or reducing CRS in cell immunotherapy, wherein cells or a therapeutic composition thereof are administered to patients, said cells being genetically modified to secrete polypeptide(s) comprising a soluble extracellular domain of GP130, sGP130Fc, an anti-IL-6 or anti-IL6R antibody, an anti-IL-8 or anti-IL8R antibody, or any fusion thereof.

Examples of preferred genotypes of the engineered immune cells are:

[CAR]$^{positive}$[GP130]$^{positive}$

[CAR]$^{positive}$[GP130]$^{positive}$

[CAR]$^{positive}$[TCR]$^{negative}$ [GP130]$^{positive}$ [PD1]$^{negative}$

[CAR]$^{positive}$[TCR]$^{negative}$ [GP130]$^{positive}$ [PD1]$^{negative}$

[CAR]$^{positive}$[GP130]$^{positive}$ [CD25]$^{negative}$

[CAR]$^{positive}$[TCR]$^{negative}$ [GP130]$^{positive}$ [CD25]$^{negative}$

Improving the Efficiency of Gene Targeted Insertion in Primary Immune Cells Using AAV Vectors The present specification provides with donor templates and sequence specific reagents as illustrated in the figures that are useful to perform efficient insertion of a coding sequence in frame with endogenous promoters, in particular PD1 and CD25, as well as means and sequences for detecting proper insertion of said exogenous sequences at said loci.

The donor templates according to the present invention are generally polynucleotide sequences which can be included into a variety of vectors described in the art prompt to deliver the donor templates into the nucleus at the time the endonuclease reagents get active to obtain their site directed insertion into the genome generally by NHEJ or homologous recombination, Specifically, the present invention provides specific donor polynucleotides for expression of IL-15 (SEQ ID NO:59) at the PD1 locus comprising one or several of the following sequences:

Sequence encoding IL-15, such as one presenting identity with SEQ ID NO:50;

Upstream and downstream (also referred to left and right) sequences homologous to the PD1 locus, comprising preferably polynucleotide sequences SEQ ID NO:45 and SEQ ID NO:46;

optionally, a sequence encoding soluble form of an IL-15 receptor (sIL-15R), such as one presenting identity with SEQ ID NO:50;

optionally, at least one 2A peptide cleavage site such as one of SEQ ID NO:53 (F2A), SEQ ID NO:54 (P2A) and/or SEQ ID NO:55 (T2A), Specifically, the present invention provides specific donor polynucleotides for expression of IL-12 (SEQ ID NO:58) at the PD1 locus comprising one or several of the following sequences:

Sequence encoding IL-12a, such as one presenting identity with SEQ ID NO:47;

Upstream and downstream (also referred to left and right) sequences homologous to the PD1 locus, comprising preferably polynucleotide sequences SEQ ID NO:45 and SEQ ID NO:46;

optionally, a sequence encoding IL-12b, such as one presenting identity with SEQ ID NO:48;

optionally, at least one 2A peptide cleavage site such as one of SEQ ID NO:53 (F2A), SEQ ID NO:54 (P2A) and/or SEQ ID NO:55 (T2A), Specifically, the present invention provides specific donor polynucleotides for expression of soluble GP130 (comprising SEQ ID NO:61) at the PD1 locus comprising one or several of the following sequences:

Sequence encoding soluble GP130, preferably a soluble gp130 fused to a Fc, such as one presenting identity with SEQ ID NO:62;

Upstream and downstream (also referred to left and right) sequences homologous to the PD1 locus, comprising preferably polynucleotide sequences SEQ ID NO:45 and SEQ ID NO:46;

optionally, at least one 2A peptide cleavage site such as one of SEQ ID NO:53 (F2A), SEQ ID NO:54 (P2A) and/or SEQ ID NO:55 (T2A), Specifically, the present invention provides specific donor polynucleotides for expression of IL-15 (SEQ ID NO:59) at the CD25 locus comprising one or several of the following sequences:

Sequence encoding IL-15, such as one presenting identity with SEQ ID NO:50;

Upstream and downstream (also referred to left and right) sequences homologous to the CD25 locus, comprising preferably polynucleotide sequences SEQ ID NO:43 and SEQ ID NO:44;

optionally, a sequence encoding soluble form of an IL-15 receptor (siL-15R), such as one presenting identity with SEQ ID NO:50;

optionally, at least one 2A peptide cleavage site such as one of SEQ ID NO:53 (F2A), SEQ ID NO:54 (P2A) and/or SEQ ID NO:55 (T2A), Specifically, the present invention provides specific donor polynucleotides for expression of IL-12 (SEQ ID NO:58) at the CD25 locus comprising one or several of the following sequences:

Sequence encoding IL-12a, such as one presenting identity with SEQ ID NO:47;

Upstream and downstream (also referred to left and right) sequences homologous to the CD25 locus, comprising preferably polynucleotide sequences SEQ ID NO:43 and SEQ ID NO:44;

optionally, a sequence encoding IL-12b, such as one presenting identity with SEQ ID NO:48;

optionally, at least one 2A peptide cleavage site such as one of SEQ ID NO:53 (F2A), SEQ ID NO:54 (P2A) and/or SEQ ID NO:55 (T2A), Specifically, the present invention provides specific donor polynucleotides for expression of soluble GP130 (comprising SEQ ID NO:61) at the CD25 locus comprising one or several of the following sequences:

Sequence encoding soluble GP130, preferably a soluble gp130 fused to a Fc, such as one presenting identity with SEQ ID NO:62;

Upstream and downstream (also referred to left and right) sequences homologous to the CD25 locus, comprising preferably polynucleotide sequences SEQ ID NO:43 and SEQ ID NO:44;

optionally, at least one 2A peptide cleavage site such as one of SEQ ID NO:53 (F2A), SEQ ID NO:54 (P2A) and/or SEQ ID NO:55 (T2A), As illustrated in the examples herein, the inventors have significantly improved the rate of gene targeted insertion into human cells by using AAV vectors, especially vectors from the AAV6 family.

One broad aspect of the present invention is thus the transduction of AAV vectors in human primary immune cells, in conjunction with the expression of sequence specific endonuclease reagents, such as TALE endonucleases, more preferably introduced under mRNA form, to increase homologous recombination events in these cells.

According to one aspect of this invention, sequence specific endonuclease reagents can be introduced into the cells by transfection, more preferably by electroporation of mRNA encoding said sequence specific endonuclease reagents, such as TALE nucleases.

Still according to this broad aspect, the invention more particularly provides a method of insertion of an exogenous nucleic acid sequence into an endogenous polynucleotide sequence in a cell, comprising at least the steps of:

transducing into said cell an AAV vector comprising said exogenous nucleic acid sequence and sequences homologous to the targeted endogenous DNA sequence, and Inducing the expression of a sequence specific endonuclease reagent to cleave said endogenous sequence at the locus of insertion.

The obtained insertion of the exogenous nucleic acid sequence may result into the introduction of genetic material, correction or replacement of the endogenous sequence, more preferably "in frame" with respect to the endogenous gene sequences at that locus.

According to another aspect of the invention, from $10^5$ to $10^7$ preferably from $10^6$ to $10^7$, more preferably about $5 \cdot 10^6$ viral genomes are transduced per cell.

According to another aspect of the invention, the cells can be treated with proteasome inhibitors, such as Bortezomib to further help homologous recombination.

As one object of the present invention, the AAV vector used in the method can comprise a promoterless exogenous coding sequence as any of those referred to in this specification in order to be placed under control of an endogenous promoter at one loci selected among those listed in the present specification.

As one object of the present invention, the AAV vector used in the method can comprise a 2A peptide cleavage site followed by the cDNA (minus the start codon) forming the exogenous coding sequence.

As one object of the present invention, said AAV vector comprises an exogenous sequence coding for a chimeric antigen receptor, especially an anti-CD19 CAR, an anti-CD22 CAR, an anti-CD123 CAR, an anti-CS1 CAR, an anti-CCL1 CAR, an anti-HSP70 CAR, an anti-GD3 CAR or an anti-ROR1 CAR.

The invention thus encompasses any AAV vectors designed to perform the method herein described, especially vectors comprising a sequence homologous to a locus of insertion located in any of the endogenous gene responsive to T-cell activation referred to in Table 4.

Many other vectors known in the art, such as plasmids, episomal vectors, linear DNA matrices, etc. . . . can also be used following the teachings to the present invention.

As stated before, the DNA vector used according to the invention preferably comprises: (1) said exogenous nucleic acid comprising the exogenous coding sequence to be inserted by homologous recombination, and (2) a sequence encoding the sequence specific endonuclease reagent that promotes said insertion. According to a more preferred aspect, said exogenous nucleic acid under (1) does not comprise any promoter sequence, whereas the sequence under (2) has its own promoter. According to an even more preferred aspect, the nucleic acid under (1) comprises an Internal Ribosome Entry Site (IRES) or "self-cleaving" 2A peptides, such as T2A, P2A, E2A or F2A, so that the endogenous gene where the exogenous coding sequence is inserted becomes multi-cistronic. The IRES of 2A Peptide can precede or follow said exogenous coding sequence.

Preferred vectors of the present invention are vectors derived from AAV6, comprising donor polynucleotides as previously described herein or illustrated in the experimental section and figures. Examples of vectors according to the invention comprise or consist of polynucleotides having identity with sequences SEQ ID NO:37 (matrix for integration of sequence coding for IL-15 into the CD25 locus), SEQ ID NO:38 (matrix for integration of sequence coding for IL-15 into the PD1 locus) SEQ ID NO:39 (matrix for integration of sequence coding for IL-12 into the CD25 locus) and SEQ ID NO:40 (matrix for integration of sequence coding for IL-12 into the PD1 locus).

Gene Targeted Integration in Immune Cells Under Transcriptional Control of Endogenous Promoters The present invention, in one of its main aspects, is taking advantage of the endogenous transcriptional activity of the immune cells to express exogenous sequences that improve their therapeutic potential.

The invention provides with several embodiments based on the profile of transcriptional activity of the endogenous promoters and on a selection of promoter loci useful to carry out the invention. Preferred loci are those, which transcription activity is generally high upon immune cell activation, especially in response to CAR activation (CAR-sensitive promoters) when the cells are endowed with CARs.

Accordingly, the invention provides with a method for producing allogeneic therapeutic immune cells by expressing a first exogenous sequence encoding a CAR at the TCR locus, thereby disrupting TCR expression, and expressing a second exogenous coding sequence under transcriptional activity of an endogenous locus, preferably dependent from either:

CD3/CD28 activation, such as dynabeads, which is useful for instance for promoting cells expansion;

CAR activation, such as through the CD3zeta pathway, which is useful for instance to activate immune cells functions on-target;

Transcriptional activity linked to the appearance of disease symptom or molecular marker. which is useful for instance for activating the cells in-situ in ill organs.

Cell differentiation, which is useful for conferring therapeutic properties to cells at a given level of differentiation or to express protein into a particular lineage (see FIG. 1), for instance at the time hematopoietic cells gain their immune functions; or/and TME (Tumor microoenvironment), which is useful for redirect cells activity and their amplification to specific tumor conditions (hypoxia, low glucose . . . ), or for preventing exhaustion and/or sustaining activation;

CRS (cytokine release syndrome), which is useful to mitigate adverse events related to CAR T-cell activity The inventors have established a first list of endogenous genes (Table 6) which have been found to be particularly appropriate for applying the targeted gene recombination as per the present invention. To draw this list, they have come across several transcriptome murine databases, in particular that from the Immunological Genome Project Consortium referred to in Best J. A. et al. (2013) "Transcriptional insights into the CD8(+) T cell response to infection and memory T cell formation" *Nat. Immunol.* 14(4):404-12, which allows comparing transcription levels of various genes upon T-cell activation, in response to ovalbumin antigens. Also, because very few data is available with respect to human T-cell activation, they had to make some extrapolations and analysis from these data and compare with the human situation by studying available literature related to the human genes. The selected loci are particularly relevant for the insertion of sequences encoding CARs. Based on the first selection of Table 6, they made subsequent selections of genes based on their expected expression profiles (Tables 7 to 10).

On another hand, the inventors have identified a selection of transcriptional loci that are mostly inactive, which would be most appropriate to insert expression cassette(s) to express exogenous coding sequence under the transcriptional control of exogenous promoters. These loci are referred to as "safe harbor loci" as those being mostly transcriptionally inactive, especially during T-Cell activation. They are useful to integrate a coding sequence by reducing at the maximum the risk of interfering with genome expression of the immune cells.

Gene Targeted Insertion Under Control of Endogenous Promoters that are Steadily Active During Immune Cell Activation A selection of endogenous gene loci related to this embodiment is listed in Table 7.

Accordingly the method of the present invention provides with the step of performing gene targeted insertion under control of an endogenous promoter that is constantly active during immune cell activation, preferably from of an endogenous gene selected from CD3G, Rn28s1, Rn18s, Rn7sk, Actg1, β2m, Rpl18a, Pabpc1, Gapdh, Rpl17, Rpl19, Rplp0, Cfl1 and Pfn1.

By "steadily active" means that the transcriptional activity observed for these promoters in the primary immune cell is not affected by a negative regulation upon the activation of the immune cell.

As reported elsewhere (Acuto, O. (2008) "Tailoring T-cell receptor signals by proximal negative feedback mechanisms". *Nature Reviews Immunology* 8:699-712), the promoters present at the TCR locus are subjected to different negative feedback mechanisms upon TCR engagement and thus may not be steadily active or up regulated during for the method of the present invention. The present invention has been designed to some extend to avoid using the TCR locus as a possible insertion site for exogenous coding sequences to be expressed during T-cell activation. Therefore, according to one aspect of the invention, the targeted insertion of the exogenous coding sequence is not performed at a TCRalpha or TCRbeta gene locus.

Examples of exogenous coding sequence that can be advantageously introduced at such loci under the control of steadily active endogenous promoters, are those encoding or positively regulating the production of a cytokine, a chemokine receptor, a molecule conferring resistance to a drug, a co-stimulation ligand, such as 4-1BRL and OX40L, or of a secreted antibody.

Gene Integration Under Endogenous Promoters that are Dependent from Immune Cell Activation or Dependent from CAR Activation As stated before, the method of the present invention provides with the step of performing gene targeted insertion under control of an endogenous promoter, which transcriptional activity is preferably up-regulated upon immune cell activation, either transiently or over more than 10 days.

By "immune cell activation" is meant production of an immune response as per the mechanisms generally described and commonly established in the literature for a given type of immune cells. With respect to T-cell, for instance, T-cell activation is generally characterized by one of the changes consisting of cell surface expression by production of a variety of proteins, including CD69, CD71 and CD25 (also a marker for Treg cells), and HLA-DR (a marker of human T cell activation), release of perforin, granzymes and granulysin (degranulation), or production of cytokine effectors IFN-γ, TNF and LT-alpha.

According to a preferred embodiment of the invention, the transcriptional activity of the endogenous gene is up-regulated in the immune cell, especially in response to an activation by a CAR. The CAR can be independently expressed in the immune cell. By "independently expressed" is meant that the CAR can be transcribed in the immune cell from an exogenous expression cassette introduced, for instance, using a retroviral vector, such as a lentiviral vector, or by transfecting capped messenger RNAs by electroporation encoding such CAR Many methods are known in the art to express a CAR into an immune cell as described for instance by (REF.)

Said endogenous gene whose transcriptional activity is up regulated are particularly appropriate for the integration of exogenous sequences to encode cytokine(s), such as IL-12 and IL-15, immunogenic peptide(s), or a secreted antibody, such as an anti-IDO1, anti-IL10, anti-PD1, anti-PDL1, anti-IL6 or anti-PGE2 antibody.

According to a preferred embodiment of the invention, the endogenous promoter is selected for its transcriptional activity being responsive to, and more preferably being dependent from CAR activation.

As shown herein, CD69, CD25 and PD1 are such loci, which are particularly appropriate for the insertion of expression of an exogenous coding sequences to be expressed when the immune cells get activated, especially into CAR positive immune cells.

The present invention thus combines any methods of expressing a CAR into an immune cell with the step of performing a site directed insertion of an exogenous coding sequence at a locus, the transcriptional activity of which is responsive to or dependent from the engagement of said CAR with a tumor antigen. Especially, the method comprises the step of introducing into a CAR positive or Recombinant TCR positive immune cell an exogenous sequence encoding IL-12 or IL-15 under transcriptional control of one promoter selected from PD1, CD25 and CD69 promoters.

In particular, CAR positive cells can obtained by following the steps of co-expressing into an immune cell, preferably a primary cell, and more preferably into a primary T-cell, at least one exogenous sequence encoding a CAR and another exogenous sequence placed under an endogenous promoter dependent, which transcriptional activity is dependent from said CAR, such a PD1, CD25 or CD71.

The expression "dependent from said CAR" means that the transcriptional activity of said endogenous promoter is necessary increased by more than 10%, preferably by more than 20%, more preferably by more than 50% and even more preferably more than 80%, as a result of the engagement of the CAR with its cognate antigen, in a situation where, in general, the antigens are exceeding the number of CARs present at the cell surface and the number of CARs expressed at the cell surface is more than 10 per cell, preferably more than 100, and more preferably more than 1000 molecules per cells.

The present invention thus teaches the expression of a CAR sequence, preferably inserted at the TCR locus and constitutively expressed, whereas another exogenous sequence integrated at another locus is co-expressed, in response to, or dependent from, the engagement of said CAR with its cognate antigen. Said another locus is for instance CD25, PD1 or CD71 or any loci being specifically transcribed upon CAR activation.

In other words, the invention provides the co-expression of a CAR and at least one exogenous coding sequence, the expression of said exogenous sequence being under control of an endogenous promoter the transcriptional activity of which is influenced by the CAR activity, this being done in view of obtaining engineered immune cells offering a better immune response.

As previously described, this can be performed by transfecting the cells with sequence-specific nuclease reagents targeting the coding regions of such loci being specifically CAR dependent, along with donor templates comprising sequences homologous to said genomic regions. The sequence specific nuclease reagents help the donor templates to be integrated by homologous recombination or NHEJ.

According to a preferred embodiment, the exogenous coding sequence is integrated in frame with the endogenous gene, so that the expression of said endogenous gene is preserved. This is the case for instance with respect to CD25 and CD69 in at least one example of the experimental section herein.

According to a preferred embodiment, the exogenous sequence disrupts the endogenous coding sequence of the gene to prevent its expression of one endogenous coding sequence, especially when this expression has a negative effect on the immune cell functions, as it the case for instance with PD1 in the experimental section herein.

According to an even more preferred embodiments, the exogenous coding sequence, which disrupts the endogenous gene sequence is placed in frame with the endogenous promoter, so that its expression is made dependent from the endogenous promoter as also shown in the experimental section.

The present invention is also drawn to the polynucleotide and polypeptide sequences encoding the different TAL-nucleases exemplified in the present patent application, especially those permitting the site directed insertion at the CD25 locus (SEQ ID NO:18 and 19), as well as their respective target and RVD sequences.

The present invention also encompasses kits for immune cells transfection comprising polynucleotides encoding the sequence-specific endonuclease reagents and the donor sequences designed to integrate the exogenous sequence at the locus targeted by said reagents. Examples of such kits are a kit comprising mRNA encoding rare-cutting endonuclease targeting PD1 locus (ex: PD1 TALEN®) and an AAV vector comprising an exogenous sequence encoding IL-12, a kit comprising mRNA encoding rare-cutting endonuclease targeting PD1 locus (ex: PD1 TALEN®) and an AAV vector comprising an exogenous sequence encoding IL-15, a kit comprising mRNA encoding rare-cutting endonuclease targeting CD25 locus (ex: CD25 TALEN®) and an AAV vector comprising an exogenous sequence encoding IL-12, a kit comprising mRNA encoding rare-cutting endonuclease targeting CD25 locus (ex: CD25 TALEN®) and an AAV vector comprising an exogenous sequence encoding IL-15, a kit comprising mRNA encoding rare-cutting endonuclease targeting PD1 locus (ex: PD1 TALEN®) and an AAV vector comprising an exogenous sequence encoding soluble gp130, a kit comprising mRNA encoding rare-cutting endonuclease targeting CD25 locus (ex: CD25 TALEN®) and an AAV vector comprising an exogenous sequence encoding soluble gp130, and any kits involving endonuclease reagents targeting a gene listed in table 6, and a donor matrix for introducing a coding sequence referred to in the present specification.

According to one aspect of the invention, the endogenous gene is selected for a weak up-regulation. The exogenous coding sequence introduced into said endogenous gene whose transcriptional activity is weakly up regulated, can be advantageously a constituent of an inhibitory CAR, or of an apoptotic CAR, which expression level has generally to remain lower than that of a positive CAR. Such combination of CAR expression, for instance one transduced with a viral vector and the other introduced according to the invention, can greatly improve the specificity or safety of CAR immune cells Some endogenous promoters are transiently up-regulated, sometimes over less than 12 hours upon immune cell activation, such as those selected from the endogenous gene loci Spata6, Itga6, Rcbtb2, Cd1d1, St8sia4, Itgae and Fam214a (Table 8). Other endogenous promoters are up-regulated over less than 24 hours upon immune cell activation, such as those selected from the endogenous gene loci IL3, IL2, Ccl4, IL21, Gp49a, Nr4a3, Lilrb4, Cd200, Cdkn1a, Gzmc, Nr4a2, Cish, Ccr8, Lad1 and Crabp2 (Table 9) and others over more than 24 hours, more generally over more than 10 days, upon immune cell activation. Such as those selected from Gzmb, Tbx21, Plek, Chek1, Slamf7, Zbtb32, Tigit, Lag3, Gzma, Wee1, IL12rb2, Eea1 and Dtl (Table 9).

Alternatively, the inventors have found that endogenous gene under transcriptional control of promoters that are down-regulated upon immune cell activation, could also be of interest for the method according to the present invention. Indeed they have conceived that exogenous coding sequences encoding anti-apoptotic factors, such as of Bcl2 family, BclXL, NF-kB, Survivin, or anti-FAP (fibroblast activation protein), such as a constituent of a CAR anti-FAP, could be introduced at said loci. Said endogenous gene under transcriptional control of promoters that are down-regulated upon immune cell activation can be more particularly selected from Slc6a19, Cd55, Xkrx, Mturn, H2-Ob, Cnr2, Itgae, Raver2, Zbtb20, Arrb1, Abca1, Tet1, Slc16a5 and Ampd3 (Table 10)

Gene Integration Under Endogenous Promoters Activated Under Tumor Microenvironment (TME) Conditions One aspect of the present invention more particularly concerns methods to prevent immune cells exhaustion in tumor microenvironment (TME) conditions. Immune cells often get exhausted in response to nutrient depletion or molecular signals found in the microoenvironment of tumors, which helps tumor resistance. The method comprises the steps of engineering immune cells by integrating exogenous coding sequences under control of endogenous promoters which are up-regulated under arginine, cysteine, tryptophan and oxygen deprivation as well as extracellular acidosis (lactate build up).

Such exogenous sequences may encode chimeric antigen receptors, interleukins, or any polypeptide given elsewhere in this specification to bolster immune cells function or activation and/or confer a therapeutic advantage.

The inventors have listed a number of loci which have been found to be upregulated in a large number of exhausted tumor infiltrating lymphocytes (TIL), which are listed in tables 12 and 13. The invention provides with the step of integrating exogenous coding sequences at these preferred loci to prevent exhaustion of the immune cells, in particular T-cells, in tumor microoenvironment.

For instance, the exogenous sequences encoding a CAR can be placed under transcriptional control of the promoter of endogenous genes that are activated by the tumor microenvironment, such as HIF1a, transcription factor hypoxia-inducible factor, or the aryl hydrocarbon receptor (AhR), These gene are sensors respectively induced by hypoxia and xenobiotics in the close environment of tumors.

The present invention is thus useful to improve the therapeutic outcome of CAR T-cell therapies by integrating exogenous coding sequences, and more generally genetic attributes/circuits, under the control of endogenous T-cell promoters influenced by tumor microenvironment (TME).

Pursuant to the invention, upregulation of endogenous genes can be "hijacked" to re-express relevant exogenous coding sequences to improve the antitumor activity of CAR T-cells in certain tumor microenvironment.

Gene Targeted Insertion and Expression in Hematopoietic Stem Cells (HSCs)

One aspect of the present invention more particularly concerns the insertion of transgenes into hematopoietic stem cells (HSCs).

Hematopoietic stem cells (HSCs) are multipotent, self-renewing progenitor cells from which all differentiated blood cell types arise during the process of hematopoiesis. These cells include lymphocytes, granulocytes, and macrophages of the immune system as well as circulating erythrocytes and platelets. Classically, HSCs are thought to differentiate into two lineage-restricted, lymphoid and myelo-erythroid, oligopotent progenitor cells. The mechanisms controlling HSC self-renewal and differentiation are thought to be influenced by a diverse set of cytokines, chemokines, receptors, and intracellular signaling molecules. Differentiation of HSCs is regulated, in part, by growth factors and cytokines including colony-stimulating factors (CSFs) and interleukins (ILs) that activate intracellular signaling pathways. The factors depicted below are known to influence HSC multipotency, proliferation, and lineage commitment. HSCs and their differentiated progeny can be identified by the expression of specific cell surface lineage markers such as cluster of differentiation (CD) proteins and cytokine receptors into hematopoietic stem cells.

Gene therapy using HSCs has enormous potential to treat diseases of the hematopoietic system including immune diseases. In this approach, HSCs are collected from a patient, gene-modified ex-vivo using integrating retroviral vectors, and then infused into a patient. To date retroviral vectors have been the only effective gene delivery system for HSC gene therapy. Gene delivery to HSCs using integrating vectors thereby allowing for efficient delivery to HSC-derived mature hematopoietic cells. However, the gene-modified cells that are infused into a patient are a polyclonal population, where the different cells have vector proviruses integrated at different chromosomal locations, which can result into many adverse mutations, which may be amplified due to some proliferative/survival advantage of these mutations (Powers and Trobridge (2013) "Identification of Hematopoietic Stem Cell Engraftment Genes in Gene Therapy Studies" *J Stem Cell Res Ther* S3:004. doi:10.4172/2157-7633.S3-00).

HSCs are commonly harvested from the peripheral blood after mobilization (patients receive recombinant human granulocyte-colony stimulating factor (G-CSF)). The patient's peripheral blood is collected and enriched for HSCs using the CD34+ marker. HSCs are then cultured ex vivo and exposed to viral vectors. The ex vivo culture period varies from 1 to 4 days. Prior to the infusion of gene-modified HSCs, patients may be treated with chemotherapy agents or irradiation to help enhance the engraftment efficiency. Gene-modified HSCs are re-infused into the patient intravenously. The cells migrate into the bone marrow before finally residing in the sinusoids and perivascular tissue. Both homing and hematopoiesis are integral aspects of engraftment. Cells that have reached the stem cell niche through homing will begin producing mature myeloid and lymphoid cells from each blood lineage. Hematopoiesis continues through the action of long-term HSCs, which are capable of self-renewal for life-long generation of the patient's mature blood cells, in particular the production of common lymphoid progenitor cells, such as T cells and NK cells, which are key immune cells for eliminating infected and malignant cells.

The present invention provides with performing gene targeted insertion in HSCs to introduce exogenous coding sequences under the control of endogenous promoters, especially endogenous promoters of genes that are specifically activated into cells of a particular hematopoietic lineage or at particular differentiation stage, preferably at a late stage of differentiation. The HSCs can be transduced with a polynucleotide vector (donor template), such as an AAV vector, during an ex-vivo treatment as referred to in the previous paragraph, whereas a sequence specific nuclease reagent is expressed as to promote the insertion of the coding sequences at the selected locus. The resulting engineered HSCs can be then engrafted into a patient in need thereof for a long term in-vivo production of engineered immune cells that will comprise said exogenous coding sequences. Depending on the activity of the selected endogenous promoter, the coding sequences will be selectively expressed in certain lineages or in response to the local environment of the immune cells in-vivo, thereby providing adoptive immunotherapy.

According to one preferred aspect of the invention, the exogenous coding sequences are placed under the control of promoters of a gene, which transcriptional activity is specifically induced in common lymphoid progenitor cells, such as CD34, CD43, Flt-3/Flk-2, IL-7 R alpha/CD127 and Neprilysin/CD10.

More preferably, the exogenous coding sequences are placed under the control of promoters of a gene, which transcriptional activity is specifically induced in NK cells, such as CD161, CD229/SLAMF3, CD96, DNAM-1/CD226, Fc gamma RII/CD32, Fc gamma RII/RIII (CD32/CD16), Fc gamma RIII (CD16), IL-2 R beta, Integrin alpha 2/CD49b, KIR/CD158, NCAM-1/CD56, NKG2A/CD159a, NKG2C/CD159c, NKG2D/CD314, NKp30/NCR3, NKp44/NCR2, NKp46/NCR1, NKp80/KLRF1, Siglec-7/CD328 and TIGIT, or induced in T-cells, such as CCR7, CD2, CD3, CD4, CD8, CD28, CD45, CD96, CD229/SLAMF3, DNAM-1/CD226, CD25/IL-2 R alpha, L-Selectin/CD62L and TIGIT.

The invention comprises as a preferred aspect the introduction of an exogenous sequence encoding a CAR, or a component thereof, into HSCs, preferably under the transcriptional control of a promoter of a gene that is not expressed in HSC, more preferably a gene that is only expressed in the hematopoietic cells produced by said HSC, and even more preferably of a gene that is only expressed in T-cells or NK cells.

Conditional CAR Expression in HSCs to Overpass the Thymus Barrier

A particular aspect of the present invention concerns the in-vivo production by the above engineered HSCs of hematopoietic immune cells, such as T-cells or NK-cells, expressing exogenous coding sequences, in particular a CAR or a component thereof.

One major bar of the production of hematopoietic CAR positive cells by engineered HSCs, for instance, is the rejection of the CAR positive cells by the immune system itself, especially by the thymus.

The blood-thymus barrier regulates exchange of substances between the circulatory system and thymus, providing a sequestered environment for immature T cells to develop. The barrier also prevents the immature T cells from contacting foreign antigens (since contact with antigens at this stage will cause the T cells to die by apoptosis).

One solution provided by the present invention is to place the sequences encoding the CAR components in the HSCs under the transcriptional control of promoters which are not significantly transcribed into the hematopoietic cells when they pass through the thymus barrier. One example of a gene that offers a conditional expression of the CAR into the hematopoietic cells with reduced or no significant transcriptional activity in the thymus is LCK (Uniprot: P06239).

According to a preferred aspect of the invention the exogenous sequence encoding a CAR, or a component thereof, is introduced into the HSC under the transcriptional control of a gene that is described as being specifically expressed in T-cells or NK cells, preferably in these types of cells only.

The invention thereby provides with a method of producing HSCs comprising an exogenous coding sequences to be expressed exclusively in selected hematopoietic lineage(s), said coding sequences encoding preferably at least one component of a CAR or of an antigen in order to stimulate the immune system.

More broadly, the invention provides with a method of engineering HSCs by gene targeted insertion of an exogenous coding sequences to be selectively expressed in the hematopoietic cells produced by said HSCs. As a preferred embodiment, said hematopoietic cells produced by said engineered HSCs express said exogenous coding sequences in response to selected environmental factors or in-vivo stimuli to improve their therapeutic potential.

Combining Targeted Sequence Insertion(s) in Immune Cells with the Inactivation of Endogenous Genomic Sequences One particular focus of the present invention is to perform gene inactivation in primary immune cells at a locus, by integrating exogenous coding sequence at said locus, the expression of which improves the therapeutic potential of said engineered cells. Examples of relevant exogenous coding sequences that can be inserted according to the invention have been presented above in connection with their positive effects on the therapeutic potential of the cells. Here below are presented the endogenous gene that are preferably targeted by gene targeted insertion and the advantages associated with their inactivation.

According to a preferred aspect of the invention, the insertion of the coding sequence has the effect of reducing or preventing the expression of genes involved into self and non-self recognition to reduce host versus graft disease (GVHD) reaction or immune rejection upon introduction of the allogeneic cells into a recipient patient. For instance, one of the sequence-specific reagents used in the method can reduce or prevent the expression of TCR in primary T-cells, such as the genes encoding TCR-alpha or TCR-beta.

As another preferred aspect, one gene editing step is to reduce or prevent the expression of the 2m protein and/or another protein involved in its regulation such as C2TA (Uniprot P33076) or in MHC recognition, such as HLA proteins. This permits the engineered immune cells to be less alloreactive when infused into patients.

By "allogeneic therapeutic use" is meant that the cells originate from a donor in view of being infused into patients having a different haplotype. Indeed, the present invention provides with an efficient method for obtaining primary cells, which can be gene edited in various gene loci involved into host-graft interaction and recognition.

Other loci may also be edited in view of improving the activity, the persistence of the therapeutic activity of the engineered primary cells as detailed here after:

Inactivation of Checkpoint Receptors and Immune Cells Inhibitory Pathways:

According to a preferred aspect of the invention, the inserted exogenous coding sequence has the effect of reducing or preventing the expression of a protein involved in immune cells inhibitory pathways, in particular those referred to in the literature as "immune checkpoint" (Pardoll, D. M. (2012) The blockade of immune checkpoints in cancer immunotherapy, *Nature Reviews Cancer*, 12:252-264). In the sense of the present invention, "immune cells inhibitory pathways" means any gene expression in immune cells that leads to a reduction of the cytotoxic activity of the lymphocytes towards malignant or infected cells. This can be for instance a gene involved into the expression of FOXP3, which is known to drive the activity of Tregs upon T cells (moderating T-cell activity).

"Immune checkpoints" are molecules in the immune system that either turn up a signal (co-stimulatory molecules) or turn down a signal of activation of an immune cell. As per the present invention, immune checkpoints more particularly designate surface proteins involved in the ligand-receptor interactions between T cells and antigen-presenting cells (APCs) that regulate the T cell response to antigen (which is mediated by peptide-major histocompatibility complex (MHC) molecule complexes that are recognized by the T cell receptor (TCR)). These interactions can occur at the initiation of T cell responses in lymph nodes (where the major APCs are dendritic cells) or in peripheral tissues or tumours (where effector responses are regulated). One important family of membrane-bound ligands that bind both co-stimulatory and inhibitory receptors is the B7 family. All of the B7 family members and their known ligands belong to the immunoglobulin superfamily. Many of the receptors for more recently identified B7 family members have not yet been identified. Tumour necrosis factor (TNF) family members that bind to cognate TNF receptor family molecules represent a second family of regulatory ligand-receptor pairs. These receptors predominantly deliver co-stimulatory signals when engaged by their cognate ligands. Another major category of signals that regulate the activation of T cells comes from soluble cytokines in the microenvironment. In other cases, activated T cells upregulate ligands, such as CD40L, that engage cognate receptors on APCs. A2aR, adenosine A2a receptor; B7RP1, B7-related protein 1; BTLA, B and T lymphocyte attenuator; GAL9, galectin 9; HVEM, herpesvirus entry mediator; ICOS, inducible T cell co-stimulator; IL, interleukin; KIR, killer cell immunoglobulin-like receptor; LAG3, lymphocyte activation gene 3; PD1, programmed cell death protein 1; PDL, PD1 ligand; TGFβ, transforming growth factor-β; TIM3, T cell membrane protein 3.

Examples of further endogenous genes, which expression could be reduced or suppressed to turn-up activation in the engineered immune cells according the present invention are listed in Table 3.

For instance, the inserted exogenous coding sequence(s) can have the effect of reducing or preventing the expression, by the engineered immune cell of at least one protein selected from PD1 (Uniprot Q15116), CTLA4 (Uniprot P16410), PPP2CA (Uniprot P67775), PPP2CB (Uniprot P62714), PTPN6 (Uniprot P29350), PTPN22 (Uniprot Q9Y2R2), LAG3 (Uniprot P18627), HAVCR2 (Uniprot Q8TDQ0), BTLA (Uniprot Q7Z6A9), CD160 (Uniprot O95971), TIGIT (Uniprot Q495A1), CD96 (Uniprot P40200), CRTAM (Uniprot O95727), LAIR1 (Uniprot Q6GTX8), SIGLEC7 (Uniprot Q9Y286), SIGLEC9 (Uniprot Q9Y336), CD244 (Uniprot Q9BZW8), TNFRSF10B (Uniprot O14763), TNFRSF10A (Uniprot O00220), CASP8 (Uniprot Q14790), CASP10 (Uniprot Q92851), CASP3 (Uniprot P42574), CASP6 (Uniprot P55212), CASP7 (Uniprot P55210), FADD (Uniprot Q13158), FAS (Uniprot P25445), TGFBRII (Uniprot P37173), TGFRBRI (Uniprot Q15582), SMAD2 (Uniprot Q15796), SMAD3 (Uniprot P84022), SMAD4 (Uniprot Q13485), SMAD10 (Uniprot B7ZSB5), SKI (Uniprot P12755), SKIL (Uniprot P12757), TGIF1 (Uniprot Q15583), IL10RA (Uniprot Q13651), IL10RB (Uniprot Q08334), HMOX2 (Uniprot P30519), IL6R (Uniprot P08887), IL6ST (Uniprot P40189), EIF2AK4 (Uniprot Q9P2K8), CSK (Uniprot P41240), PAG1 (Uniprot Q9NWQ8), SIT1 (Uniprot Q9Y3P8), FOXP3 (Uniprot Q9BZS1), PRDM1 (Uniprot Q60636), BATF (Uniprot Q16520), GUCY1A2 (Uniprot P33402), GUCY1A3 (Uniprot Q02108), GUCY1B2 (Uniprot Q8BXH3) and GUCY1B3 (Uniprot Q02153). The gene editing introduced in the genes encoding the above proteins is preferably combined with an inactivation of TCR in CAR T cells.

Preference is given to inactivation of PD1 and/or CTLA4, in combination with the expression of non-endogenous immunosuppressive polypeptide, such as a PD-L1 ligand and/or CTLA-4 Ig (see also peptides of Table 1 and 2).

TABLE 3

List of genes involved into immune cells inhibitory pathways

| Pathway | | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1(PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |
| | LAIR1(cd305) | LAIR1 |
| | SIGLECs | SIGLEC7 |
| | | SIGLEC9 |
| | CD244(2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Prevention of TCR signalling | | CSK, PAG1 SIT1 |
| Induced Treg | induced Treg | FOXP3 |
| Transcription factors controlling exhaustion | transcription factors controlling exhaustion | PRDM1 BATF |
| Hypoxia mediated tolerance | iNOS induced guanylated cyclase | GUCY1A2, GUCY1A3, GUCY1B2, GUCY1B3 |

Inhibiting Suppressive Cytokines/Metabolites

According to another aspect of the invention, the inserted exogenous coding sequence has the effect of reducing or preventing the expression of genes encoding or positively regulating suppressive cytokines or metabolites or receptors thereof, in particular TGFbeta (Uniprot:P01137), TGFbR (Uniprot:P37173), IL10 (Uniprot:P22301), IL10R (Uniprot: Q13651 and/or Q08334), A2aR (Uniprot: P29274), GCN2 (Uniprot: P15442) and PRDM1 (Uniprot: O75626).

Preference is given to engineered immune cells in which a sequence encoding IL-2, IL-12 or IL-15 replaces the sequence of at least one of the above endogenous genes.

Inducing Resistance to Chemotherapy Drugs

According to another aspect of the present method, the inserted exogenous coding sequence has the effect of reducing or preventing the expression of a gene responsible for the sensitivity of the immune cells to compounds used in standard of care treatments for cancer or infection, such as drugs purine nucleotide analogs (PNA) or 6-Mercaptopurine (6MP) and 6 thio-guanine (6TG) commonly used in chemotherapy. Reducing or inactivating the genes involved into the mode of action of such compounds (referred to as "drug sensitizing genes") improves the resistance of the immune cells to same.

Examples of drug sensitizing gene are those encoding DCK (Uniprot P27707) with respect to the activity of PNA, such a clorofarabine et fludarabine, HPRT (Uniprot P00492) with respect to the activity of purine antimetabolites such as 6MP and 6TG, and GGH (Uniprot Q92820) with respect to the activity of antifolate drugs, in particular methotrexate.

This enables the cells to be used after or in combination with conventional anti-cancer chemotherapies.

Resistance to Immune-Suppressive Treatments

According to another aspect of the present invention, the inserted exogenous coding sequence has the effect of reducing or preventing the expression of receptors or proteins, which are drug targets, making said cells resistant to immune-depletion drug treatments. Such target can be glucocorticoids receptors or antigens, to make the engineered immune cells resistant to glucocorticoids or immune depletion treatments using antibodies such as Alemtuzumab, which is used to deplete CD52 positive immune cells in many cancer treatments.

Also the method of the invention can comprise gene targeted insertion in endogenous gene(s) encoding or regulating the expression of CD52 (Uniprot P31358) and/or GR (Glucocorticoids receptor also referred to as NR3C1—Uniprot P04150).

Improving CAR Positive Immune Cells Activity and Survival

According to another aspect of the present invention, the inserted exogenous coding sequence can have the effect of reducing or preventing the expression of a surface antigen, such as BCMA, CS1 and CD38, wherein such antigen is one targeted by a CAR expressed by said immune cells.

This embodiment can solve the problem of CAR targeting antigens that are present at the surface of infected or malignant cells, but also to some extent expressed by the immune cell itself.

According to a preferred embodiment the exogenous sequence encoding the CAR or one of its constituents is integrated into the gene encoding the antigen targeted by said CAR to avoid self-destruction of the immune cells.

Engineered Immune Cells and Populations of Immune Cells

The present invention is also drawn to the variety of engineered immune cells obtainable according to one of the method described previously under isolated form or as part of populations of cells.

According to a preferred aspect of the invention the engineered cells are primary immune cells, such as NK cells or T-cells, which are generally part of populations of cells that may involve different types of cells. In general, population deriving from patients or donors isolated by leukapheresis from PBMC (peripheral blood mononuclear cells).

According to a preferred aspect of the invention, more than 50% of the immune cells comprised in said population are TCR negative T-cells. According to a more preferred aspect of the invention, more than 50% of the immune cells comprised in said population are CAR positive T-cells.

The present invention encompasses immune cells comprising any combinations of the different exogenous coding sequences and gene inactivation, which have been respectively and independently described above. Among these combinations are particularly preferred those combining the expression of a CAR under the transcriptional control of an endogenous promoter that is steadily active during immune cell activation and preferably independently from said activation, and the expression of an exogenous sequence encoding a cytokine, such as IL-2, IL-12 or IL-15, under the transcriptional control of a promoter that is up-regulated during the immune cell activation.

Another preferred combination is the insertion of an exogenous sequence encoding a CAR or one of its constituents under the transcription control of the hypoxia-inducible factor 1 gene promoter (Uniprot: Q16665).

The invention is also drawn to a pharmaceutical composition comprising an engineered primary immune cell or immune cell population as previously described for the treatment of infection or cancer, and to a method for treating a patient in need thereof, wherein said method comprises:

preparing a population of engineered primary immune cells according to the method of the invention as previously described;

optionally, purifying or sorting said engineered primary immune cells;

activating said population of engineered primary immune cells upon or after infusion of said cells into said patient.

Activation and Expansion of T Cells

Whether prior to or after genetic modification, the immune cells according to the present invention can be activated or expanded, even if they can activate or proliferate independently of antigen binding mechanisms. T-cells, in particular, can be activated and expanded using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo. T cells are generally expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF– or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Compositions and Applications

The method of the present invention described above allows producing engineered primary immune cells within a limited time frame of about 15 to 30 days, preferably between 15 and 20 days, and most preferably between 18 and 20 days so that they keep their full immune therapeutic potential, especially with respect to their cytotoxic activity.

These cells form a population of cells, which preferably originate from a single donor or patient. These populations of cells can be expanded under closed culture recipients to comply with highest manufacturing practices requirements and can be frozen prior to infusion into a patient, thereby providing "off the shelf" or "ready to use" therapeutic compositions.

As per the present invention, a significant number of cells originating from the same Leukapheresis can be obtained, which is critical to obtain sufficient doses for treating a patient. Although variations between populations of cells originating from various donors may be observed, the number of immune cells procured by a leukapheresis is generally about from $10^8$ to $10^{10}$ cells of PBMC. PBMC comprises several types of cells: granulocytes, monocytes and lymphocytes, among which from 30 to 60% of T-cells, which generally represents between $10^8$ to $10^9$ of primary T-cells from one donor. The method of the present invention generally ends up with a population of engineered cells that reaches generally more than about $10^8$ T-cells, more generally more than about $10^9$ T-cells, even more generally more than about $10^{10}$ T-cells, and usually more than $10^{11}$ T-cells.

The invention is thus more particularly drawn to a therapeutically effective population of primary immune cells, wherein at least 30%, preferably 50%, more preferably 80% of the cells in said population have been modified according to any one the methods described herein. Said therapeutically effective population of primary immune cells, as per the present invention, comprises immune cells that have integrated at least one exogenous genetic sequence under the transcriptional control of an endogenous promoter from at least one of the genes listed in Table 6.

Such compositions or populations of cells can therefore be used as medicaments; especially for treating cancer, particularly for the treatment of lymphoma, but also for solid tumors such as melanomas, neuroblastomas, gliomas or carcinomas such as lung, breast, colon, prostate or ovary tumors in a patient in need thereof.

The invention is more particularly drawn to populations of primary TCR negative T-cells originating from a single donor, wherein at least 20%, preferably 30%, more preferably 50% of the cells in said population have been modified using sequence-specific reagents in at least two, preferably three different loci.

In another aspect, the present invention relies on methods for treating patients in need thereof, said method comprising at least one of the following steps:

(a) Determining specific antigen markers present at the surface of patients tumors biopsies;

(b) providing a population of engineered primary immune cells engineered by one of the methods of the present invention previously described expressing a CAR directed against said specific antigen markers;

(c) Administrating said engineered population of engineered primary immune cells to said patient, Generally, said populations of cells mainly comprises CD4 and CD8 positive immune cells, such as T-cells, which can undergo robust in vivo T cell expansion and can persist for an extended amount of time in-vitro and in-vivo.

The treatments involving the engineered primary immune cells according to the present invention can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

In another embodiment, said isolated cell according to the invention or cell line derived from said isolated cell can be used for the treatment of liquid tumors, and preferably of T-cell acute lymphoblastic leukemia.

Adult tumors/cancers and pediatric tumors/cancers are also included.

The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The present invention thus can provide more than 10, generally more than 50, more generally more than 100 and usually more than 1000 doses comprising between $10^6$ to $10^8$ gene edited cells originating from a single donor's or patient's sampling.

The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

When CARs are expressed in the immune cells or populations of immune cells according to the present invention, the preferred CARs are those targeting at least one antigen selected from CD22, CD38, CD123, CS1, HSP70, ROR1, GD3, and CLL1.

The engineered immune cells according to the present invention endowed with a CAR or a modified TCR targeting CD22 are preferably used for treating leukemia, such as acute lymphoblastic leukemia (ALL), those with a CAR or a modified TCR targeting CD38 are preferably used for treating leukemia such as T-cell acute lymphoblastic leukemia (T-ALL) or multiple myeloma (MM), those with a CAR or a modified TCR targeting CD123 are preferably used for treating leukemia, such as acute myeloid leukemia (AML), and blastic plasmacytoid dendritic cells neoplasm (BPDCN), those with a CAR or a modified TCR targeting CS1 are preferably used for treating multiple myeloma (MM).

The present invention also encompasses means for detecting the engineered cells of the present invention comprising the desired genetic insertions, especially by carrying out steps of using PCR methods for detecting insertions of exogenous coding sequences at the endogenous loci referred to in the present specification, especially at the PD1, CD25, CD69 and TCR loci, by using probes or primers hybridizing any sequences represented by SEQ ID NO:36 to 40.

Immunological assays may also be performed for detecting the expression by the engineered cells of CARs, GP130, and to check absence or reduction of the expression of TCR, PD1, IL-6 or IL-8 in the cells where such genes have been knocked-out or their expression reduced.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 10 base pairs (bp) in length, more preferably of 14-55 bp. Rare-cutting endonucleases significantly increase homologous recombination by inducing DNA double-strand breaks (DSBs) at a defined locus thereby allowing gene repair or gene insertion therapies (Pingoud, A. and G. H. Silva (2007). Precision genome surgery. *Nat. Biotechnol.* 25(7): 743-4).

By "DNA target", "DNA target sequence", "target DNA sequence", "nucleic acid target sequence", "target sequence", or "processing site" is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of RNA guided target sequences, are those genome sequences that can hybridize the guide RNA which directs the RNA guided endonuclease to a desired locus.

By "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

By "vector" is meant a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available. Viral vectors include retrovirus, adenovirus, parvovirus (e.g. adeno-associated viruses (AAV), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

As used herein, the term "locus" is the specific physical location of a DNA sequence (e.g. of a gene) into a genome. The term "locus" can refer to the specific physical location of a rare-cutting endonuclease target sequence on a chromosome or on an infection agent's genome sequence. Such a locus can comprise a target sequence that is recognized and/or cleaved by a sequence-specific endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

Having generally described this invention, a further understanding can be obtained by reference to certain specific examples, which are provided herein for purposes of illustration only, and are not intended to limit the scope of the claimed invention.

EXAMPLES

Example 1: AAV Driven Homologous Recombination in Human Primary T-Cells at Various Loci Under Control of Endogenous Promoters with Knock-Out of the Endogenous Gene Introduction Sequence specific endonuclease reagents, such as TALEN® (Cellectis, 8 rue de la Croix Jarry, 75013 PARIS) enable the site-specific induction of double-stranded breaks (DSBs) in the genome at desired loci. Repair of DSBs by cellular enzymes occurs mainly through two pathways: non-homologous end joining (NHEJ) and homology directed repair (HDR). HDR uses a homologous piece of DNA (template DNA) to repair the DSB by recombination and can be used to introduce any genetic sequence comprised in the template DNA. As shown therein, said template DNA can be delivered by recombinant adeno-associated virus (rAAV) along with an engineered nuclease such as TALEN® to introduce a site-specific DSB.

Design of the Integration Matrices 1.1. Insertion of an Apoptosis CAR in an Upregulated Locus with Knock-Out of the Endogenous PD1 Gene Coding Sequence The location of the TALEN target site has been designed to be located in the targeted endogenous PDCD1 gene (Programmed cell death protein 1 referred to as PD1—Uniprot #Q15116). The sequence encompassing 1000 bp upstream and downstream the TALEN targets is given in SEQ ID NO:1 and SEQ ID NO:2. Target sequences of the TALEN (SEQ ID NO:3 and SEQ ID NO:4) is given in SEQ ID NO:5. The integration matrix is designed to be composed of a sequence (300 bp) homologous to the endogenous gene upstream of the TALEN site (SEQ ID NO:1), followed by a 2A regulatory element (SEQ ID NO:6), followed by a sequence encoding an apoptosis inducing CAR without the start codon (SEQ ID NO:7), followed by a STOP codon (TAG), followed by a polyadenylation sequence (SEQ ID NO:8), followed by a sequence (1000 bp) homologous to the endogenous gene downstream of the TALEN site (SEQ ID NO:2). The insertion matrix is subsequently cloned into a promoterless rAAV vector and used to produce AAV6.

1.2 Insertion of an Interleukin in an Upregulated Locus with Knock-Out of the Endogenous Gene The location of the TALEN target site is designed to be located in the targeted endogenous PDCD1 gene (Programmed cell death protein 1, PD1). The sequence encompassing 1000 bp upstream and downstream the TALEN targets is given in SEQ ID NO:1 and SEQ ID NO:2. Target sequences of the TALEN (SEQ ID NO:3 and SEQ ID NO:4) is given in SEQ ID NO:5. The integration matrix is designed to be composed of a sequence (300 bp) homologous to the endogenous gene upstream of the TALEN site (SEQ ID NO:1), followed by a 2A regulatory element (SEQ ID NO:6), followed by a sequence encoding an engineered single-chained human IL-12 p35 (SEQ ID NO:9) and p40 (SEQ ID NO:10) subunit fusion protein, followed by a STOP codon (TAG), followed by a polyadenylation sequence (SEQ ID NO:8), followed by a sequence (1000 bp) homologous to the endogenous gene downstream of the TALEN site (SEQ ID NO:2). The insertion matrix is subsequently cloned into a promoterless rAAV vector and used to produce AAV6.

1.3 Insertion of an Apoptosis CAR in a Weakly Expressed Locus without Knocking Out the Endogenous Gene—N-Terminal Insertion The location of the TALEN target site is designed to be located as close as possible to the start codon of the targeted endogenous LCK gene (LCK, LCK proto-oncogene, Src family tyrosine kinase [Homo sapiens (human)]). The sequence encompassing 1000 bp upstream and downstream the start codon is given in SEQ ID NO:11 and SEQ ID NO:12. The integration matrix is designed to be composed of a sequence (1000 bp) homologous to the endogenous gene upstream of the start codon, followed by a sequence encoding an apoptosis inducing CAR containing a start codon (SEQ ID NO:13), followed by a 2A regulatory element (SEQ ID NO:8), followed by a sequence (1000 bp) homologous to the endogenous gene downstream of the start codon (SEQ ID NO:12). The insertion matrix is subsequently cloned into a promoterless rAAV vector and used to produce AAV6.

1.4 Insertion of an Apoptosis CAR in a Weakly Expressed Locus without Knocking Out the Endogenous Gene—C-Terminal Insertion The location of the TALEN target site is designed to be located as close as possible to the stop codon of the targeted endogenous LCK gene (LCK, LCK proto-oncogene, Src family tyrosine kinase [Homo sapiens (human)]). The sequence encompassing 1000 bp upstream and downstream the stop codon is given in SEQ ID NO:14 and SEQ ID NO:15. The integration matrix is designed to be composed of a sequence (1000 bp) homologous to the endogenous gene upstream of the stop codon, followed by a 2A regulatory element (SEQ ID NO:8), followed by a sequence encoding an apoptosis inducing CAR without the start codon (SEQ ID NO:7), followed by a STOP codon (TAG), followed by a sequence (1000 bp) homologous to the endogenous gene downstream of the stop codon (SEQ ID NO:15). The insertion matrix is subsequently cloned into a promoterless rAAV vector and used to produce AAV6.

Expression of the Sequence-Specific Nuclease Reagents in the Transduced Cells

TALEN® mRNA is synthesized using the mMessage mMachine T7 Ultra kit (Thermo Fisher Scientific, Grand Island, NY) as each TALEN is cloned downstream of a T7 promoter, purified using RNeasy columns (Qiagen, Valencia, CA) and eluted in "cytoporation medium T" (Harvard Apparatus, Holliston, MA). Human T-cells are collected and activated from whole peripheral blood provided by ALL-CELLS (Alameda, CA) in X-Vivo-15 medium (Lonza, Basel, Switzerland) supplemented with 20 ng/ml human IL-2 (Miltenyi Biotech, San Diego, CA), 5% human AB serum (Gemini Bio-Products, West San Francisco, CA) and Dynabeads Human T-activator CD3/CD28 at a 1:1 bead:cell ratio (Thermo Fisher Scientific, Grand Island, NY). Beads are removed after 3 days and $5\times10^6$ cells are electroporated with 10 µg mRNA of each of the two adequate TALEN® using Cytopulse (BTX Harvard Apparatus, Holliston, MA) by applying two 0.1 mS pulses at 3,000 V/cm followed by four 0.2 mS pulses at 325 V/cm in 0.4 cm gap cuvettes in a final volume of 200 μl of "cytoporation medium T" (BTX Harvard Apparatus, Holliston, Massachusetts). Cells are immediately diluted in X-Vivo-15 media with 20 ng/mL IL-2 and incubated at 37° C. with 5% CO$_2$. After two hours, cells are incubated with AAV6 particles at 3×10^5 viral genomes (vg) per cell (37° C., 16 hours). Cells are passaged and maintained in X-Vivo-15 medium supplemented with 5% human AB serum and 20 ng/mL IL-2 until examined by flow cytometry for expression of the respective inserted gene sequences.

Table 4: Sequences referred to in example 1

TABLE 4

Sequences referred to in example 1

| Sequence name | Ref. sequences | Polynucleotide or polypeptide sequences |
|---|---|---|
| PD1 left homology | SEQ ID NO. 1 | CCAAGCCCTGACCCTGGCAGGCATATGTTTCAGGAGGTCCTTGTCTTGGGA GCCCAGGGTCGGGGGCCCCGTGTCTGTCCACATCCGAGTCAATGGCCCAT CTCGTCTCTGAAGCATCTTTGCTGTGAGCTCTAGTCCCCACTGTCTTGCTGG AAAATGTGGAGGCCCCACTGCCCACTGCCCAGGGCAGCAATGCCCATACC ACGTGGTCCCAGCTCCGAGCTTGTCCTGAAAAGGGGGCAAAGACTGGACC CTGAGCCTGCCAAGGGGCCACACTCCTCCCAGGGCTGGGGTCTCCATGGG CAGCCCCCCACCCACCCAGACCAGTTACACTCCCCTGTGCCAGAGCAGTGC AGACAGGACCAGGCCAGGATGCCCAAGGGTCAGGGGCTGGGGATGGGT AGCCCCCAAACAGCCCTTTCTGGGGGAACTGGCCTCAACGGGGAAGGGG GTGAAGGCTCTTAGTAGGAAATCAGGGAGACCCAAGTCAGAGCCAGGTG CTGTGCAGAAGCTGCAGCCTCACGTAGAAGGAAGAGGCTCTGCAGTGGA GGCCAGTGCCCATCCCCGGGTGGCAGAGGCCCCAGCAGAGACTTCTCAAT GACATTCCAGCTGGGGTGGCCCTTCCAGAGCCCTTGCTGCCCGAGGGATG TGAGCAGGTGGCCGGGGAGGCTTTGTGGGGCCACCCAGCCCCTTCCTCAC CTCTCTCCATCTCTCAGACTCCCCAGACAGGCCCTGGAACCCCCCCACCTTC TCCCCAGCCCTGCTCGTGGTGACCGAAGGGGACAACGCCACCTTCACCTGC AGCTTCTCCAACACATCGGAGAGCTTCGTGCTAAACTGGTACCGCATGAGC CCCAGCAACCAGACGGACAAGCTGGCCGCCTTCCCCGAGGACCGCAGCCA GCCCGGCCAGGACTGCCGCTTCCGTGTCACACAACTGCCCAACGGGCGTG ACTTCCACATGAGCGTGGTCAGGGCCCGGCGCAATGACAGCGGCACC |
| PD1 right homology | SEQ ID NO. 2 | GCCTGCGGGCAGAGCTCAGGGTGACAGGTGCGGCCTCGGAGGCCCCGGG GCAGGGGTGAGCTGAGCCGGTCCTGGGGTGGGTGTCCCCTCCTGCACAG GATCAGGAGCTCCAGGGTCGTAGGGCAGGGACCCCCCAGCTCCAGTCCAG GGCTCTGTCCTGCACCTGGGGAATGGTGACCGGCATCTCTGTCCTCTAGCT CTGGAAGCACCCCAGCCCCTCTAGTCTGCCCTCACCCCTGACCCTGACCCTC CACCCTGACCCCGTCCTAACCCCTGACCTTTGTGCCCTTCCAGAGAGAAGG GCAGAAGTGCCCACAGCCCACCCCAGCCCCTCACCCAGGCCAGCCGGCCA GTTCCAAACCCTGGTGGTTGGTGTCGTGGGCGGCCTGCTGGGCAGCCTGG TGCTGCTAGTCTGGGTCCTGGCCGTCATCTGCTCCCGGGCCGCACGAGGTA ACGTCATCCCAGCCCCTCGGCCTGCCCTGCCCTAACCCTGCTGGCGGCCCT CACTCCCGCCTCCCCTTCCTCCACCCTTCCCTCACCCCACCCCACCTCCCCCC ATCTCCCCGCCAGGCTAAGTCCCTGATGAAGGCCCCTGGACTAAGACCCCC CACCTAGGAGCACGGCTCAGGGTCGGCCTGGTGACCCCAAGTGTGTTTCT CTGCAGGGACAATAGGAGCCAGGCGCACCGGCCAGCCCCTGGTGAGTCTC ACTCTTTTCCTGCATGATCCACTGTGCCTTCCTTCCTGGGTGGGCAGAGGT GGAAGGACAGGCTGGGACCACACGGCCTGCAGGACTCACATTCTATTATA GCCAGGACCCCACCTCCCCAGCCCCCAGGCAGCAACCTCAATCCCTAAAGC CATGATCTGGGGCCCCAGCCCACCTGCGGTCTCCGGGGGTGCCCGGCCCA TGTGTGTGCCTGCCTGCGGTCTCCAGGGGTGCCTGGCCCACGCGTGTGCC CGCCTGCGGTCTCTGGGGGTGCCCGGCCCACATATGTGCC |
| PD1_T3C-L2 | SEQ ID NO. 3 | ATGGGCGATCCTAAAAAGAAACGTAAGGTCATCGATATCGCCGATCTACG CACGCTCGGCTACAGCCAGCAGCAACAGGAGAAGATCAAACCGAAGGTTC GTTCGACAGTGGCGCAGCACCACGAGGCACTGGTCGGCCACGGGTTTACA CACGCGCACATCGTTGCGTTAAGCCAACACCCGGCAGCGTTAGGGACCGT CGCTGTCAAGTATCAGGACATGATCGCAGCGTTGCCAGAGGCGACACACG AAGCGATCGTTGGCGTCGGCAAACAGTGGTCCGGCGCACGCGCTCTGGA GGCCTTGCTCACGGTGGCGGGAGAGTTGAGAGGTCCACCGTTACAGTTGG ACACAGGCCAACTTCTCAAGATTGCAAAACGTGGCGGCGTGACCGCAGTG GAGGCAGTGCATGCATGGCGCAATGCACTGACGGGTGCCCCGCTCAACTT GACCCCCGAGCAAGTGGTGGCTATCGCTTCCAAGCTGGGGGGAAAGCAG GCCCTGGAGACCGTCCAGGCCCTTCTCCCAGTGCTTTGCCAGGCTCACGGA CTGACCCCTGAACAGGTGGTGGCAATTGCCTCACACGACGGGGGCAAGCA GGCACTGGAGACTGTCCAGCGGCTGCTGCCTGTCCTCTGCCAGGCCCACG GACTCACTCCTGAGCAGGTCGTGGCCATTGCCAGCCACGATGGGGGCAAA CAGGCTCTGGAGACCGTGCAGCGCCTCCTCCCAGTGCTGTGCCAGGCTCAT GGGCTGACCCCACAGCAGGTCGTCGCCATTGCCAGTAACGGCGGGGGGA AGCAGGCCCTCGAAACAGTGCAGAGGCTGCTGCCCGTCTTGTGCCAAGCA CACGGCCTGACACCCGAGCAGGTGGTGGCCATCGCCTCTCATGACGGCGG CAAGCAGGCCCTTGAGACAGTGCAGAGACTGTTGCCCGTGTTGTGTCAGG CCCACGGGTTGACACCCCAGCAGGTGGTCGCCATCGCCAGCAATGGCGGG GGAAAGCAGGCCCTTGAGACCGTGCAGCGGTTGCTTCCAGTGTTGTGCCA GGCACACGGACTGACCCCTCAACAGGTGGTCGCAATCGCCAGCTACAAGG GCGGAAAGCAGGCTCTGGAGACAGTGCAGCGCCTCCTGCCCGTGCTGTGT CAGGCTCACGGACTGACACCACAGCAGGTGGTCGCCATCGCCAGTAACGG GGGCGGCAAGCAGGCTTTGGAGACCGTCCAGAGACTCCTCCCCGTCCTTT |

TABLE 4-continued

Sequences referred to in example 1

| Sequence name | Ref. sequences | Polynucleotide or polypeptide sequences |
|---|---|---|
| | | GCCAGGCCCACGGGTTGACACCTCAGCAGGTCGTCGCCATTGCCTCCAAC<br>AACGGGGGCAAGCAGGCCCTCGAAACTGTGCAGAGGCTGCTGCCTGTGCT<br>GTGCCAGGCTCATGGGCTGACACCCCAGCAGGTGGTGGCCATTGCCTCTA<br>ACAACGGCGGCAAACAGGCACTGGAGACCGTGCAAAGGCTGCTGCCCGT<br>CCTCTGCCAAGCCCACGGGCTCACTCCACAGCAGGTCGTGGCCATCGCCTC<br>AAACAATGGCGGGAAGCAGGCCCTGGAGACTGTGCAAAGGCTGCTCCCT<br>GTGCTCTGCCAGGCACACGGACTGACCCCTCAGCAGGTGGTGGCAATCGC<br>TTCCAACAACGGGGGAAAGCAGGCCCTCGAAACCGTGCAGCGCCTCCTCC<br>CAGTGCTGTGCCAGGCACATGGCCTCACACCCGAGCAAGTGGTGGCTATC<br>GCCAGCCACGACGGAGGGAAGCAGGCTCTGGAGACCGTGCAGAGGCTGC<br>TGCCTGTCCTGTGCCAGGCCCACGGGCTTACTCCAGAGCAGGTCGTCGCCA<br>TCGCCAGTCATGATGGGGGGAAGCAGGCCCTTGAGACAGTCCAGCGGCT<br>GCTGCCAGTCCTTTGCCAGGCTCACGGCTTGACTCCCGAGCAGGTCGTGGC<br>CATTGCCTCAAACATTGGGGGCAAACAGGCCCTGGAGACAGTGCAGGCCC<br>TGCTGCCCGTGTTGTGTCAGGCCCACGGCTTGACACCCCAGCAGGTGGTC<br>GCCATTGCCTCTAATGGCGGCGGGAGACCCGCCTTGGAGAGCATTGTTGC<br>CCAGTTATCTCGCCCTGATCCGGCGTTGGCCGCGTTGACCAACGACCACCT<br>CGTCGCCTTGGCCTGCCTCGGCGGGCGTCCTGCGCTGGATGCAGTGAAAA<br>AGGGATTGGGGGATCCTATCAGCCGTTCCCAGCTGGTGAAGTCCGAGCTG<br>GAGGAGAAGAAATCCGAGTTGAGGCACAAGCTGAAGTACGTGCCCCACG<br>AGTACATCGAGCTGATCGAGATCGCCCGGAACAGCACCCAGGACCGTATC<br>CTGGAGATGAAGGTGATGGAGTTCTTCATGAAGGTGTACGGCTACAGGG<br>GCAAGCACCTGGGCGGCTCCAGGAAGCCCGACGGCGCCATCTACACCGTG<br>GGCTCCCCCATCGACTACGGCGTGATCGTGGACACCAAGGCCTACTCCGG<br>CGGCTACAACCTGCCCATCGGCCAGGCCGACGAAATGCAGAGGTACGTGG<br>AGGAGAACCAGACCAGGAACAAGCACATCAACCCCAACGAGTGGTGGAA<br>GGTGTACCCCTCCAGCGTGACCGAGTTCAAGTTCCTGTTCGTGTCCGGCCA<br>CTTCAAGGGCAACTACAAGGCCCAGCTGACCAGGCTGAACCACATCACCA<br>ACTGCAACGGCGCCGTGCTGTCCGTGGAGGAGCTCCTGATCGGCGGCGA<br>GATGATCAAGGCCGGCACCCTGACCCTGGAGGAGGTGAGGAGGAAGTTC<br>AACAACGGCGAGATCAACTTCGCGGCCGACTGATAA |
| PD1T3R | SEQ ID<br>NO. 4 | ATGGGCGATCCTAAAAAGAAACGTAAGGTCATCGATATCGCCGATCTACG<br>CACGCTCGGCTACAGCCAGCAGCAACAGGAGAAGATCAAACCGAAGGTTC<br>GTTCGACAGTGGCGCAGCACCACGAGGCACTGGTCGGCCACGGGTTTACA<br>CACGCGCACATCGTTGCGTTAAGCCAACACCCGGCAGCGTTAGGGACCGT<br>CGCTGTCAAGTATCAGGACATGATCGCAGCGTTGCCAGAGGCGACACACG<br>AAGCGATCGTTGGCGTCGGCAAACAGTGGTCCGGCGCACGCGCTCTGGA<br>GGCCTTGCTCACGGTGGCGGGAGAGTTGAGAGGTCCACCGTTACAGTTGG<br>ACACAGGCCAACTTCTCAAGATTGCAAAACGTGGCGGCGTGACCGCAGTG<br>GAGGCAGTGCATGCATGGCGCAATGCACTGACGGGTGCCCCGCTCAACTT<br>GACCCCCGAGCAAGTCGTCGCAATCGCCAGCCATGATGGAGGGAAGCAA<br>GCCCTCGAAACCGTGCAGCGGTTGCTTCCTGTGCTCTGCCAGGCCCACGGC<br>CTTACCCCTCAGCAGGTGGTGGCCATCGCAAGTAACGGAGGAGGAAAGCA<br>AGCCTTGGAGACAGTGCAGCGCCTGTTGCCCGTGCTGTGCCAGGCACACG<br>GCCTCACACCAGAGCAGGTCGTGGCCATTGCCTCCCATGACGGGGGGAAA<br>CAGGCTCTGGAGACCGTCCAGAGGCTGCTGCCCGTCCTCTGTCAAGCTCAC<br>GGCCTGACTCCCCAACAAGTGGTCGCCATCGCCTCTAATGGCGGCGGGAA<br>GCAGGCACTGGAAACAGTGCAGAGACTGCTCCCTGTGCTTTGCCAAGCTC<br>ATGGGTTGACCCCCAACAGGTCGTCGCTATTGCCTCAAACGGGGGGGC<br>AAGCAGGCCCTTGAGACTGTGCAGAGGCTGTTGCCAGTGCTGTGTCAGGC<br>TCACGGCTCACTCCACAACAGGTGGTCGCAATTGCCAGCAACGGCGGCG<br>GAAAGCAAGCTCTTGAAACCGTGCAACGCCTCCTGCCCGTGCTCTGTCAGG<br>CTCATGGCCTGACACCACAACAAGTCGTGGCCATCGCCAGTAATAATGGC<br>GGGAAACAGGCTCTTGAGACCGTCCAGAGGCTGCTCCCAGTGCTCTGCCA<br>GGCACACGGGCTGACCCCGAGCAGGTGGTGGCTATCGCCAGCAATATTG<br>GGGGCAAGCAGGCCCTGGAAACAGTCCAGGCCCTGCTGCCAGTGCTTTGC<br>CAGGCTCACGGGCTCACTCCCCAGCAGGTCGTGGCCAATCGCCTCCAACGG<br>CGGAGGGAAGCAGGCTCTGGAGACCGTGCAGAGACTGCTGCCCGTCTTGT<br>GCCAGGCCCACGGACTCACACCTGAACAGGTCGTCGCCATTGCCTCTCACG<br>ATGGGGGCAAACAAGCCCTGGAGACAGTGCAGCGGCTGTTGCCTGTGTTG<br>TGCCAAGCCCACGGCTTGACTCCTCAACAAGTGGTCGCCATCGCCTCAAAT<br>GGCGGCGGAAAACAAGCTCTGGAGACAGTGCAGAGGTTGCTGCCCGTCC<br>TCTGCCAAGCCCACGCCTGACTCCCAACAGGTCGTCGCCATTGCCAGCA<br>ACAACGGAGGAAAGCAGGCTCTCGAAACTGTGCAGCGGCTGCTTCCTGTG<br>CTGTGTCAGGCTCATGGGCTGACCCCCGAGCAAGTGGTGGCTATTGCCTCT<br>AATGGAGGCAAGCAAGCCCTTGAGACAGTCCAGAGGCTGTTGCCAGTGCT<br>GTGCCAGGCCCACGGGCTCACACCCCAGCAGGTGGTCGCCATCGCCAGTA<br>ACAACGGGGGCAAACAGGCATTGGAAACCGTCCAGCGCCTGCTTCCAGTG<br>CTCTGCCAGGCACACGGACTGACACCCGAACAGGTGGTGGCCATTGCATC<br>CCATGATGGGGGCAAGCAGGCCCTGGAGACCGTGCAGAGACTCCTGCCA<br>GTGTTGTGCCAAGCTCACGGCCTCACCCCTCAGCAAGTCGTGGCCATCGCC<br>TCAAACGGGGGGGCCGGCCTGCACTGGAGAGCATTGTTGCCCAGTTATC<br>TCGCCCTGATCCGGCGTTGGCCGCGTTGACCAACGACCACCTCGTCGCCTT<br>GGCCTGCCTCGGCGGGCGTCCTGCGCTGGATGCAGTGAAAAAGGGGATTG |

TABLE 4-continued

Sequences referred to in example 1

| Sequence name | Ref. sequences | Polynucleotide or polypeptide sequences |
|---|---|---|
| | | GGGGATCCTATCAGCCGTTCCCAGCTGGTGAAGTCCGAGCTGGAGGAGAA<br>GAAATCCGAGTTGAGGCACAAGCTGAAGTACGTGCCCCACGAGTACATCG<br>AGCTGATCGAGATCGCCCGGAACAGCACCCAGGACCGTATCCTGGAGATG<br>AAGGTGATGGAGTTCTTCATGAAGGTGTACGGCTACAGGGGCAAGCACCT<br>GGGCGGCTCCAGGAAGCCCGACGGCGCCATCTACACCGTGGGCTCCCCCA<br>TCGACTACGGCGTGATCGTGGACACCAAGGCCTACTCCGGCGGCTACAAC<br>CTGCCCATCGGCCAGGCCGACGAAATGCAGAGGTACGTGGAGGAGAACC<br>AGACCAGGAACAAGCACATCAACCCCAACGAGTGGTGAAGGTGTACCCC<br>TCCAGCGTGACCGAGTTCAAGTTCCTGTTCGTGTCCGGCCACTTCAAGGGC<br>AACTACAAGGCCCAGCTGACCAGGCTGAACCACATCACCAACTGCAACGG<br>CGCCGTGCTGTCCGTGGAGGAGCTCCTGATCGGCGGCGAGATGATCAAG<br>GCCGGCACCCTGACCCTGGAGGAGGTGAGGAGGAAGTTCAACAACGGCG<br>AGATCAACTTCGCGGCCGACTGATAA |
| PD1-T3 | SEQ ID NO. 5 | TACCTCTGTGGGGCCATCTCCCTGGCCCCCAAGGCGCAGATCAAAGAGA |
| 2A-element | SEQ ID NO. 6 | TCCGGTGAGGGCAGAGGAAGTCTTCTAACATGCGGTGACGTGGAGGAGA<br>ATCCGGGCCCC |
| apoptosis CAR (without start codon) | SEQ ID NO. 7 | GCTTTGCCTGTCACTGCCTTGCTGCTTCCACTTGCTCTGTTGTTGCACGCCG<br>CAAGACCCGAGGTCAAGCTCCAGGAAAGCGGACCAGGGCTGGTGGCCCC<br>TAGTCAGTCATTGAGCGTCACTTGCACCGTCAGCGGCGTGTCTCTGCCCGA<br>TTACGCGTGAGCTGGATCAGACAGCCCCCAAGGAAGGGACTGGAGTGG<br>CTGGGCGTCATCTGGGGGAGCGAGACTACCTACTACAACAGCGCCCTGAA<br>GAGCAGGCTGACCATCATTAAGGACAACTCCAAGTCCAGGTCTTTCTGAA<br>AATGAACAGCCTGCAGACTGATGACACTGCCATCTACTACTGCGCCAAGCA<br>TTACTACTACGGGGGCAGCTACGCTATGGACTACTGGGGGCAGGGGACCT<br>CTGTCACAGTGTCAAGTGGCGGAGGAGGCAGTGGCGGAGGGGGAAGTG<br>GGGGCGGCGGCAGCGACATCCAGATGACCCAGACAACATCCAGCCTCTCC<br>GCCTCTCTGGGCGACAGAGTGACAATCAGCTGCCGGGCCAGTCAGGACAT<br>CAGCAAGTATCTCAATTGGTACCAGCAGAAACCAGACGGGACAGTGAAAT<br>TGCTGATCTACCACACATCCAGGCTGCACTCAGGAGTCCCCAGCAGGTTTT<br>CCGGCTCCGGCTCCGGGACAGATTACAGTCTGACCATTTCCAACCTGGAGC<br>AGGAGGATATTGCCACATACTTTTGCCAGCAAGGCAACACTCTGCCCTATA<br>CCTTCGGCGGAGGCACAAAACTGGAGATTACTCGGTCGGATCCCGAGCCC<br>AAATCTCCTGACAAAACTCACACATGCCCACCGTGCCCAGCACCTCCCGTG<br>GCCGGCCCGTCAGTGTTCCTCTTCCCCCCAAAACCCAAGGACACCCTCATG<br>ATCGCCCGGACCCCTGAGGTCACATGCGTGGTGGTGGACGTGAGCCACGA<br>GGACCCTGAGGTCAAGTTCAACTGGTACGTGGACGGCGTGGAGGTGCAT<br>AATGCCAAGACAAAGCCGCGGGAGGAGCAGTACAACAGCACGTACCGTG<br>TGGTCAGCGTCCTCACCGTCCTGCACCAGGACTGGCTGAATGGCAAGGAG<br>TACAAGTGCAAGGTGTCCAACAAAGCCCTCCCAGCCCCCATCGAGAAAAC<br>CATCTCCAAAGCCAAAGGGCAGCCCCGAGAACCACAGGTGTACACCCTGC<br>CCCCATCCCGGGATGAGCTGACCAAGAACCAGGTCAGCCTGACCTGCCTG<br>GTCAAAGGCTTCTATCCCAGCGACATCGCCGTGGAGTGGGAGAGCAATGG<br>GCAACCGGAGAACAACTACAAGACCACGCCTCCCGTGCTGGACTCCGACG<br>GCTCCTTCTTCCTCTACAGCAAGCTCACCGTGGACAAGAGCAGGTGGCAGC<br>AGGGGAACGTGTTCTCATGCTCCGTGATGCATGAGGCCCTGCACAATCACT<br>ATACCCAGAAATCTCTGAGTCTGAGCCCAGGCAAGAAGGATATTTTGGGG<br>TGGCTTTGCCTTCTTCTTTTGCCAATTCCACTAATTGTTTGGGTGAAGAGAA<br>AGGAAGTACAGAAAACATGCAGAAAGCACAGAAAGGAAAACCAAGGTTC<br>TCATGAATCTCCAACCTTAAATCCTGAAACAGTGGCAATAAATTTATCTGAT<br>GTTGACTTGAGTAAATATATCACCACTATTGCTGGAGTCATGACACTAAGT<br>CAAGTTAAAGGCTTTGTTCGAAAGAATGGTGTCAATGAAGCCAAAATAGA<br>TGAGATCAAGAATGACAATGTCCAAGACACAGCAGAACAGAAAGTTCAAC<br>TGCTTCGTAATTGGCATCAACTTCATGGAAAGAAAGAAGCGTATGCACAT<br>TGATTGCAGATCTCAAAAAAGCCAATCTTTGTACTCTTGCAGAGAAAATTC<br>AGACTATCATCCTCAAGGACATTACTAGTGACTCAGAAAATTCAAACTTCA<br>GAAATGAAATCCAGAGCTTGGTCGAA |
| BGH polyA | SEQ ID NO. 8 | TCTAGAGGGCCCGTTTAAACCCGCTGATCAGCCTCGACTGTGCCTTCTAGT<br>TGCCAGCCATCTGTTGTTTGCCCCTCCCCCGTGCCTTCCTTGACCCTGGAAG<br>GTGCCACTCCCACTGTCCTTTCCTAATAAAATGAGGAAATTGCATCGCATT<br>GTCTGAGTAGGTGTCATTCTATTCTGGGGGGTGGGGTGGGGCAGGACAG<br>CAAGGGGGAGGATTGGGAAGACAATAGCAGGCATGCTGGGGATGCGGT<br>GGGCTCTATGACTAGTGGCGAATTC |
| Interleukin-12 subunit alpha | SEQ ID NO. 9 | MCPARSLLLVATLVLLDHLSLARNLPVATPDPGMFPCLHHSQNLLRAVSNML<br>QKARQTLEFYPCTSEEIDHEDITKDKTSVEACLPLELTKNESCLNSRETSFITNG<br>SCLASRKTSFMMALCLSSIYEDLKMYQVEFKTMNAKLLMDPKRQIFLDQNML<br>AVIDELMQALNFNSETVPQKSSLEEPDFYKTKIKLCILLHAFRIRAVTIDRVMSYL<br>NAS |

TABLE 4-continued

Sequences referred to in example 1

| Sequence name | Ref. sequences | Polynucleotide or polypeptide sequences |
|---|---|---|
| Interleukin-12 subunit beta | SEQ ID NO. 10 | MCHQQLVISWFSLVFLASPLVAIWELKKDVYVVELDWYPDAPGEMVVLTCDT<br>PEEDGITWTLDQSSEVLGSGKTLTIQVKEFGDAGQYTCHKGGEVLSHSLLLLHK<br>KEDGIWSTDILKDQKEPKNKTFLRCEAKNYSGRFTCWWLTTISTDLTFSVKSSR<br>GSSDPQGVTCGAATLSAERVRGDNKEYEYSVECQEDSACPAAEESLPIEVMV<br>DAVHKLKYENYTSSFFIRDIIKPDPPKNLQLKPLKNSRQVEVSWEYPDTWSTPH<br>SYFSLTFCVQVQGKSKREKKDRVFTDKTSATVICRKNASISVRAQDRYYSSSWS<br>EWASVPCS |
| Lck left homology | SEQ ID NO. 11 | GGGATAGGGGTGCCTCTGTGTGTGTGTGAGAGTGTGTGTGTGTAGG<br>GTGTGTATATGTATAGGGTGTGTGTGAGTGTGTGTGTGTGAGAGAGTGTG<br>TGTGTGGCAGAATAGACTGCGGAGGTGGATTTCATCTTGATATGAAAGGT<br>CTGGAATGCATGGTACATTAAACTTTGAGGACAGCGCTTTCCAAGCACTCT<br>GAGGAGCAGCCCTAGAGAAGGAGGAGCTGCAGGGACTCCGGGGGCTTCA<br>AAGTGAGGGCCCCACTCTGCTTCAGGCAAAACAGGCACACATTTATCACTT<br>TATCTATGGAGTTCTGCTTGATTTCATCAGACAAAAATTTCCACTGCTAAA<br>ACAGGCAAATAAACAAAAAAAAAGTTATGGCCAACAGAGTCACTGGAGG<br>GTTTTCTGCTGGGGAGAAGCAAGCCCGTGTTTGAAGGAACCCTGTGAGAT<br>GACTGTGGGCTGTGTGAGGGGAACAGCGGGGGCTTGATGGTGGACTTCG<br>GGAGCAGAAGCCTCTTTCTCAGCCTCCTCAGCTAGACAGGGGAATTATAAT<br>AGGAGGTGTGGCGTGCACACCTCTCCAGTAGGGGAGGGTCTGATAAGTC<br>AGGTCTCTCCCAGGCTTGGGAAAGTGTGTGTCATCTCTAGGAGGTGGTCCT<br>CCCAACACAGGGTACTGGCAGAGGGAGAGGGAGGGGGCAGAGGCAGGA<br>AGTGGGTAACTAGACTAACAAAGGTGCCTGTGGCGGTTTGCCCATCCCAG<br>GTGGGAGGGTGGGGCTAGGGCTCAGGGGCCGTGTGTGAATTTACTTGTA<br>GCCTGAGGGCTCAGAGGGAGCACCGGTTTGGAGCTGGGACCCCCTATTTT<br>AGCTTTTCTGTGGCTGGTGAATGGGGATCCCAGGATCTCACAATCTCAGGT<br>ACTTTTGGAACTTTCCAGGGCAAGGCCCCATTATATCTGATGTTGGGGGAG<br>CAGATCTTGGGGGAGCCCCTTCAGCCCCCTCTTCCATTCCCTCAGGGACC |
| lck right homology | SEQ ID NO. 12 | GGCTGTGGCTGCAGCTCACACCCGGAAGATGACTGGATGGAAAACATCGA<br>TGTGTGTGAGAACTGCCATTATCCCATAGTCCCACTGGATGGCAAGGGCA<br>CGGTAAGAGGCGAGACAGGGGCCTTGGTGAGGGAGTTGGGTAGAGAAT<br>GCAACCCAGGAGAAAGAAATGACCAGCACTACAGGCCCTTGAAAGAATA<br>GAGTGGCCCTCTCCCCTGAAATACAGAAAGGAAAAGAGGCCCAGAGAGG<br>GGAAGGGAATCTCCTAAGATCACACAGAAAGTAGTTGGTAAACTCAGGGA<br>TAACATCTAACCAGGCTGGAGAGGCTGAGAGCAGAGCAGGGGGGAAGG<br>GGGCCAGGGTCTGACCCAATCTTCTGCTTTCTGACCCCACCCTCATCCCCCA<br>CTCCACAGCTGCTCATCCGAAATGGCTCTGAGGTGCGGGACCCACTGGTTA<br>CCTACGAAGGCTCCAATCCGCCGGCTTCCCCACTGCAAGGTGACCCCAGGC<br>AGCAGGGCCTGAAAGACAAGGCCTGCGGATCCCTGGCTGTTGGCTTCCAC<br>CTCTCCCCCACCTACTTTCTCCCCGGTCTTGCCTTCTTGTCCCCCACCCTGT<br>AACTCCAGGCTTCCTGCCGATCCCAGCTCGGTTCTCCCTGATGCCCCTTGTC<br>TTTACAGACAACCTGGTTATCGCTCTGCACAGCTATGAGCCCTCTCACGAC<br>GGAGATCTGGGCTTTGAGAAGGGGGAACAGCTCCGCATCCTGGAGCAGT<br>GAGTCCCTCTCCACCTTGCTCTGGCGGAGTCCGTGAGGGAGCGGCGATCT<br>CCGCGACCCGCAGCCCTCCTGCGCCCTTGACCAGCTCGGGGTGGCCGCC<br>CTTGGGACAAAATTCGAGGCTCAGTATTGCTGAGCCAGGGTTGGGGGAG<br>GCTGGCTTAAGGGGTGGAGGGGTCTTTGAGGGAGGGTCTCAGGTCGACG<br>GCTGAGCGAGCCACACTGACCCACCTCCGTGGCGCAGGAGCGGCGAGTG |
| apoptosis CAR (with start codon) | SEQ ID NO. 13 | ATGGCTTTGCCTGTCACTGCCTTGCTGCTTCCACTTGCTCTGTTGTTGCACG<br>CCGCAAGACCCGAGGTCAAGCTCCAGGAAAGCGGACCAGGGCTGGTGGC<br>CCCTAGTCAGTCATTGAGCGTCACTTGCACCGTCAGCGGCGTGTCTCTGCC<br>CGATTACGGCGTGAGCTGGATCAGACAGCCCCCAAGGAAGGGACTGGAG<br>TGGCTGGGCGTCATCTGGGGGAGCGAGACTACCTACTACAACAGCGCCCT<br>GAAGAGCAGGCTGACCATCATTAAGGACAACTCCAAGTCCCAGGTCTTTCT<br>GAAAATGAACAGCCTGCAGACTGATGACACTGCCATCTACTACTGCGCCAA<br>GCATTACTACTACGGGGGCAGCTACGCTATGGACTACTGGGGCCAGGGG<br>ACCTCTGTCACAGTGTCAAGTGGCGGAGGAGGCAGTGGCGGAGGGGGAA<br>GTGGGGGCGGCGGCAGCGACATCCAGATGACCCAGACAACATCCAGCCTC<br>TCCGCCTCTCTGGGCGACAGAGTGACAATCAGCTGCCGGGCCAGTCAGGA<br>CATCAGCAAGTATCTCAATTGGTACCAGCAGAAACCAGACGGGACAGTGA<br>AATTGCTGATCTACCACACATCCAGGCTGCACTCAGGAGTCCCCAGCAGGT<br>TTTCCGGCTCCGGCTCCGGGACAGATTACAGTCTGACCATTTCCAACCTGG<br>AGCAGGAGGATATTGCCACATACTTTTGCCAGCAAGGCAACACTCTGCCCT<br>ATACCTTCGGCGGAGGCACAAAACTGGAGATTACTCGGTCGGATCCCGAG<br>CCCAAATCTCCTGACAAAACTCACACATGCCCACCGTGCCCAGCACCTCCC<br>GTGGCCGGCCCGTCAGTGTTCCTCTTCCCCCCAAAACCCAAGGACACCCTC<br>ATGATCGCCCGGACCCCTGAGGTCACATGCGTGGTGGTGGACGTGAGCCA<br>CGAGGACCCTGAGGTCAAGTTCAACTGGTACGTGGACGGCGTGGAGGTG<br>CATAATGCCAAGACAAAGCCGCGGGAGGAGCAGTACAACAGCACGTACC<br>GTGTGGTCAGCGTCCTCACCGTCCTGCACCAGGACTGGCTGAATGGCAAG<br>GAGTACAAGTGCAAGGTGTCCAACAAAGCCCTCCCAGCCCCCATCGAGAA<br>AACCATCTCCAAAGCCAAAGGGCAGCCCCGAGAACCACAGGTGTACACCC |

TABLE 4-continued

Sequences referred to in example 1

| Sequence name | Ref. sequences | Polynucleotide or polypeptide sequences |
|---|---|---|
| | | TGCCCCCATCCCGGGATGAGCTGACCAAGAACCAGGTCAGCCTGACCTGC<br>CTGGTCAAAGGCTTCTATCCCAGCGACATCGCCGTGGAGTGGGAGAGCAA<br>TGGGCAACCGGAGAACAACTACAAGACCACGCCTCCCGTGCTGGACTCCG<br>ACGGCTCCTTCTTCCTCTACAGCAAGCTCACCGTGGACAAGAGCAGGTGGC<br>AGCAGGGGAACGTGTTCTCATGCTCCGTGATGCATGAGGCCCTGCACAAT<br>CACTATACCCAGAAATCTCTGAGTCTGAGCCCAGGCAAGAAGGATATTTTG<br>GGGTGGCTTTGCCTTCTTCTTTTGCCAATTCCACTAATTGTTTGGGTGAAGA<br>GAAAGGAAGTACAGAAAACATGCAGAAAGCACAGAAAGGAAAACCAAGG<br>TTCTCATGAATCTCCAACCTTAAATCCTGAAACAGTGGCAATAAATTTATCT<br>GATGTTGACTTGAGTAAATATATCACCACTATTGCTGGAGTCATGACACTA<br>AGTCAAGTTAAAGGCTTTGTTCGAAAGAATGGTGTCAATGAAGCCAAAAT<br>AGATGAGATCAAGAATGACAATGTCCAAGACACAGCAGAACAGAAAGTTC<br>AACTGCTTCGTAATTGGCATCAACTTCATGGAAAGAAAGAAGCGTATGAC<br>ACATTGATTGCAGATCTCAAAAAAGCCAATCTTTGTACTCTTGCAGAGAAA<br>ATTCAGACTATCATCCTCAAGGACATTACTAGTGACTCAGAAAATTCAAAC<br>TTCAGAAATGAAATCCAGAGCTTGGTCGAA |
| Lck left homology | SEQ ID NO. 14 | CTCATAACAATTCTATGAGGTAGGAACAGTTATTTACTCTATTTTCCAAATA<br>AGGAAACTGGGCTCGCCCAAGGTTCCACAACTAACATGTGTGTATTATTGA<br>GCATTTAATTTACACCAGGGAAGCAGGTTGTGGTGGTGTGCACCTGTTGTC<br>CAGCTATTTAGGAGGCTGAGGTGAAAGGATCACTTGAACGGAGGAGTTCA<br>AATTTGCAATGTGCTATGATTGTGCCTGTGAACAGCTGCTGCACTCCAGCC<br>TGGGCAACATAGTGAGATCCCTTATCTAAAACATTTTTTTTAAGTAAATAAT<br>CAGGTGGGCACGGTGGCTCACGCCTGTAATCCAGCACTTTGGGAGGCTGA<br>GGCGGGCGGATCACCTGAGGTCAGGAGTTCAAGACCAGCCTGACCAACAT<br>GGAGAAACCCGTCTCTACTAAAAATACAAAATTAGCTTGGCGTGGTGGTG<br>CATGCCTGTAATCCCAGCTACTCGAGAAGCTGAGGCAGGAGAATTGTTTG<br>AACCTGGGAGGTGGAGGTTGCGGTGAGCCGAGATCGCACCATTGCACTCC<br>AGCCTGGGCAACAAGAGTGAAATTGCATCTCAAAAAAAAAGAAAAGGAA<br>ATAATCTATACCAGGCACTCCAAGTGGTGTGACTGATATTCAACAAGTACC<br>TCTAGTGTGACCTTACCATTGATGAAGACCAAGATTCTTTTGGATTGGTGC<br>TCACACTGTGCCAGTTAAATATTCCGAACATTACCCTTGCCTGTGGGCTTCC<br>AGTGCCTGACCTTGATGTCCTTTCACCCATCAACCCGTAGGGATGACCAAC<br>CCGGAGGTGATTCAGAACCTGGAGCGAGGCTACCGCATGGTGCGCCCTGA<br>CAACTGTCCAGAGGAGCTGTACCAACTCATGAGGCTGTGCTGGAAGGAGC<br>GCCCAGAGGACCGGCCCACCTTTGACTACCTGCGCAGTGTGCTGGAGGAC<br>TTCTTCACGGCCACAGAGGGCCAGTACCAGCCTCAGCCT |
| lck right homology | SEQ ID NO. 15 | GAGGCCTTGAGAGGCCCTGGGGTTCTCCCCCTTTCTCTCCAGCCTGACTTG<br>GGGAGATGGAGTTCTTGTGCCATAGTCACATGGCCTATGCACATATGGAC<br>TCTGCACATGAATCCCACCCACATGTGACACATATGCACCTTGTGTCTGTAC<br>ACGTGTCCTGTAGTTGCGTGGACTCTGCACATGTCTTGTACATGTGTAGCC<br>TGTGCATGTATGTCTTGGACACTGTACAAGGTACCCTTTCTGGCTCTCCCA<br>TTTCCTGAGACCACAGAGAGAGGGGAGAAGCCTGGGATTGACAGAAGCT<br>TCTGCCCACCTACTTTTCTTTCCTCAGATCATCCAGAAGTTCCTCAAGGGCC<br>AGGACTTTATCTAATACCTCTGTGTGCTCCTCCTTGGTGCCTGGCCTGGCAC<br>ACATCAGGAGTTCAATAAATGTCTGTTGATGACTGTTGTACATCTCTTTGCT<br>GTCCACTCTTTGTGGGTGGGCAGTGGGGGTTAAGAAAATGGTAATTAGGT<br>CACCCTGAGTTGGGGTGAAAGATGGGATGAGTGGATGTCTGGAGGCTCT<br>GCAGACCCCTTCAAATGGGACAGTGCTCCTCACCCCTCCCCAAAGGATTCA<br>GGGTGACTCCTACCTGGAATCCCTTAGGGAATGGGTGCGTCAAAGGACCT<br>TCCTCCCCATTATAAAAGGGCAACAGCATTTTTTACTGATTCAAGGGCTATA<br>TTTGACCTCAGATTTTGTTTTTTAAGGCTAGTCAAATGAAGCGGCGGGAA<br>TGGAGGAGGAACAAATAAATCTGTAACTATCCTCAGATTTTTTTTTTTTTT<br>GAGACTGGGTCTCACTTTTTCATCCAGGCTGGAGTGCAGTCGCATGATCAC<br>GGCTCACTGTAGCCTCAACCTCTCCAGCTCAAATGCTCCTCCTGTCTCAGCC<br>TCCCGAGTACCTGGGACTACTTTCTTGAGGCCAGGAATTCAAGAACAGAG<br>TAAGATCCTGGTCTCCAAAAAAAGTTTTAAA |

Example 2: TALEN®-Mediated Double Targeted Integration of IL-15 and CAR Encoding Matrices in T-Cells

Materials

X-vivo-15 was obtained for Lonza (cat #BE04-418Q), IL-2 from Miltenyi Biotech (cat #130-097-748), human serum AB from Seralab (cat #GEM-100-318), human T activator CD3/CD28 from Life Technology (cat #11132D), QBEND10-APC from R&D Systems (cat #FAB7227A), vioblue-labeled anti-CD3, PE-labeled anti-LNGFR, APC-labeled anti-CD25 and PE-labeled anti-PD1 from Miltenyi (cat #130-094-363, 130-112-790, 130-109-021 and 130-104-892 respectively) 48 wells treated plates (CytoOne, cat #CC7682-7548), human IL-15 Quantikine ELISA kit from R&D systems (cat #S1500), ONE-Glo from Promega (cat #E6110). AAV6 batches containing the different matrices were obtained from Virovek, PBMC cells were obtained from Allcells, (cat #PB004F) and Raji-Luciferase cells were obtained after Firefly Luciferase-encoding lentiviral particles transduction of Raji cells from ATCC (cat #CCL-86).

Methods 2.1—Transfection-Transduction

The double targeted integration at TRAC and PD1 or CD25 loci were performed as follows. PBMC cells were first thawed, washed, resuspended and cultivated in X-vivo-15 complete media (X-vivo-15, 5% AB serum, 20 ng/mL IL-2). One day later, cells were activated by Dynabeads human T activator CD3/CD28 (25 uL of beads/1$E^6$ CD3 positive cells) and cultivated at a density of 1$E^6$ cells/mL for 3 days in X-vivo complete media at 37° C. in the presence of 5% $CO_2$. Cells were then split in fresh complete media and transduced/transfected the next day according to the following procedure. On the day of transduction-transfection, cells were first de-beaded by magnetic separation (EasySep), washed twice in Cytoporation buffer T (BTX Harvard Apparatus, Holliston, Massachusetts) and resuspended at a final concentration of 28$E^6$ cells/mL in the same solution. Cellular suspension was mixed with 5 µg mRNA encoding TRAC TALEN® arms (SEQ ID NO:16 and 17) in the presence or in the absence of 15 µg of mRNA encoding arms of either CD25 or PD1 TALEN® (SEQ ID NO:18 and 19 and SEQ ID NO:20 and 21 respectively) in a final volume of 200 µl. TALEN® is a standard format of TALE-nucleases resulting from a fusion of TALE with Fok-1 Transfection was performed using Pulse Agile technology, by applying two 0.1 mS pulses at 3,000 V/cm followed by four 0.2 mS pulses at 325 V/cm in 0.4 cm gap cuvettes and in a final volume of 200 µl of Cytoporation buffer T (BTX Harvard Apparatus, Holliston, Massachusetts). Electroporated cells were then immediately transferred to a 12-well plate containing 1 mL of prewarm X-vivo-15 serum-free media and incubated for 37° C. for 15 min. Cells were then concentrated to 8$E^6$ cells/mL in 250 µL of the same media in the presence of AAV6 particles (MOI=3$E^5$ vg/cells) comprising the donor matrices in 48 wells regular treated plates. After 2 hours of culture at 30° C., 250 µL of Xvivo-15 media supplemented by 10% AB serum and 40 ng/ml IL-2 was added to the cell suspension and the mix was incubated 24 hours in the same culture conditions. One day later, cells were seeded at 1$E^6$ cells/mL in complete X-vivo-15 media and cultivated at 37° C. in the presence of 5% $CO_2$.

2.2—Activation-Dependent Expression of ΔLNGFR and Secretion of IL15

Engineered T-cells were recovered from the transfection-transduction process described earlier and seeded at 1$E^6$ cells/mL alone or in the presence of Raji cells (E:T=1:1) or Dynabeads (12.5 uL/1$E^6$ cells) in 100 µL final volume of complete X-vivo-15 media. Cells were cultivated for 48 hours before being recovered, labeled and analyzed by flow cytometry. Cells were labeled with two independent sets of antibodies. The first sets of antibodies, aiming at detecting the presence of ΔLNGFR, CAR and CD3 cells, consisted in QBEND10-APC (diluted 1/10), vioblue-labeled anti CD3 (diluted 1/25) and PE-labeled anti-ΔLNGFR (diluted 1/25). The second sets of antibodies, aiming at detecting expression of endogenous CD25 and PD1, consisted in APC-labeled anti-CD25 (diluted 1/25) and vioblue-labeled anti PD1 (diluted 1/25).

The same experimental set up was used to study IL-15 secretion in the media. Cells mixture were kept in co-culture for 2, 4, 7 and 10 days before collecting and analyzing supernatant using an IL-15 specific ELISA kit.

2.3—Serial Killing Assay

To assess the antitumor activity of engineered CAR T-cells, a serial killing assay was performed. The principle of this assay is to challenge CAR T-cell antitumor activity everyday by a daily addition of a constant amount of tumor cells. Tumor cell proliferation, control and relapse could be monitored via luminescence read out thanks to a Luciferase marker stably integrated in Tumor cell lines.

Typically, CAR T-cells are mixed to a suspension of 2.5×$10^5$ Raji-luc tumor cells at variable E:T ratio (E:T=5:1 or 1:1) in a total volume of 1 mL of Xvivo 5% AB, 20 ng/uL IL-2. The mixture is incubated 24 hours before determining the luminescence of 25 uL of cell suspension using ONE-Glo reagent. Cells mixture are then spun down, the old media is discarded and substituted with 1 mL of fresh complete X-vivo-15 media containing 2.5×$10^5$ Raji-Luc cells and the resulting cell mixture is incubated for 24 hours. This protocol is repeated 4 days.

Experiments and Results

This example describes methods to improve the therapeutic outcome of CAR T-cell therapies by integrating an IL-15/soluble IL-15 receptor alpha heterodimer (IL15/sIL15rα) expression cassette under the control of the endogenous T-cell promoters regulating PD1 and CD25 genes. Because both genes are known to be upregulated upon tumor engagement by CAR T-cells, they could be hijacked to re-express IL-IL15/sIL15rα only in vicinity of a tumor. This method aims to reduce the potential side effects of IL15/sIL15rα systemic secretion while maintaining its capacity to reduced activation induced T-cell death (AICD), promote T-cell survival, enhance T-cell antitumor activity and to reverse T-cell anergy.

The method developed to integrate IL15/sIL15rα at PD1 and CD25 loci consisted in generating a double-strand break at both loci using TALEN in the presence of a DNA repair matrix vectorized by AAV6. This matrix consists of two homology arms embedding IL15/sIL15rα coding regions separated by a 2A cis acting elements and regulatory elements (stop codon and polyA sequences). Depending on the locus targeted and its involvement in T-cell activity, the targeted endogenous gene could be inactivated or not via specific matrix design. When CD25 gene was considered as targeted locus, the insertion matrix was designed to knock-in (KI) IL15/sIL15rα without inactivating CD25 because the protein product of this gene is regarded as essential for T-cell function. By contrast, because PD1 is involved in T-cell inhibition/exhaustion of T-cells, the insertion matrix was designed to prevent its expression while enabling the expression and secretion of IL15/sIL15rα.

To illustrate this approach and demonstrate the feasibility of double targeted insertion in primary T-cells, three different matrices were designed (FIGS. 2A, 2B and 2C). The first one named CARm represented by SEQ ID NO:36 was designed to insert an anti-CD22 CAR cDNA at the TRAC locus in the presence of TRAC TALEN® (SEQ ID NO:16 and 17). The second one, IL-15_CD25m (SEQ ID NO:37) was designed to integrate IL15, sIL15rα and the surface marker named ΔLNGFR cDNAs separated by 2A cis-acting elements just before the stop codon of CD25 endogenous coding sequence using CD25 TALEN® (SEQ ID NO:18 and 19). The third one, IL-15_PD1m (SEQ ID NO:38), contained the same expression cassette and was designed to integrate in the middle of the PD1 open reading frame using PD1 TALEN® (SEQ ID NO:20 and 21). The three matrices contained an additional 2A cis-acting element located upstream expression cassettes to enable co-expression of IL15/sIL15rα and CAR with the endogenous gene targeted.

We first assessed the efficiency of double targeted insertion in T-cells by transducing them with one of the AAV6 encoding IL15/sIL15rα matrices (SEQ ID NO:41; pCLS30519) along with the one encoding the CAR and subsequently transfected the corresponding TALEN®. AAV6-assisted vectorization of matrices in the presence of mRNA encoding TRAC TALEN® (SEQ ID NO:22 and 23) and PD1 TALEN® (SEQ ID NO:24 and 25) or CD25

TALEN® (SEQ ID NO:26 and 27) enabled expression of the anti CD22 CAR in up to 46% of engineered T-cells (FIG. 3).

To determine the extent of IL15m integration at CD25 and PD1 locus, engineered T-cells were activated with either antiCD3/CD28 coated beads or with CD22 expressing Raji tumor cells. 2 days post activation, cells were recovered and analyzed by FACS using LNGFR expression as IL15/sIL15rα secretion surrogate (FIGS. 4 and 5). Our results showed that antiCD3/CD28 coated beads induced expression of ΔLNGFR by T-cells containing IL-15m_CD25 or IL-15m_PD1, independently of the presence of the anti CD22 CAR (FIG. 4A-B). Tumor cells however, only induced expression of ΔLNGFR by T-cell treated by both CARm and IL-15m. This indicated that expression of ΔLNGFR could be specifically induced through tumor cell engagement by the CAR (FIGS. 5 and 6).

As expected the endogenous CD25 gene was still expressed in activated treated T-cells (FIGS. 7 and 8) while PD1 expression was strongly impaired (FIG. 12).

To verify that expression of ΔLNGFR correlated with secretion of IL15 in the media, T-cells expressing the anti-CD22 CAR and ΔLNGFR were incubated in the presence of CD22 expressing Raji tumor cells (E:T ratio=1:1) for a total of 10 days. Supernatant were recovered at day 2, 4, 7 and 10 and the presence of IL15 was quantified by ELISA assay. Our results showed that IL15 was secreted in the media only by T-cells that were co-treated by both CARm and IL15m matrices along with their corresponding TALEN® (FIG. 13). T-cell treated with either one of these matrices were unable to secrete any significant level of IL15 with respect to resting T-cells. Interestingly, IL-15 secretion level was found transitory, with a maximum peak centered at day 4 (FIG. 14).

To assess whether the level of secreted IL-15 (SEQ ID NO:59) could impact CAR T-cell activity, CAR T-cell were co-cultured in the presence of tumor cells at E:T ratio of 5:1 for 4 days. Their antitumor activity was challenged everyday by pelleting and resuspended them in a culture media lacking IL-2 and containing fresh tumor cells. Antitumor activity of CAR T-cell was monitored everyday by measuring the luminescence of the remaining Raji tumor cells expressing luciferase. Our results showed that CAR T-cells co-expressing IL-15 had a higher antitumor activity than those lacking IL15 at all time points considered (FIG. 15).

Thus, together our results showed that we have developed a method allowing simultaneous targeted insertions of CAR and IL15 cDNA at TRAC and 0025 or PD1 loci. This double targeted insertion led to robust expression of an antiCD22 CAR and to the secretion of IL15 in the media. Levels of secreted IL15 were sufficient to enhance the activity of CAR T-cells.

TABLE 5

Sequences referred to in example 2.

| SEQ ID NO# | Sequence Name | Polypeptide sequence | RVD sequence |
|---|---|---|---|
| 16 | TALEN right TRAC | MGDPKKKRKVIDYPYDVPDYAIDIADLRTLGYSQQQQEKIKPKVRSTVAQHHEALVGHGFTHAHIVALSQHPAALGTVAVKYQDMIAALPEATHEAIVGVGKQWSGARALEALLTVAGELRGPPLQLDTGQLLKIAKRGGVTAVEAVHAWRNALTGAPLNLTPQQVVAIASNGGGKQALETVQRLLPVLCQAHGLTPQQVVAIASNNGGKQALETVQRLLPVLCQAHGLTPQQVVAIASNGGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASNIGGKQALETVQALLPVLCQAHGLTPEQVVAIASHDGGKQALETVQRLLPVLCQAHGLTPEQVVAIASNIGGKQALETVQALLPVLCQAHGLTPQQVVAIASNNGGKQALETVQRLLPVLCQAHGLTPEQVVAIASNIGGKQALETVQALLPVLCQAHGLTPQQVVAIASNGGGKQALETVQRLLPVLCQAHGLTPEQVVAIASNIGGKQALETVQALLPVLCQAHGLTPQQVVAIASNGGGKQALETVQRLLPVLCQAHGLTPEQVVAIASHDGGKQALETVQRLLPVLCQAHGLTPQQVVAIASNGGGRPALESIVAQLSRPDPALAALTNDHLVALACLGGRPALDAVKKGLGDPISRSQLVKSELEEKKSELRHKLKYVPHEYIELIEIARNSTQDRILEMKVMEFFMKVYGYRGKHLGGSRKPDGAIYTVGSPIDYGVIVDTKAYSGGYNLPIGQADEMQRYVEENQTRNKHINPNEWWKVYPSSVTEFKFLFVSGHFKGNYKAQLTRLNHITNCNGAVLSVEELLIGGEMIKAGTLTLEEVRRKFNNGEINFAAD | NG-NN-NG-HD-HD-HD-NI-HD-NI-NN-NI-NG-NI-NG-HD-NG# |
| 17 | TALEN Left TRAC | MGDPKKKRKVIDKETAAAKFERQHMDSIDIADLRTLGYSQQQQEKIKPKVRSTVAQHHEALVGHGFTHAHIVALSQHPAALGTVAVKYQDMIAALPEATHEAIVGVGKQWSGARALEALLTVAGELRGPPLQLDTGQLLKIAKRGGVTAVEAVHAWRNALTGAPLNLTPEQVVAIASHDGGKQALETVQRLLPVLCQAHGLTPQQVVAIASNGGGKQALETVQRLLPVLCQAHGLTPEQVVAIASHDGGKQALETVQRLLPVLCQAHGLTPEQVVAIASNIGGKQALETVQALLPVLCQAHGLTPQQVVAIASNNGGKQALETVQRLLPVLCQAHGLTPEQVVAIASHDGGKQALETVQRLLPVLCQAHGLTPQQVVAIASNGGGKQALETVQRLLPVLCQAHGLTPQQVVAIASNNGGKQALETVQRLLPVLCQAHGLTPQQVVAIASNGGGKQALETVQRLLPVLCQAHGLTPQQVVAIASNNGGKQALETVQRLLPVLCQAHGLTPQQVVAIASNGGGKQALETVQRLLPVLCQAHGLTPEQVVAIASNIGGKQALETVQALLPVLCQAHGLTPEQVVAIASHDGGKQALETVQRLLPVLCQAHGLTPEQVVAIASNIGGKQALETVQALLPVLCQAHGLTPEQVVAIASHDGGKQALETVQRLLPVLCQAHGLTPQQVVAIASNNGGKQALETVQRLLPVLCQAHGLTPQQVVAIASNGGGRPALESIVAQLSRPDPALAALTNDHLVALACLGGRPALDAVKKGLGDPISRSQLVKSELEEKKSELRHKLKYVPHEYIELIEIARNSTQDRILEMKVMEFFMKVYGYRGKHLGGSRKPDGAIYTVGSPIDYGVIVDTKAYSGGYNLPIGQADEMQRYVEENQTRNKHINPNEWWKVYPSSVTEFKFLFVSGHFKGNYKAQLTRLNHITNCNGAVLSVEELLIGGEMIKAGTLTLEEVRRKFNNGEINFAAD | HD-NG-HD-NI-NN-HD-NG-NN-NN-NG-NI-HD-NI-HD-NN-NG# |

TABLE 5-continued

Sequences referred to in example 2.

| | | | |
|---|---|---|---|
| 18 | TALEN right CD25 | MGDPKKKRKVIDYPYDVPDYAIDIADLRTLGYSQQQQEKIKPKVRSTVA QHHEALVGHGFTHAHIVALSQHPAALGTVAVKYQDMIAALPEATHEAIV GVGKQWSGARALEALLTVAGELRGPPLQLDTGQLLKIAKRGGVTAVEA VHAWRNALTGAPLNLTPQQVVAIASNNGGKQALETVQRLLPVLCQAHG LTPQQVVAIASNGGGKQALETVQRLLPVLCQAHGLTPQQVVAIASNGG GKQALETVQRLLPVLCQAHGLTPEQVVAIASHDGGKQALETVQRLLPVL CQAHGLTPQQVVAIASNGGGKQALETVQRLLPVLCQAHGLTPQQVVAI ASNGGGKQALETVQRLLPVLCQAHGLTPQQVVAIASNGGGKQALETVQ RLLPVLCQAHGLTPQQVVAIASNNGGKQALETVQRLLPVLCQAHGLTP QQVVAIASNNGGKQALETVQRLLPVLCQAHGLTPQQVVAIASNNGGKQ ALETVQRLLPVLCQAHGLTPQQVVAIASNGGGKQALETVQRLLPVLCQ AHGLTPQQVVAIASNGGGKQALETVQRLLPVLCQAHGLTPQQVVAIAS NGGGKQALETVQRLLPVLCQAHGLTPQQVVAIASNGGGKQALETVQRL LPVLCQAHGLTPEQVVAIASHDGGKQALETVQRLLPVLCQAHGLTPQQ VVAIASNGGGRPALESIVAQLSRPDPSGSGSGGDPISRSQLVKSELEEK KSELRHKLKYVPHEYIELIEIARNSTQDRILEMKVMEFFMKVYGYRGKHL GGSRKPDGAIYTVGSPIDYGVIVDTKAYSGGYNLPIGQADEMQRYVEEN QTRNKHINPNEWWKVYPSSVTEFKFLFVSGHFKGNYKAQLTRLNHITN CNGAVLSVEELLIGGEMIKAGTLTLEEVRRKFNNGEINFAAD | NN-NG-NG-HD-NG-NG-NG-NG-NN-NN-NG-NG-NG-NG-HD-NG# |
| 19 | TALEN left CD25 | MGDPKKKRKVIDYPYDVPDYAIDIADLRTLGYSQQQQEKIKPKVRSTVA QHHEALVGHGFTHAHIVALSQHPAALGTVAVKYQDMIAALPEATHEAIV GVGKQWSGARALEALLTVAGELRGPPLQLDTGQLLKIAKRGGVTAVEA VHAWRNALTGAPLNLTPEQVVAIASNIGGKQALETVQALLPVLCQAHGL TPEQVVAIASHDGGKQALETVQRLLPVLCQAHGLTPEQVVAIASNIGGK QALETVQALLPVLCQAHGLTPQQVVAIASNNGGKQALETVQRLLPVLC QAHGLTPQQVVAIASNNGGKQALETVQRLLPVLCQAHGLTPEQVVAIAS NIGGKQALETVQALLPVLCQAHGLTPQQVVAIASNNGGKQALETVQRLL PVLCQAHGLTPQQVVAIASNNGGKQALETVQRLLPVLCQAHGLTPEQV VAIASNIGGKQALETVQALLPVLCQAHGLTPEQVVAIASNIGGKQALETV QALLPVLCQAHGLTPQQVVAIASNNGGKQALETVQRLLPVLCQAHGLT PEQVVAIASNIGGKQALETVQALLPVLCQAHGLTPQQVVAIASNNGGKQ ALETVQRLLPVLCQAHGLTPQQVVAIASNGGGKQALETVQRLLPVLCQ AHGLTPEQVVAIASNIGGKQALETVQALLPVLCQAHGLTPQQVVAIASN GGGRPALESIVAQLSRPDPSGSGSGGDPISRSQLVKSELEEKKSELRH KLKYVPHEYIELIEIARNSTQDRILEMKVMEFFMKVYGYRGKHLGGSRK PDGAIYTVGSPIDYGVIVDTKAYSGGYNLPIGQADEMQRYVEENQTRNK HINPNEWWKVYPSSVTEFKFLFVSGHFKGNYKAQLTRLNHITNCNGAV LSVEELLIGGEMIKAGTLTLEEVRRKFNNGEINFAAD | NI-HD-NI-NN-NN-NI-NN-NN-NI-NI-NN-NI-NN-NG-NI-NG# |
| 20 | TALEN right PD1 | MGDPKKKRKVIDYPYDVPDYAIDIADLRTLGYSQQQQEKIKPKVRSTVA QHHEALVGHGFTHAHIVALSQHPAALGTVAVKYQDMIAALPEATHEAIV GVGKQWSGARALEALLTVAGELRGPPLQLDTGQLLKIAKRGGVTAVEA VHAWRNALTGAPLNLTPEQVVAIASKLGGKQALETVQALLPVLCQAHGL TPEQVVAIASHDGGKQALETVQRLLPVLCQAHGLTPEQVVAIASHDGG KQALETVQRLLPVLCQAHGLTPQQVVAIASNGGGKQALETVQRLLPVL CQAHGLTPEQVVAIASNGGGKQALETVQRLLPVLCQAHGLTPQQVVAI ASNGGGKQALETVQRLLPVLCQAHGLTPQQVVAIASYKGGKQALETVQ RLLPVLCQAHGLTPQQVVAIASNGGGKQALETVQRLLPVLCQAHGLTP QQVVAIASNNGGKQALETVQRLLPVLCQAHGLTPQQVVAIASNNGGKQ ALETVQRLLPVLCQAHGLTPQQVVAIASNNGGKQALETVQRLLPVLCQA HGLTPQQVVAIASNNGGKQALETVQRLLPVLCQAHGLTPEQVVAIASHD GGKQALETVQRLLPVLCQAHGLTPEQVVAIASHDGGKQALETVQRLLP VLCQAHGLTPEQVVAIASNIGGKQALETVQALLPVLCQAHGLTPQQVVA IASNGGGRPALESIVAQLSRPDPALAALTNDHLVALACLGGRPALDAVK KGLGDPISRSQLVKSELEEKKSELRHKLKYVPHEYIELIEIARNSTQDRIL EMKVMEFFMKVYGYRGKHLGGSRKPDGAIYTVGSPIDYGVIVDTKAYS GGYNLPIGQADEMQRYVEENQTRNKHINPNEWWKVYPSSVTEFKFLFV SGHFKGNYKAQLTRLNHITNCNGAVLSVEELLIGGEMIKAGTLTLEEVRR KFNNGEINFAAD | KL-HD-HD-NG-HD-NG-YK-NG-NN-NN-NN-NN-HD-HD-NI-NG# |
| 21 | TALEN Left PD1 | MGDPKKKRKVIDKETAAAKFERQHMDSIDIADLRTLGYSQQQQEKIKPK VRSTVAQHHEALVGHGFTHAHIVALSQHPAALGTVAVKYQDMIAALPEA THEAIVGVGKQWSGARALEALLTVAGELRGPPLQLDTGQLLKIAKRGGV TAVEAVHAWRNALTGAPLNLTPEQVVAIASHDGGKQALETVQRLLPVL CQAHGLTPQQVVAIASNGGGKQALETVQRLLPVLCQAHGLTPEQVVAI ASHDGGKQALETVQRLLPVLCQAHGLTPQQVVAIASNGGGKQALETVQ RLLPVLCQAHGLTPQQVVAIASNGGGKQALETVQRLLPVLCQAHGLTP QQVVAIASNGGGKQALETVQRLLPVLCQAHGLTPQQVVAIASNNGGKQ ALETVQRLLPVLCQAHGLTPEQVVAIASNIGGKQALETVQALLPVLCQA HGLTPQQVVAIASNGGGKQALETVQRLLPVLCQAHGLTPEQVVAIASH DGGKQALETVQRLLPVLCQAHGLTPQQVVAIASNGGGKQALETVQRLL PVLCQAHGLTPQQVVAIASNNGGKQALETVQRLLPVLCQAHGLTPEQV VAIASNGGGKQALETVQRLLPVLCQAHGLTPQQVVAIASNNGGKQALETV QRLLPVLCQAHGLTPEQVVAIASHDGGKQALETVQRLLPVLCQAHGLT PQQVVAIASNGGGRPALESIVAQLSRPDPALAALTNDHLVALACLGGRP ALDAVKKGLGDPISRSQLVKSELEEKKSELRHKLKYVPHEYIELIEIARNS | HD-NG-HD-NG-NG-NG-NN-NI-NG-HD-NG-NN-N-NN-HD-NG# |

TABLE 5-continued

Sequences referred to in example 2.

TQDRILEMKVMEFFMKVYGYRGKHLGGSRKPDGAIYTVGSPIDYGVIVD
TKAYSGGYNLPIGQADEMQRYVEENQTRNKHINPNEWWKVYPSSVTE
FKFLFVSGHFKGNYKAQLTRLNHITNCNGAVLSVEELLIGGEMIKAGTLT
LEEVRRKFNNGEINFAAD

| SEQ ID NO# | Sequence Name | Polynucleotide sequence |
|---|---|---|
| 22 | TALEN TRAC pCLS11370 | ATGGGCGATCCTAAAAAGAAACGTAAGGTCATCGATTACCCATACGATGTTCCAGATTACGCTAT<br>CGATATCGCCGATCTACGCACGCTCGGCTACAGCCAGCAGCAACAGGAGAAGATCAAACCGAA<br>GGTTCGTTCGACAGTGGCGCAGCACCACGAGGCACTGGTCGGCCACGGGTTTACACACGCGC<br>ACATCGTTGCGTTAAGCCAACACCCGGCAGCGTTAGGGACCGTCGCTGTCAAGTATCAGGACA<br>TGATCGCAGCGTTGCCAGAGGCGACACACGAAGCGATCGTTGGCGTCGGCAAACAGTGGTCC<br>GGCGCACGCGCTCTGGAGGCCTTGCTCACGGTGGCGGGAGAGTTGAGAGGTCCACCGTTACA<br>GTTGGACACAGGCCAACTTCTCAAGATTGCAAAACGTGGCGGCGTGACCGCAGTGGAGGCAGT<br>GCATGCATGGCGCAATGCACTGACGGGTGCCCCGCTCAACTTGACCCCCCAGCAGGTGGTGG<br>CCATCGCCAGCAATGGCGGTGGCAAGCAGGCGCTGGAGACGGTCCAGCGGCTGTTGCCGGTG<br>CTGTGCCAGGCCCACGGCTTGACCCCCCAGCAGGTGGTGGCCATCGCCAGCAATAATGGTGG<br>CAAGCAGGCGCTGGAGACGGTCCAGCGGCTGTTGCCGGTGCTGTGCCAGGCCCACGGCTTGA<br>CCCCCCAGCAGGTGGTGGCCATCGCCAGCAATGGCGGTGGCAAGCAGGCGCTGGAGACGGT<br>CCAGCGGCTGTTGCCGGTGCTGTGCCAGGCCCACGGCTTGACCCCGGAGCAGGTGGTGGCCA<br>TCGCCAGCACGATGGCGGCAAGCAGGCGCTGGAGACGGTCCAGCGGCTGTTGCCGGTGCTG<br>TGCCAGGCCCACGGCTTGACCCCGGAGCAGGTGGTGGCCATCGCCAGCCACGATGGCGGCAA<br>GCAGGCGCTGGAGACGGTCCAGCGGCTGTTGCCGGTGCTGTGCCAGGCCCACGGCTTGACCC<br>CGGAGCAGGTGGTGGCCATCGCCAGCCACGATGGCGGCAAGCAGGCGCTGGAGACGGTCCA<br>GCGGCTGTTGCCGGTGCTGTGCCAGGCCCACGGCTTGACCCCGGAGCAGGTGGTGGCCATCG<br>CCAGCAATATTGGTGGCAAGCAGGCGCTGGAGACGGTGCAGGCGCTGTTGCCGGTGCTGTGC<br>CAGGCCCACGGCTTGACCCCGGAGCAGGTGGTGGCCATCGCCAGCCACGATGGCGGCAAGCA<br>GGCGCTGGAGACGGTCCAGCGGCTGTTGCCGGTGCTGTGCCAGGCCCACGGCTTGACCCCG<br>GAGCAGGTGGTGGCCATCGCCAGCAATATTGGTGGCAAGCAGGCGCTGGAGACGGTCCAGGC<br>GCTGTTGCCGGTGCTGTGCCAGGCCCACGGCTTGACCCCCAGCAGGTGGTGGCCATCGCCA<br>GCAATAATGGTGGCAAGCAGGCGCTGGAGACGGTCCAGCGGCTGTTGCCGGTGCTGTGCCAG<br>GCCCACGGCTTGACCCCGGAGCAGGTGGTGGCCATCGCCAGCAATATTGGTGGCAAGCAGGC<br>GCTGGAGACGGTGCAGGCGCTGTTGCCGGTGCTGTGCCAGGCCCACGGCTTGACCCCCCAGC<br>AGGTGGTGGCCATCGCCAGCAATGGCGGTGGCAAGCAGGCGCTGGAGACGGTCCAGCGGCT<br>GTTGCCGGTGCTGTGCCAGGCCCACGGCTTGACCCCGGAGCAGGTGGTGGCCATCGCCAGCA<br>ATATTGGTGGCAAGCAGGCGCTGGAGACGGTGCAGGCGCTGTTGCCGGTGCTGTGCCAGGCC<br>CACGGCTTGACCCCCAGCAGGTGGTGGCCATCGCCAGCAATGGCGGTGGCAAGCAGGCGCT<br>GGAGACGGTCCAGCGGCTGTTGCCGGTGCTGTGCCAGGCCCACGGCTTGACCCCGGAGCAG<br>GTGGTGGCCATCGCCAGCCACGATGGCGGCAAGCAGGCGCTGGAGACGGTCCAGCGGCTGTT<br>GCCGGTGCTGTGCCAGGCCCACGGCTTGACCCCTCAGCAGGTGGTGGCCATCGCCAGCAATG<br>GCGGCGGCAGGCCGGCGCTGGAGAGCATTGTTGCCCAGTTATCTCGCCCTGATCCGGCGTTG<br>GCCGCGTTGACCAACGACCACCTCGTCGCCTTGGCCTGCCTCGGCGGGCGTCCTCGCGTGGA<br>TGCAGTGAAAAAGGGATTGGGGGATCCTATCAGCCGTTCCCAGCTGGTGAAGTCCGAGCTGGA<br>GGGAGAAGAAATCCGAGTTGAGGCACAAGCTGAAGTACGTGCCCCACGAGTACATCGAGCTGAT<br>CGAGATCGCCCGGAACAGCACCCAGGACCGTATCCTGGAGATGAAGGTGATGGAGTTCTTCAT<br>GAAGGTGTACGGCTACAGGGGCAAGCACCTGGGCGGCTCCAGGAAGCCCGACGGCGCCATCT<br>ACACCGTGGGCTCCCCCATCGACTACGGCGTGATCGTGGACACCAAGGCCTACTCCGGCGGC<br>TACAACCTGCCCATCGGCCAGGCCGACGAAATGCAGAGGTACGTGGAGGAGAACCAGACCAG<br>GAACAAGCACATCAACCCCAACGAGTGGTGGAAGGTGTACCCCTCCAGCGTGACCGAGTTCAA<br>GTTCCTGTTCGTGTCCGGCCACTTCAAGGGCAACTACAAGGCCCAGCTGACCAGGCTGAACCA<br>CATCACCAACTGCAACGGCGCCGTGCTGTCCGTGGAGGAGCTCCTGATCGGCGGCGAGATGA<br>TCAAGGCCGGCACCCTGACCCTGGAGGAGGTGAGGAGGAAGTTCAACAACGGCGAGATCAAC<br>TTCGCGGCCGACTGATAA |
| 23 | TALEN TRAC pCLS11369 | ATGGGCGATCCTAAAAAGAAACGTAAGGTCATCGATAAGGAGACCGCCGCTGCCAAGTTCGAG<br>AGACAGCACATGGACAGCATCGATATCGCCGATCTACGCACGCTCGGCTACAGCCAGCAGCAA<br>CAGGAGAAGATCAAACCGAAGGTTCGTTCGACAGTGGCGCAGCACCACGAGGCACTGGTCGG<br>CCACGGGTTTACACACGCGCACATCGTTGCGTTAAGCCAACACCCGGCAGCGTTAGGGACCGT<br>CGCTGTCAAGTATCAGGACATGATCGCAGCGTTGCCAGAGGCGACACACGAAGCGATCGTTGG<br>CGTCGGCAAACAGTGGTCCGGCGCACGCGCTCTGGAGGCCTTGCTCACGGTGGCGGGAGAGT<br>TGAGAGGTCCACCGTTACAGTTGGACACAGGCCAACTTCTCAAGATTGCAAAACGTGGCGGCG<br>TGACCGCAGTGGAGGCAGTGCATGCATGGCGCAATGCACTGACGGGTGCCCCGCTCAACTTG<br>ACCCCGGAGCAGGTGGTGGCCATCGCCAGCCACGATGGCGGCAAGCAGGCGCTGGAGACGG<br>TCCAGCGGCTGTTGCCGGTGCTGTGCCAGGCCCACGGCTTGACCCCCCAGCAGGTGGTGGCC<br>ATCGCCAGCAATGGCGGTGGCAAGCAGGCGCTGGAGACGGTCCAGCGGCTGTTGCCGGTGCT<br>GTGCCAGGCCCACGGCTTGACCCCGGAGCAGGTGGTGGCCATCGCCAGCCACGATGGCGGC<br>AAGCAGGCGCTGGAGACGGTCCAGCGGCTGTTGCCGGTGCTGTGCCAGGCCCACGGCTTGAC<br>CCCGGAGCAGGTGGTGGCCATCGCCAGCAATATTGGTGGCAAGCAGGCGCTGGAGACGGTGC<br>AGGCGCTGTTGCCGGTGCTGTGCCAGGCCCACGGCTTGACCCCCAGCAGGTGGTGGCCATC<br>GCCAGCAATAATGGTGGCAAGCAGGCGCTGGAGACGGTCCAGCGGCTGTTGCCGGTGCTGTG<br>CCAGGCCCACGGCTTGACCCCGGAGCAGGTGGTGGCCATCGCCAGCCACGATGGCGGCAAG<br>CAGGCGCTGGAGACGGTCCAGCGGCTGTTGCCGGTGCTGTGCCAGGCCCACGGCTTGACCCC<br>CAGCAGGTGGTGGCCATCGCCAGCAATGGCGGTGGCAAGCAGGCGCTGGAGACGGTCCAG<br>CGGCTGTTGCCGGTGCTGTGCCAGGCCCACGGCTTGACCCCCAGCAGGTGGTGGCCATCGC<br>CAGCAATAATGGTGGCAAGCAGGCGCTGGAGACGGTCCAGCGGCTGTTGCCGGTGCTGTGCC<br>AGGCCCACGGCTTGACCCCCAGCAGGTGGTGGCCATCGCCAGCAATAATGGTGGCAAGCAG |

TABLE 5-continued

Sequences referred to in example 2.

|  |  |  |
|---|---|---|
|  |  | GCGCTGGAGACGGTCCAGCGGCTGTTGCCGGTGCTGTGCCAGGCCCACGGCTTGACCCCCCA
GCAGGTGGTGGCCATCGCCAGCAATGGCGGTGGCAAGCAGGCGCTGGAGACGGTCCAGCGG
CTGTTGCCGGTGCTGTGCCAGGCCCACGGCTTGACCCCGGAGCAGGTGGTGGCCATCGCCAG
CAATATTGGTGGCAAGCAGGCGCTGGAGACGGTGCAGGCGCTGTTGCCGGTGCTGTGCCAGG
CCCACGGCTTGACCCCGGAGCAGGTGGTGGCCATCGCCAGCCACGATGGCGGCAAGCAGGC
GCTGGAGACGGTCCAGCGGCTGTTGCCGGTGCTGTGCCAGGCCCACGGCTTGACCCCGGAGC
AGGTGGTGGCCATCGCCAGCAATATTGGTGGCAAGCAGGCGCTGGAGACGGTGCAGGCGCTG
TTGCCGGTGCTGTGCCAGGCCCACGGCTTGACCCCGGAGCAGGTGGTGGCCATCGCCAGCCA
CGATGGCGGCAAGCAGGCGCTGGAGACGGTCCAGCGGCTGTTGCCGGTGCTGTGCCAGGCC
CACGGCTTGACCCCCAGCAGGTGGTGGCCATCGCCAGCAATAATGGTGGCAAGCAGGCGCT
GGGAGACGGTCCAGCGGCTGTTGCCGGTGCTGTGCCAGGCCCACGGCTTGACCCCTCAGCAGG
TGGTGGCCATCGCCAGCAATGGCGGCGGCAGGCCGGCGCTGGAGAGCATTGTTGCCCAGTTA
TCTCGCCCTGATCCGGCGTTGGCCGCGTTGACCAACGACCACCTCGTCGCCTTGGCCTGCCTC
GGCGGGCGTCCTGCGCTGGATGCAGTGAAAAAGGGATTGGGGGATCCTATCAGCCGTTCCCA
GCTGGTGAAGTCCGAGCTGGAGGAGAAGAAATCCGAGTTGAGGCACAAGCTGAAGTACGTGCC
CCACGAGTACATCGAGCTGATCGAGATCGCCCGGAACAGCACCCAGGACCGTATCCTGGAGAT
GAAGGTGATGGAGTTCTTCATGAAGGTGTACGGCTACAGGGGCAAGCACCTGGGCGGCTCCA
GGAAGCCCGACGGCGCCATCTACACCGTGGGCTCCCCCATCGACTACGGCGTGATCGTGGAC
ACCAAGGCCTACTCCGGCGGCTACAACCTGCCCATCGGCCAGGCCGACGAAATGCAGAGGTA
CGTGGAGGAGAACCAGACCAGGAACAAGCACATCAACCCCAACGAGTGGTGGAAGGTGTACC
CCTCCAGCGTGACCGAGTTCAAGTTCCTGTTCGTGTCCGGCCACTTCAAGGGCAACTACAAGG
CCCAGCTGACCAGGCTGAACCACATCACCAACTGCAACGGCGCCGTGCTGTCCGTGGAGGAG
CTCCTGATCGGCGGCGAGATGATCAAGGCCGGCACCCTGACCCTGGAGGAGGTGAGGAGGAA
GTTCAACAACGGCGAGATCAACTTCGCGGCCGACTGATAA |
| 24 | TALEN CD25
pCLS30480 | ATGGGCGATCCTAAAAAGAAACGTAAGGTCATCGATTACCCATACGATGTTCCAGATTACGCTAT
CGATATCGCCGATCTACGCACGCTCGGCTACAGCCAGCAGCAACAGGAGAAGATCAAACCGAA
GGTTCGTTCGACAGTGGCGCAGCACCACGAGGCACTGGTCGGCCACGGGTTTACACACGCGC
ACATCGTTGCGTTAAGCCAACACCCGGCAGCGTTAGGGACCGTCGCTGTCAAGTATCAGGACA
TGATCGCAGCGTTGCCAGAGGCGACACACGAAGCGATCGTTGGCGTCGGCAAACAGTGGTCC
GGCGCACGCGCTCTGGAGGCCTTGCTCACGGTGGCGGGAGAGTTGAGAGGTCCACCGTTACA
GTTGGACACAGGCCAACTTCTCAAGATTGCAAAACGTGGCGGCGTGACCGCAGTGGAGGCAGT
GCATGCATGGCGCAATGCACTGACGGGTGCCCCGCTCAACTTGACCCCCCAGCAGGTGGTGG
CCATCGCCAGCAATAATGGTGGCAAGCAGGCGCTGGAGACGGTCCAGCGGCTGTTGCCGGTG
CTGTGCCAGGCCCACGGCTTGACCCCCCAGCAGGTGGTGGCCATCGCCAGCAATGGCGGTGG
CAAGCAGGCGCTGGAGACGGTCCAGCGGCTGTTGCCGGTGCTGTGCCAGGCCCACGGCTTGA
CCCCCCAGCAGGTGGTGGCCATCGCCAGCAATGGCGGTGGCAAGCAGGCGCTGGAGACGGT
CCAGCGGCTGTTGCCGGTGCTGTGCCAGGCCCACGGCTTGACCCCGGAGCAGGTGGTGGCCA
TCGCCAGCCACGATGGCGGCAAGCAGGCGCTGGAGACGGTCCAGCGGCTGTTGCCGGTGCTG
TGCCAGGCCCACGGCTTGACCCCCCAGCAGGTGGTGGCCATCGCCAGCAATGGCGGTGGCAA
GCAGGCGCTGGAGACGGTCCAGCGGCTGTTGCCGGTGCTGTGCCAGGCCCACGGCTTGACCC
CCAGCAGGTGGTGGCCATCGCCAGCAATGGCGGTGGCAAGCAGGCGCTGGAGACGGTCCA
GCGGCTGTTGCCGGTGCTGTGCCAGGCCCACGGCTTGACCCCCAGCAGGTGGTGGCCATCG
CCAGCAATGGCGGTGGCAAGCAGGCGCTGGAGACGGTCCAGCGGCTGTTGCCGGTGCTGTGC
CAGGCCCACGGCTTGACCCCCCAGCAGGTGGTGGCCATCGCCAGCAATGGCGGTGGCAAGCA
GGCGCTGGAGACGGTCCAGCGGCTGTTGCCGGTGCTGTGCCAGGCCCACGGCTTGACCCCCC
AGCAGGTGGTGGCCATCGCCAGCAATAATGGTGGCAAGCAGGCGCTGGAGACGGTCCAGCGG
CTGTTGCCGGTGCTGTGCCAGGCCCACGGCTTGACCCCCAGCAGGTGGTGGCCATCGCCAG
CAATAATGGTGGCAAGCAGGCGCTGGAGACGGTCCAGCGGCTGTTGCCGGTGCTGTGCCAGG
CCCACGGCTTGACCCCCCAGCAGGTGGTGGCCATCGCCAGCAATGGCGGTGGCAAGCAGGCG
CTGGAGACGGTCCAGCGGCTGTTGCCGGTGCTGTGCCAGGCCCACGGCTTGACCCCCCAGCA
GGTGGTGGCCATCGCCAGCAATGGCGGTGGCAAGCAGGCGCTGGAGACGGTCCAGCGGCTG
TTGCCGGTGCTGTGCCAGGCCCACGGCTTGACCCCCAGCAGGTGGTGGCCATCGCCAGCAA
TGGCGGTGGCAAGCAGGCGCTGGAGACGGTCCAGCGGCTGTTGCCGGTGCTGTGCCAGGCC
CACGGCTTGACCCCCAGCAGGTGGTGGCCATCGCCAGCAATGGCGGTGGCAAGCAGGCGCT
GGAGACGGTCCAGCGGCTGTTGCCGGTGCTGTGCCAGGCCCACGGCTTGACCCCGGAGCAG
GTGGTGGCCATCGCCAGCCACGATGGCGGCAAGCAGGCGCTGGAGACGGTCCAGCGGCTGTT
GCCGGTGCTGTGCCAGGCCCACGGCTTGACCCCTCAGCAGGTGGTGGCCATCGCCAGCAATG
GCGGCGGCAGGCCGGCGCTGGAGAGCATTGTTGCCCAGTTATCTCGCCCTGATCCGAGTGGC
AGCGGAAGTGGCGGGGATCCTATCAGCCGTTCCCAGCTGGTGAAGTCCGAGCTGGAGGAGAA
GAAATCCGAGTTGAGGCACAAGCTGAAGTACGTGCCCCACGAGTACATCGAGCTGATCGAGAT
CGCCCGGAACAGCACCCAGGACCGTATCCTGGAGATGAAGGTGATGGAGTTCTTCATGAAGGT
GTACGGCTACAGGGGCAAGCACCTGGGCGGCTCCAGGAAGCCCGACGGCGCCATCTACACCG
TGGGCTCCCCCATCGACTACGGCGTGATCGTGGACACCAAGGCCTACTCCGGCGGCTACAACC
TGCCCATCGGCCAGGCCGACGAAATGCAGAGGTACGTGGAGGAGAACCAGACCAGGAACAAG
CACATCAACCCCAACGAGTGGTGGAAGGTGTACCCCTCCAGCGTGACCGAGTTCAAGTTCCTG
TTCGTGTCCGGCCACTTCAAGGGCAACTACAAGGCCCAGCTGACCAGGCTGAACCACATCACC
AACTGCAACGGCGCCGTGCTGTCCGTGGAGGAGCTCCTGATCGGCGGCGAGATGATCAAGGC
CGGCACCCTGACCCTGGAGGAGGTGAGGAGGAAGTTCAACAACGGCGAGATCAACTTCGCGG
CCGACTGATAA |
| 25 | TALEN CD25
pCLS30479 | ATGGGCGATCCTAAAAAGAAACGTAAGGTCATCGATTACCCATACGATGTTCCAGATTACGCTAT
CGATATCGCCGATCTACGCACGCTCGGCTACAGCCAGCAGCAACAGGAGAAGATCAAACCGAA
GGTTCGTTCGACAGTGGCGCAGCACCACGAGGCACTGGTCGGCCACGGGTTTACACACGCGC
ACATCGTTGCGTTAAGCCAACACCCGGCAGCGTTAGGGACCGTCGCTGTCAAGTATCAGGACA
TGATCGCAGCGTTGCCAGAGGCGACACACGAAGCGATCGTTGGCGTCGGCAAACAGTGGTCC
GGCGCACGCGCTCTGGAGGCCTTGCTCACGGTGGCGGGAGAGTTGAGAGGTCCACCGTTACA
GTTGGACACAGGCCAACTTCTCAAGATTGCAAAACGTGGCGGCGTGACCGCAGTGGAGGCAGT |

TABLE 5-continued

Sequences referred to in example 2.

|  |  |  |
|---|---|---|
|  |  | GCATGCATGGCGCAATGCACTGACGGGTGCCCCGCTCAACTTGACCCCGGAGCAGGTGGTGG<br>CCATCGCCAGCAATATTGGTGGCAAGCAGGCGCTGGAGACGGTGCAGGCGCTGTTGCCGGTG<br>CTGTGCCAGGCCCACGGCTTGACCCCGGAGCAGGTGGTGGCCATCGCCAGCCACGATGGCGG<br>CAAGCAGGCGCTGGAGACGGTCCAGCGGCTGTTGCCGGTGCTGTGCCAGGCCCACGGCTTGA<br>CCCCGGAGCAGGTGGTGGCCATCGCCAGCAATATTGGTGGCAAGCAGGCGCTGGAGACGGTG<br>CAGGCGCTGTTGCCGGTGCTGTGCCAGGCCCACGGCTTGACCCCCCAGCAGGTGGTGGCCAT<br>CGCCAGCAATAATGGTGGCAAGCAGGCGCTGGAGACGGTCCAGCGGCTGTTGCCGGTGCTGT<br>GCCAGGCCCACGGCTTGACCCCCAGCAGGTGGTGGCCATCGCCAGCAATAATGGTGGCAAG<br>CAGGCGCTGGAGACGGTCCAGCGGCTGTTGCCGGTGCTGTGCCAGGCCCACGGCTTGACCCC<br>GGAGCAGGTGGTGGCCATCGCCAGCAATATTGGTGGCAAGCAGGCGCTGGAGACGGTGCAGG<br>CGCTGTTGCCGGTGCTGTGCCAGGCCCACGGCTTGACCCCCCAGCAGGTGGTGGCCATCGCC<br>AGCAATAATGGTGGCAAGCAGGCGCTGGAGACGGTCCAGCGGCTGTTGCCGGTGCTGTGCCA<br>GGCCCACGGCTTGACCCCCCAGCAGGTGGTGGCCATCGCCAGCAATAATGGTGGCAAGCAGG<br>CGCTGGAGACGGTCCAGCGGCTGTTGCCGGTGCTGTGCCAGGCCCACGGCTTGACCCCGGAG<br>CAGGTGGTGGCCATCGCCAGCAATATTGGTGGCAAGCAGGCGCTGGAGACGGTGCAGGCGCT<br>GTTGCCGGTGCTGTGCCAGGCCCACGGCTTGACCCCGGAGCAGGTGGTGGCCATCGCCAGCA<br>ATATTGGTGGCAAGCAGGCGCTGGAGACGGTGCAGGCGCTGTTGCCGGTGCTGTGCCAGGCC<br>CACGGCTTGACCCCCAGCAGGTGGTGGCCATCGCCAGCAATAATGGTGGCAAGCAGGCGCT<br>GGAGACGGTCCAGCGGCTGTTGCCGGTGCTGTGCCAGGCCCACGGCTTGACCCCGGAGCAG<br>GTGGTGGCCATCGCCAGCAATATTGGTGGCAAGCAGGCGCTGGAGACGGTGCAGGCGCTGTT<br>GCCGGTGCTGTGCCAGGCCCACGGCTTGACCCCCAGCAGGTGGTGGCCATCGCCAGCAATA<br>ATGGTGGCAAGCAGGCGCTGGAGACGGTCCAGCGGCTGTTGCCGGTGCTGTGCCAGGCCCAC<br>GGCTTGACCCCCAGCAGGTGGTGGCCATCGCCAGCAATGGCGGTGGCAAGCAGGCGCTGGA<br>GACGGTCCAGCGGCTGTTGCCGGTGCTGTGCCAGGCCCACGGCTTGACCCCGGAGCAGGTGG<br>TGGCCATCGCCAGCAATATTGGTGGCAAGCAGGCGCTGGAGACGGTGCAGGCGCTGTTGCCG<br>GTGCTGTGCCAGGCCCACGGCTTGACCCCTCAGCAGGTGGTGGCCATCGCCAGCAATGGCGG<br>CGGCAGGCCGGCGCTGGAGAGCATTGTTGCCCAGTTATCTCGCCCTGATCCGAGTGGCAGCG<br>GAAGTGGCGGGGATCCTATCAGCCGTTCCCAGCTGGTGAAGTCCGAGCTGGAGGAGAAGAAT<br>CCGAGTTGAGGCACAAGCTGAAGTACGTGCCCCACGAGTACATCGAGCTGATCGAGATCGCCC<br>GGAACAGCACCCAGGACCGTATCCTGGAGATGAAGGTGATGGAGTTCTTCATGAAGGTGTACG<br>GCTACAGGGGCAAGCACCTGGGCGGCTCCAGGAAGCCCGACGGCGCCATCTACACCGTGGGC<br>TCCCCCATCGACTACGCGTGATCGTGGACACCAAGGCCTACTCCGGCGGCTACAACCTGCCC<br>ATCGGCCAGGCCGACGAAATGCAGAGGTACGTGGAGGAGAACCAGACCAGGAACAAGCACAT<br>CAACCCCAACGAGTGGTGGAAGGTGTACCCCTCCAGCGTGACCGAGTTCAAGTTCCTGTTCGT<br>GTCCGGCCACTTCAAGGGCAACTACAAGGCCCAGCTGACCAGGCTGAACCACATCACCAACTG<br>CAACGGCGCCGTGCTGTCCGTGGAGGAGCTCCTGATCGGCGGCGAGATGATCAAGGCCGGCA<br>CCCTGACCCTGGAGGAGGTGAGGAGGAAGTTCAACAACGGCGAGATCAACTTCGCGGCCGAC<br>TGATAA |
| 26 | TALEN PD1<br>pCLS28959 | ATGGGCGATCCTAAAAAGAAACGTAAGGTCATCGATTACCCATACGATGTTCCAGATTACGCTAT<br>CGATATCGCCGATCTACGCACGCTCGGCTACAGCCAGCAGCAACAGGAGAAGATCAAACCGAA<br>GGTTCGTTCGACAGTGGCGCAGCACCACGAGGCACTGGTCGGCCACGGGTTTACACACGCGC<br>ACATCGTTGCGTTAAGCCAACACCCGGCAGCGTTAGGGACCGTCGCTGTCAAGTATCAGGACA<br>TGATCGCAGCGTTGCCAGAGGCGACACACGAAGCGATCGTTGGCGTCGGCAAACAGTGGTCC<br>GGCGCACGCGCTCTGGAGGCCTTGCTCACGGTGGCGGGAGAGTTGAGAGGTCCACCGTTACA<br>GTTGGACACAGGCCAACTTCTCAAGGATTGCAAAACGTGGCGGCGTGACCGCAGTGGAGGCAGT<br>GCATGCATGGCGCAATGCACTGACGGGTGCCCCGCTCAACTTGACCCCGAGCAAGTGGTGG<br>CTATCGCTTCCAAGCTGGGGGGAAAGCAGGCCCTGGAGACCGTCCAGGCCCTTCTCCCAGTG<br>CTTTGCCAGGCTCACGGACTGACCCCTGAACAGGTGGTGGCAATTGCCTCACACGACGGGGG<br>CAAGCAGGCACTGGAGACTGTCCAGCGGCTGCTGCCTGTCCTCTGCCAGGCCCACGGACTCA<br>CTCCTGAGCAGGTCGTGGCCATTGCCAGCCACGATGGGGGCAAACAGGCTCTGGAGACCGTG<br>CAGCGCCTCCTCCCAGTGCTGTGCCAGGCTCATGGGCTGACCCCACAGCAGGTCGTCGCCATT<br>GCCAGTAACGGCGGGGGGAAGCAGGCCCTCGAAACAGTGCAGAGGCTGCTGCCCGTCTTGTG<br>CCAAGCACACGGCCTGACACCCGAGCAGGTGGTGGCCATCGCCTCTCATGACGGCGGCAAGC<br>AGGCCCTTGAGACAGTGCAGAGACTGTTGCCCGTGTTGTGTCAGGCCCACGGGTTGACACCCC<br>AGCAGGTGGTCGCCATCGCCAGCAATGGCGGGGGAAAGCAGGCCCTTGAGACCGTGCAGCGG<br>TTGCTTCCAGTGTTGTGCCAGGCACACGGACTGACCCCTCAACAGGTGGTCGCAATCGCCAGC<br>TACAAGGGCGGAAAGCAGGCTCTGGAGACAGTGCAGCGCCTCCTGCCCGTGCTGTGTCAGGC<br>TCACGGACTGACACCACAGCAGGTGGTCGCCATCGCCAGTAACGGGGGCGGCAAGCAGGCTT<br>TGGAGACCGTCCAGAGACTCCTCCCCGTCCTTTGCCAGGCCCACGGGTTGACACCTCAGCAGG<br>TCGTCGCCATTGCCTCCAACAACGGGGGCAAGCAGGCCCTCGAAACTGTGCAGAGGCTGCTG<br>CCTGTGCTGTGCCAGGCTCATGGGCTGACACCCCAGCAGGTGGTGGCCATTGCCTCTAACAAC<br>GGCGGCAAACAGGCACTGGAGACCGTGCAAGGCTGCTGCCCGTCCTCTGCCAAGCCCACGG<br>GCTCACTCCACAGCAGGTCGTGGCCATCGCCTCAAACAATGGCGGGAAGCAGGCCCTGGAGA<br>CTGTGCAAAGGCTGCTCCCTGTGCTCTGCAGGCACACGGACTGACCCCTCAGCAGGTGGTTG<br>GCAATCGCTTCCAACAACGGGGAAAGCAGGCCCTCGAAACCGTGCAGCGCCTCCTCCCAGT<br>GCTGTGCCAGGCACATGGCCTCACACCCGAGCAAGTGGTGGCTATCGCCAGCCACGACGGAG<br>GGAAGCAGGCTCTGGAGACCGTGCAGAGGCTGCTGCCTGTCCTGTGCCAGGCCCACGGGCTT<br>ACTCCAGAGCAGGTCGTCGCCATCGCCAGTCATGATGGGGGAAGCAGGCCCTTGAGACAGT<br>CCAGCGGCTGCTGCCAGTCCTTTGCCAGGCTCACGGCTTGACTCCCGAGCAGGTCGTGGCCAT<br>TGCCTCAAACATTGGGGGCAAACAGGCCCTGGAGACAGTGCAGGCCCTGCTGCCCGTGTTGTG<br>TCAGGCCCACGGCTTGACACCCCAGCAGGTGGTCGCCATTGCCTCTAATGGCGGCGGGAGAC<br>CCGCCTTGGAGAGCATTGTTGCCCAGTTATCTCGCCCTGATCCGAGTGGCAGTGAAAAAG<br>GGATTGGGGATCCTATCAGCCGTTCCCAGCTGGTGAAGTCCGAGCTGGAGGAGAAGAAATCC<br>GAGTTGAGGCACAAGCTGAAGTACGTGCCCCACGAGTACATCGAGCTGATCGAGATCGCCCGG<br>AACAGCACCCAGGACCGTATCCTGGAGATGAAGGTGATGGAGTTCTTCATGAAGGTGTACGGC<br>TACAGGGGCAAGCACCTGGGCGGCTCCAGGAAGCCCGACGGCGCCATCTACACCGTGGGCTC |

TABLE 5-continued

Sequences referred to in example 2.

|  |  |  |
|---|---|---|
|  |  | CCCCATCGACTACGGCGTGATCGTGGACACCAAGGCCTACTCCGGCGGCTACAACCTGCCCAT CGGCCAGGCCGACGAAATGCAGAGGTACGTGGAGGAGAACCAGACCAGGAACAAGCACATCA ACCCCAACGAGTGGTGGAAGGTGTACCCCTCCAGCGTGACCGAGTTCAAGTTCCTGTTCGTGT CCGGCCACTTCAAGGGCAACTACAAGGCCCAGCTGACCAGGCTGAACCACATCACCAACTGCA ACGGCGCCGTGCTGTCCGTGGAGGAGCTCCTGATCGGCGGCGAGATGATCAAGGCCGGCACC CTGACCCTGGAGGAGGTGAGGAGGAAGTTCAACAACGGCGAGATCAACTTCGCGGCCGACTG ATAA |
| 27 | TALEN PD1 pCLS18792 | ATGGGCGATCCTAAAAAGAAACGTAAGGTCATCGATAAGGAGACCGCCGCTGCCAAGTTCGAG AGACAGCACATGGACAGCATCGATATCGCCGATCTACGCACGCTCGGCTACAGCCAGCAGCAA CAGGAGAAGATCAAACCGAAGGTTCGTTCGACAGTGGCGCAGCACCACGAGGCACTGGTCGG CCACGGGTTTACACACGCGCACATCGTTGCGTTAAGCCAACACCCGGCAGCGTTAGGGACCGT CGCTGTCAAGTATCAGGACATGATCGCAGCGTTGCCAGAGGCGACACACGAAGCGATCGTTGG CGTCGGCAAACAGTGGTCCGGCGCACGCGCTCTGGAGGCCTTGCTCACGGTGGCGGGAGAGT TGAGAGGTCCACCGTTACAGTTGGACACAGGCCAACTTCTCAAGGATTGCAAAACGTGGCGGCG TGACCGCAGTGGAGGCAGTGCATGCATGGCGCAATGCACTGACGGGTGCCCCGCTCAACTTG ACCCCCGAGCAAGTCGTCGCAATCGCCAGCCATGATGGAGGGAAGCAAGCCCTCGAAACCGT GCAGCGGTTGCTTCCTGTGCTCTGCCAGGCCCACGGCCTTACCCCTCAGCAGGTGGTGGCCAT CGCAAGTAACGGAGGAGGAAAGCAAGCCTTGGAGACAGTGCAGCGCCTGTTGCCCGTGCTGT GCCAGGCACACGGCCTCACACCAGAGCAGGTCGTGGCCATTGCCTCCCATGACGGGGGGAAA CAGGCTCTGGAGACCGTCCAGAGGCTGCTGCCCGTCCTCTGTCAAGCTCACGGCCTGACTCCC CAACAAGTGGTCGCCATCGCCTCTAATGGCGGCGGGAAGCAGGCACTGGAAACAGTGCAGAG ACTGCTCCCTGTGCTTTGCCAAGCTCATGGGTTGACCCCCAACAAGGTCGTCGCTATTGCCTCA AACGGGGGGGCAAGCAGGCCCTTGAGACTGTGCAGAGGCTGTTGCCAGTGCTGTGTCAGGC TCACGGGCTCACTCCACAACAGGTGGTCGCAATTGCCAGCAACGGCGGCGGAAAGCAAGCTCT TGAAACCGTGCAACGCCTCCTGCCCGTGCTCTGTCAGGCTCATGGCCTGACACCACAACAAGT CGTGGCCATCGCCAGTAATAATGGCGGGAAACAGGCTCTTGAGACCGTCCAGAGGCTGCTCCC AGTGCTCTGCCAGGCACACGGGCTGACCCCCGAGCAGGTGGTGGCTATCGCCAGCAATATTG GGGGCAAGCAGGCCCTGGAAACAGTCCAGGCCCTGCTGCCAGTGCTTTGCCAGGCTCACGGG CTCACTCCCCAGCAGGTCGTGGCAATCGCCTCCAACGGCGGAGGGAAGCAGGCTCTGGAGAC CGTGCAGAGACTGCTGCCCGTCTTGTGCCAGGCCCACGGACTCACACCTGAACAGGTCGTCGC CATTGCCTCTCACGATGGGGGCAAACAAGCCCTGGAGACAGTGCAGCGGCTGTTGCCTGTGTT GTGCCAAGCCCACGGCTTGACTCCTCAACAAGTGGTCGCCATCGCCTCAAATGGCGGCGGAAA ACAAGCTCTGGAGACAGTGCAGAGGTTGCTGCCCGTCCTCTGCCAAGCCCACGGCCTGACTCC CCAACAGGTCGTCGCCATTGCCAGCAACAACGGAGGAAAGCAGGCTCTCGAAACTGTGCAGCG GCTGCTTCCTGTGCTGTGTCAGGCTCATGGGCTGACCCCCGAGCAAGTGGTGGCTATTGCCTC TAATGGAGGCAAGCAAGCCCTTGAGACAGTCCAGAGGCTGTTGCCAGTGCTGTGCCAGGCCCA CGGGCTCACACCCCAGCAGGTGGTCGCCATCGCCAGTAACAACGGGGGCAAACAGGCATTGG AAACCGTCCAGCGCCTGCTTCCAGTGCTCTGCCAGGCACACGGACTGACACCCGAACAGGTGG TGGCCATTGCATCCATGATGGGGCAAGCAGGCCCTGGAGACCGTGCAGAGACTCCTGCCA GTGTTGTGCCAAGCTCACGGCCTCACCCCTCAGCAAGTCGTGGCCATCGCCTCAAACGGGGG GGGCCGGCCTGCACTGGAGAGCATTGTTGCCCAGTTATCTCGCCCTGATCCGGCGTTGGCCG CGTTGACCAACGACCACCTCGTCGCCTTGGCCTGCCTCGGCGGGCGTCCTGCGCTGGATGCA GTGAAAAAGGGATTGGGGGATCCTATCAGCCGTTCCCAGCTGGTGAAGTCCAGCGTGGAGGAG AAGAAATCCGAGTTGAGGCACAAGCTGAAGTACGTGCCCCACGAGTACATCGAGCTGATCGAG ATCGCCCGGAACAGCACCCAGGACCGTATCCTGGAGATGAAGGTGATGGAGTTCTTCATGAAG GTGTACGGCTACAGGGGCAAGCACCTGGGCGGCTCCAGGAAGCCCGACGGCGCCATCTACAC CGTGGGCTCCCCCATCGACTACGGCGTGATCGTGGACACCAAGGCCTACTCCGGCGGCTACA ACCTGCCCATCGGCCAGGCCGACGAAATGCAGAGGTACGTGGAGGAGAACCAGACCAGGAAC AAGCACATCAACCCCAACGAGTGGTGGAAGGTGTACCCCTCCAGCGTGACCGAGTTCAAGTTC CTGTTCGTGTCCGGCCACTTCAAGGGCAACTACAAGGCCCAGCTGACCAGGCTGAACCACATC ACCAACTGCAACGGCGCCGTGCTGTCCGTGGAGGAGCTCCTGATCGGCGGCGAGATGATCAA GGCCGGCACCCTGACCCTGGAGGAGGTGAGGAGGAAGTTCAACAACGGCGAGATCAACTTCG CGGCCGACTGATAA |
| 28 | TALE N target TRAC | TTGTCCCACAGATATCCAGAACCCTGACCCTGCCGTGTACCAGCTGAGA |
| 29 | TALE N target CD25 | TACAGGAGGAAGAGTAGAAGAACAATCTAGAAAACCAAAAGAACA |
| 30 | TALE N target PD1 | TACCTCTGTGGGGCCATCTCCCTGGCCCCCAAGGCGCAGATCAAAGAGA |
| 31 | Matrice TRAC locus_CubiCAR CD22 pCLS30056 | TTGCTGGGCCTTTTTCCCATGCCTGCCTTTACTCTGCCAGAGTTATATTGCTGGGGTTTTGAAGA AGATCCTATTAAATAAAAGAATAAGCAGTATTATTAAGTAGCCCTGCATTTCAGGTTTCCTTGAGT GGCAGGCCAGGCCTGGCCGTGAACGTTCACTGAAATCATGGCCTCTTGGCCAAGATTGATAGC TTGTGCCTGTCCCTGAGTCCCAGTCCATCACGAGCAGCTGGTTTCTAAGATGCTATTTCCCGTA TAAAGCATGAGACCGTGACTTGCCAGCCCCACAGAGCCCCGCCCTTGTCCATCACTGGCATCT GGACTCCAGCCTGGGTTGGGGCAAAGAGGGAAATGAGATCATGTTCCTAACCCTGATCCTCTTG TCCCACAGATATCCAGTACCCCTACGACGTGCCCGACTACGCCTCCGGTGAGGGCAGAGGAAG TCTTCTAACATGCGGTGACGTGGAGGAGAATCCGGGCCCCGGATCCGCTCTGCCCGTCACCGC TCTGCTGCTGCCACTGGCACTGCTGCTGCACGCTGCTAGGCCCGGAGGGGGAGGCAGCTGCC CCTACAGCAACCCCAGCCTGTGCAGCGGAGGCGGCGGCAGCGGCGGAGGGGGTAGCAGGT GCAGCTGCAGCAGAGCGGCCCTGGCCTGGTGAAGCCAAGCCAGACACTGTCCCTGACCTGCG CCATCAGCGGCGATTCCGTGAGCTCCAACTCCGCCGCCTGGAATTGGATCAGGCAGTCCCCTT CTCGGGGCCTGGAGTGGCTGGGAAGGACATACTATCGGTCTAAGTGGTACAACGATTATGCCG TGTCTGTGAAGAGCAGAATCACAATCAACCCTGACACCTCCAAGAATCAGTTCTCTCTGCAGCT |

TABLE 5-continued

Sequences referred to in example 2.

```
GAATAGCGTGACACCAGAGGACACCGCCGTGTACTATTGCGCCAGGGAGGTGACCGGCGACC
TGGAGGATGCCTTTGACATCTGGGGCCAGGGCACAATGGTGACCGTGAGCTCCGGAGGCGGC
GGATCTGGCGGAGGAGGAAGTGGGGGCGGCGGGAGTGATATCCAGATGACACAGTCCCCATC
CTCTCTGAGCGCCTCCGTGGGCGACAGAGTGACAATCACCTGTAGGGCCTCCCAGACCATCTG
GTCTTACCTGAACTGGTATCAGCAGAGGCCCGGCAAGGCCCCTAATCTGCTGATCTACGCAGC
AAGCTCCCTGCAGAGCGGAGTGCCATCCAGATTCTCTGGCAGGGGCTCCGGCACAGACTTCAC
CCTGACCATCTCTAGCCTGCAGGCCGAGGACTTCGCCACCTACTATTGCCAGCAGTCTTATAGC
ATCCCCCAGACATTTGGCCAGGGCACCAAGCTGGAGATCAAGTCGGATCCCGGAAGCGGAGG
GGGAGGCAGCTGCCCCTACAGCAACCCCAGCCTGTGCAGCGGAGGCGGCGGCAGCGAGCTG
CCCACCCAGGGCACCTTCTCCAACGTGTCCACCAACGTGAGCCCAGCCAAGCCCACCACCACC
GCCTGTCCTTATTCCAATCCTTCCCTGTGTGCTCCCACCACAACCCCCGCTCCAAGGCCCCCTA
CCCCCGCACCAACTATTGCCTCCCAGCCACTCTCACTGCGGCCTGAGGCCTGTCGGCCCGCTG
CTGGAGGCGCAGTGCATACAAGGGGCCTCGATTTCGCCTGCGATATTTACATCTGGGCACCCC
TCGCCGGCACCTGCGGGGTGCTTCTCCTCTCCCTGGTGATTACCCTGTATTGCAGACGGGGCC
GGAAGAAGCTCCTCTACATTTTTAAGCAGCCTTTCATGCGGCCAGTGCAGACAACCCAAGAGGA
GGATGGGTGTTCCTGCAGATTCCCTGAGGAAGAGGAAGGCGGGTGCGAGCTGAGAGTGAAGT
CTCCAGGAGCGCAGATGCCCCCGCCTATCAACAGGGCCAGAACCAGCTCTACAACGAGCTTA
ACCTCGGGAGGCGCGAAGAATACGACGTGTTGGATAAGAGAAGGGGGCGGGACCCCGAGATG
GGAGGAAAGCCCCGGAGGAAGAACCCTCAGGAGGGCCTGTACAACGAGCTGCAGAAGGATAA
GATGGCCGAGGCCTACTCAGAGATCGGGATGAAGGGGGAGCGGCGCCGCGGGAAGGGGCAC
GATGGGCTCTACCAGGGGCTGAGCACAGCCACAAAGGACACATACGACGCCTTGCACATGCAG
GCCCTTCCACCCCGGGAATAGTCTAGAGGGCCCGTTTAAACCCGCTGATCAGCCTCGACTGTG
CCTTCTAGTTGCCAGCCATCTGTTGTTTGCCCCTCCCCCGTGCCTTCTTGACCCTGGAAGGTG
CCACTCCCACTGTCCTTTCCTAATAAAATGAGGAAATTGCATCGCATTGTCTGAGTAGGTGTCAT
TCTATTCTGGGGGGTGGGGTGGGGCAGGACAGCAAGGGGGAGGATTGGGAAGACAATAGCAG
GCATGCTGGGGATGCGGTGGGCTCTATGACTAGTGGCGAATTCCCGTGTACCAGCTGAGAGAC
TCTAAATCCAGTGACAAGTCTGTCTGCCTATTCACCGATTTTGATTCTCAAACAAATGTGTCACA
AAGTAAGGATTCTGATGTGTATATCACAGACAAAACTGTGCTAGACATGAGGTCTATGGACTTCA
AGAGCAACAGTGCTGTGGCCTGGAGCAACAAATCTGACTTTGCATGTGCAAACGCCTTCAACAA
CAGCATTATTCCAGAAGACACCTTCTTCCCCAGCCCAGGTAAGGGCAGCTTTGGTGCCTTCGCA
GGCTGTTTCCTTGCTTCAGGAATGGCCAGGTTCTGCCCAGAGCTCTGGTCAATGATGTCTAAAA
CTCCTCTGATTGGTGGTCTCGGCCTTATCCATTGCCACCAAAACCCTCTTTTTACTAA
```

| 32 | Matrice CD25 locus_IL15_ 2A_sIL15Ra pCLS0519 | GTTTATTATTCCTGTTCCACAGCTATTGTCTGCCATATAAAACTTAGGCCAGGCACAGTGGCTC
ACACCTGTAATCCCAGCACTTTGGAAGGCCGAGGCAGGCAGATCACAAGGTCAGGAGTTCGAG
ACCAGCCTGGCCAACATAGCAAAACCCCATCTCTACTAAAAATACAAAAATTAGCCAGGCATGG
TGGCGTGTGCACTGGTTTAGAGTGAGGACCACATTTTTTTGGTGCCGTGTTACACATATGACCG
TGACTTTGTTACACCACTACAGGAGGAAGAGTAGAAGAACAATCGGTTCTGGCGTGAAACAGAC
TTTGAATTTTGACCTTCTCAAGTTGGCGGGAGACGTGGAGTCCAACCCAGGGCCCGGTACCGG
GTCCGCCACCATGGACTGGACCTGGATTCTGTTCCTCGTGGCTGCTGCTACAGAGTGCACAG
CGGCATTCATGTCTTCATTTTGGGCTGTTTCAGTGCAGGGCTTCCTAAAACAGAAGCCAACTGG
GTGAATGTAATAAGTGATTTGAAAAAAATTGAAGATCTTATTCAATCTATGCATATTGATGCTACT
TTATATACGGAAAGTGATGTTCACCCCAGTTGCAAAGTAACAGCAATGAAGTGCTTTCTCTTGGA
GTTACAAGTTATTTCACTTGAGTCCGGAGATGCAAGTATTCATGATACAGTAGAAAATCTGATCA
TCCTAGCAAACAACAGTTTGTCTTCTAATGGGAATGTAACAGAATCTGGATGCAAAGAATGTGAG
GAACTGGAGGAAAAAAATATTAAAGAATTTTTTGCAGAGTTTTGTACATATTGTCCAAATGTTCATC
AACACTTCTGGAAGCGGAGCTACTAACTTCAGCCTGCTGAAGCAGGCTGGAGACGTGGAGGAG
AACCCTGGACCTGGGACCGGCTCTGCAACCATGGATTGGACGTGGATCCTGTTTCTCGTGGCA
GCTGCCACAAGAGTTCACAGTATCACGTGCCCTCCCCCCATGTCCGTGGAACACGCAGACATC
TGGGTCAAGAGCTACAGCTTGTACTCCAGGGAGCGGTACATTTGTAACTCTGGTTTCAAGCGTA
AAGCCGGCACGTCCAGCCTGACGGAGTGCGTGTTGAACAAGGCCACGAATGTCGCCCACTGG
ACAACCCCCAGTCTCAAATGCATTAGAGACCCTGCCCTGGTTCACCAAAGGCCAGCGCCACCC
TCCACAGTAACGACGGCAGGGGTGACCCCACAGCCAGAGAGCCTCTCCCCTTCTGGAAAAGAG
CCCGCAGCTTCATCTCCCAGCTCAAACAACACAGCGGCCACAACAGCAGCTATTGTCCCGGGC
TCCCAGCTGATGCCTTCAAAATCACCTTCCACAGGAACCACAGAGATAAGCAGTCATGAGTCCT
CCCACGGCACCCCCTCTCAGACAACAGCCAAGAACTGGGAACTCACACGCATCCGCCTCCCACC
AGCCGCCAGGTGTGTATCCACAGGGCCACAGCGACACCACTGAGGGCAGAGGCAGCCTGCTG
ACCTGCGGCGACGTCGAGGAGAACCCCGGGCCCATGGGGGCAGGTGCCACCGGCCGCGCCA
TGGACGGGCCGCGCCTGCTGCTGTTGCTGCTTCTGGGGGTGTCCCTTGGAGGTGCCAAGGAG
GCATGCCCCACAGGCCTGTACACACACAGCGGTGAGTGCTGCAAAGCCTGCAACCTGGGCGA
GGGTGTGGCCCAGCCTTGTGGAGCCAACCAGACCGTGTGTGAGCCCTGCCTGGACAGCGTGA
CGTTCTCCGACGTGGTGAGCGCGACCGAGCCGTGCAAGCCGTGCACCGAGTGCGTGGGGCTC
CAGAGCATGTCGGCGCCGTGCGTGGAGGCCGATGACGCCGTGCCGCTGCGCCTACGGCTA
CTACCAGGATGAGACGACTGGGCGCTGCGAGGCGTGCCGCGTGTGCGAGGCGGGCTCGGGC
CTCGTGTTCTCCTGCCAGGACAAGCAGAACACCGTGTGTGAGGAGTGCCCCGACGGCACGTAT
TCCGACGAGGCCAACCACGTGGACCCGTGCCTGCCCTGCACCGTGTGCGAGGACACCGAGCG
CCAGCTCCGCGAGTGCACACGCTGGGCCGACGCCGAGTGCGAGGAGATCCCTGGCCGTTGGA
TTACACGGTCCACACCCCCAGAGGGCTCGGACAGCACAGCCCCCAGCACCCAGGAGCCTGAG
GCACCTCCAGAACAAGACCTCATAGCCAGCACGGTGGCAGGTGTGGTGACCACAGTGATGGG
CAGCTCCCAGCCCGTGGTGACCCGAGGCACCACCGACAACCTCATCCCTGTCTATTGCTCCAT
CCTGGCTGCTGTGGTTGTGGGTCTTGTGGCCTACATAGCCTTCAAGAGGTGAAAAACCAAAGA
ACAAGAATTTCTTGGTAAGAAGCCGGGAACAGACAACAGAAGTCATGAAGCCCAAGTGAAATCA
AAGGTGCTAAATGGTCGCCCAGGAGACATCCGTTGTGCTTGCCTGCGTTTTGGAAGCTCTGAA
GTCACATCACAGGACACGGGGCAGTGGCAACCTTGTCTCTATGCCAGCTCAGTCCCATCAGAG
AGCGAGCGCTACCCACTTCTAAATAGCAATTTCGCCGTTGAAGAGGAAGGGCAAAACCACTAGA
ACTCTCCATCTTATTTTCATGTATATGTGTTCAT |

TABLE 5-continued

Sequences referred to in example 2.

| 33 | MatriCe PD1 locus_IL15_ 2A_sIL15Ra pCLS30513 | GACTCCCCAGACAGGCCCTGGAACCCCCCCACCTTCTCCCCAGCCCTGCTCGTGGTGACCGAA
GGGGACAACGCCACCTTCACCTGCAGCTTCTCCAACACATCGGAGAGCTTCGTGCTAAACTGG
TACCGCATGAGCCCCAGCAACCAGACGGACAAGCTGGCCGCCTTCCCCGAGGACCGCAGCCA
GCCCGGCCAGGACTGCCGCTTCCGTGTCACACAACTGCCCAACGGGCGTGACTTCCACATGAG
CGTGGTCAGGGCCCGGCGCAATGACAGCGGCACCTACCTCTGTGGGGCCGGTTCTGGCGTGA
AACAGACTTTGAATTTTGACCTTCTCAAGTTGGCGGGAGACGTGGAGTCCAACCCAGGGCCCG
GTACCGGGTCCGCCACCATGGACTGGACCTGGATTCTGTTCCTCGTGGCTGCTGCTACAAGAG
TGCACAGCGGCATTCATGTCTTCATTTTGGGCTGTTTCAGTGCAGGGCTTCCTAAAACAGAAGC
CAACTGGGTGAATGTAATAAGTGATTTGAAAAAAATTGAAGATCTTATTCAATCTATGCATATTGA
TGCTACTTTATATACGGAAAGTGATGTTCACCCCAGTTGCAAAGTAACAGCAATGAAGTGCTTTC
TCTTGGAGTTACAAGTTATTTCACTTGAGTCCGGAGATGCAAGTATTCATGATACAGTAGAAAAT
CTGATCATCCTAGCAAACAACAGTTTGTCTTCTAATGGGAATGTAACAGAATCTGGATGCAAAGA
ATGTGAGGAACTGGAGGAAAAAAATATTAAAGAATTTTTGCAGAGTTTTGTACATATTGTCCAAAT
GTTCATCAACACTTCTGGAAGCGGAGCTACTAACTTCAGCCTGCTGAAGCAGGCTGGAGACGT
GGAGGAGAACCCTGGACCTGGGACCGGCTCTGCAACCATGGATTGGACGTGGATCCTGTTTCT
CGTGGCAGCTGCCACAAGAGTTCACAGTATCACGTGCCCTCCCCCCATGTCCGTGGAACACGC
AGACATCTGGGTCAAGAGCTACAGCTTGTACTCCAGGGAGCGGTACATTTGTAACTCTGGTTTC
AAGCGTAAAGCCGGCACGTCCAGCCTGACGGAGTGCGTGTTGAACAAGGCCACGAATGTCGC
CCACTGGACAACCCCCAGTCTCAAATGCATTAGAGACCCTGCCCTGGTTCACCAAAGGCCAGC
GCCACCCTCCACAGTAACGACGGCAGGGGTGACCCCACAGCCAGAGAGCCTCTCCCCTTCTG
GAAAAGAGCCCGCAGCTTCATCTCCCAGCTCAAACAACACAGCGGCCACAACAGCAGCTATTG
TCCCGGGCTCCCAGCTGATGCCTTCAAAATCACCTTCCACAGGAACCACAGAGATAAGCAGTCA
TGAGTCCTCCCACGGCACCCCCTCTCAGACAACAGCCAAGAACTGGGAACTCACAGCATCCGC
CTCCCACCAGCCGCCAGGTGTGTATCCACAGGGCCACAGCGACACCACTGAGGGCAGAGGCA
GCCTGCTGACCTGCGGCGACGTCGAGGAGAACCCCGGGCCCATGGGGCAGGTGCCACCGG
CCGCGCCATGGACGGGCCGCGCCTGCTGCTGTTGCTGCTTCTGGGGGTGTCCCTTGGAGGTG
CCAAGGAGGCATGCCCCACAGGCCTGTACACACACAGCGGTGAGTGCTGCAAAGCCTGCAAC
CTGGGCGAGGGTGTGGCCCAGCCTTGTGGAGCCAACCAGACCGTGTGTGAGCCCTGCCTGGA
CAGCGTGACGTTCTCCGACGTGGTGAGCGCGACCGAGCCGTGCAAGCCGTGCACCGAGTGCG
TGGGGCTCCAGAGCATGTCGGCGCCGTGCGTGGAGGCCGATGACGCCGTGTGCAGGTGCGC
CTACGGCTACTACCAGGATGAGACGACTGGGCGCTGCGAGGCGTGCCGCGTGTGCGAGGCGG
GCTCGGGCCTCGTGTTCTCCTGCCAGGACAAGCAGAACACCGTGTGCGAGGAGTGCCCCGAC
GGCACGTATTCCGACGAGGCCAACCACGTGGACCCGTGCCTGCCCTGCACCGTGTGCGAGGA
CACCGAGCGCCAGCTCCGCGAGTGCACACGCTGGGCCGACGCCGAGTGCGAGGAGATCCCT
GGCCGTTGGATTACACGGTCCACACCCCCAGAGGGCTCGGACAGCACAGCCCCCAGCACCCA
GGAGCCTGAGGCACCTCCAGAACAAGACCTCATAGCCAGCACGGTGGCAGGTGTGGTGACCA
CAGTGATGGGCAGCTCCCAGCCCGTGGTGACCCGAGGCACCACCGACAACCTCATCCCTGTCT
ATTGCTCCATCCTGGCTGCTGTGGTTGTGGGTCTTGTGGCCTACATAGCCTTCAAGAGGTGATC
TAGAGGGCCCGTTTAAACCCGCTGATCAGCCTCGACTGTGCCTTCTAGTTGCCAGCCATCTGTT
GTTTGCCCCTCCCCCGTGCCTTCCTTGACCCTGGAAGGTGCCACTCCCACTGTCCTTTCCTAAT
AAAATGAGGAAATTGCATCGCATTGTCTGAGTAGGTGTCATTCTATTCTGGGGGGTGGGGTGGG
GCAGGACAGCAAGGGGGAGGATTGGGAAGACAATAGCAGGCATGCTGGGGATGCGGTGGGCT
CTATGACTAGTGGCGAATTCGGCGCAGATCAAAGAGAGCCTGCGGGCAGAGCTCAGGGTGACA
GGTGCGGCCTCGGAGGCCCCGGGGCAGGGGTGAGCTGAGCCGGTCCTGGGGTGGGTGTCCC
CTCCTGCACAGGATCAGGAGCTCCAGGGTCGTAGGGCAGGGACCCCCCAGCTCCAGTCCAGG
GCTCTGTCCTGCACCTGGGGAATGGTGACCGGCATCTCTGTCCTCTAGCTCTGGAAGCACCCC
AGCCCCTCTAGTCTGCCCTCACCCCTGACCCTGACCCTCCACCCTGACCCCGTCCTAACCCCT
GACCTTTG |
| 34 | Matrice CD25 locus_IL12a_ 2A_IL12b pCLS30520 | GTTTATTATTCCTGTTCCACAGCTATTGTCTGCCATATAAAAACTTAGGCCAGGCACAGTGGCTC
ACACCTGTAATCCCAGCACTTTGGAAGGCCGAGGCAGGCAGATCACAAGGTCAGGAGTTCGAG
ACCAGCCTGGCCAACATAGCAAAACCCCATCTCTACTAAAAATACAAAAATTAGCCAGGCATGG
TGGCGTGTGCACTGGTTTAGAGTGAGGACCACATTTTTTTGGTGCCGTGTTACACATATGACCG
TGACTTTGTTACACCACTACAGGAGGAAGAGTAGAAGAACAATCGGTTCTGGCGTGAAACAGAC
TTTGAATTTTGACCTTCTCAAGTTGGCGGGAGACGTGGAGTCCAACCCAGGGCCCATGTGCC
CCCTGGGTCAGCCTCCCAGCCACCGCCCTCACCTGCCGCGGCCACAGGTCTGCATCCAGCGG
CTCGCCCTGTGTCCCTGCAGTGCCGGCTCAGCATGTGTCCAGCGCGCAGCCTCCTCCTTGTGG
CTACCCTGGTCCTCCTGGACCACCTCAGTTTGGCCAGAAACCTCCCCGTGGCCACTCCAGACC
CAGGAATGTTCCCATGCCTTCACCACTCCCAAAACCTGCTGAGGGCCGTCAGCAACATGCTCCA
GAAGGCCAGACAAACTCTAGAATTTTACCCTTGCACTTCTGAAGAGATTGATCATGAAGATATCA
CAAAAGATAAAACCAGCACAGTGGAGGCTGTTTACCATTGGAATTAACCAAGAATGAGAGTTG
CCTAAATTCCAGAGAGACCTCTTTCATAACTAATGGGAGTTGCCTGGCCTCCAGAAAGACCTCT
TTTATGATGGCCCTGTGCCTTAGTAGTATTTATGAAGACTTGAAGATGTACCAGGTGGAGTTCAA
GACCATGAATGCAAAGCTTCTGATGGATCCTAAGAGGCAGATCTTTCTAGATCAAAACATGCTG
GCAGTTATTGATGAGCTGATGCAGGCCCTGAATTTCAACAGTGAGACTGTGCCACAAAAATCCT
CCCTTGAAGAACCGGATTTTTATAAAACTAAAATCAAGCTCTGCATACTTCTTCATGCTTTCAGAA
TTCGGGCAGTGACTATTGATAGAGTGATGAGCTATCTGAATGCTTCCGGAAGCGGAGCTACTAA
CTTCAGCCTGCTGAAGCAGGCTGGAGACGTGGAGGAGAACCCTGGACCTATGTGTCACCAGCA
GTTGGTCATCTCTTGGTTTTCCCTGGTTTTTCTGGCATCTCCCCTCGTGGCCATATGGGAACTGA
AGAAAGATGTTTATGTCGTAGAATTGGATTGGTATCCGGATGCCCCTGGAGAAATGGTGGTCCT
CACCTGTGACACCCCTGAAGAAGATGGTATCACCTGGACCTTGGACCAGAGCAGTGAGGTCTT
AGGCTCTGGCAAAACCCTGACCATCCAAGTCAAAGAGTTTGGAGATGCTGGCCAGTACACCTGT
CACAAAGGAGGCGAGGTTCTAAGCCATTCGCTCCTGCTGCTTCACAAAAAGGAAGATGGAATTT
GGTCCACTGATATTTTAAAGGACCAGAAAGAACCCAAAAATAAGACCTTTCTAAGATGCGAGGC
CAAGAATTATTCTGGACGTTTCACCTGCTGGTGGCTGACGACAATCAGTACTGATTTGACATTCA
GTGTCAAAAGCAGCAGAGGCTCTTCTGACCCCAAGGGTGACGTGCGGAGCTGCTACACTCT
CTGCAGAGAGAGTCAGAGGGACAACAAGGAGTATGAGTACTCAGTGGAGTGCCAGGAGGAC |

TABLE 5-continued

Sequences referred to in example 2.

| | | |
|---|---|---|
| | | AGTGCCTGCCCAGCTGCTGAGGAGAGTCTGCCCATTGAGGTCATGGTGGATGCCGTTCACAAG<br>CTCAAGTATGAAAACTACACCAGCAGCTTCTTCATCAGGGACATCATCAAACCTGACCCACCCA<br>AGAACTTGCAGCTGAAGCCATTAAAGAATTCTCGGCAGGTGGAGGTCAGCTGGGAGTACCCTG<br>ACACCTGGAGTACTCCACATTCCTACTTCTCCCTGACATTCTGCGTTCAGGTCCAGGGCAAGAG<br>CAAGAGAGAAAAGAAAGATAGAGTCTTCACGGACAAGACCTCAGCCACGGTCATCTGCCGCAA<br>AAATGCCAGCATTAGCGTGCGGGCCCAGGACCGCTACTATAGCTCATCTTGGAGCGAATGGGC<br>ATCTGTGCCCTGCAGTGAGGGCAGAGGCAGCCTGCTGACCTGCGGCGACGTCGAGGAGAACC<br>CCGGGCCCATGGGGGCAGGTGCCACCGGCCGCGCCATGGACGGGCCGCGCCTGCTGCTGTT<br>GCTGCTTCTGGGGGTGTCCCTTGGAGGTGCCAAGGAGGCATGCCCCACAGGCCTGTACACAC<br>ACAGCGGTGAGTGCTGCAAAGCCTGCAACCTGGGCGAGGGTGTGGCCCAGCCTTGTGGAGCC<br>AACCAGACCGTGTGTGAGCCCTGCCTGGACAGCGTGACGTTCTCCGACGTGGTGAGCGCGAC<br>CGAGCCGTGCAAGCCGTGCACCGAGTGCGTGGGGCTCCAGAGCATGTCGGCGCCGTGCGTG<br>GAGGCCGATGACGCCGTGTGCCGCTGCGCCTACGGCTACTACCAGGATGAGACGACTGGGCG<br>CTGCGAGGCGTGCCGCGTGTGCGAGGCGGGCTCGGGCCTCGTGTTCTCCTGCCAGGACAAGC<br>AGAACACCGTGTGCGAGGAGTGCCCCGACGGCACGTATTCCGACGAGGCCAACCACGTGGAC<br>CCGTGCCTGCCCTGCACCGTGTGCGAGGACACCGAGCGCCAGCTCCGCGAGTGCACACGCTG<br>GGCCGACGCCGAGTGCGAGGAGATCCCTGGCCGTTGGATTACACGGTCCACACCCCCAGAGG<br>GCTCGGACAGCACAGCCCCAGCACCCAGGAGCCTGAGGCACCTCCAGAACAAGACCTCATA<br>GCCAGCACGGTGGCAGGTGTGGTGACCACAGTGATGGGCAGCTCCCAGCCCGTGGTGACCCG<br>AGGCACCACCGACAACCTCATCCCTGTCTATTGCTCCATCCTGGCTGCTGTGGTTGTGGGTCTT<br>GTGGCCTACATAGCCTTCAAGAGGTGAAAAACCAAAGAACAAGAATTTCTTGGTAAGAAGCCG<br>GGAACAGACAACAGAAGTCATGAAGCCCAAGTGAAATCAAAGGTGCTAAATGGTCGCCCAGGA<br>GACATCCGTTGTGCTTGCCTGCGTTTTGGAAGCTCTGAAGTCACATCACAGGACACGGGGCAG<br>TGGCAACCTTGTCTCTATGCCAGCTCAGTCCCATCAGAGAGCGAGCGCTACCCACTTCTAAATA<br>GCAATTTCGCCGTTGAAGAGGAAGGGCAAAACCACTAGAACTCTCCATCTTATTTTCATGTATAT<br>GTGTTCAT |
| 35 | Matrice PD1<br>locus_IL12a_<br>2A_IL12b<br>pCLS30511 | GACTCCCCAGACAGGCCCTGGAACCCCCCCACCTTCTCCCCAGCCCTGCTCGTGGTGACCGAA<br>GGGGACAACGCCACCTTCACCTGCAGCTTCTCCAACACATCGGAGAGCTTCGTGCTAAACTGG<br>TACCGCATGAGCCCCAGCAACCAGACGGACAAGCTGGCCGCCTTCCCCGAGGACCGCAGCCA<br>GCCCGGCCAGGACTGCCGCTTCCGTGTGCACACAACTGCCCAACGGGCGTGACTTCCACATGAG<br>CGTGGTCAGGGCCCGGCGCAATGACAGCGGCACCTACCTCTGTGGGGCCGGTTCTGGCGTGA<br>AACAGACTTTGAATTTTGACCTTCTCAAGTTGGCGGGAGACGTGGAGTCCAACCCAGGGCCCAT<br>GTGGCCCCCTGGGTCAGCCTCCCAGCCACCGCCCTCACCTGCCGCGGCCACAGGTCTGCATC<br>CAGCGGCTCGCCCTGTGTCCCTGCAGTGCCGGCTCAGCATGTGTCCAGCGCGCAGCCTCCTC<br>CTTGTGGCTACCCTGGTCCTCCTGGACCACCTCAGTTTGGCCAGAAACCTCCCCGTGGCCACT<br>CCAGACCCAGGAATGTTCCCATGCCTTCACCACTCCCAAAACCTGCTGAGGGCCGTCAGCAAC<br>ATGCTCCAGAAGGCCAGACAAACTCTAGAATTTTACCCTTGCACTTCTGAAGAGATTGATCATGA<br>AGAGTTGCTAAATTCCAGAGAGACCTCTTTCATAACTAATGGGAGTTGCCTGGCCTCCAGAA<br>AGACCTCTTTTATGATGGCCCTGTGCCTTAGTAGTATTTATGAAGACTTGAAGATGTACCAGGTG<br>GAGTTCAAGACCATGAATGCAAAGCTTCTGATGGATCCTAAGAGGCAGATCTTTCTAGATCAAAA<br>CATGCTGGCAGTTATTGATGAGCTGATGCAGGCCCTGAATTTCAACAGTGAGACTGTGCCACAA<br>AAATCCTCCCTTGAAGAACCGGATTTTTATAAAACTAAAATCAAGCTCTGCATACTTCTTCATGCT<br>TTCAGAATTCGGGCAGTGACTATTGATAGAGTGATGAGCTATCTGAATGCTTCCGGAAGCGGAG<br>CTACTAACTTCAGCCTGCTGAAGCAGGCTGGAGACGTGGAGGAGAACCCTGGACCTATGTGTC<br>ACCAGCAGTTGGTCATCTCTTGGTTTTCCCTGGTTTTTCTGGCATCTCCCCTCGTGGCCATATGG<br>GAACTGAAGAAAGATGTTTATGTCGTAGAATTGGATTGGTATCCGGATGCCCCTGGAGAAATGG<br>TGGTCCTCACCTGTGACACCCCTGAAGAAGATGGTATCACCTGGACCTTGGACCAGAGCAGTG<br>AGGTCTTAGGCTCTGGCAAAACCCTGACCATCCAAGTCAAAGAGTTTGGAGATGCTGGCCAGTA<br>CACCTGTCACAAAGGAGGCGAGGTTCTAAGCCATTCGCTCCTGCTGCTTCACAAAAAGGAAGAT<br>GGAATTTGGTCCACTGATATTTTAAAGGACCAGAAAGAACCCAAAAATAAGACCTTTCTAAGATG<br>CGAGGCCAAGAATTATTCTGGACGTTTCACCTGCTGGTGGCTGACGACAATCAGTACTGATTTG<br>ACATTCAGTGTCAAAAGCAGCAGAGGCTCTTCTGACCCCCAAGGGGTGACGTGCGGAGCTGCT<br>ACACTCTCTGCAGAGAGAGTCAGAGGGGACAACAAGGAGTATGAGTACTCAGTGGAGTGCCAG<br>GAGGACAGTGCCTGCCCAGCTGCTGAGGAGAGTCTGCCCATTGAGGTCATGGTGGATGCCGTT<br>CACAAGCTCAAGTATGAAAACTACACCAGCAGCTTCTTCATCAGGGACATCATCAAACCTGACC<br>CACCCAAGAACTTGCAGCTGAAGCCATTAAAGAATTCTCGGCAGGTGGAGGTCAGCTGGGAGT<br>ACCCTGACACCTGGAGTACTCCACATTCCTACTTCTCCCTGACATTCTGCGTTCAGGTCCAGGG<br>CAAGAGCAAGAGAGAAAAGAAAGATAGAGTCTTCACGGACAAGACCTCAGCCACGGTCATCTG<br>CCGCAAAAATGCCAGCATTAGCGTGCGGGCCCAGGACCGCTACTATAGCTCATCTTGGAGCGA<br>ATGGGCATCTGTGCCCTGCAGTGAGGGCAGAGGCAGCCTGCTGACCTGCGGCGACGTCGAGG<br>AGAACCCCGGGCCCATGGGGGCAGGTGCCACCGGCCGCGCCATGGACGGGCCGCGCCTGCT<br>GCTGTTGCTGCTTCTGGGGGTGTCCCTTGGAGGTGCCAAGGAGGCATGCCCCACAGGCCTGTA<br>CACACACAGCGGTGAGTGCTGCAAAGCCTGCAACCTGGGCGAGGGTGTGGCCCAGCCTTGTG<br>GAGCCAACCAGACCGTGTGTGAGCCCTGCCTGGACAGCGTGACGTTCTCCGACGTGGTGAGC<br>GCGACCGAGCCGTGCAAGCCGTGCACCGAGTGCGTGGGGCTCCAGAGCATGTCGGCGCCGT<br>GCGTGGAGGCCGATGACGCCGTGTGCCGCTGCGCCTACGGCTACTACCAGGATGAGACGACT<br>GGGCGCTGCGAGGCGTGCCGCGTGTGCGAGGCGGGCTCGGGCCTCGTGTTCTCCTGCCAGG<br>ACAAGCAGAACACCGTGTGCGAGGAGTGCCCCGACGGCACGTATTCCGACGAGGCCAACCAC<br>GTGGACCCGTGCCTGCCCTGCACCGTGTGCGAGGACACCGAGCGCCAGCTCCGCGAGTGCAC<br>ACGCTGGGCCGACGCCGAGTGCGAGGAGATCCCTGGCCGTTGGATTACACGGTCCACACCCC<br>CAGAGGGCTCGGACAGCACAGCCCCAGCACCCAGGAGCCTGAGGCACCTCCAGAACAAGAC<br>CTCATAGCCAGCACGGTGGCAGGTGTGGTGACCACAGTGATGGGCAGCTCCCAGCCCGTGGT<br>GACCCGAGGCACCACCGACAACCTCATCCCTGTCTATTGCTCCATCCTGGCTGCTGTGGTTGT<br>GGGTCTTGTGGCCTACATAGCCTTCAAGAGGTGATCTAGAGGGCCCGTTTAAACCCGCTGATCA<br>GCCTCGACTGTGCCTTCTAGTTGCCAGCCATCTGTTGTTTGCCCCTCCCCCGTGCCTTCCTTGA<br>CCCTGGAAGGTGCCACTCCCACTGTCCTTTCCTAATAAAATGAGGAAATTGCATCGCATTGTCT |

TABLE 5-continued

Sequences referred to in example 2.

| | | |
|---|---|---|
| | | GAGTAGGTGTCATTCTATTCTGGGGGGTGGGGTGGGGCAGGACAGCAAGGGGGAGGATTGGG<br>AAGACAATAGCAGGCATGCTGGGGATGCGGTGGGCTCTATGACTAGTAGTGGCGAATTCGGCGCAG<br>ATCAAAGAGAGCCTGCGGGCAGAGCTCAGGGTGACAGGTGCGGCCTCGGAGGCCCCGGGGC<br>AGGGGTGAGCTGAGCCGGTCCTGGGGTGGGTGTCCCCTCCTGCACAGGATCAGGAGCTCCAG<br>GGTCGTAGGGCAGGGACCCCCAGCTCCAGTCCAGGGCTCTGTCCTGCACCTGGGGAATGGT<br>GACCGGCATCTCTGTCCTCTAGCTCTGGAAGCACCCCAGCCCCTCTAGTCTGCCCTCACCCCT<br>GACCCTGACCCTCCACCCTGACCCCGTCCTAACCCCTGACCTTTG |
| 36 | Inserted<br>matrice TRAC<br>locus_CubiCAR<br>CD22 (60<br>nucleotides<br>upstream and<br>downstream) | ATGAGATCATGTCCTAACCCTGATCCTCTTGTCCCACAGATATCCAGAACCCTGACCCTGTTGCT<br>GGGCCTTTTTCCCATGCCTGCCTTTACTCTGCCAGAGTTATATTGCTGGGGTTTTGAAGAAGATC<br>CTATTAAATAAAAGAATAAGCAGTATTATTAAGTAGCCCTGCATTTCAGGTTTCCTTGAGTGGCA<br>GGCCAGGCCTGGCCGTGAACGTTCACTGAAATCATGGCCTCTTGGCCAAGATTGATAGCTTGT<br>GCCTGTCCCTGAGTCCCAGTCCATCACGAGCAGCTGGTTTCTAAGATGCTATTTCCCGTATAAA<br>GCATGAGACCGTGACTTGCCAGCCCCACAGAGCCCCGCCCTTGTCCATCACTGGCATCTGGAC<br>TCCAGCCTGGGTTGGGGCAAAGAGGGAAATGATCATGTCCTAACCCTGATCCTCTTGTCCCA<br>CAGATATCCAGTACCCCTACGACGTGCCCGACTACGCCTCCGGTGAGGGCAGAGGAAGTCTTC<br>TAACATGCGGTGACGTGGAGGAGAATCCGGGCCCCGGATCCGCTCTGCCCGTCACCGCTCTG<br>CTGCTGCCACTGGCACTGCTGCTGCACGCTGCTAGGCCCGGAGGGGGAGGCAGCTGCCCCTA<br>CAGCAACCCCAGCCTGTGCAGCGGAGGCGGCGGCAGCGGCGGAGGGGGTAGCCAGGTGCAG<br>CTGCAGCAGAGCGGCCCTGGCCTGGTGAAGCCAAGCCAGACACTGTCCCTGACCTGCGCCAT<br>CAGCGGCGATTCCGTGAGCTCCAACTCCGCCGCCTGGAATTGGATCAGGCAGTCCCCTTCTCG<br>GGGCCTGGAGTGGCTGGGAAGGACATACTATCGGTCTAAGTGGTACAACGATTATGCCGTGTC<br>TGTGAAGAGCAGAATCACAATCAACCCTGACACCTCCAAGAATCAGTTCTCTCTGCAGCTGAAT<br>AGCGTGACACCAGAGGACACCGCCGTGTACTATTGCGCCAGGGAGGTGACCGGCGACCTGGA<br>GGATGCCTTTGACATCTGGGGCCAGGGCACAATGGTGACCGTGAGCTCCGGAGGCGGCGGAT<br>CTGGCGGAGGAGGAAGTGGGGGCGGCGGGAGTGATATCCAGATGACACAGTCCCCATCCTCT<br>CTGAGCGCCTCCGTGGGCGACAGAGTGACAATCACCTGTAGGGCCTCCCAGACCATCTGGTCT<br>TACCTGAACTGGTATCAGCAGAGGCCCGGCAAGGCCCCTAATCTGCTGATCTACGCAGCAAGC<br>TCCCTGCAGAGCGGAGTGCCATCCAGATTCTCTGGCAGGGGCTCCGGCACAGACTTCACCCTG<br>ACCATCTCTAGCCTGCAGGCCGAGGACTTCGCCACCTACTATTGCCAGCAGTCTTATAGCATCC<br>CCCAGACATTTGGCCAGGGCACCAAGCTGGAGATCAAGTCGGATCCCGGAAGCGGAGGGGGA<br>GGCAGCTGCCCCTACAGCAACCCCAGCCTGTGCAGCGGAGGCGGCGGCAGCGAGCTGCCCA<br>CCCAGGGCACCTTCTCCAACGTGTCCACCAACGTGAGCCCAGCCAAGCCCACCACCACCGCCT<br>GTCCTTATTCCAATCCTTCCCTGTGTGCTCCCACCACAACCCCGCTCCAAGGCCCCCTACCCC<br>CGCACCAACTATTGCCTCCCAGCCACTCTCACTGCGGCCTGAGGCCTGTCGGCCCGCTGCTGG<br>AGGCGCAGTGCATACAAGGGGCCTCGATTTCGCCTGCGATATTTACATCTGGGCACCCCTCGC<br>CGGCACCTGCGGGGTGCTTCTCCTCTCCCTGGTGATTACCCTGTATTGCAGACGGGGCCGGAA<br>GAAGCTCCTCTACATTTTTAAGCAGCCTTTCATGCGGCCAGTGCAGACAACCCAAGAGGAGGAT<br>GGGTGTTCCTGCAGATTCCCTGAGGAAGAGGAAGGCGGGTGCGAGCTGAGAGTGAAGTTCTC<br>CAGGAGCGCAGATGCCCCCGCCTATCAACAGGGCCAGAACCAGCTCTACAACGAGCTTAACCT<br>CGGGAGGCGCGAAGAATACGACGTGTTGGATAAGAGAAGGGGGCGGGACCCCGAGATGGGA<br>GGAAAGCCCCGGAGGAAGAACCCTCAGGAGGGCCTGTACAACGAGCTGCAGAAGGATAAGAT<br>GGCCGAGGCCTACTCAGAGATCGGGATGAAGGGGGAGCGGCGCCGCGGGAAGGGGCACGAT<br>GGGCTCTACCAGGGGCTGAGCACAGCCACAAAGGACACATACGACGCCTTGCACATGCAGGC<br>CCTTCCACCCCGGGAATAGTCTAGAGGGCCCGTTTAAACCCGCTGATCAGCCTCGACTGTGCC<br>TTCTAGTTGCCAGCCATCTGTTGTTTGCCCCTCCCCCGTGCCTTCCTTGACCCTGGAAGGTGCC<br>ACTCCCACTGTCCTTTCCTAATAAAATGAGGAAATTGCATCGCATTGTCTGAGTAGGTGTCATTC<br>TATTCTGGGGGGTGGGGTGGGGCAGGACAGCAAGGGGGAGGATTGGGAAGACAATAGCAGGC<br>ATGCTGGGGATGCGGTGGGCTCTATGACTAGTGGCGAATTCCCGTGTACCAGCTGAGAGACTC<br>TAAATCCAGTGACAAGTCTGTCTGCCTATTCACCGATTTTGATTCTCAAACAAATGTGTCACAAA<br>GTAAGGATTCTGATGTGTATATCACAGACAAAACTGTGCTAGACATGAGGTCTATGGACTTCAAG<br>AGCAACAGTGCTGTGGCCTGGAGCAACAAATCTGACTTTGCATGTGCAAACGCCTTCAACAACA<br>GCATTATTCCAGAAGACACCTTCTTCCCCAGCCCAGGTAAGGGCAGCTTTGGTGCCTTCGCAG<br>GCTGTTTCCTTGCTTCAGGAATGGCCAGGTTCTGCCCAGAGCTCTGGTCAATGATGTCTAAAAC<br>TCCTCTGATTGGTGGTCTCGGCCTTATCCATTGCCACCAAAACCCTCTTTTTACTAAGAAACAGT<br>GAGCCTTGTTCTGGCAGTCCAGAGAATGACACGGGAAAAAAGCAGATGAAGA |
| 37 | Inserted<br>matrice CD25<br>locus_IL15_<br>2A_sIL15Ra<br>(60<br>nucleotides<br>upstream and<br>downstream) | AGTGCTGGCTAGAAACCAAGTGCTTTACTGCATGCACATCATTTAGCACAGTTAGTTGCTGTTTA<br>TTATTCCTGTTCCACAGCTATTGTCTGCCATATAAAAACTTAGGCCAGGCACAGTGGCTCACACC<br>TGTAATCCCAGCACTTTGGAAGGCCGAGGCAGGCAGATCACAAGGTCAGGAGTTCGAGACCAG<br>CCTGGCCAACATAGCAAAACCCCATCTCTACTAAAAATACAAAAATTAGCCAGGCATGGTGGCG<br>TGTGCACTGGTTTAGAGTGAGGACCACATTTTTTTGGTGCCGTGTTACACATATGACCGTGACTT<br>TGTTACACCACTACAGGAGGAAGAGTAGAAGAACAATCGGTTCTGGCGTGAAACAGACTTTGAA<br>TTTTGACCTTCTCAAGTTGGCGGGAGACGTGGAGTCCAACCCAGGGCCCGGTACCGGGTCCGC<br>CACCATGGACTGGACCTGGATTCTGTTCCTCGTGGCTGCTGCTACAAGAGTGCACAGCGGCAT<br>TCATGTCTTCATTTTGGGCTGTTTCAGTGCAGGGCTTCCTAAAACAGAAGCCAACTGGGTGAAT<br>GTAATAAGTGATTTGAAAAAAATTGAAGATCTTATTCAATCTATGCATATTGATGCTACTTTATATA<br>CGGAAAGTGATGTTCACCCCAGTTGCAAAGTAACAGCAATGAAGTGCTTTCTCTTGGAGTTACA<br>AGTTATTTCACTTGAGTCCGGAGATGCAAGTATTCATGATACAGTAGAAAATCTGATCATCCTAG<br>CAAACAACAGTTTGTCTTCTAATGGGAATGTAACAGAATCTGGATGCAAAGAATGTGAGGAACT<br>GGAGGAAAAAATATTAAAGAATTTTTGCAGATTTTGTACATATTGTCCAAATGTTCATCAACAC<br>TTCTGGAAGCGGAGCTACTAACTTCAGCCTGCTGAAGCAGGCTGGAGACGTGGAGGAGAACCC<br>TGGACCTGGGACCGGCTCTGCAACCATGGATTGGACGTGGATCCTGTTTCTCGTGGCAGCTGC<br>CACAAGAGTTCACAGTATCACGTGCCCTCCCCCATGTCCGTGGAACACGCAGACATCTGGGT<br>CAAGAGCTACAGCTTGTACTCCAGGGAGCGGTACATTTGTAACTCTGGTTTCAAGCGTAAAGCC<br>GGCACGTCCAGCCTGACGGAGTGCGTGTTAACAAGGCCACGAATGTCGCCCACTGGACAAC<br>CCCAGTCTCAAATGCATTAGAGACCCTGCCCTGGTTCACCAAAGGCCAGCGCCACCCTCCAC<br>AGTAACGACGGCAGGGGTGACCCCACAGCCAGAGAGCCTCTCCCCTTCTGGAAAAGAGCCCG |

TABLE 5-continued

Sequences referred to in example 2.

| | | |
|---|---|---|
| | | CAGCTTCATCTCCCAGCTCAAACAACACAGCGGCCACAACAGCAGCTATTGTCCCGGGCTCCC<br>AGCTGATGCCTTCAAAATCACCTTCCACAGGAACCACAGAGATAAGCAGTCATGAGTCCTCCCA<br>CGGCACCCCCTCTCAGACAACAGCCAAGAACTGGGAACTCACAGCATCCGCCTCCCACCAGCC<br>GCCAGGTGTGTATCCACAGGGCCACAGCGACACCACTGAGGGCAGAGGCAGCCTGCTGACCT<br>GCGGCGACGTCGAGGAGAACCCCGGGCCCATGGGGGCAGGTGCCACCGGCCGCGCCATGGA<br>CGGGCCGCGCCTGCTGCTGTTGCTGCTTCTGGGGGTGTCCCTTGGAGGTGCCAAGGAGGCAT<br>GCCCCACAGGCCTGTACACACACAGCGGTGAGTGCTGCAAAGCCTGCAACCTGGGCGAGGGT<br>GTGGCCCAGCCTTGTGGAGCCAACCAGACCGTGTGTGAGCCCTGCCTGGACAGCGTGACGTT<br>CTCCGACGTGGTGAGCGCGACCGAGCCGTGCAAGCCGTGCACCGAGTGCGTGGGGCTCCAGA<br>GCATGTCGGCGCCGTGCGTGGAGGCCGATGACGCCGTGTGCCGCTGCGCCTACGGCTACTAC<br>CAGGATGAGACGACTGGGCGCTGCGAGGCGTGCCGCGTGTGCGAGGCGGGCTCGGGCCTCG<br>TGTTCTCCTGCCAGGACAAGCAGAACACCGTGTGCGAGGAGTGCCCCGACGGCACGTATTCCG<br>ACGAGGCCAACCACGTGGACCCGTGCCTGCCCTGCACCGTGTGCGAGGACACCGAGCGCCAG<br>CTCCGCGAGTGCACACGCTGGGCCGACGCCGAGTGCGAGGAGATCCCTGGCCGTTGGATTAC<br>ACGGTCCACACCCCCAGAGGGCTCGGACAGCACAGCCCCCAGCACCCAGGAGCCTGAGGCAC<br>CTCCAGAACAAGACCTCATAGCCAGCACGGTGGCAGGTGTGGTGACCACAGTGATGGGCAGCT<br>CCCAGCCCGTGGTGACCCGAGGCACCACCGACAACCTCATCCCTGTCTATTGCTCCATCCTGG<br>CTGCTGTGGTTGTGGGTCTTGTGGCCTACATAGCCTTCAAGAGGTGAAAAACCAAAAGAACAAG<br>AATTTCTTGGTAAGAAGCCGGGAACAGACAACAGAAGTCATGAAGCCCAAGTGAAATCAAAGGT<br>GCTAAATGGTCGCCCAGGAGACATCCGTTGTGCTTGCCTGCGTTTTGGAAGCTCTGAAGTCACA<br>TCACAGGACACGGGGCAGTGGCAACCTTGTCTCTATGCCAGCTCAGTCCCATCAGAGAGCGAG<br>CGCTACCCACTTCTAAATAGCAATTTCGCCGTTGAAGAGGAAGGGCAAAACCACTAGAACTCTC<br>CATCTTATTTTCATGTATATGTGTTCATTAAAGCATGAATGGTATGGAACTCTCTCCACCCTATAT<br>GTAGTATAAAGAAAAGTAGGTT |
| 38 | Inserted<br>matrice PD1<br>locus_IL15_<br>2A_sIL15Ra<br>(60<br>nucleotides<br>upstream and<br>downstream) | GGTGGCCGGGGAGGCTTTGTGGGGCCACCCAGCCCCTTCCTCACCTCTCTCCATCTCTCAGAC<br>TCCCCAGACAGGCCCTGGAACCCCCCACCTTCTCCCCAGCCCTGCTCGTGGTGACCGAAGG<br>GGACAACGCCACCTTCACCTGCAGCTTCTCCAACACATCGGAGAGCTTCGTGCTAAACTGGTAC<br>CGCATGAGCCCCAGCAACCAGACGGACAAGCTGGCCGCCTTCCCCGAGGACCGCAGCCAGCC<br>CGGCCAGGACTGCCGCTTCCGTGTCACACAACTGCCCAACGGGCGTGACTTCCACATGAGCGT<br>GGTCAGGGCCCGGCGCAATGACAGCGGCACCTACCTCTGTGGGGCCGGTTCTGGCGTGAAAC<br>AGACTTTGAATTTTGACCTTCTCAAGTTGGCGGGAGACGTGGAGTCCAACCCAGGGCCCGGTA<br>CCGGGTCCGCCACCATGGACTGGACCTGGATTCTGTTCCTCGTGGCTGCCTGCTACAAGAGTGC<br>ACAGCGGCATTCATGTCTTCATTTTGGGCTGTTTCAGTGCAGGGCTTCCTAAAACAGAAGCCAA<br>CTGGGTGAATGTAATAAGTGATTTGAAGAAAAATTGAAGATCTTATTCAATCTATGCATATTGATGC<br>TACTTTATATACGGAAAGTGATGTTCACCCCAGTTGCAAAGTAACAGCAATGAAGTGCTTTCTCT<br>TGGAGTTACAAGTTATTTCACTTGAGTCCGGAGATGCAAGTATTCATGATACAGTAGAAAATCTG<br>ATCATCCTAGCAAACAACAGTTTGTCTTCTAATGGAATGTAACAGAATCTGGATGCAAAGAATG<br>TGAGGAACTGGAGGAAAAAAATATTAAAGAATTTTTGCAGAGTTTTGTACATATTGTCCAAATGTT<br>CATCAACACTTCTGGAAGCGGAGCTACTAACTTCAGCCTGCTGAAGCAGGCTGGAGACGTGGA<br>GGAGAACCCTGGACCTGGGACCGGCTCTGCAACCATGGATTGGACGTGGATCCTGTTTCTCGT<br>GGCAGCTGCCACAAGAGTTCACAGTATCACGTGCCCTCCCCCATGTCCGTGGAACACGCAGA<br>CATCTGGGTCAAGAGCTACAGCTTGTACTCCAGGGAGCGGTACATTTGTAACTCTGGTTTCAAG<br>CGTAAAGCCGGCACGTCCAGCCTGACGGAGTGCGTGTTGAACAAGGCCACGAATGTCGCCCA<br>CTGGACAACCCCCAGTCTCAAATGCATTAGAGACCCTGCCCTGGTTCACCAAAGGCCAGCGCC<br>ACCCTCCACAGTAACGACGGCAGGGGTGACCCCACAGCCAGAGAGCCTCTCCCCTTCTGGAAA<br>AGAGCCCGCAGCTTCATCTCCCAGCTCAAACAACACAGCGGCCACAACAGCAGCTATTGTCCC<br>GGGCTCCCAGCTGATGCCTTCAAAATCACCTTCCACAGGAACCACAGAGATAAGCAGTCATGAG<br>TCCTCCCACGGCACCCCCTCTCAGACAACAGCCAAGAACTGGGAACTCACAGCATCCGCCTCC<br>CACCAGCCGCCAGGTGTGTATCCACAGGGCCACAGCGACACCACTGAGGGCAGAGGCAGCCT<br>GCTGACCTGCGGCGACGTCGAGGAGAACCCCGGGCCCATGGGGGCAGGTGCCACCGGCCGC<br>GCCATGGACGGGCCGCGCCTGCTGCTGTTGCTGCTTCTGGGGGTGTCCCTTGGAGGTGCCAA<br>GGAGGCATGCCCCACAGGCCTGTACACACACAGCGGTGAGTGCTGCAAAGCCTGCAACCTGG<br>GCGAGGGTGTGGCCCAGCCTTGTGGAGCCAACCAGACCGTGTGTGAGCCCTGCCTGGACAGC<br>GTGACGTTCTCCGACGTGGTGAGCGCGACCGAGCCGTGCAAGCCGTGCACCGAGTGCGTGGG<br>GCTCCAGAGCATGTCGGCGCCGTGCGTGGAGGCCGATGACGCCGTGTGCCGCTGCGCCTACG<br>GCTACTACCAGGATGAGACGACTGGGCGCTGCGAGGCGTGCCGCGTGTGCGAGGCGGGCTC<br>GGGCCTCGTGTTCTCCTGCCAGGACAAGCAGAACACCGTGTGCGAGGAGTGCCCCGACGGCA<br>CGTATTCCGACGAGGCCAACCACGTGGACCCGTGCCTGCCCTGCACCGTGTGCGAGGACACC<br>GAGCGCCAGCTCCGCGAGTGCACACGCTGGGCCGACGCCGAGTGCGAGGAGATCCCTGGCC<br>GTTGGATTACACGGTCCACACCCCCAGAGGGCTCGGACAGCACAGCCCCCAGCACCCAGGAG<br>CCTGAGGCACCTCCAGAACAAGACCTCATAGCCAGCACGGTGGCAGGTGTGGTGACCACAGTG<br>ATGGGCAGCTCCCAGCCCGTGGTGACCCGAGGCACCACCGACAACCTCATCCCTGTCTATTGC<br>TCCATCCTGGCTGCTGTGGTTGTGGGTCTTGTGGCCTACATAGCCTTCAAGAGGTGAAAAACC<br>AAAAGAACAAGAATTTCTTGGTAAGAAGCCGGGAACAGACAACAGAAGTCATGAAGCCCAAGTG<br>AAATCAAAGGGCCCGTTTAAACCCGCTGATCAGCCTCGACTGTGCCTTCTAGTTGCCAGCCATCTGTTGTTTG<br>CCCCTCCCCCGTGCCTTCCTTGACCCTGGAAGGTGCCACTCCCACTGTCCTTTCCTAATAAAAT<br>GAGGAAATTGCATCGCATTGTCTGAGTAGGTGTCATTCTATTCTGGGGGGTGGGTGGGGCAG<br>GACAGCAAGGGGGAGGATTGGGAAGACAATAGCAGGCATGCTGGGGATGCGGTGGGCTCTAT<br>GACTAGTGGCGAATTCGGCGCAGATCAAAGAGAGCCTGCGGGCAGAGCTCAGGGTGACAGGT<br>GCGGCCTCGGAGGCCCCGGGGCAGGGGTGAGCTGAGCCGGTCCTGGGGTGGGTGTCCCCTC<br>CTGCACAGGATCAGGAGCTCCAGGGTCGTAGGGCAGGGACCCCCAGCTCCAGTCCAGGGCT<br>CTGTCCTGCACCTGGGGAATGGTGACCGGCATCTCTGTCCTCTAGCTCTGGAAGCACCCCAGC<br>CCCTCTAGTCTGCCCTCACCCCTGACCCTGACCCTCCACCCTGACCCCGTCCTAACCCCTGAC<br>CTTTGTGCCCTTCCAGAGAGAAGGGCAGAAGTGCCCACAGCCCACCCCAGCCCCTCACCCAGG<br>CC |

TABLE 5-continued

Sequences referred to in example 2.

| 39 | Inserted matrice CD25 locus_IL12a_ 2A_IL12b (60 nucleotides upstream and downstream) | AGTGCTGGCTAGAAACCAAGTGCTTTACTGCATGCACATCATTTAGCACAGTTAGTTGCTGTTTA<br>TTATTCCTGTTCCACAGCTATTGTCTGCCATATAAAAACTTAGGCCAGGCACAGTGGCTCACACC<br>TGTAATCCCAGCACTTTGGAAGGCCGAGGCAGGCAGATCACAAGGTCAGGAGTTCGAGACCAG<br>CCTGGCCAACATAGCAAAACCCCATCTCTACTAAAAATACAAAAATTAGCCAGGCATGGTGGCG<br>TGTGCACTGGTTTAGAGTGAGGACCACATTTTTTTGGTGCCGTGTTACACATATGACCGTGACTT<br>TGTTACACCACTACAGGAGGAAGAGTAGAAGAACAATCGGTTCTGGCGTGAAACAGACTTTGAA<br>TTTTGACCTTCTCAAGTTGGCGGGAGACGTGGAGTCCAACCCAGGGCCCATGTGGCCCCTGG<br>GTCAGCCTCCCAGCCACCGCCCTCACCTGCCGCGGCCACAGGTCTGCATCCAGCGGCTCGCC<br>CTGTGTCCCTGCAGTGCCGGCTCAGCATGTGTCCAGCGCGCAGCCTCCTCCTTGTGGCTACCC<br>TGGTCCTCCTGGACCACCTCAGTTTGGCCAGAAACCTCCCCGTGGCCACTCCAGACCCAGGAA<br>TGTTCCCATGCCTTCACCACTCCCAAAACCTGCTGAGGGCCGTCAGCAACATGCTCCAGAAGG<br>CCAGACAAACTCTAGAATTTTACCCTTGCACTTCTGAAGAGATTGATCATGAAGATATCACAAAA<br>GATAAAACCAGCACAGTGGAGGCCTGTTTACCATTGGAATTAACCAAGAATGAGAGTTGCCTAA<br>ATTCCAGAGAGACCTCTTTCATAACTAATGGGAGTTGCCTGGCCTCCAGAAAGACCTCTTTTATG<br>ATGGCCCTGTGCCTTAGTAGTATTTATGAAGACTTGAAGATGTACCAGGTGGAGTTCAAGACCA<br>TGAATGCAAAGCTTCTGATGGATCCTAAGAGGCAGATCTTTCTAGATCAAACATGCTGGCAGTT<br>ATTGATGAGCTGATGCAGGCCCTGAATTTCAACAGTGAGACTGTGCCACAAAAATCCTCCCTTG<br>AAGAACCGGATTTTTATAAAACTAAAATCAAGCTCTGCATACTTCTTCATGCTTTCAGAATTCGGG<br>CAGTGACTATTGATAGAGTGATGAGCTATCTGAATGCTTCCGGAAGCGGAGCTACTAACTTCAG<br>CCTGCTGAAGCAGGCTGGAGACGTGGAGGAGAACCCTGGACCTATGTGTCACCAGCAGTTGGT<br>CATCTCTTGGTTTTCCCTGGTTTTTCTGGCATCTCCCCTCGTGGCCATATGGGAACTGAAGAAA<br>GATGTTTATGTCGTAGAATTGGATTGGTATCCGGATGCCCCTGGAGAAATGGTGGTCCTCACCT<br>GTGACACCCCTGAAGAAGATGGTATCACCTGGACCTTGGACCAGAGCAGTGAGGTCTTAGGCT<br>CTGGCAAAACCCTGACCATCCAAGTCAAAGAGTTTGGAGATGCTGGCCAGTACACCTGTCACAA<br>AGGAGGCGAGGTTCTAAGCCATTCGCTCCTGCTGCTTCACAAAAAGGAAGATGGAATTTGGTCC<br>ACTGATATTTTAAAGGACCAGAAAGAACCCAAAAATAAGACCTTTCTAAGATGCGAGGCCAAGAA<br>TTATTCTGGACGTTTCACCTGCTGGTGGCTGACGACAATCAGTACTGATTTGACATTCAGTGTCA<br>AAAGCAGCAGAGGCTCTTCTGACCCCCAAGGGGTGACGTGCGGAGCTGCTACACTCTCTGCAG<br>AGAGAGTCAGAGGGGACAACAAGGAGTATGAGTACTCAGTGGAGTGCCAGGAGGACAGTGCC<br>TGCCCAGCTGCTGAGGAGAGTCTGCCCATTGAGGTCATGGTGGATGCCGTTCACAAGCTCAAG<br>TATGAAAACTACACCAGCAGCTTCTTCATCAGGGACATCATCAAACCTGACCCACCCAAGAACTT<br>GCAGCTGAAGCCATTAAAGAATTCTCGGCAGGTGGAGGTCAGCTGGGAGTACCCTGACACCTG<br>GAGTACTCCACATTCCTACTTCTCCCTGACATTCTGCGTTCAGGTCCAGGGCAAGAGCAAGAGA<br>GAAAAGAAAGATAGAGTCTTCACGGACAAGACCTCAGCCACGGTCATCTGCCGCAAAAATGCCA<br>GCATTAGCGTGCGGGCCCAGGACCGCTACTATAGCTCATCTTGGAGCGAATGGGCATCTGTGC<br>CCTGCAGTGAGGGCAGAGGCAGCCTGCTGACCTGCGGCGACGTCGAGGAGAACCCCGGGCC<br>CATGGGGGCAGGTGCCACCGGCCGCGCCATGGACGGGCCGCGCCTGCTGCTGTTGCTGCTTC<br>TGGGGGTGTCCCTTGGAGGTGCCAAGGAGGCATGCCCCACAGGCCTGTACACACACAGCGGT<br>GAGTGCTGCAAAGCCTGCAACCTGGGCGAGGGTGTGGCCCAGCCTTGTGGAGCCAACCAGAC<br>CGTGTGTGAGCCCTGCCTGGACAGCGTGACGTTCTCCGACGTGGTGAGCGCGACCGAGCCGT<br>GCAAGCCGTGCACCGAGTGCGTGGGGCTCCAGAGCATGTCGGCGCCGTGCGTGGAGGCCGA<br>TGACGCCGTGTGCCGCTGCGCCTACGGCTACTACCAGGATGAGACGACTGGGCGCTGCGAGG<br>CGTCCGCGTGTGCGAGGCGGGCTCGGGCCTCGTGTTCTCCTGCCAGGACAAGCAGAACACC<br>GTGTGCGAGGAGTGCCCCGACGGCACGTATTCCGACGAGGCCAACCACGTGGACCCGTGCCT<br>GCCCCTGCACCGTGTGCGAGGACACCGAGCGCCAGCTCCGCGAGTGCACACGCTGGGCCGAC<br>GCCGAGTGCGAGGAGATCCCTGGCCGTTGGATTACACGGTCCACACCCCCAGAGGGCTCGGA<br>CAGCACAGCCCCCAGCACCCAGGAGCCTGAGGCACCTCCAGAACAAGACCTCATAGCCAGCA<br>CGGTGGCAGGTGTGGTGACCACAGTGATGGGCAGCTCCCAGCCCGTGGTGACCCGAGGCACC<br>ACCGACAACCTCATCCCTGTCTATTGCTCCATCCTGGCTGCTGTGGTTGTGGGTCTTGTGGCCT<br>ACATAGCCTTCAAGAGGTGAAAAACCAAAAGAACAAGAATTTCTTGGTAAGAAGCCGGGAACAG<br>ACAACAGAAGTCATGAAGCCCAAGTGAAATCAAAGGTGCTAAATGGTCGCCCAGGAGACATCC<br>GTTGTGCTTGCCTGCGTTTTGGAAGCTCTGAAGTCACATCACAGGACACGGGGCAGTGGCAAC<br>CTTGTCTCTATGCCAGCTCAGTCCCATCAGAGAGCGAGCGCTACCCACTTCTAAATAGCAATTT<br>CGCCGTTGAAGAGGAAGGGCAAAACCACTAGAACTCTCCATCTTATTTTCATGTATATGTGTTCA<br>TGAATGGTATGGAACTCTCTCCACCCTATATGTAGTATAAAGAAAAGTAGGTT |
| 40 | Inserted matrice PD1 locus_IL12a_ 2A_IL12b (60 nucleotides upstream and downstream) | GGTGGCCGGGAGGCTTTGTGGGGCCACCCAGCCCCTTCCTCACCTCTCTCCATCTCTCAGAC<br>TCCCCAGACAGGCCCTGGAACCCCCCACCTTCTCCCCAGCCCTGCTCGTGGTGACCGAAGG<br>GGACAACGCCACCTTCACCTGCAGCTTCTCCAACACATCGGAGAGCTTCGTGCTAAACTGGTAC<br>CGCATGAGCCCCAGCAACCAGACGGACAAGCTGGCCGCCTTCCCGGAGGACCGCAGCCAGCC<br>CGGCCAGGACTGCCGCTTCCGTGTCACACAACTGCCCAACGGGCGTGACTTCCACATGAGCGT<br>GGTCAGGGCCCGGCGCAATGACAGCGGCACCTACCTCTGTGGGGCCGGTTCTGGCGTGAAAC<br>AGACTTTGAATTTTGACCTTCTCAAGTTGGCGGGAGACGTGGAGTCCAACCCAGGGCCCATGT<br>GGCCCCTGGGTCAGCCTCCCAGCCACCGCCCTCACCTGCCGCGGCCACAGGTCTGCATCCA<br>GCGGCTCGCCCTGTGTCCCTGCAGTGCCGGCTCAGCATGTGTCCAGCGCGCAGCCTCCTCCTT<br>GTGGCTACCCTGGTCCTCCTGGACCACCTCAGTTTGGCCAGAAACCTCCCCGTGGCCACTCCA<br>GACCCAGGAATGTTCCCATGCCTTCACCACTCCCAAAACCTGCTGAGGGCCGTCAGCAACATG<br>CTCCAGAAGGCCAGACAAACTCTAGAATTTTACCCTTGCACTTCTGAAGAGATTGATCATGAAGA<br>TATCACAAAAGATAAAACCAGCACAGTGGAGGCCTGTTTACCATTGGAATTAACCAAGAATGAG<br>AGTTGCCTAAATTCCAGAGAGACCTCTTTCATAACTAATGGGAGTTGCCTGGCCTCCAGAAAGA<br>CCTCTTTTATGATGGCCCTGTGCCTTAGTAGTATTTATGAAGACTTGAAGATGTACCAGGTGGAG<br>TTCAAGACCATGAATGCAAAGCTTCTGATGGATCCTAAGAGGCAGATCTTTCTAGATCAAACAT<br>GCTGGCAGTTATTGATGAGCTGATGCAGGCCCTGAATTTCAACAGTGAGACTGTGCCACAAAAA<br>TCCTCCCTTGAAGAACCGGATTTTTATAAAACTAAATCAAGCTCTGCATACTTCTTCATGCTTTC<br>AGAATTCGGGCAGTGACTATTGATAGAGTGATGAGCTATCTGAATGCTTCCGGAAGCGGAGCTA<br>CTAACTTCAGCCTGCTGAAGCAGGCTGGAGACGTGGAGGAGAACCCTGGACCTATGTGTCACC<br>AGCAGTTGGTCATCTCTTGGTTTTCCCTGGTTTTTCTGGCATCTCCCCTCGTGGCCATATGGGAA |

TABLE 5-continued

Sequences referred to in example 2.

| | | |
|---|---|---|
| | | CTGAAGAAAGATGTTTATGTCGTAGAATTGGATTGGTATCCGGATGCCCCTGGAGAAATGGTGG<br>TCCTCACCTGTGACACCCCTGAAGAAGATGGTATCACCTGGACCTTGGACCAGAGCAGTGAGG<br>TCTTAGGCTCTGGCAAAACCCTGACCATCCAAGTCAAAGAGTTTGGAGATGCTGGCCAGTACAC<br>CTGTCACAAAGGAGGCGAGGTTCTAAGCCATTCGCTCCTGCTGCTTCACAAAAAGGAAGATGGA<br>ATTTGGTCCACTGATATTTTAAAGGACCAGAAAGAACCCAAAAATAAGACCTTTCTAAGATGCGA<br>GGCCAAGAATTATTCTGGACGTTTCACCTGCTGGTGGCTGACGACAATCAGTACTGATTTTGACA<br>TTCAGTGTCAAAAGCAGCAGAGGCTCTTCTGACCCCCAAGGGGTGACGTGCGGAGCTGCTACA<br>CTCTCTGCAGAGAGAGTCAGAGGGGACAACAAGGAGTATGAGTACTCAGTGGAGTGCCAGGAG<br>GACAGTGCCTGCCCAGCTGCTGAGGAGAGTCTGCCCATTGAGGTCATGGTGGATGCCGTTCAC<br>AAGCTCAAGTATGAAAACTACACCAGCAGCTTCTTCATCAGGGACATCATCAAACCTGACCCAC<br>CCAAGAACTTGCAGCTGAAGCCATTAAAGAATTCTCGGCAGGTGGAGGTCAGCTGGGAGTACC<br>CTGACACCTGGAGTACTCCACATTCCTACTTCTCCCTGACATTCTGCGTTCAGGTCCAGGGCAA<br>GAGCAAGAGAGAAAGAAAGATAGAGTCTTCACGGACAAGACCTCAGCCACGGTCATCTGCCG<br>CAAAAATGCCAGCATTAGCGTGCGGGCCCAGGACCGCTACTATAGCTCATCTTGGAGCGAATG<br>GGCATCTGTGCCCTGCAGTGAGGGCAGAGGCAGCCTGCTGACCTGCGGCGACGTCGAGGAGA<br>ACCCCGGGCCCATGGGGGCAGGTGCCACCGGCCGCGCCATGGACGGGCCGCGCCTGCTGCT<br>GTTGCTGCTTCTGGGGGTGTCCCTTGGAGGTGCCAAGGAGGCATGCCCCACAGGCCTGTACAC<br>ACACAGCGGTGAGTGCTGCAAAGCCTGCAACCTGGGCGAGGGTGTGGCCCAGCCTTGTGGAG<br>CCAACCAGACCGTGTGTGAGCCCTGCCTGGACAGCGTGACGTTCTCCGACGTGGTGAGCGCG<br>ACCGAGCCGTGCAAGCCGTGCACCGAGTGCGTGGGGCTCCAGAGCATGTCGGCGCCGTCGT<br>GGAGGCCGATGACGCCGTGTGCCGCTGCGCCTACGGCTACTACCAGGATGAGACGACTGGGC<br>GCTGCGAGGCGTGCCGCGTGTGCGAGGCGGGCTCGGGCCTCGTGTTCTCCTGCCAGGACAAG<br>CAGAACACCGTGTGCGAGGAGTGCCCCGACGGCACGTATTCCGACGAGGCCAACCACGTGGA<br>CCCGTGCCTGCCCTGCACCGTGTGCGAGGACACCGAGCGCCAGCTCCGCGAGTGCACACGCT<br>GGGCCGACGCCGAGTGCGAGGAGATCCCTGGCCGTTGGATTACACGGTCCACACCCCCAGAG<br>GGCTCGGACAGCACAGCCCCAGCACCCAGGAGCCTGAGGCACCTCCAGAACAAGACCTCAT<br>AGCCAGCACGGTGGCAGGTGTGGTGACCAGTGATGGGCAGCTCCCAGCCCGTGGTGACCC<br>GAGGCACCACCGACAACCTCATCCCTGTCTATTGCTCCATCCTGGCTGCTGTGGTTGTGGGTCT<br>TGTGGCCTACATAGCCTTCAAGAGGTGATCTAGAGGGCCCGTTTAAACCCGCTGATCAGCCTC<br>GACTGTGCCTTCTAGTTGCCAGCCATCTGTTGTTTGCCCCTCCCCCGTGCCTTCCTTGACCCTG<br>GAAGGTGCCACTCCCACTGTCCTTTCCTAATAAAATGAGGAAATTGCATCGCATTGTCTGAGTA<br>GGTGTCATTCTATTCTGGGGGGTGGGTGGGCAGGACAGCAAGGGGGAGGATTGGGAAGAC<br>AATAGCAGGCATGCTGGGGATGCGGTGGGCTCTATGACTAGTGGCGAATTCGGCGCAGATCAA<br>AGAGAGCCTGCGGGCAGAGCTCAGGGTGACAGGTGCGGCCTCGGAGGCCCCGGGGCAGGGG<br>TGAGCTGAGCCGGTCCTGGGGTGGGTGTCCCCTCCTGCACAGGATCAGGAGCTCCAGGGTCG<br>TAGGGCAGGGACCCCCCAGCTCCAGTCCAGGGCTCTGTCCTGCACCTGGGGAATGGTGACCG<br>GCATCTCTGTCCTCTAGCTCTGGAAGCACCCCAGCCCCTCTAGTCTGCCCTCACCCCTGACCCT<br>GACCCTCCACCCTGACCCGTCCTAACCCTGACCTTTGTGCCCTTCCAGAGAGAAGGGCAGA<br>AGTGCCCACAGCCCACCCCAGCCCCTCACCCAGGCC |
| 41 | upstream<br>TRAC locus<br>polynucleotide<br>sequence | ATGAGATCATGTCCTAACCCTGATCCTCTTGTCCCACAGATATCCAGAACCCTGACC<br>CTG |
| 42 | downstream<br>TRAC locus<br>polynucleotide<br>sequence | GAAACAGTGAGCCTTGTTCTGGCAGTCCAGAGAATGACACGGGAAAAAAGCAGATG<br>AAGA |
| 43 | upstream<br>CD25 locus<br>polynucleotide<br>sequence | AGTGCTGGCTAGAAACCAAGTGCTTTACTGCATGCACATCATTTAGCACAGTTAGTT<br>GCT |
| 44 | downstream<br>CD25 locus<br>polynucleotide<br>sequence | GAATGGTATGGAACTCTCTCCACCCTATATGTAGTATAAAGAAAAGTAGGTT |
| 45 | upstream PD1<br>locus<br>polynucleotide<br>sequence | GGTGGCCGGGGAGGCTTTGTGGGGCCACCCAGCCCCTTCCTCACCTCTCTCCATCT<br>CTCA |
| 46 | downstream<br>PD1 locus<br>polynucleotide<br>sequence | TGCCCTTCCAGAGAGAAGGGCAGAAGTGCCCACAGCCCACCCCAGCCCCTCACCC<br>AGGCC |
| 47 | IL-12a<br>polynucleotide | ATGTGGCCCCCTGGGTCAGCCTCCCAGCCACCGCCCTCACCTGCCGCGGCCACAG<br>GTCTGCATCCAGCGGCTCGCCCTGTGTCCCTGCAGTGCCGGCTCAGCATGTGTCCA<br>GCGCGCAGCCTCCTCCTTGTGGCTACCCTGGTCCTCCTGGACCACCTCAGTTTGGC<br>CAGAAACCTCCCCGTGGCCACTCCAGACCCAGGAATGTTCCCATGCCTTCACCACT<br>CCCAAAACCTGCTGAGGGCCGTCAGCAACATGCTCCAGAAGGCCAGACAAACTCTA<br>GAATTTTACCCTTGCACTTCTGAAGAGATTGATCATGAAGATATCACAAAAGATAAA<br>CCAGCACAGTGGAGGCCTGTTTACCATTGGAATTAACCAAGAATGAGAGTTGCCTAA<br>ATTCCAGAGAGACCTCTTTCATAACTAATGGGAGTTGCCTGGCCTCCAGAAAGACCT |

TABLE 5-continued

Sequences referred to in example 2.

|  |  |  |
|---|---|---|
|  |  | CTTTTATGATGGCCCTGTGCCTTAGTAGTATTTATGAAGACTTGAAGATGTACCAGGT<br>GGAGTTCAAGACCATGAATGCAAAGCTTCTGATGGATCCTAAGAGGCAGATCTTTCT<br>AGATCAAAACATGCTGGCAGTTATTGATGAGCTGATGCAGGCCCTGAATTTCAACAG<br>TGAGACTGTGCCACAAAAATCCTCCCTTGAAGAACCGGATTTTTATAAAACTAAAATC<br>AAGCTCTGCATACTTCTTCATGCTTTCAGAATTCGGGCAGTGACTATTGATAGAGTGA<br>TGAGCTATCTGAATGCTTCC |
| 48 | IL12b<br>polynucleotide | ATGTGTCACCAGCAGTTGGTCATCTCTTGGTTTTCCCTGGTTTTTCTGGCATCTCCCC<br>TCGTGGCCATATGGGAACTGAAGAAAGATGTTTATGTCGTAGAATTGGATTGGTATC<br>CGGATGCCCCTGGAGAAATGGTGGTCCTCACCTGTGACACCCCTGAAGAAGATGGT<br>ATCACCTGGACCTTGGACCAGAGCAGTGAGGTCTTAGGCTCTGGCAAAACCCTGAC<br>CATCCAAGTCAAAGAGTTTGGAGATGCTGGCCAGTACACCTGTCACAAAGGAGGCG<br>AGGTTCTAAGCCATTCGCTCCTGCTGCTTCACAAAAAGGAAGATGGAATTTGGTCCA<br>CTGATATTTTAAAGGACCAGAAAGAACCCAAAAATAAGACCTTTCTAAGATGCGAGG<br>CCAAGAATTATTCTGGACGTTTCACCTGCTGGTGGCTGACGACAATCAGTACTGATT<br>TGACATTCAGTGTCAAAAGCAGCAGAGGCTCTTCTGACCCCCAAGGGGTGACGTGC<br>GGAGCTGCTACACTCTCTGCAGAGAGAGTCAGAGGGGACAACAAGGAGTATGAGTA<br>CTCAGTGGAGTGCCAGGAGGACAGTGCCTGCCCAGCTGCTGAGGAGAGTCTGCCC<br>ATTGAGGTCATGGTGGATGCCGTTCACAAGCTCAAGTATGAAAACTACACCAGCAGC<br>TTCTTCATCAGGGACATCATCAAACCTGACCCACCCAAGAACTTGCAGCTGAAGCCA<br>TTAAAGAATTCTCGGCAGGTGGAGGTCAGCTGGGAGTACCCTGACACCTGGAGTAC<br>TCCACATTCCTACTTCTCCCTGACATTCTGCGTTCAGGTCCAGGGCAAGAGCAAGAG<br>AGAAAAGAAAGATAGAGTCTTCACGGACAAGACCTCAGCCACGGTCATCTGCCGCA<br>AAAATGCCAGCATTAGCGTGCGGGCCCAGGACCGCTACTATAGCTCATCTTGGAGC<br>GAATGGGCATCTGTGCCCTGCAGT |
| 49 | IL15<br>polynucleotide | GGCATTCATGTCTTCATTTTGGGCTGTTTCAGTGCAGGGCTTCCTAAAACAGAAGCC<br>AACTGGGTGAATGTAATAAGTGATTTGAAAAAAATTGAAGATCTTATTCAATCTATGC<br>ATATTGATGCTACTTTATATACGGAAAGTGATGTTCACCCCAGTTGCAAAGTAACAGC<br>AATGAAGTGCTTTCTCTTGGAGTTACAAGTTATTTCACTTGAGTCCGGAGATGCAAGT<br>ATTCATGATACAGTAGAAAATCTGATCATCCTAGCAAACAACAGTTTGTCTTCTAATG<br>GGAATGTAACAGAATCTGGATGCAAAGAATGTGAGGAACTGGAGGAAAAAAATATTA<br>AAGAATTTTTGCAGAGTTTTGTACATATTGTCCAAATGTTCATCAACACTTCT |
| 50 | sIL15ra<br>polynucleotide | ATCACGTGCCCTCCCCCCATGTCCGTGGAACACGCAGACATCTGGGTCAAGAGCTA<br>CAGCTTGTACTCCAGGGAGCGGTACATTTGTAACTCTGGTTTCAAGCGTAAAGCCGG<br>CACGTCCAGCCTGACGGAGTGCGTGTTGAACAAGGCCACGAATGTCGCCCACTGGA<br>CAACCCCCAGTCTCAAATGCATTAGAGACCCTGCCCTGGTTCACCAAAGGCCAGCG<br>CCACCCCTCCACAGTAACGACGGCAGGGGTGACCCCACAGCCAGAGAGCCTCTCCC<br>CTTCTGGAAAAGAGCCCGCAGCTTCATCTCCCAGCTCAAACAACACAGCGGCCACA<br>ACAGCAGCTATTGTCCCGGGCTCCCAGCTGATGCCTTCAAAATCACCTTCCACAGGA<br>ACCACAGAGATAAGCAGTCATGAGTCCTCCCACGGCACCCCCTCTCAGACAACAGC<br>CAAGAACTGGGAACTCACAGCATCCGCCTCCCACCAGCCGCCAGGTGTGTATCCAC<br>AGGGCCACAGCGACACCACT |
| 51 | soluble<br>GP130<br>polynucleotide | ATGCTGACACTGCAGACTTGGCTGGTGCAGGCACTGTTTATTTTTCTGACTACTGAA<br>TCAACTGGCGAACTGCTGGACCCTTGTGGCTACATCAGCCCTGAGTCCCCAGTGGT<br>GCAGCTGCACAGCAACTTCACCGCCGTGTGCGTGCTGAAGGAGAAGTGTATGGACT<br>ACTTTCACGTGAACGCCAATTATATCGTGTGGAAAACCAACCACTTCACAATCCCCAA<br>GGAGCAGTACACCATCATCAATAGGACAGCCAGCTCCGTGACCTTTACAGACATCG<br>CCTCCCTGAACATCCAGCTGACCTGCAATATCCTGACATTCGGCCAGCTGGAGCAG<br>AACGTGTATGGCATCACCATCATCTCTGGCTGCCCCCTGAGAAGCCTAAGAACCTG<br>AGCTGCATCGTGAATGAGGGCAAGAAGATGCGGTGTGAGTGGGACGGCGGCAGAG<br>AGACACACCTGGAGACAAACTTCACCCTGAAGTCCGAGTGGGCCACACACAAGTTT<br>GCCGACTGCAAGGCCAAGCGCGATACCCCAACATCCTGTACCGTGGATTACTCTAC<br>AGTGTATTTTGTGAACATCGAAGTGTGGGTGGAGGCCGAGAATGCCCTGGGCAGG<br>TGACCTCCGACCACATCAACTTCGATCCCGTGTACAAGGTGAAGCCTAACCCACCCC<br>ACAATCTGAGCGTGATCAATTCCGAGGAGCTGTCTAGCATCCTGAAGCTGACCTGGA<br>CAAACCCATCTATCAAGAGCGTGATCATCCTGAAGTACAATATCCAGTATCGGACCA<br>AGGACGCCTCCACATGGAGCCAGATCCCTCCAGAGGATACCGCCAGCACAAGATCC<br>TCTTTCACCGTGCAGGACCTGAAGCCCTTCACAGAGTACGTGTTTCGGATCAGATGT<br>ATGAAGGAGGACGGCAAGGGCTACTGGAGCGATTGGTCCGAGGAGGCCAGCGGCA<br>TCACCTATGAGGACAGGCCTTCTAAGGCCCCCAGCTTCTGGTACAAGATCGATCCAT<br>CCCACACCCAGGGCTATCGCACAGTGCAGCTGGTGTGGAAAACCCTGCCCCCTTTC<br>GAGGCCAACGGCAAGATCCTGGACTACGAGGTGACCCTGACACGGTGGAAGTCCC<br>ACCTGCAGAACTATACCGTGAATGCCACCAAGCTGACAGTGAACCTGACAAATGATC<br>GGTACCTGGCCACCCTGACAGTGAGAAACCTGGTGGGCAAGTCTGACGCCGCCGT<br>GCTGACCATCCCTGCCTGCGATTTCCAGGCCACACACCCAGTGATGGACCTGAAGG<br>CCTTTCCCAAGGATAATATGCTGTGGGTGGAGTGGACCACACCTAGAGAGTCCGTG<br>AAGAAGTACATCCTGGAGTGGTGCGTGCTGTCTGACAAGGCCCCATGTATCACCGA<br>CTGGCAGCAGGAGGATGGCACCGTGCACAGGACATATCTGCGCGGCAACCTGGCC<br>GAGTCTAAGTGTTACCTGATCACCGTGACACCCGTGTATGCAGACGGACCAGGCTC<br>TCCTGAGAGCATCAAGGCCTACCTGAAGCAGGCACCACCAAGACAAGGGACCAACCG<br>TGCGGACAAAGAAGGTCGGCAAGAATGAGGCCGTGCTGGAGTGGGACCAGCTGCC<br>TGTGGATGTGCAGAACGCTTCATCAGGAATTACACCATCTTTTATCGCACAATCATC<br>GGCAACGAGACAGCCGTGAATGTGGACAGCTCCCACACCGAGTATACACTGTCTAG<br>CCTGACCTCCGATACACTGTACATGGTGAGGATGGCCGCCTATACAGACGAGGGCG<br>GCAAGGATGGCCCCGAGTTT |

TABLE 5-continued

Sequences referred to in example 2.

| 52 | IgE signal sequence | GGTACCGGGTCCGCCACCATGGACTGGACCTGGATTCTGTTCCTCGTGGCTGCTGC<br>TACAAGAGTGCACAGC |
| --- | --- | --- |
| 53 | F2A | GGTTCTGGCGTGAAACAGACTTTGAATTTTGACCTTCTCAAGTTGGCGGGAGACGTG<br>GAGTCCAACCCAGGGCCC |
| 54 | P2A | GGAAGCGGAGCTACTAACTTCAGCCTGCTGAAGCAGGCTGGAGACGTGGAGGAGA<br>ACCCTGGACCT |
| 55 | T2A | GAGGGCAGAGGCAGCCTGCTGACCTGCGGCGACGTCGAGGAGAACCCCGGGCCC |
| 56 | LNGFR | ATGGGGGCAGGTGCCACCGGCCGCGCCATGGACGGGCCGCGCCTGCTGCTGTTG<br>CTGCTTCTGGGGGTGTCCCTTGGAGGTGCCAAGGAGGCATGCCCCACAGGCCTGT<br>ACACACACAGCGGTGAGTGCTGCAAAGCCTGCAACCTGGGCGAGGGTGTGGCCCA<br>GCCTTGTGGAGCCAACCAGACCGTGTGTGAGCCCTGCCTGGACAGCGTGACGTTCT<br>CCGACGTGGTGAGCGCGACCGAGCCGTGCAAGCCGTGCACCGAGTGCGTGGGGC<br>TCCAGAGCATGTCGGCGCCGTGCGTGGAGGCCGATGACGCCGTGTGCCGCTGCGC<br>CTACGGCTACTACCAGGATGAGACGACTGGGCGCTGCGAGGCGTGCCGCGTGTGC<br>GAGGCGGGCTCGGGCCTCGTGTTCTCCTGCCAGGACAAGCAGAACACCGTGTGCG<br>AGGAGTGCCCCGACGGCACGTATTCCGACGAGGCCAACCACGTGGACCCGTGCCT<br>GCCCTGCACCGTGTGCGAGGACACCGAGCGCCAGCTCCGCGAGTGCACACGCTGG<br>GCCGACGCCGAGTGCGAGGAGATCCCTGGCCGTTGGATTACACGGTCCACACCCC<br>CAGAGGGCTCGGACAGCACAGCCCCCAGCACCCAGGAGCCTGAGGCACCTCCAGA<br>ACAAGACCTCATAGCCAGCACGGTGGCAGGTGTGGTGACCACAGTGATGGGCAGCT<br>CCCAGCCCGTGGTGACCCGAGGCACCACCGACAACCTCATCCCTGTCTATTGCTCC<br>ATCCTGGCTGCTGTGGTTGTGGGTCTTGTGGCCTACATAGCCTTCAAGAGGTGA |
| 57 | IL-12a polypeptide | MWPPGSASQPPPSPAAATGLHPAARPVSLQCRLSMCPARSLLLVATLVLLDHLSARNL<br>PVATPDPGMFPCLHHSQNLLRAVSNMLQKARQTLEFYPCTSEEIDHEDITKDKTSTVEA<br>CLPLELTKNESCLNSRETSFITNGSCLASRKTSFMMALCLSSIYEDLKMYQVEFKTMNAK<br>LLMDPKRQIFLDQNMLAVIDELMQALNFNSETVPQKSSLEEPDFYKTKIKLCILLHAFRIRA<br>VTIDRVMSYLNAS |
| 58 | IL12b polypeptide | MCHQQLVISWFSLVFLASPLVAIWELKKDVYVVELDWYPDAPGEMVVLTCDTPEEDGIT<br>WTLDQSSEVLGSGKTLTIQVKEFGDAGQYTCHKGGEVLSHSLLLLHKKEDGIWSTDILKD<br>QKEPKNKTFLRCEAKNYSGRFTCWWLTTISTDLTFSVKSSRGSSDPQGVTCGAATLSAE<br>RVRGDNKEYEYSVECQEDSACPAAEESLPIEVMVDAVHKLKYENYTSSFFIRDIIKPDPP<br>KNLQLKPLKNSRQVEVSWEYPDTWSTPHSYFSLTFCVQVQGKSKREKKDRVFTDKTSA<br>TVICRKNASISVRAQDRYYSSSWSEWASVPCS |
| 59 | IL15 polypeptide | GIHVFILGCFSAGLPKTEANWVNVISDLKKIEDLIQSMHIDATLYTESDVHPSCKVTAMKC<br>FLLELQVISLESGDASIHDTVENLIILANNSLSSNGNVTESGCKECEELEEKNIKEFLQSFV<br>HIVQMFINTS |
| 60 | sIL15ra polypeptide | ITCPPPMSVEHADIWVKSYSLYSRERYICNSGFKRKAGTSSLTECVLNKATNVAHWTTPS<br>LKCIRDPALVHQRPAPPSTVTTAGVTPQPESLSPSGKEPAASSPSSNNTAATTAAIVPGS<br>QLMPSKSPSTGTTEISSHESSHGTPSQTTAKNWELTASASHQPPGVYPQGHSDTT |
| 61 | soluble gp130 | MLTLQTWLVQALFIFLTTESTGELLDPCGYISPESPVVQLHSNFTAVCVLKEKCMDYFHV<br>NANYIVWKTNHFTIPKEQYTIINRTASSVTFTDIASLNIQLTCNILTFGQLEQNVYGITIISGL<br>PPEKPKNLSCIVNEGKKMRCEWDGGRETHLETNFTLKSEWATHKFADCKAKRDTPTSC<br>TVDYSTVYFVNIEVWVEAENALGKVTSDHINFDPVYKVKPNPPHNLSVINSEELSSILKLT<br>WTNPSIKSVIILKYNIQYRTKDASTWSQIPPEDTASTRSSFTVQDLKPFTEYVFRIRCMKE<br>DGKGYWSDWSEEASGITYEDRPSKAPSFWYKIDPSHTQGYRTVQLVWKTLPPFEANGK<br>ILDYEVTLTRWKSHLQNYTVNATKLTVNLTNDRYLATLTVRNLVGKSDAAVLTIPACDFQA<br>THPVMDLKAFPKDNMLWVEWTTPRESVKKYILEWCVLSDKAPCITDWQQEDGTVHRTY<br>LRGNLAESKCYLITVTPVYADGPGSPESIKAYLKQAPPSKGPTVRTKKVGKNEAVLEWD<br>QLPVDVQNGFIRNYTIFYRTIIGNETAVNVDSSHTEYTLSSLTSDTLYMVRMAAYTDEGG<br>KDGPEF |
| 62 | soluble gp130 fused to a Fc | MLTLQTWLVQALFIFLTTESTGELLDPCGYISPESPVVQLHSNFTAVCVLKEKCMDYFHV<br>NANYIVWKTNHFTIPKEQYTIINRTASSVTFTDIASLNIQLTCNILTFGQLEQNVYGITIISGL<br>PPEKPKNLSCIVNEGKKMRCEWDGGRETHLETNFTLKSEWATHKFADCKAKRDTPTSC<br>TVDYSTVYFVNIEVWVEAENALGKVTSDHINFDPVYKVKPNPPHNLSVINSEELSSILKLT<br>WTNPSIKSVIILKYNIQYRTKDASTWSQIPPEDTASTRSSFTVQDLKPFTEYVFRIRCMKE<br>DGKGYWSDWSEEASGITYEDRPSKAPSFWYKIDPSHTQGYRTVQLVWKTLPPFEANGK<br>ILDYEVTLTRWKSHLQNYTVNATKLTVNLTNDRYLATLTVRNLVGKSDAAVLTIPACDFQA<br>THPVMDLKAFPKDNMLWVEWTTPRESVKKYILEWCVLSDKAPCITDWQQEDGTVHRTY<br>LRGNLAESKCYLITVTPVYADGPGSPESIKAYLKQAPPSKGPTVRTKKVGKNEAVLEWD<br>QLPVDVQNGFIRNYTIFYRTIIGNETAVNVDSSHTEYTLSSLTSDTLYMVRMAAYTDEGG<br>KDGPEFRSCDKTHTCPPCPAPEAEGGPSVFLFPPKPKDTLMISRTPEVTCVVVDVSHED<br>PEVKFNWYVDGVEVHNAKTKPREEQYNSTYRVVSVLTVLHQDWLNGKEYKCKVSNKAL<br>PAPIEKTISKAKGQPREPQVYTLPPSREEMTKNQVSLTCLVKGFYPSDIAVEWESNGQP<br>ENNYKTTPPVLDSDGSFFLYSKLTVDKSRWQQGNVFSCSVMHEALHNHYTQKSLSLSP<br>GK |

TABLE 5-continued

Sequences referred to in example 2.

| 63 | Matrice TRAC locus_CubiCAR CD22 pCLS30056 full sequence | GTGGCACTTTTCGGGGAAATGTGCGCGGAACCCCTATTTGTTTATTTTTCTAAATACA TTCAAATATGTATCCGCTCATGAGACAATAACCCTGATAAATGCTTCAATAATATTGAA AAAGGAAGAGTATGAGTATTCAACATTTCCGTGTCGCCCTTATTCCCTTTTTTGCGGC ATTTTGCCTTCCTGTTTTTGCTCACCCAGAAACGCTGGTGAAAGTAAAAGATGCTGAA GATCAGTTGGGTGCACGAGTGGGTTACATCGAACTGGATCTCAACAGCGGTAAGAT CCTTGAGAGTTTTCGCCCCGAAGAACGTTTTCCAATGATGAGCACTTTTAAAGTTCTG CTATGTGGCGCGGTATTATCCCGTATTGACGCCGGGCAAGAGCAACTCGGTCGCCG CATACACTATTCTCAGAATGACTTGGTTGAGTACTCACCAGTCACAGAAAAGCATCTT ACGGATGGCATGACAGTAAGAGAATTATGCAGTGCTGCCATAACCATGAGTGATAAC ACTGCGGCCAACTTACTTCTGACAACGATCGGAGGACCGAAGGAGCTAACCGCTTT TTTGCACAACATGGGGGATCATGTAACTCGCCTTGATCGTTGGGAACCGGAGCTGA ATGAAGCCATACCAAACGACGAGCGTGACACCACGATGCCTGTAGCAATGGCAACA ACGTTGCGCAAACTATTAACTGGCGAACTACTTACTCTAGCTTCCCGGCAACAATTAA TAGACTGGATGGAGGCGGATAAAGTTGCAGGACCACTTCTGCGCTCGGCCCTTCCG GCTGGCTGGTTTATTGCTGATAAATCTGGAGCCGGTGAGCGTGGTTCTCGCGGTAT CATTGCAGCACTGGGGCCAGATGGTAAGCCCTCCCGTATCGTAGTTATCTACACGA CGGGGAGTCAGGCAACTATGGATGAACGAAATAGACAGATCGCTGAGATAGGTGCC TCACTGATTAAGCATTGGTAACTGTCAGACCAAGTTTACTCATATATACTTTAGATTGA TTTAAAACTTCATTTTTAATTTAAAAGGATCTAGGTGAAGATCCTTTTTGATAATCTCAT GACCAAAATCCCTTAACGTGAGTTTTCGTTCCACTGAGCGTCAGACCCCGTAGAAAA GATCAAAGGATCTTCTTGAGATCCTTTTTTTCTGCGCGTAATCTGCTGCTTGCAAACA AAAAAACCACCGCTACCAGCGGTGGTTTGTTTGCCGGATCAAGAGCTACCAACTCTT TTTCCGAAGGTAACTGGCTTCAGCAGAGCGCAGATACCAAATACTGTTCTTCTAGTG TAGCCGTAGTTAGGCCACCACTTCAAGAACTCTGTAGCACCGCCTACATACCTCGCT CTGCTAATCCTGTTACCAGTGGCTGCTGCCAGTGGCGATAAGTCGTGTCTTACCGG GTTGGACTCAAGACGATAGTTACCGGATAAGGCGCAGCGGTCGGGCTGAACGGGG GGTTCGTGCACACAGCCCAGCTTGGAGCGAACGACCTACACCGAACTGAGATACCT ACAGCGTGAGCTATGAGAAAGCGCCACGCTTCCCGAAGGGAGAAAGGCGGACAGG TATCCGGTAAGCGGCAGGGTCGGAACAGGAGAGCGCACGAGGGAGCTTCCAGGGG GAAACGCCTGGTATCTTTATAGTCCTGTCGGGTTTCGCCACCTCTGACTTGAGCGTC GATTTTTGTGATGCTCGTCAGGGGGCGGAGCCTATGGAAAAACGCCAGCAACGCG GCCTTTTTACGGTTCCTGGCCTTTTGCTGGCCTTTTGCTCACATGGTCTTTCCTGCGT TATCCCCTGATTCTGTGGATAACCGTATTACCGCCTTTGAGTGAGCTGATACCGCTC GCCGCAGCCGAACGACCGAGCGCAGCGAGTCAGTGAGCGAGGAAGCGGAGAGCG CCCAATACGCAAACCGCCTCTCCCCGCGCGTTGGCCGATTCATTAATGCAGCTGGC ACGACAGGTTTCCCGACTGGAAAGCGGGCAGTGAGCGCAACGCAATTAATGTGAGT TAGCTCACTCATTAGGCACCCCAGGCTTTACACTTTATGCTTCCGGCTCGTATGTTGT GTGGAATTGTGAGCGGATAACAATTTCACACAGGAAACAGCTATGACCATGATTACG CCAAGCGCGTCAATTAACCCTCACTAAAGGGAACAAAAGCTGTTAATTAATTGCTGG GCCTTTTTCCCATGCCTGCCTTTACTCTGCCAGAGTTATATTGCTGGGGTTTTGAAGA AGATCCTATTAAATAAAAGAATAAGCAGTATTATTAAGTAGCCCTGCATTTCAGGTTT CCTTGAGTGGCAGGCCAGGCCTGGCCGTGAACGTTCACTGAAATCATGGCCTCTTG GCCAAGATTGATAGCTTGTGCCTGTCCCTGAGTCCCAGTCCATCACGAGCAGCTGG TTTCTAAGATGCTATTTCCCGTATAAAGCATGAGACCGTGACTTGCCAGCCCCACAG AGCCCCGCCCTTGTCCATCACTGGCATCTGGACTCCAGCCTGGGTTGGGGCAAAGA GGGAAATGAGATCATGTCCTAACCCTGATCCTCTTGTCCCACAGATATCCAGTACCC CTACGACGTGCCCGACTACGCCTCCGGTGAGGGCAGAGGAAGTCTTCTAACATGCG GTGACGTGGAGGAGAATCCGGGCCCCGGATCCGCTCTGCCCGTCACCGCTCTGCT GCTGCCACTGGCACTGCTGCTGCACGCTGCTAGGCCCGGAGGGGGAGGCAGCTGC CCCTACAGCAACCCCAGCCTGTGCAGCGGAGGCGGCGGCAGCGGCGGAGGGGGT AGCCAGGTGCAGCTGCAGCAGAGCGGCCCTGGCCTGGTGAAGCCAAGCCAGACAC TGTCCCTGACCTGCGCCATCAGCGGCGATTCCGTGAGCTCCAACTCCGCCGCCTGG AATTGGATCAGGCAGTCCCCTTCTCGGGGCCTGGAGTGGCTGGGAAGGACATACTA TCGGTCTAAGTGGTACAACGATTATGCCGTGTCTGTGAAGAGCAGAATCACAATCAA CCCTGACACCTCCAAGAATCAGTTCTCTCTGCAGCTGAATAGCGTGACACCAGAGGA CACCGCCGTGTACTATTGCGCCAGGGAGGTGACCGGCGACCTGGAGGATGCCTTT GACATCTGGGGCCAGGGCACAATGGTGACCGTGAGCTCCGGAGGCGGCGGATCTG GCGGAGGAGGAAGTGGGGCGGCGGGAGTGATATCCAGATGACACAGTCCCCATC CTCTCTGAGCGCCTCCGTGGGCGACAGAGTGACAATCACCTGTAGGGCCTCCCAGA CCATCTGGTCTTACCTGAACTGGTATCAGCAGAGGCCCGGCAAGGCCCCTAATCTG CTGATCTACGCAGCAAGCTCCCTGCAGAGCGGAGTGCCATCCAGATTCTCTGGCAG GGGCTCCGGCACAGACTTCACCCTGACCATCTCTAGCCTGCAGGCCGAGGACTTCG CCACCTACTATTGCCAGCAGTCTTATAGCATCCCCCAGACATTTGGCCAGGGCACCA AGCTGGAGATCAAGTCGGATCCGGAAGCGGAGGGGGAGGCAGCTGCCCCTACAG CAACCCCAGCCTGTGCAGCGGAGGCGGCGGCAGCGAGCTGCCCACCCAGGGCAC CTTCTCCAACGTGTCCACCAACGTGAGCCCAGCCAAGCCCACCACCACCGCCTGTC CTTATTCCAATCCTTCCCTGTGTGCTCCCACCACAACCCCGCTCCAAGGCCCCCTA CCCCCGCACCAACTATTGCCTCCCAGCCACTCTCACTGCGGCCTGAGGCCTGTCGG CCCGCTGCTGGAGGCGCAGTGCATACAAGGGGCCTCGATTTCGCCTGCGATATTTA CATCTGGGCACCCCTCGCCGGCACCTGCGGGGTGCTTCTCCTCTCCCTGGTGATTA CCCTGTATTGCAGACGGGGCCGGAAGAAGCTCCTCTACATTTTTAAGCAGCCTTTCA TGCGGCCAGTGCAGACAACCCAAGAGGAGGATGGGTGTTCCTGCAGATTCCCTGAG GAAGAGGAAGGCGGGTGCGAGCTGAGAGTGAAGTTCTCCAGGAGCGCAGATGCCC CCGCCTATCAACAGGGCCAGAACCAGCTCTACAACGAGCTTAACCTCGGGAGGCGC GAAGAATACGACGTGTTGGATAAGAGAAGGGGGCGGGACCCCGAGATGGGAGGAA AGCCCCGGAGGAAGAACCCTCAGGAGGGCCTGTACAACGAGCTGCAGAAGGATAA GATGGCCGAGGCCTACTCAGAGATCGGGATGAAGGGGGAGCGGCGCCGCGGGAA |

TABLE 5-continued

Sequences referred to in example 2.

```
GGGGCACGATGGGCTCTACCAGGGGCTGAGCACAGCCACAAAGGACACATACGAC
GCCTTGCACATGCAGGCCCTTCCACCCCGGGAATAGTCTAGAGGGCCCGTTTAAAC
CCGCTGATCAGCCTCGACTGTGCCTTCTAGTTGCCAGCCATCTGTTGTTTGCCCCTC
CCCCGTGCCTTCCTTGACCCTGGAAGGTGCCACTCCCACTGTCCTTTCCTAATAAAA
TGAGGAAATTGCATCGCATTGTCTGAGTAGGTGTCATTCTATTCTGGGGGGTGGGGT
GGGGCAGGACAGCAAGGGGGAGGATTGGGAAGACAATAGCAGGCATGCTGGGGAT
GCGGTGGGCTCTATGACTAGTGGCGAATTCCCGTGTACCAGCTGAGAGACTCTAAA
TCCAGTGACAAGTCTGTCTGCCTATTCACCGATTTTGATTCTCAAACAAATGTGTCAC
AAAGTAAGGATTCTGATGTGTATATCACAGACAAAACTGTGCTAGACATGAGGTCTAT
GGACTTCAAGAGCAACAGTGCTGTGGCCTGGAGCAACAAATCTGACTTTGCATGTG
CAAACGCCTTCAACAACAGCATTATTCCAGAAGACACCTTCTTCCCCAGCCCAGGTA
AGGGCAGCTTTGGTGCCTTCGCAGGCTGTTTCCTTGCTTCAGGAATGGCCAGGTTC
TGCCCAGAGCTCTGGTCAATGATGTCTAAAACTCCTCTGATTGGTGGTCTCGGCCTT
ATCCATTGCCACCAAAACCCTCTTTTTACTAAGCGATCGCTCCGGTGCCCGTCAGTG
GGCAGAGCGCACATCGCCCACAGTCCCCGAGAAGTTGGGGGGAGGGGTCGGCAAT
TGAACGGGTGCCTAGAGAAGGTGGCGCGGGGTAAACTGGGAAAGTGATGTCGTGT
ACTGGCTCCGCCTTTTTCCCGAGGGTGGGGGAGAACCGTATATAAGTGCAGTAGTC
GCCGTGAACGTTCTTTTTCGCAACGGGTTTGCCGCCAGAACACAGCTGAAGCTTCG
AGGGGCTCGCATCTCTCCTTCACGCGCCCGCCGCCCTACCTGAGGCCGCCATCCA
CGCCGGTTGAGTCGCGTTCTGCCGCCTCCCGCCTGTGGTGCCTCCTGAACTGCGTC
CGCCGTCTAGGTAAGTTTAAAGCTCAGGTCGAGACCGGGCCTTTGTCCGGCGCTCC
CTTGGAGCCTACCTAGACTCAGCCGGCTCTCCACGCTTTGCCTGACCCTGCTTGCT
CAACTCTACGTCTTTGTTTCGTTTTCTGTTCTGCGCCGTTACAGATCCAAGCTGTGAC
CGGCGCCTACCTGAGATCACCGGCGCCACCATGGCTTCTTACCCTGGACACCAGCA
TGCTTCTGCCTTTGACCAGGCTGCCAGATCCAGGGGCCACTCCAACAGGAGAACTG
CCCTAAGACCCAGAAGACAGCAGGAAGCCACTGAGGTGAGGCCTGAGCAGAAGAT
GCCAACCCTGCTGAGGGTGTACATTGATGGACCTCATGGCATGGGCAAGACCACCA
CCACTCAACTGCTGGTGGCACTGGGCTCCAGGGATGACATTGTGTATGTGCCTGAG
CCAATGACCTACTGGAGAGTGCTAGGAGCCTCTGAGACCATTGCCAACATCTACACC
ACCCAGCACAGGCTGGACCAGGGAGAAATCTCTGCTGGAGATGCTGCTGTGGTGAT
GACCTCTGCCCAGATCACAATGGGAATGCCCTATGCTGTGACTGATGCTGTTCTGGC
TCCTCACATTGGAGGAGAGGCTGGCTCTTCTCATGCCCCTCCACCTGCCCTGACCC
TGATCTTTGACAGACACCCCATTGCAGCCCTGCTGTGCTACCCAGCAGCAAGGTAC
CTCATGGGCTCCATGACCCCACAGGCTGTGCTGGCTTTTGTGGCCCTGATCCCTCC
AACCCTCCCTGGCACCAACATTGTTCTGGGAGCACTGCCTGAAGACAGACACATTGA
CAGGCTGGCAAAGAGGCAGAGACCTGGAGAGAGACTGGACCTGGCCATGCTGGCT
GCAATCAGAAGGGTGTATGGACTGCTGGCAAACACTGTGAGATACCTCCAGTGTGG
AGGCTCTTGGAGAGAGGACTGGGGACAGCTCTCTGGAACAGCAGTGCCCCCTCAA
GGAGCTGAGCCCCAGTCCAATGCTGGTCCAAGACCCCACATTGGGGACACCCTGTT
CACCCTGTTCAGAGCCCCTGAGCTGCTGGCTCCCAATGGAGACCTGTACAATGTGT
TTGCCTGGGCTCTGGATGTTCTAGCCAAGAGGCTGAGGTCCATGCATGTGTTCATCC
TGGACTATGACCAGTCCCCTGCTGGATGCAGAGATGCTCTGCTGCAACTAACCTCTG
GCATGGTGCAGACCCATGTGACCACCCCTGGCAGCATCCCCACCATCTGTGACCTA
GCCAGAACCTTTGCCAGGGAGATGGGAGAGGCCAACTAAGGCGCGCCACTCGAGA
GCTAGCTGGCCAGACATGATAAGATACATTGATGAGTTTGGACAAACCACAACTAGA
ATGCAGTGAAAAAAATGCTTTATTTGTGAAATTTGTGATGCTATTGCTTTATTTGTAAC
CATTATAAGCTGCAATAAACAAGTTAACAACAACAATTGCATTCATTTTATGTTTCAGG
TTCAGGGGGAGGTGTGGGAGGTTTTTTAAAGCAAGTAAAACCTCTACAAATGTGGTA
TGGAAGGCGCGCCCAATTCGCCCTATAGTGAGTCGTATTACGTCGCGCTCACTGGC
CGTCGTTTTACAACGTCGTGACTGGGAAAACCCTGGCGTTACCCAACTTAATCGCCT
TGCAGCACATCCCCCTTTCGCCAGCTGGCGTAATAGCGAAGAGGCCCGCACCGAAA
CGCCCTTCCCAACAGTTGCGCAGCCTGAATGGCGAATGGGAGCGCCCTGTAGCGG
CGCATTAAGCGCGGCGGGTGTGGTGGTTACGCGCAGCGTGACCGCTACACTTGCC
AGCGCCCTAGCGCCCGCTCCTTTCGCTTTCTTCCCTTCCTTTCTCGCCACGTTCGCC
GGCTTTCCCCGTCAAGCTCTAAATCGGGGGCTCCCTTTAGGGTTCCGATTTAGTGCT
TTACGGCACCTCGACCCCAAAAAACTTGATTAGGGTGATGGTTGGCCTGTAGTGGG
CCATAGCCCTGATAGACGGTTTTTCGCCCTTTGACGTTGGAGTCCACGTTCTTTAATA
GTGGACTCTTGTTCCAAACTGGAACAACACTCAACCCTATCTCGGTCTATTCTTTTGA
TTTATAAGGGATTTTGCCGATTTCGGCCTATTGGTTAAAAAATGAGCTGATTTAACAA
AAATTTAACGCGAATTTTAACAAAATATTAACGCTTACAATTTAG
```

| 64 | Matrice CD25 locus_IL15_ 2A_sIL15Ra pCLS30519 full sequence | GTTTATTATTCCTGTTCCACAGCTATTGTCTGCCATATAAAAACTTAGGCCAGGCACA<br>GTGGCTCACACCTGTAATCCCAGCACTTTGGAAGGCCGAGGCAGGCAGATCACAAG<br>GTCAGGAGTTCGAGACCAGCCTGGCCAACATAGCAAAACCCCATCTCTACTAAAAAT<br>ACAAAAATTAGCCAGGCATGGTGGCGTGTGCACTGGTTTAGAGTGAGGACCCACATTT<br>TTTTGGTGCCGTGTTACACATATGACCGTGACTTTGTTACACCACTACAGGAGGAAG<br>AGTAGAAGAACAATCGGTTCTGGCGTGAAACAGACTTTGAATTTTGACCTTCTCAAGT<br>TGGCGGGAGACGTGGAGTCCAACCCAGGGCCCGGTACCGGGTCCGCCACCATGGA<br>CTGGACCTGGATTCTGTTCCTCGTGGCTGCTGCTACAAGAGTGCACAGCGGCATTC<br>ATGTCTTCATTTTGGGCTGTTTCAGTCAGGGCTTCCTAAAACAGAAGCCAACTGGG<br>TGAATGTAATAAGTGATTTGAAAAAAATTGAAGATCTTATTCAATCTATGCATATTGAT<br>GCTACTTTATATACGGAAAGTGATGTTCACCCCAGTTGCAAAGTAACAGCAATGAAG<br>TGCTTTCTCTTGGAGTTACAAGTTATTTCACTTGAGTCCGGAGATGCAAGTATTCATG<br>ATACAGTAGAAAATCTGATCATCCTAGCAAACAACAGTTTGTCTTCTAATGGGAATGT<br>AACAGAATCTGGATGCAAAGAATGTGAGGAACTGGAGGAAAAAAATATTAAAGAATT<br>TTTGCAGAGTTTTGTACATATTGTCCAAATGTTCATCAACACTTCGGAAGCGGAGCT<br>ACTAACTTCAGCCTGCTGAAGCAGGCTGGAGACGTGGAGGAGAACCCTGGACCTGG<br>GACCGGCTCTGCAACCATGGATTGGACCTGGATCCTGTTTCTCGTGGCAGCTGCCA |

TABLE 5-continued

Sequences referred to in example 2.

```
CAAGAGTTCACAGTATCACGTGCCCTCCCCCCATGTCCGTGGAACACGCAGACATC
TGGGTCAAGAGCTACAGCTTGTACTCCAGGGAGCGGTACATTTGTAACTCTGGTTTC
AAGCGTAAAGCCGGCACGTCCAGCCTGACGGAGTGCGTGTTGAACAAGGCCACGA
ATGTCGCCCACTGGACAACCCCCAGTCTCAAATGCATTAGAGACCCTGCCCTGGTTC
ACCAAAGGCCAGCGCCACCCTCCACAGTAACGACGGCAGGGGTGACCCCACAGCC
AGAGAGCCTCTCCCCTTCTGGAAAAGAGCCCGCAGCTTCATCTCCCAGCTCAAACAA
CACAGCGGCCACAACAGCAGCTATTGTCCCGGGCTCCCAGCTGATGCCTTCAAAAT
CACCTTCCACAGGAACCACAGAGATAAGCAGTCATGAGTCCTCCCACGGCACCCCC
TCTCAGACAACAGCCAAGAACTGGGAACTCACAGCATCCGCCTCCCACCAGCCGCC
AGGTGTGTATCCACAGGGCCACAGCGACACCACTGAGGGCAGAGGCAGCCTGCTG
ACCTGCGGCGACGTCGAGGAGAACCCCGGGCCCATGGGGGCAGGTGCCACCGGC
CGCGCCATGGACGGGCCGCGCCTGCTGCTGTTGCTGCTTCTGGGGGTGTCCCTTG
GAGGTGCCAAGGAGGCATGCCCCACAGGCCTGTACACACACAGCGGTGAGTGCTG
CAAAGCCTGCAACCTGGGCGAGGGTGTGGCCCAGCCTTGTGGAGCCAACCAGACC
GTGTGTGAGCCCTGCCTGGACAGCGTGACGTTCTCCGACGTGGTGAGCGCGACCG
AGCCGTGCAAGCCGTGCACCGAGTGCGTGGGGCTCCAGAGCATGTCGGCGCCGTG
CGTGGAGGCCGATGACGCCGTGTGCCGCTGCGCCTACGGCTACTACCAGGATGAG
ACGACTGGGCGCTGCGAGGCGTGCCGCGTGTGCGAGGCGGGCTCGGGCCTCGTG
TTCTCCTGCCAGGACAAGCAGAACACCGTGTGCGAGGAGTGCCCCGACGGCACGT
ATTCCGACGAGGCCAACCACGTGGACCCGTGCCTGCCCTGCACCGTGTGCGAGGA
CACCGAGCGCCAGCTCCGCGAGTGCACACGCTGGGCCGACGCCGAGTGCGAGGA
GATCCCTGGCCGTTGGATTACACGGTCCACACCCCCAGAGGGCTCGGACAGCACA
GCCCCCAGCACCCAGGAGCCTGAGGCACCTCCAGAACAAGACCTCATAGCCAGCA
CGGTGGCAGGTGTGGTGACCACAGTGATGGGCAGCTCCCAGCCCGTGGTGACCCG
AGGCACCACCGACAACCTCATCCCTGTCTATTGCTCCATCCTGGCTGCTGTGGTTGT
GGGTCTTGTGGCCTACATAGCCTTCAAGAGGTGAAAAACCAAAAGAACAAGAATTTC
TTGGTAAGAAGCCGGGAACAGACAACAGAAGTCATGAAGCCCAAGTGAAATCAAAG
GTGCTAAATGGTCGCCCAGGAGACATCCGTTGTGCTTGCCTGCGTTTTGGAAGCTCT
GAAGTCACATCACAGGACACGGGGCAGTGGCAACCTTGTCTCTATGCCAGCTCAGT
CCCATCAGAGAGCGAGCGCTACCCACTTCTAAATAGCAATTTCGCCGTTGAAGAGGA
AGGGCAAAACCACTAGAACTCTCCATCTTATTTTCATGTATATGTGTTCATGCGATCG
CTCCGGTGCCCGTCAGTGGGCAGAGCGCACATCGCCCACAGTCCCCGAGAAGTTG
GGGGGAGGGGTCGGCAATTGAACGGGTGCCTAGAGAAGGTGGCGCGGGGTAAACT
GGGAAAGTGATGTCGTGTACTGGCTCCGCCTTTTTCCCGAGGGTGGGGGAGAACCG
TATATAAGTGCAGTAGTCGCCGTGAACGTTCTTTTTCGCAACGGGTTTGCCGCCAGA
ACACAGCTGAAGCTTCGAGGGGCTCGCATCTCTCCTTCACGCGCCCGCCGCCCTAC
CTGAGGCCGCCATCCACGCCGGTTGAGTCGCGTTCTGCCGCCTCCCGCCTGTGGT
GCCTCCTGAACTGCGTCCGCCGTCTAGGTAAGTTTAAAGCTCAGGTCGAGACCGGG
CCTTTGTCCGGCGCTCCCTTGGAGCCTACCTAGACTCAGCCGGCTCTCCACGCTTT
GCCTGACCCTGCTTGCTCAACTCTACGTCTTTGTTTCGTTTTCTGTTCTGCGCCGTTA
CAGATCCAAGCTGTGACCGGCGCCTACCTGAGATCACCGGCGCCACCATGGCTTCT
TACCCTGGACACCAGCATGCTTCTGCCTTTGACCAGGCTGCCAGATCCAGGGGCCA
CTCCAACAGGAGAACTGCCCTAAGACCCAGAAGACAGCAGGAAGCCACTGAGGTGA
GGCCTGAGCAGAAGATGCCAACCCTGCTGAGGGTGTACATTGATGGACCTCATGGC
ATGGGCAAGACCACCACCACTCAACTGCTGGTGGCACTGGGCTCCAGGGATGACAT
TGTGTATGTGCCTGAGCCAATGACCTACTGGAGAGTGCTAGGAGCCTCTGAGACCA
TTGCCAACATCTACACCACCCAGCACAGGCTGGACCAGGGAGAAATCTCTGCTGGA
GATGCTGCTGTGGTGATGACCTCTGCCCAGATCACAATGGGAATGCCCTATGCTGT
GACTGATGCTGTTCTGGCTCCTCACATTGGAGGAGAGGCTGGCTCTTCTCATGCCC
CTCCACCTGCCCTGACCCTGATCTTTGACAGACACCCCATTGCAGCCCTGCTGTGCT
ACCCAGCAGCAAGGTACCTCATGGGCTCCATGACCCCACAGGCTGTGCTGGCTTTT
GTGGCCCTGATCCCTCCAACCCTCCCTGGCACCAACATTGTTCTGGGAGCACTGCC
TGAAGACAGACACATTGACAGGCTGGCAAAGAGGCAGAGACCTGGAGAGAGACTG
GACCTGGCCATGCTGGCTGCAATCAGAAGGGTGTATGGACTGCTGGCAAACACTGT
GAGATACCTCCAGTGTGGAGGCTCTTGGAGAGAGGACTGGGGACAGCTCTCTGGAA
CAGCAGTGCCCCCTCAAGGAGCTGAGCCCCAGTCCAATGCTGGTCCAAGACCCCAC
ATTGGGGACACCCTGTTCACCCTGTTCAGAGCCCCTGAGCTGCTGGCTCCCAATGG
AGACCTGTACAATGTGTTTGCCTGGGCTCTGGATGTTCTAGCCAAGAGGCTGAGGT
CCATGCATGTGTTCATCCTGGACTATGACCAGTCCCTGCTGGATGCAGAGATGCTC
TGCTGCAACTAACCTCTGGCATGGTGCAGACCCATGTGACCACCCCTGGCAGCATC
CCCACCATCTGTGACCTAGCCAGAACCTTTGCCAGGGAGATGGGAGAGGCCAACTA
AGGCGCGCCACTCGAGCGCTAGCTGGCCAGACATGATAAGATACATTGATGAGTTT
GGACAAACCACAACTAGAATGCAGTGAAAAAAATGCTTTATTTGTGAAATTTGTGATG
CTATTGCTTTATTTGTAACCATTATAAGCTGCAATAAACAAGTTAACAACAACAATTGC
ATTCATTTTATGTTTCAGGTTCAGGGGGAGGTGTGGGAGGTTTTTTAAAGCAAGTAAA
ACCTCTACAAATGTGGTATGGAAGGCGCGCCCAATTCGCCCTATAGTGAGTCGTATT
ACGTCGCGCTCACTGGCCGTCGTTTTACAACGTCGTGACTGGGAAAACCCTGGCGT
TACCCAACTTAATCGCCTTGCAGCACATCCCCCTTTCGCCAGCTGGCGTAATAGCGA
AGAGGCCCGCACCGAAACGCCCTTCCCAACAGTTGCGCAGCCTGAATGGCGAATG
GGAGCGCCCTGTAGCGGCGCATTAAGCGCGGCGGGTGTGGTGGTTACGCGCAGCG
TGACCGCTACACTTGCCAGCGCCCTAGCGCCCGCTCCTTTCGCTTTCTTCCCTTCCT
TTCTCGCCACGTTCGCCGGCTTTCCCCGTCAAGCTCTAAATCGGGGGCTCCCTTTAG
GGTTCCGATTTAGTGCTTTACGGCACCTCGACCCCAAAAAACTTGATTAGGGTGATG
GTTGGCCTGTAGTGGGCCATAGCCCTGATAGACGGTTTTTCGCCCTTTGACGTTGGA
GTCCACGTTCTTTAATAGTGGACTCTTGTTCCAAACTGGAACAACACTCAACCCTATC
TCGGTCTATTCTTTTGATTTATAAGGGATTTTGCCGATTTCGGCCTATTGGTTAAAAAA
TGAGCTGATTTAACAAAAATTTAACGCGAATTTTAACAAAATATTAACGCTTACAATTT
AGGTGGCACTTTTCGGGGAAATGTGCGCGGAACCCCTATTTGTTTATTTTTCTAAATA
```

TABLE 5-continued

Sequences referred to in example 2.

|  |  |  |
|---|---|---|
|  |  | CATTCAAATATGTATCCGCTCATGAGACAATAACCCTGATAAATGCTTCAATAATATT<br>GAAAAAGGAAGAGTATGAGTATTCAACATTTCCGTGTCGCCCTTATTCCCTTTTTTGC<br>GGCATTTTGCCTTCCTGTTTTTGCTCACCCAGAAACGCTGGTGAAAGTAAAAGATGC<br>TGAAGATCAGTTGGGTGCACGAGTGGGTTACATCGAACTGGATCTCAACAGCGGTA<br>AGATCCTTGAGAGTTTTCGCCCCGAAGAACGTTTTCCAATGATGAGCACTTTTAAAGT<br>TCTGCTATGTGGCGCGGTATTATCCCGTATTGACGCCGGGCAAGAGCAACTCGGTC<br>GCCGCATACACTATTCTCAGAATGACTTGGTTGAGTACTCACCAGTCACAGAAAAGC<br>ATCTTACGGATGGCATGACAGTAAGAGAATTATGCAGTGCTGCCATAACCATGAGTG<br>ATAACACTGCGGCCAACTTACTTCTGACAACGATCGGAGGACCGAAGGAGCTAACC<br>GCTTTTTTGCACAACATGGGGGATCATGTAACTCGCCTTGATCGTTGGGAACCGGAG<br>CTGAATGAAGCCATACCAAACGACGAGCGTGACACCACGATGCCTGTAGCAATGGC<br>AACAACGTTGCGCAAACTATTAACTGGCGAACTACTTACTCTAGCTTCCCGGCAACA<br>ATTAATAGACTGGATGGAGGCGGATAAAGTTGCAGGACCACTTCTGCGCTCGGCCC<br>TTCCGGCTGGCTGGTTTATTGCTGATAAATCTGGAGCCGGTGAGCGTGGTTCTCGC<br>GGTATCATTGCAGCACTGGGGCCAGATGGTAAGCCCTCCCGTATCGTAGTTATCTAC<br>ACGACGGGGAGTCAGGCAACTATGGATGAACGAAATAGACAGATCGCTGAGATAGG<br>TGCCTCACTGATTAAGCATTGGTAACTGTCAGACCAAGTTTACTCATATATACTTTAG<br>ATTGATTTAAAACTTCATTTTTAATTTAAAAGGATCTAGGTGAAGATCCTTTTTGATAAT<br>CTCATGACCAAAATCCCTTAACGTGAGTTTTCGTTCCACTGAGCGTCAGACCCCGTA<br>GAAAAGATCAAAGGATCTTCTTGAGATCCTTTTTTTCTGCGCGTAATCTGCTGCTTGC<br>AAACAAAAAAACCACCGCTACCAGCGGTGGTTTGTTTGCCGGATCAAGAGCTACCAA<br>CTCTTTTTCCGAAGGTAACTGGCTTCAGCAGAGCGCAGATACCAAATACTGTTCTTCT<br>AGTGTAGCCGTAGTTAGGCCACCACTTCAAGAACTCTGTAGCACCGCCTACATACCT<br>CGCTCTGCTAATCCTGTTACCAGTGGCTGCTGCCAGTGGCGATAAGTCGTGTCTTAC<br>CGGGTTGGACTCAAGACGATAGTTACCGGATAAGGCGCAGCGGTCGGGCTGAACG<br>GGGGGTTCGTGCACACAGCCCAGCTTGGAGCGAACGACCTACACCGAACTGAGATA<br>CCTACAGCGTGAGCTATGAGAAAGCGCCACGCTTCCCGAAGGGAGAAAGGCGGAC<br>AGGTATCCGGTAAGCGGCAGGGTCGGAACAGGAGAGCGCACGAGGGAGCTTCCAG<br>GGGGAAACGCCTGGTATCTTTATAGTCCTGTCGGGTTTCGCCACCTCTGACTTGAGC<br>GTCGATTTTTGTGATGCTCGTCAGGGGGCGGAGCCTATGGAAAAACGCCAGCAAC<br>GCGGCCTTTTTACGGTTCCTGGCCTTTTGCTGGCCTTTTGCTCACATGGTCTTTCCT<br>GCGTTATCCCCTGATTCTGTGGATAACCGTATTACCGCCTTTGAGTGAGCTGATACC<br>GCTCGCCGCAGCCGAACGACCGAGCGCAGCGAGTCAGTGAGCGAGGAAGCGGAG<br>AGCGCCCAATACGCAAACCGCCTCTCCCCGCGCGTTGGCCGATTCATTAATGCAGC<br>TGGCACGACAGGTTTCCCGACTGGAAAGCGGGCAGTGAGCGCAACGCAATTAATGT<br>GAGTTAGCTCACTCATTAGGCACCCCAGGCTTTACACTTTATGCTTCCGGCTCGTAT<br>GTTGTGTGGAATTGTGAGCGGATAACAATTTCACACAGGAAACAGCTATGACCATGA<br>TTACGCCAAGCGCGTCAATTAACCCTCACTAAAGGGAACAAAAGCTGTTAATTAA |
| 65 | Matrice PD1<br>locus_IL15_<br>2A_sIL15Ra<br>pCLS30513<br>full sequence | GACTCCCCAGACAGGCCCTGGAACCCCCCCACCTTCTCCCCAGCCCTGCTCGTGGT<br>GACCGAAGGGGACAACGCCACCTTCACCTGCAGCTTCTCCAACACATCGGAGAGCT<br>TCGTGCTAAACTGGTACCGCATGAGCCCCAGCAACCAGACGGACAAGCTGGCCGCC<br>TTCCCCGAGGACCGCAGCCAGCCCGGCCAGGACTGCCGCTTCCGTGTCACACAAC<br>TGCCCAACGGGCGTGACTTCCACATGAGCGTGGTCAGGGCCCGGCGCAATGACAG<br>CGGCACCTACCTCTGTGGGGCCGGTTCTGGCGTGAAACAGACTTTGAATTTTGACCT<br>TCTCAAGTTGGCGGGAGACGTGGAGTCCAACCCAGGGCCCGGTACCGGGTCCGCC<br>ACCATGGACTGGACCTGGATTCTGTTCCTCGTGGCTGCTGCTACAAGAGTGCACAG<br>CGGCATTCATGTCTTCATTTTGGGCTGTTTCAGTGCAGGGCTTCCTAAAACAGAAGC<br>CAACTGGGTGAATGTAATAAGTGATTTGAAAAAAATTGAAGATCTTATTCAATCTATG<br>CATATTGATGCTACTTTATATACGGAAAGTGATGTTCACCCCAGTTGCAAAGTAACAG<br>CAATGAAGTGCTTTCTCTTGGAGTTACAAGTTATTTCACTTGAGTCCGGAGATGCAAG<br>TATTCATGATACAGTAGAAAATCTGATCATCCTAGCAAACAACAGTTTGTCTTCTAAT<br>GGGAATGTAACAGAATCTGGATGCAAAGAATGTGAGGAACTGGAGGAAAAAAATATT<br>AAAGAATTTTTGCAGAGTTTTGTACATATTGTCCAAATGTTCATCAACACTTCTGGAA<br>GCGGAGCTACTAACTTCAGCCTGCTGAAGCAGGCTGGAGACGTGGAGGAGAACCCT<br>GGACCTGGGACCGGCTCTGCAACCATGGATTGGACGTGGATCCTGTTTCTCGTGGC<br>AGCTGCCACAAGAGTTCACAGTATCACGTGCCCTCCCCCATGTCCGTGGAACACG<br>CAGACATCTGGGTCAAGAGCTACAGCTTGTACTCCAGGGAGCGGTACATTTGTAACT<br>CTGGTTTCAAGCGTAAAGCCGGCACGTCCAGCCTGACGGAGTGCGTGTTGAACAAG<br>GCCACGAATGTCGCCCACTGGACAACCCCCAGTCTCAAATGCATTAGAGACCCTGC<br>CCTGGTTCACCAAAGGCCAGCGCCACCCTCCACAGTAACGACGGCAGGGGTGACC<br>CCACAGCCAGAGAGCCTCTCCCCTTCTGGAAAAGAGCCCGCAGCTTCATCTCCCAG<br>CTCAAACAACACAGCGGCCACAACAGCAGCTATTGTCCCGGGCTCCCAGCTGATGC<br>CTTCAAAATCACCTTCCACAGGAACCACAGAGATAAGCAGTCATGAGTCCTCCCACG<br>GCACCCCCTCTCAGACAACAGCCAAGAACTGGGAACTCACAGCATCCGCTCCCAC<br>CAGCCGCCAGGTGTGTATCCACAGGGCCACAGCGACACCACTGAGGGCAGAGGCA<br>GCCGCTGACCTGCGGCGACGTCGAGGAGAACCCCGGGCCCATGGGGGCAGGTG<br>CCACCGGCCGCGCCATGGACGGGCCGCGCCTGCTGCTGTTGCTGCTTCTGGGGGT<br>GTCCCTTGGAGGTGCCAAGGAGGCATGCCCCACAGGCCTGTACACACACAGCGGT<br>GAGTGCTGCAAAGCCTGCAACCTGGGCGAGGGTGTGGCCCAGCCTTGTGGAGCCA<br>ACCAGACCGTGTGTGAGCCCTGCCTGGACAGCGTGACGTTCTCCGACGTGGTGAG<br>CGCGACCGAGCCGTGCAAGCCGTGCACCGAGTGCGTGGGGCTCCAGAGCATGTCG<br>GCGCCGTGCGTGGAGGCCGATGACGCCGTGTGCCGCTGCGCCTACGGCTACTACC<br>AGGATGAGACGACTGGGCGCTGCGAGGCGTGCCGCGTGTGCGAGGCGGGCTCGG<br>GCCTCGTGTTCTCCTGCCAGGACAAGCAGAACACCGTGTGCGAGGAGTGCCCCGA<br>CGGCACGTATTCCGACGAGGCCAACCACGTGGACCCGTGCCTGCCCTGCACCGTG<br>TGCGAGGACACCGAGCGCCAGCTCCGCGAGTGCACACGCTGGGCCGACGCCGAGT<br>GCGAGGAGATCCCTGGCCGTTGGATTACACGGTCCACACCCCCAGAGGGCTCGGA |

TABLE 5-continued

Sequences referred to in example 2.

```
CAGCACAGCCCCCAGCACCCAGGAGCCTGAGGCACCTCCAGAACAAGACCTCATAG
CCAGCACGGTGGCAGGTGTGGTGACCACAGTGATGGGCAGCTCCCAGCCCGTGGT
GACCCGAGGCACCACCGACAACCTCATCCCTGTCTATTGCTCCATCCTGGCTGCTG
TGGTTGTGGGTCTTGTGGCCTACATAGCCTTCAAGAGGTGATCTAGAGGGCCCGTTT
AAACCCGCTGATCAGCCTCGACTGTGCCTTCTAGTTGCCAGCCATCTGTTGTTTGCC
CCTCCCCCGTGCCTTCCTTGACCCTGGAAGGTGCCACTCCCACTGTCCTTTCCTAAT
AAAATGAGGAAATTGCATCGCATTGTCTGAGTAGGTGTCATTCTATTCTGGGGGGTG
GGGTGGGGCAGGACAGCAAGGGGGAGGATTGGGAAGACAATAGCAGGCATGCTGG
GGATGCGGTGGGCTCTATGACTAGTGGCGAATTCGGCGCAGATCAAAGAGAGCCTG
CGGGCAGAGCTCAGGGTGACAGGTGCGGCCTCGGAGGCCCCGGGGCAGGGGTGA
GCTGAGCCGGTCCTGGGGTGGGTGTCCCCTCCTGCACAGGATCAGGAGCTCCAGG
GTCGTAGGGCAGGGACCCCCCAGCTCCAGTCCAGGGCTCTGTCCTGCACCTGGGG
AATGGTGACCGGCATCTCTGTCCTCTAGCTCTGGAAGCACCCCAGCCCCTCTAGTCT
GCCCTCACCCCTGACCCTGACCCTCCACCCTGACCCGTCCTAACCCCTGACCTTT
GGCGATCGCTCCGGTGCCCGTCAGTGGGCAGAGCGCACATCGCCCACAGTCCCG
AGAAGTTGGGGGGAGGGGTCGGCAATTGAACGGGTGCCTAGAGAAGGTGGCGCGG
GGTAAACTGGGAAAGTGATGTCGTGTACTGGCTCCGCCTTTTTCCCGAGGGTGGGG
GAGAACCGTATATAAGTGCAGTAGTCGCCGTGAACGTTCTTTTTCGCAACGGGTTTG
CCGCCAGAACACAGCTGAAGCTTCGAGGGGCTCGCATCTCTCCTTCACGCGCCCGC
CGCCCTACCTGAGGCCGCCATCCACGCCGGTTGAGTCGCGTTCTGCCGCCTCCCG
CCTGTGGTGCCTCCTGAACTGCGTCCGCCGTCTAGGTAAGTTTAAAGCTCAGGTCG
AGACCGGGCCTTTGTCCGGCGCTCCCTTGGAGCCTACCTAGACTCAGCCGGCTCTC
CACGCTTTGCCTGACCCTGCTTGCTCAACTCTACGTCTTTGTTTCGTTTTCTGTTCTG
CGCCGTTACAGATCCAAGCTGTGACCGGCGCCTACCTGAGATCACCGGCGCCACCA
TGGCTTCTTACCCTGGACACCAGCATGCTTCTGCCTTTGACCAGGCTGCCAGATCCA
GGGGCCACTCCAACAGGAGAACTGCCCTAAGACCCAGAAGACAGCAGGAAGCCAC
TGAGGTGAGGCCTGAGCAGAAGATGCCAACCCTGCTGAGGGTGTACATTGATGGAC
CTCATGGCATGGGCAAGACCACCACCACTCAACTGCTGGTGGCACTGGGCTCCAGG
GATGACATTGTGTATGTGCCTGAGCCAATGACCTACTGGAGAGTGCTAGGAGCCTCT
GAGACCATTGCCAACATCTACACCACCCAGCACAGGCTGGACCAGGGAGAAATCTC
TGCTGGAGATGCTGCTGTGGTGATGACCTCTGCCCAGATCACAATGGGAATGCCCT
ATGCTGTGACTGATGCTGTTCTGGCTCCTCACATTGGAGGAGAGGCTGGCTCTTCTC
ATGCCCCTCCACCTGCCCTGACCCTGATCTTTGACAGACACCCCATTGCAGCCCTG
CTGTGCTACCCAGCAGCAAGGTACCTCATGGGCTCCATGACCCCACAGGCTGTGCT
GGCTTTTGTGGCCCTGATCCCTCCAACCCTCCCTGGCACCAACATTGTTCTGGGAG
CACTGCCTGAAGACAGACACATTGACAGGCTGGCAAAGAGGCAGAGACCTGGAGAG
AGACTGGACCTGGCCATGCTGGCTGCAATCAGAAGGGTGTATGGACTGCTGGCAAA
CACTGTGAGATACCTCCAGTGTGGAGGCTCTTGGAGAGAGGACTGGGGACAGCTCT
CTGGAACAGCAGTGCCCCCTCAAGGAGCTGAGCCCCAGTCCAATGCTGGTCCAAGA
CCCCACATTGGGGACACCCTGTTCACCCTGTTCAGAGCCCCTCGAGCTGCTGGCTCC
CAATGGAGACCTGTACAATGTGTTTGCCTGGGCTCTGGATGTTCTAGCCAAGAGGCT
GAGGTCCATGCATGTGTTCATCCTGGACTATGACCAGTCCCTGCTGGATGCAGAG
ATGCTCTGCTGCAACTAACCTCTGGCATGGTGCAGACCCATGTGACCACCCCTGGC
AGCATCCCCACCATCTGTGACCTAGCCAGAACCTTTGCCAGGGAGATGGGAGAGGC
CAACTAAGGCGCGCCACTCGAGCGCTAGCTGGCCAGACATGATAAGATACATTGAT
GAGTTTGGACAAACCACAACTAGAATGCAGTGAAAAAAATGCTTTATTTGTGAAATTT
GTGATGCTATTGCTTTATTTGTAACCATTATAAGCTGCAATAAACAAGTTAACAACAAC
AATTGCATTCATTTTATGTTTCAGGTTCAGGGGGAGGTGTGGGAGGTTTTTTAAAGCA
AGTAAAACCTCTACAAATGTGGTATGGAAGGCGCGCCCAATTCGCCCTATAGTGAGT
CGTATTACGTCGCGCTCACTGGCCGTCGTTTTACAACGTCGTGACTGGGAAAACCCT
GGCGTTACCCAACTTAATCGCCTTGCAGCACATCCCCCTTTCGCCAGCTGGCGTAAT
AGCGAAGAGGCCCGCACCGAAACGCCCTTCCCAACAGTTGCGCAGCCTGAATGGC
GAATGGGAGCGCCCTGTAGCGGCGCATTAAGCGCGGCGGGTGTGGTGGTTACGCG
CAGCGTGACCGCTACACTTGCCAGCGCCCTAGCGCCCGCTCCTTTCGCTTTCTTCC
CTTCCTTTCTCGCCACGTTCGCCGGCTTTCCCCGTCAAGCTCTAAATCGGGGGCTCC
CTTTAGGGTTCCGATTTAGTGCTTTACGGCACCTCGACCCCAAAAAACTTGATTAGG
GTGATGGTTGGCCTGTAGTGGGCCATAGCCCTGATAGACGGTTTTTCGCCCTTTGAC
GTTGGAGTCCACGTTCTTTAATAGTGGACTCTTGTTCCAAACTGGAACAACACTCAAC
CCTATCTCGGTCTATTCTTTTGATTTATAAGGGATTTTGCCGATTTCGGCCTATTGGT
TAAAAAATGAGCTGATTTAACAAAAATTTAACGCGAATTTTAACAAAATATTAACGCTT
ACAATTTAGGTGGCACTTTTCGGGGAAATGTGCGCGGAACCCCTATTTGTTTATTTTT
CTAAATACATTCAAATATGTATCCGCTCATGAGACAATAACCCTGATAAATGCTTCAA
TAATATTGAAAAAGGAAGAGTATGAGTATTCAACATTTCCGTGTCGCCCTTATTCCCT
TTTTTGCGGCATTTTGCCTTCCTGTTTTTGCTCACCCAGAAACGCTGGTGAAAGTAAA
AGATGCTGAAGATCAGTTGGGTGCACGAGTGGGTTACATCGAACTGGATCTCAACA
GCGGTAAGATCCTTGAGAGTTTTCGCCCCGAAGAACGTTTTCCAATGATGAGCACTT
TTAAAGTTCTGCTATGTGGCGCGGTATTATCCCGTATTGACGCCGGGCAAGAGCAAC
TCGGTCGCCGCATACACTATTCTCAGAATGACTTGGTTGAGTACTCACCAGTCACAG
AAAAGCATCTTACGGATGGCATGACAGTAAGAGAATTATGCAGTGCTGCCATAACCA
TGAGTGATAACACTGCGGCCAACTTACTTCTGACAACGATCGGAGGACCGAAGGAG
CTAACCGCTTTTTTGCACAACATGGGGGATCATGTAACTCGCCTTGATCGTTGGGAA
CCGGAGCTGAATGAAGCCATACCAAACGACGAGCGTGACACCACGATGCCTGTAGC
AATGGCAACAACGTTGCGCAAACTATTAACTGGCGAACTACTTACTCTAGCTTCCCG
GCAACAATTAATAGACTGGATGGAGGCGGATAAAGTTGCAGGACCACTTCTGCGCT
CGGCCCTTCCGGCTGGCTGGTTTATTGCTGATAAATCTGGAGCCGGTGAGCGTGGT
TCTCGCGGTATCATTGCAGCACTGGGGCCAGATGGTAAGCCCTCCCGTATCGTAGT
TATCTACACGACGGGGAGTCAGGCAACTATGGATGAACGAAATAGACAGATCGCTG
AGATAGGTGCCTCACTGATTAAGCATTGGTAACTGTCAGACCAAGTTTACTCATATAT
```

TABLE 5-continued

Sequences referred to in example 2.

|  |  |  |
|---|---|---|
|  |  | ACTTTAGATTGATTTAAAACTTCATTTTTAATTTAAAAGGATCTAGGTGAAGATCCTTT<br>TTGATAATCTCATGACCAAAATCCCTTAACGTGAGTTTTCGTTCCACTGAGCGTCAGA<br>CCCCGTAGAAAAGATCAAAGGATCTTCTTGAGATCCTTTTTTTCTGCGCGTAATCTGC<br>TGCTTGCAAACAAAAAAACCACCGCTACCAGCGGTGGTTTGTTTGCCGGATCAAGAG<br>CTACCAACTCTTTTTCCGAAGGTAACTGGCTTCAGCAGAGCGCAGATACCAAATACT<br>GTTCTTCTAGTGTAGCCGTAGTTAGGCCACCACTTCAAGAACTCTGTAGCACCGCCT<br>ACATACCTCGCTCTGCTAATCCTGTTACCAGTGGCTGCTGCCAGTGGCGATAAGTCG<br>TGTCTTACCGGGTTGGACTCAAGACGATAGTTACCGGATAAGGCGCAGCGGTCGGG<br>CTGAACGGGGGGTTCGTGCACACAGCCCAGCTTGGAGCGAACGACCTACACCGAA<br>CTGAGATACCTACAGCGTGAGCTATGAGAAAGCGCCACGCTTCCCGAAGGGAGAAA<br>GGCGGACAGGTATCCGGTAAGCGGCAGGGTCGGAACAGGAGAGCGCACGAGGGA<br>GCTTCCAGGGGGAAACGCCTGGTATCTTTATAGTCCTGTCGGGTTTCGCCACCTCTG<br>ACTTGAGCGTCGATTTTTGTGATGCTCGTCAGGGGGCGGAGCCTATGGAAAAACG<br>CCAGCAACGCGGCCTTTTTACGGTTCCTGGCCTTTTGCTGGCCTTTTGCTCACATGG<br>TCTTTCCTGCGTTATCCCCTGATTCTGTGGATAACCGTATTACCGCCTTTGAGTGAGC<br>TGATACCGCTCGCCGCAGCCGAACGACCGAGCGCAGCGAGTCAGTGAGCGAGGAA<br>GCGGAGAGCGCCCAATACGCAAACCGCCTCTCCCCGCGCGTTGGCCGATTCATTAA<br>TGCAGCTGGCACGACAGGTTTCCCGACTGGAAAGCGGGCAGTGAGCGCAACGCAA<br>TTAATGTGAGTTAGCTCACTCATTAGGCACCCCAGGCTTTACACTTTATGCTTCCGGC<br>TCGTATGTTGTGTGGAATTGTGAGCGGATAACAATTTCACACAGGAAACAGCTATGA<br>CCATGATTACGCCAAGCGCGTCAATTAACCCTCACTAAAGGGAACAAAAGCTGTTAA<br>TTAA |
| 66 | Matrice CD25<br>locus_IL12a_<br>2A_IL12b<br>pCLS30520<br>full sequence | GTTTATTATTCCTGTTCCACAGCTATTGTCTGCCATATAAAAACTTAGGCCAGGCACA<br>GTGGCTCACACCTGTAATCCCAGCACTTTGGAAGGCCGAGGCAGGCAGATCACAAG<br>GTCAGGAGTTCGAGACCAGCCTGGCCAACATAGCAAAACCCCATCTCTACTAAAAAT<br>ACAAAAATTAGCCAGGCATGGTGGCGTGTGCACTGGTTTAGAGTGAGGACCACATTT<br>TTTTGGTGCCGTGTTACACATATGACCGTGACTTTGTTACACCACTACAGGAGGAAG<br>AGTAGAAGAACAATCGGTTCTGGCGTGAAACAGACTTTGAATTTTGACCTTCTCAAGT<br>TGGCGGGAGACGTGGAGTCCAACCCAGGGCCCATGTGGCCCCCTGGGTCAGCCTC<br>CCAGCCACCGCCCTCACCTGCCGCGGCCACAGGTCTGCATCCAGCGGCTCGCCCT<br>GTGTCCCTGCAGTGCCGGCTCAGCATGTGTCCAGCGCGCAGCCTCCTCCTTGTGGC<br>TACCCTGGTCCTCCTGGACCACCTCAGTTTGGCCAGAAACCTCCCCGTGGCCACTC<br>CAGACCCAGGAATGTTCCCATGCCTTCACCACTCCCAAAACCTGCTGAGGGCCGTC<br>AGCAACATGCTCCAGAAGGCCAGACAAACTCTAGAATTTTACCCTTGCACTTCTGAA<br>GAGATTGATCATGAAGATATCACAAAAGATAAAACCAGCACAGTGGAGGCCTGTTTA<br>CCATTGGAATTAACCAAGAATGAGAGTTGCCTAAATTCCAGAGAGACCTCTTTCATAA<br>CTAATGGGAGTTGCCTGGCCTCCAGAAAGACCTCTTTTATGATGGCCCTGTGCCTTA<br>GTAGTATTTATGAAGACTTGAAGATGTACCAGGTGGAGTTCAAGACCATGAATGCAA<br>AGCTTCTGATGGATCCTAAGAGGCAGATCTTTCTAGATCAAAACATGCTGGCAGTTA<br>TTGATGAGCTGATGCAGGCCCTGAATTTCAACAGTGAGACTGTGCCACAAAAATCCT<br>CCCTTGAAGAACCGGATTTTTATAAAACTAAAATCAAGCTCTGCATACTTCTTCATGC<br>TTTCAGAATTCGGGCAGTGACTATTGATAGAGTGATGAGCTATCTGAATGCTTCCGG<br>AAGCGGAGCTACTAACTTCAGCCTGCTGAAGCAGGCTGGAGACGTGGAGGAGAACC<br>CTGGACCTATGTGTCACCAGCAGTTGGTCATCTCTTGGTTTTCCCTGGTTTTTCTGG<br>CATCTCCCCTCGTGGCCATATGGGAACTGAAGAAAGATGTTTATGTCGTAGAATTGG<br>ATTGGTATCCGGATGCCCCTGGAGAAATGGTGGTCCTCACCTGTGACACCCCTGAA<br>GAAGATGGTATCACCTGGACCTTGGACCAGAGCAGTGAGGTCTTAGGCTCTGGCAA<br>AACCCTGACCATCCAAGTCAAAGAGTTTGGAGATGCTGGCCAGTACACCTGTCACAA<br>AGGAGGCGAGGTTCTAAGCCATTCGCTCCTGCTGCTTCACAAAAAGGAAGATGGAA<br>TTTGGTCCACTGATATTTTAAAGGACCAGAAAGAACCCAAAAATAAGACCTTTCTAAG<br>ATGCGAGGCCAAGAATTATTCTGGACGTTTCACCTGCTGGTGGCTGACGACAATCAG<br>TACTGATTTGACATTCAGTGTCAAAAGCAGCAGAGGCTCTTCTGACCCCCAAGGGGT<br>GACGTGCGGAGCTGCTACACTCTCTGCAGAGAGAGTCAGAGGGGACAACAAGGAG<br>TATGAGTACTCAGTGGAGTGCCAGGAGGACAGTGCCTGCCCAGCTGCTGAGGAGA<br>GTCTGCCCATTGAGGTCATGGTGGATGCCGTTCACAAGCTCAAGTATGAAAACTACA<br>CCAGCAGCTTCTTCATCAGGGACATCATCAAACCTGACCCACCCAAGAACTTGCAGC<br>TGAAGCCATTAAAGAATTCTCGGCAGGTGGAGGTCAGCTGGGAGTACCCTGACACC<br>TGGAGTACTCCACATTCCTACTTCTCCCTGACATTCTGCGTTCAGGTCCAGGGCAAG<br>AGCAAGAGAGAAAGAAAGATAGAGTCTTCACGGACAAGGACCTCAGCCACGGTCAT<br>CTGCCCGCAAAAATGCCAGCATTAGCGTGCGGGCCCAGGACCGCTACTATAGCTCAT<br>CTTGGAGCGAATGGGCATCTGTGCCCTGCAGTGAGGGCAGAGGCAGCCTGCTGAC<br>CTGCGGCGACGTCGAGGAGAACCCCGGGCCCATGGGGGCAGGTGCCACCGGCCG<br>CGCCATGGACGGGCCGCGCCTGCTGCTGTTGCTGCTTCTGGGGGTGTCCCTTGGA<br>GGTGCCAAGGAGGCATGCCCCACAGGCCTGTACACACACAGCGGTGAGTGCTGCA<br>AAGCCTGCAACCTGGGCGAGGGTGTGGCCCAGCCTTGTGGAGCCAACCAGACCGT<br>GTGTGAGCCCTGCCTGGACAGCGTGACGTTCTCCGACGTGGTGAGCGCGACCGAG<br>CCGTGCAAGCCGTGCACCGAGTGCGTGGGGCTCCAGAGCATGTCGGCGCCGTGCG<br>TGGAGGCCGATGACGCCGTGTGCCGCTGCGCCTACGGCTACTACCAGGATGAGAC<br>GACTGGGCGCTGCGAGGCGTGCCGCGTGTGCGAGGCGGGCTCGGGCCTCGTGTT<br>CTCCTGCCAGGACAAGCAGAACACCGTGTGCGAGGAGTGCCCCGACGGCACGTAT<br>TCCGACGAGGCCAACCACGTGGACCCGTGCCTGCCCTGCACCGTGTGCGAGGACA<br>CCGAGCGCCAGCTCCGCGAGTGCACACGTGGGCCGACGCCGAGTGCGAGGAGA<br>TCCCTGGCCGTTGGATTACACGGTCCACACCCCCAGAGGGCTCGGACAGCACAGC<br>CCCCAGCACCCAGGAGCCTGAGGCACCTCCAGAACAAGACCTCATAGCCAGCACG<br>GTGGCAGGTGTGGTGACCACAGTGATGGGCAGCTCCCAGCCCGTGGTGACCCGAG<br>GCACCACCGACAACCTCATCCCTGTCTATTGCTCCATCCTGGCTGCTGTGGTTGTGG<br>GTCTTGTGGCCTACATAGCCTTCAAGAGGTGAAAAACCAAAAGAACAAGAATTTCTT |

TABLE 5-continued

Sequences referred to in example 2.

```
GGTAAGAAGCCGGGAACAGACAACAGAAGTCATGAAGCCCAAGTGAAATCAAAGGT
GCTAAATGGTCGCCCAGGAGACATCCGTTGTGCTTGCCTGCGTTTTGGAAGCTCTG
AAGTCACATCACAGGACACGGGGCAGTGGCAACCTTGTCTCTATGCCAGCTCAGTC
CCATCAGAGAGCGAGCGCTACCCACTTCTAAATAGCAATTTCGCCGTTGAAGAGGAA
GGGCAAAACCACTAGAACTCTCCATCTTATTTTCATGTATATGTGTTCATGCGATCGC
TCCGGTGCCCGTCAGTGGGCAGAGCGCACATCGCCCACAGTCCCCGAGAAGTTGG
GGGGAGGGGTCGGCAATTGAACGGGTGCCTAGAGAAGGTGGCGCGGGGTAAACTG
GGAAAGTGATGTCGTGTACTGGCTCCGCCTTTTTCCCGAGGGTGGGGGAGAACCGT
ATATAAGTGCAGTAGTCGCCGTGAACGTTCTTTTTCGCAACGGGTTTGCCGCCAGAA
CACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTG
CCTCCTGAACTGCGTCCGCCGTCTAGGTAAGTTTAAAGCTCAGGTCGAGACCGGGC
CTTTGTCCGGCGCTCCCTTGGAGCCTACCTAGACTCAGCCGGCTCTCCACGCTTTG
CCTGACCCTGCTTGCTCAACTCTACGTCTTTGTTTCGTTTTCTGTTCTGCGCCGTTAC
AGATCCAAGCTGTGACCGGCGCCTACCTGAGATCACCGGCGCCACCATGGCTTCTT
ACCCTGGACACCAGCATGCTTCTGCCTTTGACCAGGCTGCCAGATCCAGGGGCCAC
TCCAACAGGAGAACTGCCCTAAGACCCAGAAGACAGCAGGAAGCCACTGAGGTGAG
GCCTGAGCAGAAGATGCCAACCCTGCTGAGGGTGTACATTGATGGACCTCATGGCA
TGGGCAAGACCACCACCACTCAACTGCTGGTGGCACTGGGCTCCAGGGATGACATT
GTGTATGTGCCTGAGCCAATGACCTACTGGAGAGTGCTAGGAGCCTCTGAGACCAT
TGCCAACATCTACACCACCCAGCACAGGCTGGACCAGGGAGAAATCTCTGCTGGAG
ATGCTGCTGTGGTGATGACCTCTGCCCAGATCACAATGGGAATGCCCTATGCTGTGA
CTGATGCTGTTCTGGCTCCTCACATTGGAGGAGAGGCTGGCTCTTCTCATGCCCCTC
CACCTGCCCTGACCCTGATCTTTGACAGACACCCCATTGCAGCCCTGCTGTGCTACC
CAGCAGCAAGGTACCTCATGGGCTCCATGACCCCACAGGCTGTGCTGGCTTTTGTG
GCCCTGATCCCTCCAACCCTCCCTGGCACCAACATTGTTCTGGGAGCACTGCCTGA
AGACAGACACATTGACAGGCTGGCAAAGAGGCAGAGACCTGGAGAGAGACTGGAC
CTGGCCATGCTGGCTGCAATCAGAAGGGTGTATGGACTGCTGGCAAACACTGTGAG
ATACCTCCAGTGTGGAGGCTCTTGGAGAGAGGACTGGGGACAGCTCTCTGGAACAG
CAGTGCCCCTCAAGGAGCTGAGCCCCAGTCCAATGCTGGTCCAAGACCCCACATT
GGGGACACCCTGTTCACCCTGTTCAGAGCCCCTGAGCTGCTGGCTCCCAATGGAGA
CCTGTACAATGTGTTTGCCTGGGCTCTGGATGTTCTAGCCAAGAGGCTGAGGTCCAT
GCATGTGTTCATCCTGGACTATGACCAGTCCCCTGCTGGATGCAGAGATGCTCTGCT
GCAACTAACCTCTGGCATGGTGCAGACCCATGTGACCACCCCTGGCAGCATCCCCA
CCATCTGTGACCTAGCCAGAACCTTTGCCAGGGAGATGGGAGAGGCCAACTAAGGC
GCGCCACTCGAGCGCTAGCTGGCCAGACATGATAAGATACATTGATGAGTTTGGAC
AAACCACAACTAGAATGCAGTGAAAAAAATGCTTTATTTGTGAAATTTGTGATGCTAT
TGCTTTATTTGTAACCATTATAAGCTGCAATAAACAAGTTAACAACAACAATTGCATTC
ATTTTATGTTTCAGGTTCAGGGGGAGGTGTGGGAGGTTTTTTAAAGCAAGTAAAACC
TCTACAAATGTGGTATGAAGGCGCGCCCAATTCGCCCTATAGTGAGTCGTATTACG
TCGCGCTCACTGGCCGTCGTTTTACAACGTCGTGACTGGGAAAACCCTGGCGTTAC
CCAACTTAATCGCCTTGCAGCACATCCCCCTTTCGCCAGCTGGCGTAATAGCGAAGA
GGCCCGCACCGAAACGCCCTTCCCAACAGTTGCGCAGCCTGAATGGCGAATGGGA
GCGCCCTGTAGCGGCGCATTAAGCGCGGCGGGTGTGGTGGTTACGCGCAGCGTGA
CCGCTACACTTGCCAGCGCCCTAGCGCCCGCTCCTTTCGCTTTCTTCCCTTCCTTTC
TCGCCACGTTCGCCGGCTTTCCCCGTCAAGCTCTAAATCGGGGGCTCCCTTTAGGG
TTCCGATTTAGTGCTTTACGGCACCTCGACCCCAAAAAACTTGATTAGGGTGATGGT
TGGCCTGTAGTGGGCCATAGCCCTGATAGACGGTTTTTCGCCCTTTGACGTTGGAGT
CCACGTTCTTTAATAGTGGACTCTTGTTCCAAACTGGAACAACACTCAACCCTATCTC
GGTCTATTCTTTTGATTTATAAGGGATTTTGCCGATTTCGGCCTATTGGTTAAAAAAT
GAGCTGATTTAACAAAAATTTAACGCGAATTTTAACAAAATATTAACGCTTACAATTTA
GGTGGCACTTTTCGGGGAAATGTGCGCGGAACCCCTATTTGTTTATTTTTCTAAATAC
ATTCAAATATGTATCCGCTCATGAGACAATAACCCTGATAAATGCTTCAATAATATTGA
AAAAGGAAGAGTATGAGTATTCAACATTTCCGTGTCGCCCTTATTCCCTTTTTTGCGG
CATTTTGCCTTCCTGTTTTTGCTCACCCAGAAACGCTGGTGAAAGTAAAAGATGCTGA
AGATCAGTTGGGTGCACGAGTGGGTTACATCGAACTGGATCTCAACAGCGGTAAGA
TCCTTGAGAGTTTTCGCCCCGAAGAACGTTTTCCAATGATGAGCACTTTTAAAGTTCT
GCTATGTGGCGCGGTATTATCCCGTATTGACGCCGGGCAAGAGCAACTCGGTCGCC
GCATACACTATTCTCAGAATGACTTGGTTGAGTACTCACCAGTCACAGAAAAGCATCT
TACGGATGGCATGACAGTAAGAGAATTATGCAGTGCTGCCATAACCATGAGTGATAA
CACTGCGGCCAACTTACTTCTGACAACGATCGGAGGACCGAAGGAGCTAACCGCTT
TTTTGCACAACATGGGGGATCATGTAACTCGCCTTGATCGTTGGGAACCGGAGCTGA
ATGAAGCCATACCAAACGACGAGCGTGACACCACGATGCCTGTAGCAATGGCAACA
ACGTTGCGCAAACTATTAACTGGCGAACTACTTACTCTAGCTTCCCGGCAACAATTAA
TAGACTGGATGGAGGCGGATAAAGTTGCAGGACCACTTCTGCGCTCGGCCCTTCCG
GCTGGCTGGTTTATTGCTGATAAATCTGGAGCCGGTGAGCGTGGTTCTCGCGGTAT
CATTGCAGCACTGGGGCCAGATGGTAAGCCCTCCCGTATCGTAGTTATCTACACGA
CGGGGAGTCAGGCAACTATGGATGAACGAAATAGACAGATCGCTGAGATAGGTGCC
TCACTGATTAAGCATTGGTAACTGTCAGACCAAGTTTACTCATATATACTTTAGATTGA
TTTAAAACTTCATTTTTAATTTAAAAGGATCTAGGTGAAGATCCTTTTTGATAATCTCAT
GACCAAAATCCCTTAACGTGAGTTTTCGTTCCACTGAGCGTCAGACCCCGTAGAAAA
GATCAAAGGATCTTCTTGAGATCCTTTTTTTCTGCGCGTAATCTGCTGCTTGCAAACA
AAAAAACCACCGCTACCAGCGGTGGTTTGTTTGCCGGATCAAGAGCTACCAACTCTT
TTTCCGAAGGTAACTGGCTTCAGCAGAGCGCAGATACCAAATACTGTTCTTCTAGTG
TAGCCGTAGTTAGGCCACCACTTCAAGAACTCTGTAGCACCGCCTACATACCTCGCT
CTGCTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACGGG
GGTTCGTGCACACAGCCCAGCTTGGAGCGAACGACCTACACCGAACTGAGATACCT
```

TABLE 5-continued

Sequences referred to in example 2.

```
ACAGCGTGAGCTATGAGAAAGCGCCACGCTTCCCGAAGGGAGAAAGGCGGACAGG
TATCCGGTAAGCGGCAGGGTCGGAACAGGAGAGCGCACGAGGGAGCTTCCAGGGG
GAAACGCCTGGTATCTTTATAGTCCTGTCGGGTTTCGCCACCTCTGACTTGAGCGTC
GATTTTTGTGATGCTCGTCAGGGGGCGGAGCCTATGAAAAACGCCAGCAACGCG
GCCTTTTTACGGTTCCTGGCCTTTTGCTGGCCTTTTGCTCACATGGTCTTTCCTGCGT
TATCCCCTGATTCTGTGGATAACCGTATTACCGCCTTTGAGTGAGCTGATACCGCTC
GCCGCAGCCGAACGACCGAGCGCAGCGAGTCAGTGAGCGAGGAAGCGGAGAGCG
CCCAATACGCAAACCGCCTCTCCCCGCGCGTTGGCCGATTCATTAATGCAGCTGGC
ACGACAGGTTTCCCGACTGGAAAGCGGGCAGTGAGCGCAACGCAATTAATGTGAGT
TAGCTCACTCATTAGGCACCCCAGGCTTTACACTTTATGCTTCCGGCTCGTATGTTGT
GTGGAATTGTGAGCGGATAACAATTTCACACAGGAAACAGCTATGACCATGATTACG
CCAAGCGCGTCAATTAACCCTCACTAAAGGGAACAAAAGCTGTTAATTAA
```

| 67 | Matrice PD1 locus_IL12a_2A_IL12b pCLS30511 full sequence | ```
TCGCGCGTTTCGGTGATGACGGTGAAAACCTCTGACACATGCAGCTCCCGGAGACG
GTCACAGCTTGTCTGTAAGCGGATGCCGGGAGCAGACAAGCCCGTCAGGGCGCGT
CAGCGGGTGTTGGCGGGTGTCGGGGCTGGCTTAACTATGCGGCATCAGAGCAGAT
TGTACTGAGAGTGCACCATATGCGGTGTGAAATACCGCACAGATGCGTAAGGAGAA
AATACCGCATCAGGCGCCATTCGCCATTCAGGCTGCGCAACTGTTGGGAAGGGCGA
TCGGTGCGGGCCTCTTCGCTATTACGCCAGCTGGCGAAAGGGGGATGTGCTGCAA
GGCGATTAAGTTGGGTAACGCCAGGGTTTTCCCAGTCACGACGTTGTAAAACGACG
GCCAGTGAATTCGAGCTCGGTACCTCGCGAATGCATCTAGATGACTCCCCAGACAG
GCCCTGGAACCCCCCACCTTCTCCCCAGCCCTGCTCGTGGTGACCGAAGGGGAC
AACGCCACCTTCACCTGCAGCTTCTCCAACACATCGGAGAGCTTCGTGCTAAACTGG
TACCGCATGAGCCCCAGCAACCAGACGGACAAGCTGGCCGCCTTCCCCGAGGACC
GCAGCCAGCCCGGCCAGGACTGCCGCTTCCGTGTCACACAACTGCCCAACGGGCG
TGACTTCCACATGAGCGTGGTCAGGGCCCGGCGCAATGACAGCGGCACCTACCTCT
GTGGGGCCGGTTCTGGCGTGAAACAGACTTTGAATTTTGACCTTCTCAAGTTGGCG
GGAGACGTGGAGTCCAACCCAGGGCCCATGTGGCCCCCTGGGTCAGCCTCCCAGC
CACCGCCCTCACCTGCCGCGGCCACAGGTCTGCATCCAGCGGCTCGCCCTGTGTC
CCTGCAGTGCCGGCTCAGCATGTGTCCAGCGCGCAGCCTCCTCCTTGTGGCTACCC
TGGTCCTCCTGGACCACCTCAGTTTGGCCAGAAACCTCCCCGTGGCCACTCCAGAC
CCAGGAATGTTCCCATGCCTTCACCACTCCCAAAACCTGCTGAGGGCCGTCAGCAA
CATGCTCCAGAAGGCCAGACAAACTCTAGAATTTTACCCTTGCACTTCTGAAGAGAT
TGATCATGAAGATATCACAAAAGATAAAACCAGCACAGTGGAGGCCTGTTTACCATT
GGAATTAACCAAGAATGAGAGTTGCCTAAATTCCAGAGAGACCTCTTTCATAACTAAT
GGGAGTTGCCTGGCCTCCAGAAAGACCTCTTTTATGATGGCCCTGTGCCTTAGTAGT
ATTTATGAAGACTTGAAGATGTACCAGGTGGAGTTCAAGACCATGAATGCAAAGCTT
CTGATGGATCCTAAGAGGCAGATCTTTCTAGATCAAAACATGCTGGCAGTTATTGAT
GAGCTGATGCAGGCCCTGAATTTCAACAGTGAGACTGTGCCACAAAAATCCTCCCTT
GAAGAACCGGATTTTTATAAAACTAAAATCAAGCTCTGCATACTTCTTCATGCTTTCA
GAATTCGGGCAGTGACTATTGATAGAGTGATGAGCTATCTGAATGCTTCCGGAAGCG
GAGCTACTAACTTCAGCCTGCTGAAGCAGGCTGGAGACGTGGAGGAGAACCCTGGA
CCTATGTGTCCACCAGCAGTTGGTCATCTCTTGGTTTTCCCTGGTTTTTCTGGCATCTC
CCCTCGTGGCCATATGGGAACTGAAGAAAGATGTTTATGTCGTAGAATTGGATTGGT
ATCCGGATGCCCCTGGAGAAATGGTGGTCCTCACCTGTGACACCCCTGAAGAAGAT
GGTATCACCTGGACCTTGGACCAGAGCAGTGAGGTCTTAGGCTCTGGCAAAACCCT
GACCATCCAAGTCAAAGAGTTTGGAGATGCTGGCCAGTACACCTGTCACAAAGGAG
GCGAGGTTCTAAGCCATTCGCTCCTGCTGCTTCACAAAAAGGAAGATGGAATTTGGT
CCACTGATATTTTAAAGGACCAGAAAGAACCCAAAAATAAGACCTTTCTAAGATGCGA
GGCCAAGAATTATTCTGGACGTTTCACCTGCTGGTGGCTGACGACAATCAGTACTGA
TTTGACATTCAGTGTCAAAAGCAGCAGAGGCTCTTCTGACCCCCAAGGGGTGACGT
GCGGAGCTGCTACACTCTCTGCAGAGAGAGTCAGAGGGGACAACAAGGAGTATGAG
TACTCAGTGGAGTGCCAGGAGGACAGTGCCTGCCCAGCTGCTGAGGAGAGTCTGC
CCATTGAGGTCATGGTGGATGCCGTTCACAAGCTCAAGTATGAAAACTACACCAGCA
GCTTCTTCATCAGGGACATCATCAAACCTGACCCACCCAAGAACTTGCAGCTGAAGC
CATTAAAGAATTCTCGGCAGGTGGAGGTCAGCTGGGAGTACCCTGACACCTGGAGT
ACTCCACATTCCTACTTCTCCCTGACATTCTGCGTTCAGGTCCAGGGCAAGAGCAAG
AGAGAAAAGAAAGATAGAGTCTTCACGGACAAGACCTCAGCCACGGTCATCTGCCG
CAAAAATGCCAGCATTAGCGTGCGGGCCCAGGACCGCTACTATAGCTCATCTTGGA
GCGAATGGGCATCTGTGCCCTGCAGTGAGGGCAGAGGCAGCCTGCTGACCTGCGG
CGACGTCGAGGAGAACCCCGGGCCCATGGGGGCAGGTGCCACCGGCCGCGCCAT
GGACGGGCCGCGCCTGCTGCTGTTGCTGCTTCTGGGGGTGTCCCTTGGAGGTGCC
AAGGAGGCATGCCCCACAGGCCTGTACACACACAGCGGTGAGTGCTGCAAAGCCT
GCAACCTGGGCGAGGGTGTGGCCCAGCCTTGTGGAGCCAACCAGACCGTGTGTGA
GCCCTGCCTGGACAGCGTGACGTTCTCCGACGTGGTGAGCGCGACCGAGCCGTGC
AAGCCGTGCACCGAGTGCGTGGGGCTCCAGAGCATGTCGGCGCCGTGCGTGGAGG
CCGATGACGCCGTGTGCCGCTGCGCCTACGGCTACTACCAGGATGAGACGACTGG
GCGCTGCGAGGCGTGCCGCGTGTGCGAGGCGGGCTCGGGCCTCGTGTTCTCCTGC
CAGGACAAGCAGAACACCGTGTGCGAGGAGTGCCCCGACGGCACGTATTCCGACG
AGGCCAACCACGTGGACCCGTGCCTGCCCTGCACCGTGTGCGAGGACACCGAGCG
CCAGCTCCGCGAGTGCACACGCTGGGCCGACGCCGAGTGCGAGGAGATCCCTGGC
CGTTGGATTACACGGTCCACACCCCCAGAGGGCTCGGACAGCACAGCCCCCAGCA
CCCAGGAGCCTGAGGCACCTCCAGAACAGACCTCTATGCACGACGGTGGCAGG
TGTGGTGACCACAGTGATGGGCAGCTCCCAGCCCGTGGTGACCCGAGGCACCACC
GACAACCTCATCCCTGTCTATTGCTCCATCCTGGCTGCTGTGGTTGTGGGTCTTGTG
GCCTACATAGCCTTCAAGAGGTGATCTAGAGGGCCCGTTTAAACCCGCTGATCAGC
CTCGACTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGC
``` |

TABLE 5-continued

Sequences referred to in example 2.

```
ATCGCATTGTCTGAGTAGGTGTCATTCTATTCTGGGGGGTGGGGTGGGGCAGGACA
GCAAGGGGGAGGATTGGGAAGACAATAGCAGGCATGCTGGGGATGCGGTGGGCTC
TATGACTAGTGGCGAATTCGGCGCAGATCAAAGAGAGCCTGCGGGCAGAGCTCAGG
GTGACAGGTGCGGCCTCGGAGGCCCCGGGGCAGGGGTGAGCTGAGCCGGTCCTG
GGGTGGGTGTCCCCTCCTGCACAGGATCAGGAGCTCCAGGGTCGTAGGGCAGGGA
CCCCCCAGCTCCAGTCCAGGGCTCTGTCCTGCACCTGGGGAATGGTGACCGGCAT
CTCTGTCCTCTAGCTCTGGAAGCACCCCAGCCCCTCTAGTCTGCCCTCACCCCTGA
CCCTGACCCTCCACCCTGACCCCGTCCTAACCCCTGACCTTTGATCGGATCCCGGG
CCCGTCGACTGCAGAGGCCTGCATGCAAGCTTGGCGTAATCATGGTCATAGCTGTT
TCCTGTGTGAAATTGTTATCCGCTCACAATTCCACACAACATACGAGCCGGAAGCAT
AAAGTGTAAAGCCTGGGGTGCCTAATGAGTGAGCTAACTCACATTAATTGCGTTGCG
CTCACTGCCCGCTTTCCAGTCGGGAAACCTGTCGTGCCAGCTGCATTAATGAATCG
GCCAACGCGCGGGGAGAGGCGGTTTGCGTATTGGGCGCTCTTCCGCTTCCTCGCT
CACTGACTCGCTGCGCTCGGTCGTTCGGCTGCGGCGAGCGGTATCAGCTCACTCAA
AGGCGGTAATACGGTTATCCACAGAATCAGGGGATAACGCAGGAAAGAACATGTGA
GCAAAAGGCCAGCAAAAGGCCAGGAACCGTAAAAAGGCCGCGTTGCTGGCGTTTTT
CCATAGGCTCCGCCCCCTGACGAGCATCACAAAAATCGACGCTCAAGTCAGAGGT
GGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCT
TCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCGACCGCT
GCGCCTTATCCGGTAACTATCGTCTTGAGTCCAACCCGGTAAGACACGACTTATCGC
CACTGGCAGCAGCCACTGGTAACAGGATTAGCAGAGCGAGGTATGTAGGCGGTGCT
ACAGAGTTCTTGAAGTGGTGGCCTAACTACGGCTACACTAGAAGAACAGTATTTGGT
ATCTGCGCTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCT
CAGTGGAACGAAAACTCACGTTAAGGGATTTTGGTCATGAGATTATCAAAAAGGATC
TTCACCTAGATCCTTTTAAATTAAAAATGAAGTTTTAAATCAATCTAAAGTATATATGA
GTAAACTTGGTCTGACAGTTACCAATGCTTAATCAGTGAGGCACCTATCTCAGCGAT
CTGTCTATTTCGTTCATCCATAGTTGCCTGACTCCCCGTCGTGTAGATAACTACGATA
CGGGAGGGCTTACCATCTGGCCCCAGTGCTGCAATGATACCGCGAGACCCACGCTC
ACCGGCTCCAGATTTATCAGCAATAAACCAGCCAGCCGGAAGGGCCGAGCGCAGAA
GTGGTCCTGCAACTTTATCCGCCTCCATCCAGTCTATTAATTGTTGCCGGGAAGCTA
GAGTAAGTAGTTCGCCAGTTAATAGTTTGCGCAACGTTGTTGCCATTGCTACAGGCA
TCGTGGTGTCACGCTCGTCGTTTGGTATGGCTTCATTCAGCTCCGGTTCCCAACGAT
CAAGGCGAGTTACATGATCCCCCATGTTGTGCAAAAAAGCGGTTAGCTCCTTCGGTC
CTCCGATCGTTGTCAGAAGTAAGTTGGCCGCAGTGTTATCACTCATGGTTATGGCAG
CACTGCATAATTCTCTTACTGTCATGCCATCCGTAAGATGCTTTTCTGTGACTGGTGA
GTACTCAACCAAGTCATTCTGAGAATAGTGTATGCGGCGACCGAGTTGCTCTTGCCC
GGCGTCAATACGGGATAATACCGCGCCACATAGCAGAACTTTAAAAGTGCTCATCAT
TGGAAAACGTTCTTCGGGGCGAAAACTCTCAAGGATCTTACCGCTGTTGAGATCCAG
TTCGATGTAACCCACTCGTGCACCCAACTGATCTTCAGCATCTTTTACTTTCACCAGC
GTTTCTGGGTGAGCAAAAACAGGAAGGCAAATGCCGCAAAAAAGGGAATAAGGGC
GACACGGAAATGTTGAATACTCATACTCTTCCTTTTTCAATATTATTGAAGCATTTATC
AGGGTTATTGTCTCATGAGCGGATACATATTTGAATGTATTTAGAAAAATAAACAAAT
AGGGGTTCCGCGCACATTTCCCCGAAAAGTGCCACCTGACGTCTAAGAAACCATTAT
TATCATGACATTAACCTATAAAAATAGGCGTATCACGAGGCCCTTTCGTC
```

TABLE 6

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d6.LisOva |
|---|---|---|---|---|---|---|
| Il3 | interleukin 21 | 16.4 | 12.8 | 208.9 | 18.4 | 13.6 |
| Il2 | interleukin 3 | 97.0 | 16.0 | 1554.4 | 17.7 | 18.1 |
| Ccl4 | isopentenyl-diphosphate delta isomerase 2 | 2.1 | 16.8 | 35.6 | 17.6 | 19.7 |
| Il21 | granzyme C | 9.2 | 17.4 | 160.5 | 20.4 | 24.9 |
| Gp49a | chemokine (C-C motif) receptor 8 | 5.9 | 18.5 | 108.4 | 31.5 | 20.9 |
| Cxcl10 | interleukin 2 | 58.4 | 21.1 | 1229.6 | 32.7 | 17.9 |
| Nr4a3 | interleukin 1 receptor, type I | 2.6 | 21.2 | 54.6 | 35.5 | 21.7 |
| Lilrb4 | tumor necrosis factor (ligand) superfamily, member 4 | 4.1 | 21.8 | 88.8 | 29.3 | 20.0 |
| Cd200 | neuronal calcium sensor 1 | 4.5 | 24.1 | 109.6 | 46.3 | 23.2 |
| Cdkn1a | CDK5 and Abl enzyme substrate 1 | 3.1 | 26.2 | 80.9 | 49.1 | 32.8 |
| Gzmc | transmembrane and tetratricopeptide repeat containing 2 | 2.0 | 26.8 | 53.9 | 26.2 | 29.4 |
| Nr4a2 | LON peptidase N-terminal domain and ring finger 1 | 3.2 | 28.4 | 90.4 | 50.4 | 28.3 |
| Cish | glycoprotein 49 A | 15.0 | 31.6 | 472.4 | 30.6 | 212.5 |
| Nr4a1 | polo-like kinase 2 | 3.6 | 31.7 | 114.3 | 39.0 | 32.5 |
| Tnf | lipase, endothelial | 2.1 | 32.4 | 66.7 | 35.9 | 33.3 |
| Ccr8 | cyclin-dependent kinase inhibitor 1A (P21) | 9.7 | 34.6 | 335.4 | 54.4 | 71.0 |

TABLE 6-continued

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d6.LisOva |
|---|---|---|---|---|---|---|
| Lad1 | grainyhead-like 1 (Drosophila) | 2.1 | 35.1 | 73.4 | 52.0 | 44.1 |
| Slamf1 | cellular retinoic acid binding protein II | 5.3 | 35.4 | 187.2 | 43.3 | 36.3 |
| Crabp2 | adenylate kinase 4 | 2.2 | 35.9 | 80.4 | 58.5 | 39.8 |
| Furin | microtubule-associated protein 1B | 2.1 | 36.2 | 77.7 | 36.4 | 38.4 |
| Gadd45g | acyl-CoA synthetase long-chain family member 6 | 2.0 | 37.2 | 76.0 | 45.2 | 41.3 |
| Bcl2l1 | zinc finger E-box binding homeobox 2 | 2.1 | 38.6 | 80.7 | 44.9 | 455.8 |
| Ncs1 | CD200 antigen | 9.8 | 41.2 | 404.3 | 70.4 | 36.8 |
| Ciart | carboxypeptidase D | 3.1 | 41.6 | 127.7 | 71.4 | 71.6 |
| Ahr | thioredoxin reductase 3 | 3.6 | 43.4 | 157.8 | 61.7 | 28.8 |
| Spry1 | myosin IE | 2.3 | 43.6 | 100.2 | 61.3 | 77.0 |
| Tnfsf4 | RNA binding protein with multiple splicing 2 | 2.1 | 43.6 | 91.5 | 49.8 | 36.5 |
| Myo10 | mitogen-activated protein kinase kinase 3, opposite strand | 2.9 | 44.8 | 127.9 | 66.4 | 43.1 |
| Dusp5 | PERP, TP53 apoptosis effector | 2.8 | 44.9 | 127.2 | 78.4 | 72.4 |
| Myc | myosin X | 4.1 | 45.5 | 184.9 | 81.6 | 57.5 |
| Psrc1 | immediate early response 3 | 2.7 | 45.6 | 121.6 | 63.9 | 66.2 |
| St6galnac4 | folliculin interacting protein 2 | 2.6 | 47.5 | 124.2 | 87.4 | 96.6 |
| Nfkbid | leukocyte immunoglobulin-like receptor, subfamily B, member 4 | 9.9 | 48.9 | 483.3 | 64.5 | 179.1 |
| Bst2 | circadian associated repressor of transcription | 4.5 | 50.6 | 225.5 | 100.3 | 33.8 |
| Txnrd3 | RAR-related orphan receptor gamma | 2.1 | 51.7 | 106.7 | 47.5 | 52.8 |
| Plk2 | proline/serine-rich coiled-coil 1 | 3.9 | 52.9 | 205.9 | 92.3 | 79.6 |
| Gfi1 | cysteine rich protein 2 | 2.4 | 54.2 | 127.7 | 90.3 | 182.9 |
| Pim1 | cAMP responsive element modulator | 2.0 | 55.7 | 112.6 | 54.4 | 57.3 |
| Pvt1 | chemokine (C-C motif) ligand 4 | 20.2 | 55.8 | 1125.8 | 103.1 | 89.0 |
| Nfkbib | nuclear receptor subfamily 4, group A, member 2 | 7.8 | 58.5 | 457.6 | 78.7 | 72.0 |
| Gnl2 | transglutaminase 2, C polypeptide | 2.3 | 58.7 | 132.1 | 69.8 | 64.7 |
| Cd69 | synapse defective 1, Rho GTPase, homolog 2 (C, elegans) | 2.1 | 62.5 | 132.7 | 111.3 | 31.0 |
| Dgat2 | sprouty homolog 1 (Drosophila) | 4.2 | 63.8 | 268.5 | 76.8 | 61.4 |
| Atf3 | activating transcription factor 3 | 3.2 | 65.8 | 210.3 | 88.3 | 75.8 |
| Tnfrsf21 | pogo transposable element with KRAB domain | 2.9 | 68.6 | 196.9 | 91.1 | 293.2 |
| Lonrf1 | tumor necrosis factor receptor superfamily, member 21 | 3.2 | 70.6 | 224.5 | 126.5 | 72.9 |
| Cables1 | cytokine inducible SH2-containing protein | 7.5 | 74.3 | 558.7 | 82.5 | 133.9 |
| Cpd | lymphotoxin A | 2.6 | 74.6 | 197.2 | 93.4 | 58.6 |
| Qtrtd1 | FBJ osteosarcoma oncogene | 3.0 | 74.9 | 224.1 | 89.0 | 61.1 |
| Polr3d | signaling lymphocytic activation molecule family member 1 | 5.4 | 75.6 | 412.0 | 108.4 | 190.4 |
| Kcnq5 | syndecan 3 | 2.4 | 76.0 | 180.0 | 77.2 | 85.3 |
| Fos | mitochondrial ribosomal protein L47 | 2.1 | 77.2 | 161.7 | 152.0 | 72.3 |
| Slc19a2 | ladinin | 5.5 | 77.3 | 423.2 | 152.5 | 70.4 |
| Hif1a | E2F transcription factor 5 | 2.5 | 77.7 | 198.0 | 92.0 | 65.2 |
| Il15ra | ISG15 ubiquitin-like modifier | 2.8 | 77.9 | 221.0 | 88.9 | 45.1 |
| Nfkb1 | aryl-hydrocarbon receptor | 4.2 | 78.7 | 333.2 | 145.7 | 91.4 |
| PhIda3 | diacylglycerol O-acyltransferase 2 | 3.2 | 81.0 | 259.2 | 150.0 | 84.4 |
| Mtrr | FBJ osteosarcoma oncogene B | 2.0 | 81.3 | 163.7 | 139.3 | 98.5 |
| Pogk | pleckstrin homology-like domain, family A, member 3 | 2.9 | 84.8 | 244.5 | 126.9 | 83.8 |
| Map2k3os | potassium voltage-gated channel, subfamily Q, member 5 | 3.0 | 86.3 | 261.0 | 118.1 | 63.4 |
| Egr2 | tumor necrosis factor receptor superfamily, member 10b | 2.5 | 88.6 | 219.0 | 106.1 | 51.0 |
| Isg15 | Mir17 host gene 1 (non-protein coding) | 2.1 | 90.4 | 190.1 | 120.0 | 51.2 |
| Perp | glucose-fructose oxidoreductase domain containing 1 | 2.2 | 92.9 | 208.5 | 168.7 | 237.4 |
| Ipo4 | plexin A1 | 2.1 | 94.8 | 200.7 | 118.0 | 90.3 |
| Mphosph10 | heat shock factor 2 | 2.4 | 96.8 | 233.2 | 191.0 | 104.8 |
| Plk3 | carbohydrate sulfotransferase 11 | 2.4 | 96.8 | 235.1 | 180.8 | 385.7 |
| Ifitm3 | growth arrest and DNA-damage-inducible 45 gamma | 4.8 | 104.6 | 504.8 | 109.3 | 95.0 |
| Polr1b | solute carrier family 5 (sodium-dependent vitamin transporter), member 6 | 2.1 | 107.0 | 227.3 | 192.8 | 75.8 |
| Usp18 | interferon induced transmembrane protein 3 | 2.8 | 109.2 | 302.6 | 43.9 | 106.4 |
| Top1mt | DENN/MADD domain containing 5A | 2.6 | 109.5 | 279.9 | 102.0 | 517.4 |
| Dkc1 | plasminogen activator, urokinase receptor | 2.1 | 112.4 | 234.8 | 55.7 | 57.3 |
| Polr1c | solute carrier family 19 (thiamine transporter), member 2 | 3.0 | 115.4 | 343.1 | 221.7 | 138.4 |
| Cdk6 | ubiquitin domain containing 2 | 2.2 | 117.4 | 255.7 | 198.9 | 122.2 |
| Ier3 | nuclear receptor subfamily 4, group A, member 3 | 11.8 | 118.0 | 1394.1 | 114.2 | 69.6 |

TABLE 6-continued

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d6.LisOva |
|---|---|---|---|---|---|---|
| Lta | zinc finger protein 52 | 2.5 | 118.8 | 295.6 | 160.9 | 167.4 |
| Ptprs | SH3 domain containing ring finger 1 | 2.4 | 119.3 | 280.9 | 116.5 | 156.5 |
| Fnip2 | dihydrouridine synthase 2 | 2.1 | 122.7 | 260.3 | 237.7 | 202.8 |
| Asna1 | cyclin-dependent kinase 5, regulatory subunit 1 (p35) | 2.1 | 122.7 | 259.3 | 168.4 | 124.0 |
| Mybbp1a | processing of precursor 7, ribonuclease P family, (S, cerevisiae) | 2.1 | 125.9 | 264.9 | 235.7 | 150.6 |
| Il1r1 | growth factor independent 1 | 3.5 | 126.8 | 437.7 | 212.0 | 156.6 |
| Dennd5a | interleukin 15 receptor, alpha chain | 2.9 | 130.9 | 380.1 | 144.3 | 167.8 |
| E2f5 | BCL2-like 1 | 4.7 | 133.7 | 627.4 | 257.4 | 231.2 |
| Rcl1 | protein tyrosine phosphatase, receptor type, S | 2.6 | 136.6 | 358.8 | 157.5 | 125.0 |
| FosI2 | plasmacytoma variant translocation 1 | 3.4 | 136.7 | 465.5 | 179.8 | 140.7 |
| Atad3a | fos-like antigen 2 | 2.5 | 137.0 | 347.5 | 107.2 | 177.8 |
| Bax | BCL2-associated X protein | 2.5 | 138.0 | 347.3 | 260.1 | 150.2 |
| Phf6 | solute carrier family 4, sodium bicarbonate cotransporter, member 7 | 2.3 | 140.3 | 328.2 | 258.7 | 397.5 |
| Zfp52 | tumor necrosis factor receptor superfamily, member 4 | 2.2 | 141.7 | 311.1 | 161.7 | 111.6 |
| Crtam | chemokine (C—X—C motif) ligand 10 | 12.7 | 141.7 | 1798.3 | 242.1 | 59.4 |
| Nop14 | polo-like kinase 3 | 2.8 | 144.8 | 406.3 | 200.1 | 119.9 |
| Rel | CD3E antigen, epsilon polypeptide associated protein | 2.2 | 158.7 | 350.2 | 260.9 | 111.4 |
| Gramd1b | tumor necrosis factor (ligand) superfamily, member 11 | 2.1 | 162.4 | 342.1 | 242.1 | 169.7 |
| Ifi27l2a | polymerase (RNA) III (DNA directed) polypeptide D | 3.0 | 166.3 | 503.7 | 296.1 | 121.6 |
| Tnfrsf10b | early growth response 2 | 2.8 | 173.5 | 494.0 | 136.3 | 68.2 |
| Rpl7l1 | DnaJ (Hsp40) homolog, subfamily C, member 2 | 2.1 | 173.6 | 369.4 | 346.2 | 254.3 |
| Eif1a | DNA topoisomerase 1, mitochondrial | 2.7 | 182.2 | 498.2 | 338.6 | 114.4 |
| Nfkb2 | tripartite motif-containing 30D | 2.3 | 182.6 | 423.4 | 65.8 | 90.6 |
| Heatr1 | DnaJ (Hsp40) homolog, subfamily C, member 21 | 2.0 | 190.1 | 389.4 | 285.5 | 228.2 |
| Utp20 | SAM domain, SH3 domain and nuclear localization signals, 1 | 2.2 | 191.5 | 422.1 | 222.8 | 304.1 |
| Chst11 | solute carrier family 5 (inositol transporters), member 3 | 2.1 | 191.6 | 400.2 | 210.0 | 123.4 |
| Ddx21 | mitochondrial ribosomal protein L15 | 2.1 | 191.6 | 396.3 | 329.8 | 137.7 |
| Hsf2 | dual specificity phosphatase 5 | 4.0 | 203.5 | 818.1 | 307.5 | 560.7 |
| Bccip | apoptosis enhancing nuclease | 2.3 | 211.1 | 478.5 | 288.2 | 137.9 |
| Tagap | ets variant 6 | 2.3 | 218.3 | 508.1 | 220.5 | 297.3 |
| Sdc3 | DIM1 dimethyladenosine transferase 1-like (S, cerevisiae) | 2.2 | 218.4 | 486.0 | 356.0 | 129.7 |
| SytI3 | 2'-5' oligoadenylate synthetase-like 1 | 2.1 | 229.0 | 473.3 | 130.7 | 124.3 |
| Gtpbp4 | UTP18, small subunit (SSU) processome component, homolog (yeast) | 2.1 | 232.0 | 494.3 | 384.9 | 189.5 |
| Crip2 | BRCA2 and CDKN1A interacting protein | 2.4 | 234.6 | 563.3 | 437.5 | 269.8 |
| Sh3rf1 | synaptotagmin-like 3 | 2.4 | 242.4 | 572.9 | 316.7 | 700.7 |
| Nsfl1c | 5-methyltetrahydrofolate-homocysteine methyltransferase reductase | 2.9 | 245.7 | 706.5 | 334.6 | 150.6 |
| Gtf2f1 | URB2 ribosome biogenesis 2 homolog (S, cerevisiae) | 2.0 | 245.7 | 500.2 | 489.8 | 184.6 |
| Slc4a7 | ubiquitin-conjugating enzyme E2C binding protein | 2.1 | 251.2 | 530.5 | 288.2 | 85.2 |
| Etv6 | lysine (K)-specific demethylase 2B | 2.2 | 251.8 | 547.1 | 332.7 | 262.1 |
| Trim30d | queuine tRNA-ribosyltransferase domain containing 1 | 3.0 | 260.3 | 788.7 | 358.0 | 75.5 |
| Ddx27 | ubiquitin specific peptidase 31 | 2.0 | 265.2 | 533.2 | 277.1 | 176.2 |
| Pwp2 | eukaryotic translation initiation factor 2-alpha kinase 2 | 2.0 | 267.7 | 540.5 | 260.8 | 244.8 |
| Chchd2 | ATPase family, AAA domain containing 3A | 2.5 | 268.8 | 679.7 | 523.1 | 147.1 |
| Myo1e | adhesion molecule, interacts with CXADR antigen 1 | 2.3 | 269.5 | 610.9 | 272.9 | 182.8 |
| Eif5b | SUMO/sentrin specific peptidase 3 | 2.0 | 272.5 | 548.7 | 544.5 | 298.4 |
| Stat5a | ESF1, nucleolar pre-rRNA processing protein, homolog (S, cerevisiae) | 2.2 | 276.3 | 610.4 | 482.2 | 266.5 |
| Cops6 | deoxynucleotidyltransferase, terminal, interacting protein 2 | 2.1 | 282.9 | 600.4 | 359.9 | 326.1 |
| D19Bwg1357e | TGFB-induced factor homeobox 1 | 2.1 | 300.5 | 618.9 | 217.5 | 210.6 |
| Aatf | eukaryotic translation initiation factor 1A | 2.5 | 300.8 | 738.7 | 597.7 | 262.8 |
| Aen | interferon-stimulated protein | 2.1 | 305.7 | 651.2 | 144.3 | 138.4 |
| Amica1 | pleiomorphic adenoma gene-like 2 | 2.1 | 311.5 | 651.9 | 376.2 | 405.9 |
| Wdr43 | PWP2 periodic tryptophan protein homolog (yeast) | 2.3 | 321.8 | 743.3 | 586.5 | 189.3 |

TABLE 6-continued

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d6.LisOva |
|---|---|---|---|---|---|---|
| Cct4 | furin (paired basic amino acid cleaving enzyme) | 5.2 | 329.7 | 1728.3 | 271.7 | 421.5 |
| Nifk | tumor necrosis factor | 6.6 | 330.7 | 2188.4 | 489.9 | 213.3 |
| Tgm2 | apoptosis antagonizing transcription factor | 2.3 | 331.4 | 754.8 | 523.1 | 221.5 |
| Ero1l | interferon, alpha-inducible protein 27 like 2A | 2.5 | 334.0 | 828.1 | 296.0 | 221.4 |
| Gfod1 | ST6 (alpha-N-acetyl-neuraminyl-2,3-beta-galactosyl-1,3)-N-acetylgalactosaminide alpha-2,6-sialyltransferase 4 | 3.9 | 338.4 | 1311.3 | 636.0 | 298.2 |
| Ak4 | methyltransferase like 1 | 2.2 | 339.4 | 744.7 | 662.8 | 94.5 |
| Sdad1 | notchless homolog 1 (*Drosophila*) | 2.0 | 339.4 | 690.3 | 610.3 | 158.1 |
| Dimt1 | mitochondrial ribosomal protein L3 | 2.1 | 340.0 | 725.5 | 651.4 | 359.8 |
| Esf1 | UBX domain protein 2A | 2.1 | 343.8 | 732.9 | 532.1 | 428.5 |
| Cd3eap | guanine nucleotide binding protein-like 2 (nucleolar) | 3.2 | 347.6 | 1124.7 | 647.4 | 227.5 |
| Samsn1 | programmed cell death 11 | 2.0 | 353.9 | 711.8 | 435.9 | 287.4 |
| Tnfrsf4 | cyclin-dependent kinase 8 | 2.0 | 364.0 | 731.1 | 702.5 | 346.2 |
| Mettl1 | eukaryotic translation initiation factor 5B | 2.3 | 365.1 | 838.2 | 544.5 | 355.5 |
| Cd274 | RNA terminal phosphate cyclase-like 1 | 2.5 | 373.3 | 948.8 | 746.4 | 155.8 |
| Ubtd2 | NSFL1 (p97) cofactor (p47) | 2.3 | 374.1 | 876.1 | 725.9 | 369.7 |
| Icos | nuclear factor of kappa light polypeptide gene enhancer in B cells inhibitor, delta | 3.9 | 378.5 | 1465.1 | 389.9 | 224.0 |
| Kdm2b | M-phase phosphoprotein 10 (U3 small nucleolar ribonucleoprotein) | 2.8 | 379.8 | 1069.3 | 738.4 | 290.8 |
| Larp4 | GRAM domain containing 1B | 2.5 | 382.7 | 949.6 | 363.4 | 659.2 |
| Eif3d | ERO1-like (*S, cerevisiae*) | 2.2 | 387.7 | 872.3 | 773.0 | 520.9 |
| Tnfaip3 | nuclear receptor subfamily 4, group A, member 1 | 6.8 | 387.8 | 2639.0 | 343.7 | 220.7 |
| Map1b | surfeit gene 2 | 2.1 | 399.8 | 852.2 | 696.3 | 204.0 |
| Cdv3 | N(alpha)-acetyltransferase 25, NatB auxiliary subunit | 2.1 | 405.7 | 847.3 | 669.5 | 194.1 |
| Plac8 | yrdC domain containing (*E, coli*) | 2.0 | 406.7 | 830.8 | 635.3 | 267.0 |
| Mrpl3 | La ribonucleoprotein domain family, member 4 | 2.2 | 408.8 | 887.9 | 586.6 | 358.3 |
| Surf2 | SDA1 domain containing 1 | 2.2 | 419.8 | 939.9 | 631.4 | 284.7 |
| Ubxn2a | importin 4 | 2.8 | 420.3 | 1183.6 | 777.8 | 173.5 |
| Utp18 | inducible T cell co-stimulator | 2.2 | 423.9 | 920.9 | 818.8 | 796.9 |
| Isg20 | solute carrier family 7 (cationic amino acid transporter, y+ system), member 1 | 2.1 | 439.4 | 934.4 | 842.6 | 344.6 |
| Dnajc2 | arsA arsenite transporter, ATP-binding, homolog 1 (bacterial) | 2.6 | 446.6 | 1165.0 | 717.9 | 963.9 |
| Jak2 | polymerase (RNA) I polypeptide C | 2.7 | 447.8 | 1208.4 | 854.0 | 295.9 |
| Slc7a1 | spermatogenesis associated 5 | 2.0 | 450.8 | 920.2 | 516.0 | 361.6 |
| Syde2 | ubiquitin specific peptidase 18 | 2.7 | 451.8 | 1240.5 | 296.0 | 250.7 |
| Slc5a6 | placenta-specific 8 | 2.1 | 452.4 | 967.3 | 888.6 | 590.8 |
| Dnttip2 | general transcription factor IIF, polypeptide 1 | 2.3 | 454.8 | 1063.9 | 890.0 | 680.8 |
| Idi2 | nuclear factor of kappa light polypeptide gene enhancer in B cells inhibitor, beta | 3.4 | 456.4 | 1535.5 | 679.1 | 502.7 |
| Dus2 | PHD finger protein 6 | 2.5 | 462.0 | 1159.5 | 775.8 | 510.4 |
| Pitrm1 | RRN3 RNA polymerase I transcription factor homolog (yeast) | 2.1 | 462.2 | 948.4 | 913.2 | 388.9 |
| Plxna1 | cytotoxic and regulatory T cell molecule | 2.5 | 473.7 | 1177.8 | 586.8 | 431.8 |
| Cdk5r1 | COP9 (constitutive photomorphogenic) homolog, subunit 6 (*Arabidopsis thaliana*) | 2.3 | 483.6 | 1101.9 | 947.8 | 560.3 |
| Ube2cbp | asparagine-linked glycosylation 3 (alpha-1,3-mannosyltransferase) | 2.1 | 485.9 | 1006.3 | 758.7 | 339.4 |
| Tnfsfl1 | tryptophanyl-tRNA synthetase | 2.0 | 486.1 | 987.1 | 897.1 | 504.7 |
| Pop7 | hypoxia up-regulated 1 | 2.0 | 494.3 | 996.6 | 802.4 | 690.3 |
| Psme3 | family with sequence similarity 60, member A | 2.0 | 500.8 | 1002.1 | 834.7 | 417.6 |
| Mir17hg | bone marrow stromal cell antigen 2 | 3.8 | 502.5 | 1922.9 | 925.5 | 246.0 |
| Tsr1 | nuclear factor of kappa light polypeptide gene enhancer in B cells 2, p49/p100 | 2.4 | 503.2 | 1231.8 | 494.0 | 341.8 |
| Rbpms2 | UTP20, small subunit (SSU) processome component, homolog (yeast) | 2.4 | 510.5 | 1240.2 | 696.4 | 245.8 |
| Mrpl47 | CD274 antigen | 2.2 | 516.6 | 1128.7 | 246.9 | 220.2 |
| Rab8b | proviral integration site 1 | 3.4 | 518.4 | 1766.4 | 676.9 | 970.0 |
| Plagl2 | signal transducer and activator of transcription 5A | 2.3 | 530.0 | 1210.4 | 496.6 | 507.8 |
| Grhl1 | CD69 antigen | 3.2 | 535.7 | 1725.8 | 289.5 | 153.9 |
| Zeb2 | pitrilysin metallepetidase 1 | 2.1 | 544.9 | 1153.8 | 968.4 | 349.3 |
| sept-02 | cyclin-dependent kinase 6 | 2.7 | 550.3 | 1476.5 | 1064.0 | 642.1 |
| Slc5a3 | DEAD (Asp-Glu-Ala-Asp) box polypeptide 27 | 2.3 | 556.2 | 1286.9 | 987.2 | 480.4 |

TABLE 6-continued

Preferred human endogenous gene loci responsive to T-cell activation

| symbol | description | inductionRatio12 hr | T.8Nve.Sp.OT1 | T.8Eff.Sp.OT1. 12 hr.LisOva | T.8Eff.Sp.OT1. 48 hr.LisOva | T.8Eff.Sp.OT1. d6.LisOva |
|---|---|---|---|---|---|---|
| Naa25 | polymerase (RNA) I polypeptide B | 2.8 | 556.2 | 1536.0 | 1070.4 | 201.3 |
| Plaur | tumor necrosis factor, alpha-induced protein 3 | 2.2 | 560.6 | 1212.2 | 255.5 | 446.0 |
| Metap1 | nodal modulator 1 | 2.1 | 563.0 | 1161.0 | 988.9 | 439.8 |
| Alg3 | NOP14 nucleolar protein | 2.5 | 570.9 | 1418.9 | 925.3 | 398.0 |
| Mrpl15 | ribosomal protein L7-like 1 | 2.5 | 586.7 | 1448.7 | 1030.2 | 687.2 |
| Oasl1 | methionyl aminopeptidase 1 | 2.1 | 597.5 | 1244.1 | 1139.3 | 433.4 |
| Rorc | hypoxia inducible factor 1, alpha subunit | 3.0 | 624.2 | 1854.6 | 809.4 | 838.4 |
| Nomo1 | Janus kinase 2 | 2.1 | 624.5 | 1328.7 | 390.6 | 917.8 |
| Tgif1 | nuclear factor of kappa light polypeptide gene enhancer in B cells 1, p105 | 2.9 | 661.5 | 1913.3 | 713.9 | 720.5 |
| Lipg | reticuloendotheliosis oncogene | 2.5 | 678.9 | 1686.4 | 409.8 | 580.5 |
| Rrn3 | septin 2 | 2.1 | 687.3 | 1436.0 | 1354.1 | 1181.3 |
| Dnajc21 | nucleolar protein interacting with the FHA domain of MKI67 | 2.3 | 733.4 | 1658.2 | 1280.0 | 407.2 |
| Yrdc | elongation factor Tu GTP binding domain containing 2 | 2.0 | 739.3 | 1483.5 | 1439.0 | 904.3 |
| Acsl6 | myelocytomatosis oncogene | 4.0 | 761.0 | 3022.8 | 1064.0 | 211.5 |
| Spata5 | dyskeratosis congenita 1, dyskerin | 2.7 | 778.2 | 2112.0 | 1549.5 | 484.2 |
| Urb2 | carnitine deficiency-associated gene expressed in ventricle 3 | 2.1 | 801.6 | 1718.2 | 1274.7 | 1010.3 |
| Nle1 | GTP binding protein 4 | 2.4 | 824.2 | 1942.6 | 1578.7 | 567.3 |
| Wars | HEAT repeat containing 1 | 2.4 | 830.3 | 2020.6 | 1235.5 | 495.4 |
| Crem | proteaseome (prosome, macropain) activator subunit 3 (PA28 gamma, Ki) | 2.1 | 838.4 | 1763.5 | 1471.1 | 936.1 |
| Larp1 | La ribonucleoprotein domain family, member 1 | 2.0 | 861.7 | 1742.1 | 1250.9 | 854.3 |
| Eif2ak2 | DNA segment, Chr 19, Brigham & Women's Genetics 1357 expressed | 2.3 | 868.6 | 1978.4 | 1218.0 | 653.4 |
| Hyou1 | eukaryotic translation initiation factor 3, subunit D | 2.2 | 909.1 | 1971.6 | 1641.9 | 920.6 |
| Senp3 | TSR1 20S rRNA accumulation | 2.1 | 913.9 | 1915.9 | 1474.6 | 477.2 |
| Tmtc2 | MYB binding protein (P160) 1a | 2.6 | 1140.0 | 2962.9 | 2200.7 | 459.8 |
| Fosb | T cell activation Rho GTPase activating protein | 2.4 | 1176.7 | 2794.4 | 489.3 | 704.2 |
| Pdcd11 | RAB8B, member RAS oncogene family | 2.1 | 1189.5 | 2492.2 | 1671.3 | 2512.5 |
| Usp31 | DEAD (Asp-Glu-Ala-Asp) box polypeptide 21 | 2.4 | 1210.2 | 2928.0 | 2221.1 | 1098.2 |
| Cdk8 | chaperonin containing Tcp1, subunit 4 (delta) | 2.3 | 1321.4 | 2989.7 | 2462.5 | 1294.8 |
| Eftud2 | coiled-coil-helix-coiled-coil-helix domain containing 2 | 2.3 | 1374.2 | 3171.2 | 2636.9 | 1008.9 |
| Fam60a | WD repeat domain 43 | 2.3 | 1727.6 | 3912.6 | 2927.5 | 1014.9 |

TABLE 7

Selection of preferred endogenous genes that are constantly active during immune cell activation (dependent or independent from T-cell activation).

| Symbol | Gene description |
|---|---|
| CD3G | CD3 gamma |
| Rn28s1 | 28S ribosomal RNA |
| Rn18s | 18S ribosomal RNA |
| Rn7sk | RNA, 7SK, nuclear |
| Actg1 | actin, gamma, cytoplasmic 1 |
| B2m | beta-2 microglobulin |
| Rpl18a | ribosomal protein L18A |
| Pabpc1 | poly(A) binding protein, cytoplasmic 1 |
| Gapdh | glyceraldehyde-3-phosphate dehydrogenase |
| Rpl19 | ribosomal protein L19 |
| Rpl17 | ribosomal protein L17 |
| Rplp0 | ribosomal protein, large, P0 |
| Cfl1 | cofilin 1, non-muscle |
| Pfn1 | profilin 1 |

TABLE 8

Selection of genes that are transiently upregulated upon T-cell activation.

| Symbol | Gene description |
|---|---|
| Il3 | interleukin 3 |
| Il2 | interleukin 2 |
| Ccl4 | chemokine (C-C motif) ligand 4 |
| Il21 | interleukin 21 |
| Gp49a | glycoprotein 49 A |
| Nr4a3 | nuclear receptor subfamily 4, group A, member 3 |
| Lilrb4 | leukocyte immunoglobulin-like receptor, subfamily B, member 4 |
| Cd200 | CD200 antigen |
| Cdkna | cyclin-dependent kinase inhibitor 1A (P21) |
| Gzmc | granzyme C |
| Nr4a2 | nuclear receptor subfamily 4, group A, member 2 |
| Cish | cytokine inducible SH2-containing protein |
| Ccr8 | chemokine (C-C motif) receptor 8 |
| Lad1 | ladinin |
| Crabp2 | cellular retinoic acid binding protein 11 |

TABLE 9

Selection of genes that are upregulated over more than 24 hours upon T-cell activation.

| Symbol | Description |
|---|---|
| Gzmb | granzyme B |
| Tbx21 | T-box 21 |
| Pdcd1 | programmed cell death 1 |
| Plek | pleckstrin |
| Chek1 | checkpoint kinase 1 |
| Slamf7 | SLAM family member 7 |
| Zbtb32 | zinc finger and BTB domain containing 32 |
| Tigit | T cell immunoreceptor with Ig and ITIM domains |
| Lag3 | lymphocyte-activation gene 3 |
| Gzma | granzyme A |
| Wee1 | WEE 1 homolog 1 (S. pombe) |
| Il12rb2 | interleukin 12 receptor, beta 2 |
| Ccr5 | chemokine (C-C motif) receptor 5 |
| Eea1 | early endosome antigen 1 |
| Dtl | denticleless homolog (Drosophila) |

TABLE 10

Selection of genes that are down-regulated upon immune cell activation.

| Symbol | Gene description |
|---|---|
| Apata6 | spermatogenesis associated 6 |
| Itga6 | integrin alpha 6 |
| Rcbtb2 | regulator of chromosome condensation (RCC1) and BTB (POZ) domain containing protein 2 |
| Cd1d1 | CD1d1 antigen |
| St8sia4 | 5T8 alpha-N-acetyl-neuraminide alpha-2,8-sialyltransferase 4 |
| Itgae | integrin alpha E, epithelial-associated |
| Fam214a | family with sequence similarity 214, member A |
| Slc6a19 | solute carrier family 6 (neurotransmitter transporter), member 19 |
| Cd55 | CD55 antigen |
| Xkrx | X Kell blood group precursor related X linked |
| Mturn | maturin, neural progenitor differentiation regulator homolog (Xenopus) |
| H2-Ob | histocompatibility 2, O region beta locus |
| Cnr2 | cannabinoid receptor 2 (macrophage) |
| Itgae | integrin alpha E, epithelial-associated |
| Raver2 | ribonucleoprotein, PTB-binding 2 |
| Zbtb20 | zinc finger and BTB domain containing 20 |
| Arrb1 | arrestin, beta 1 |
| Abca1 | ATP-binding cassette, sub-family A (ABC1), member 1 |
| Tet1 | tet methylcytosine dioxygenase 1 |
| Slc16a5 | solute carrier family 16 (monocarboxylic acid transporters), member 5 |
| Trav14-1 | T cell receptor alpha variable 14-1 |
| Ampd3 | adenosine monophosphate deaminase 3 |

TABLE 11

Selection of human genes that are silent upon T-cell activation (safe harbor gene targeted integration loci).

| Symbol | Gene description |
|---|---|
| Zfp640 | zinc finger protein 640 |
| LOC100038422 | uncharacterized LOC100038422 |
| Zfp600 | zinc finger protein 600 |
| Serpinb3a | serine (or cysteine) peptidase inhibitor, clade B (ovalbumin), member 3A |
| Tas2r106 | taste receptor, type 2, member 106 |
| Magea3 | melanoma antigen, family A, 3 |
| Omt2a | oocyte maturation, alpha |
| Cpxcr1 | CPX chromosome region, candidate 1 |
| Hsf3 | heat shock transcription factor 3 |
| Pbsn | Probasin |
| Sbp | spermine binding protein |
| Wfdc6b | WAP four-disulfide core domain 6B |
| Meiob | meiosis specific with OB domains |
| Dnm3os | dynamin 3, opposite strand |
| Skint11 | selection and upkeep of intraepithelial T cells 11 |

TABLE 12

List of gene loci upregulated in tumor exhausted infiltrating lymphocytes from multiple tumors) useful for gene integration of exogenous (compiled coding sequences as per the present invention

| Gene names | Uniprot ID (human) |
|---|---|
| CXCL13 | O43927 |
| TNFRSF1B | P20333 |
| RGS2 | P41220 |
| TIGIT | Q495A1 |
| CD27 | P26842 |
| TNFRSF9 | Q12933 |
| SLA | Q13239 |
| INPP5F | Q01968 |
| XCL2 | Q9UBD3 |
| HLA-DMA | P28067 |
| FAM3C | Q92520 |
| WARS | P23381 |
| EIF3L | Q9Y262 |
| KCN K5 | O95279 |
| TMBIM6 | P55061 |
| CD200 | P41217 |
| C3H7A | O60880 |
| SH2D1A | O60880 |
| ATP1B3 | P54709 |
| THADA | Q6YHU6 |
| PARK7 | Q99497 |
| EGR2 | P11161 |
| FDFT1 | P37268 |
| CRTAM | O95727 |
| IFO16 | Q16666 |

TABLE 13

List of gene loci upregulated in hypoxic tumor conditions useful for gene integration of exogenous coding sequences as per the present invention

| Gene names | Strategy | |
|---|---|---|
| CTLA-4 | KO/KI | Target shown to be upregulated |
| LAG-3 (CD223) | KO/KI | in T-cells upon hypoxia exposure |
| PD1 | KO/KI | and T cell exhaustion |
| 4-1BB (CD137) | KI | |
| GITR | KI | |
| OX40 | KI | |
| IL10 | KO/KI | |
| ABCB1 | KI | HIF target |
| ABCG2 | KI | |
| ADM | KI | |
| ADRA1B | KI | |
| AK3 | KI | |
| ALDOA | KI | |
| BHLHB2 | KI | |
| BHLHB3 | KI | |
| BNIP3 | KI | |
| BNIP3L | KI | |
| CA9 | KI | |
| CCNG2 | KI | |
| CD99 | KI | |
| CDKN1A | KI | |
| CITED2 | KI | |
| COL5A1 | KI | |
| CP | KI | |

TABLE 13-continued

List of gene loci upregulated in hypoxic tumor conditions useful for gene integration of exogenous coding sequences as per the present invention

| Gene names | Strategy |
| --- | --- |
| CTGF | KI |
| CTSD | KI |
| CXCL12 | KI |
| CXCR4 | KI |
| CYP2S1 | KI |
| DDIT4 | KI |
| DEC1 | KI |
| EDN1 | KI |
| EGLN1 | KI |
| EGLN3 | KI |
| ENG | KI |
| EN01 | KI |
| EPO | KI |
| ETS1 | KI |
| FECH | KI |
| FN1 | KI |
| FURIN | KI |
| GAPDH | KI |
| GPI | KI |
| GPX3 | KI |
| HK1 | KI |
| HK2 | KI |
| HMOX1 | KI |
| HSP90B1 | KI |
| ID2 | KI |
| IGF2 | KI |
| IGFBP1 | KI |
| IGFBP2 | KI |
| IGFBP3 | KI |
| ITGB2 | KI |
| KRTI4 | KI |
| KRTI8 | KI |
| KRTI9 | KI |
| LDHA | KI |
| LEP | KI |
| LOX | KI |
| LRPI | KI |
| MCLI | KI |
| MET | KI |
| MMPI4 | KI |
| MMP2 | KI |
| MXI1 | KI |
| NOS2A | KI |
| NOS3 | KI |
| NPMI | KI |
| NR4A1 | KI |
| NT5E | KI |
| PDGFA | KI |
| PDKI | KI |
| PFKFB3 | KI |
| PFKL | KI |
| PGKI | KI |
| PH-4 | KI |
| PKM2 | KI |
| PLAUR | KI |
| PMAIPI | KI |
| PPP5C | KI |
| PROKI | 12 |
| SERPINE1 | KI |
| SLC2A1 | KI |
| TERT | KI |
| TF | KI |
| TFF3 | KI |
| TFRC | KI |
| TGFA | KI |
| TGFB3 | KI |
| TGM2 | KI |
| TPI1 | KI |
| VEGFA | KI |
| VIM | KI |
| TMEM45A | KI |
| AKAP12 | KI |
| SEC24A | KI |
| ANKRD37 | KI |
| RSBN1 | KI |
| GOPC | KI |
| SAMD12 | KI |
| CRKL | KI |
| EDEM3 | KI |
| TRIM9 | KI |
| GOSR2 | KI |
| MIF | KI |
| ASPH | KI |
| WDR33 | KI |
| DHX40 | KI |
| KLF10 | KI |
| R3HDM1 | KI |
| RARA | KI |
| L0C162073 | KI |
| PGRMC2 | KI |
| ZWILCH | KI |
| TPCN1 | KI |
| WSB1 | KI |
| SPAG4 | KI |
| GYS1 | KI |
| RRP9 | KI |
| SLC25A28 | KI |
| NTRK2 | KI |
| NARF | KI |
| ASCC1 | KI |
| UFM1 | KI |
| TXN I P | KI |
| MGAT2 | KI |
| VDAC1 | KI |
| SEC61G | KI |
| SRP19 | KI |
| JMJD2C | KI |
| SNRPD1 | KI |
| RASSF4 | KI |

SEQUENCE LISTING

<160> NUMBER OF SEQ ID NOS: 80

<210> SEQ ID NO 1
<211> LENGTH: 1000
<212> TYPE: DNA
<213> ORGANISM: artificial sequence
<220> FEATURE:
<223> OTHER INFORMATION: PD1 left homology

<400> SEQUENCE: 1
ccaagccctg accctggcag gcatatgttt caggaggtcc ttgtcttggg agcccagggt    60

| | |
|---|---|
| cggggggcccc gtgtctgtcc acatccgagt caatggccca tctcgtctct gaagcatctt | 120 |
| tgctgtgagc tctagtcccc actgtcttgc tggaaaatgt ggaggcccca ctgcccactg | 180 |
| cccagggcag caatgcccat accacgtggt cccagctccg agcttgtcct gaaaagggggg | 240 |
| caaagactgg accctgagcc tgccaagggg ccacactcct cccagggctg gggtctccat | 300 |
| gggcagcccc ccacccaccc agaccagtta cactcccctg tgccagagca gtgcagacag | 360 |
| gaccaggcca ggatgcccaa gggtcagggg ctggggatgg gtagccccca aacagccctt | 420 |
| tctggggaa ctggcctcaa cggggaaggg ggtgaaggct cttagtagga aatcagggag | 480 |
| acccaagtca gagccaggtg ctgtgcagaa gctgcagcct cacgtagaag gaagaggctc | 540 |
| tgcagtggag gccagtgccc atccccgggt ggcagaggcc ccagcagaga cttctcaatg | 600 |
| acattccagc tggggtggcc cttccagagc ccttgctgcc cgagggatgt gagcaggtgg | 660 |
| ccggggaggc tttgtggggc cacccagccc cttcctcacc tctctccatc tctcagactc | 720 |
| cccagacagg ccctggaacc cccccacctt ctccccagcc ctgctcgtgg tgaccgaagg | 780 |
| ggacaacgcc accttcacct gcagcttctc caacacatcg gagagcttcg tgctaaactg | 840 |
| gtaccgcatg agccccagca accagacgga caagctggcc gccttccccg aggaccgcag | 900 |
| ccagcccggc caggactgcc gcttccgtgt cacacaactg cccaacgggc gtgacttcca | 960 |
| catgagcgtg gtcagggccc ggcgcaatga cagcggcacc | 1000 |

<210> SEQ ID NO 2
<211> LENGTH: 1000
<212> TYPE: DNA
<213> ORGANISM: artificial sequence
<220> FEATURE:
<223> OTHER INFORMATION: PD1 right homology

<400> SEQUENCE: 2

| | |
|---|---|
| gcctgcgggc agagctcagg gtgacaggtg cggcctcgga ggccccgggg caggggtgag | 60 |
| ctgagccggt cctggggtgg gtgtcccctc ctgcacagga tcaggagctc cagggtcgta | 120 |
| gggcagggac ccccccagctc cagtccaggg ctctgtcctg cacctgggga atggtgaccg | 180 |
| gcatctctgt cctctagctc tggaagcacc ccagcccctc tagtctgccc tcaccccctga | 240 |
| ccctgaccct ccaccctgac cccgtcctaa ccctgacct ttgtgccctt ccagagagaa | 300 |
| gggcagaagt gccacagcc cacccagcc cctcacccag gccagccggc cagttccaaa | 360 |
| ccctggtggt tggtgtcgtg ggcggcctgc tgggcagcct ggtgctgcta gtctgggtcc | 420 |
| tggccgtcat ctgctcccgg gccgcacgag gtaacgtcat cccagcccct cggcctgccc | 480 |
| tgccctaacc ctgctggcgg ccctcactcc cgcctcccct tcctccaccc ttccctcacc | 540 |
| ccaccccacc tccccccatc tccccgccag gctaagtccc tgatgaaggc ccctggacta | 600 |
| agaccccca cctaggagca cggctcaggg tcggcctggt gaccccaagt gtgtttctct | 660 |
| gcagggacaa taggagccag gcgcaccggc cagcccctgg tgagtctcac tcttttcctg | 720 |
| catgatccac tgtgccttcc ttcctgggtg ggcagaggtg gaaggacagg ctgggaccac | 780 |
| acggcctgca ggactcacat tctattatag ccaggacccc acctccccag cccccaggca | 840 |
| gcaacctcaa tccctaaagc catgatctgg ggccccagcc cacctgcggt ctccgggggt | 900 |
| gccggcccca tgtgtgtgcc tgcctgcggt ctccaggggt gcctggccca cgcgtgtgcc | 960 |
| cgcctgcggt ctctgggggt gcccggccca catatgtgcc | 1000 |

<210> SEQ ID NO 3
<211> LENGTH: 2781

<212> TYPE: DNA
<213> ORGANISM: artificial sequence
<220> FEATURE:
<223> OTHER INFORMATION: PD1_T3C-L2

<400> SEQUENCE: 3

| | | | | | |
|---|---|---|---|---|---|
| atgggcgatc | ctaaaaagaa | acgtaaggtc | atcgatatcg | ccgatctacg | cacgctcggc | 60 |
| tacagccagc | agcaacagga | gaagatcaaa | ccgaaggttc | gttcgacagt | ggcgcagcac | 120 |
| cacgaggcac | tggtcggcca | cgggtttaca | cacgcgcaca | tcgttgcgtt | aagccaacac | 180 |
| ccggcagcgt | tagggaccgt | cgctgtcaag | tatcaggaca | tgatcgcagc | gttgccagag | 240 |
| gcgacacacg | aagcgatcgt | tggcgtcggc | aaacagtggt | ccggcgcacg | cgctctggag | 300 |
| gccttgctca | cggtggcggg | agagttgaga | ggtccaccgt | tacagttgga | cacaggccaa | 360 |
| cttctcaaga | ttgcaaaacg | tggcggcgtg | accgcagtgg | aggcagtgca | tgcatggcgc | 420 |
| aatgcactga | cgggtgcccc | gctcaacttg | accccgagc | aagtggtggc | tatcgcttcc | 480 |
| aagctggggg | gaaagcaggc | cctggagacc | gtccaggccc | ttctcccagt | gctttgccag | 540 |
| gctcacggac | tgacccctga | acaggtggtg | gcaattgcct | cacacgacgg | gggcaagcag | 600 |
| gcactggaga | ctgtccagcg | gctgctgcct | gtcctctgcc | aggcccacgg | actcactcct | 660 |
| gagcaggtcg | tggccattgc | cagccacgat | gggggcaaac | aggctctgga | gaccgtgcag | 720 |
| cgcctcctcc | cagtgctgtg | ccaggctcat | gggctgaccc | cacagcaggt | cgtcgccatt | 780 |
| gccagtaacg | gcggggggaa | gcaggccctc | gaaacagtgc | agaggctgct | gcccgtcttg | 840 |
| tgccaagcac | acggcctgac | acccgagcag | gtggtggcca | tcgcctctca | tgacggcggc | 900 |
| aagcaggccc | ttgagacagt | gcagagactg | ttgccgtgt | tgtgtcaggc | ccacgggttg | 960 |
| acaccccagc | aggtggtcgc | catcgccagc | aatggcgggg | gaaagcaggc | ccttgagacc | 1020 |
| gtgcagcggt | tgcttccagt | gttgtgccag | gcacacggac | tgaccctca | acaggtggtc | 1080 |
| gcaatcgcca | gctacaaggg | cggaaagcag | gctctggaga | cagtgcagcg | cctcctgccc | 1140 |
| gtgctgtgtc | aggctcacgg | actgacacca | cagcaggtgg | tcgccatcgc | cagtaacggg | 1200 |
| ggcggcaagc | aggctttgga | gaccgtccag | agactcctcc | ccgtcctttg | ccaggcccac | 1260 |
| gggttgacac | ctcagcaggt | cgtcgccatt | gcctccaaca | acgggggcaa | gcaggccctc | 1320 |
| gaaactgtgc | agaggctgct | gcctgtgctg | tgccaggctc | atgggctgac | accccagcag | 1380 |
| gtggtggcca | ttgcctctaa | caacggcggc | aaacaggcac | tggagaccgt | gcaaaggctg | 1440 |
| ctgcccgtcc | tctgccaagc | ccacgggctc | actccacagc | aggtcgtggc | catcgcctca | 1500 |
| aacaatggcg | gaagcaggc | cctggagact | gtgcaaaggc | tgctccctgt | gctctgccag | 1560 |
| gcacacggac | tgacccctca | gcaggtggtg | gcaatcgctt | ccaacaacgg | gggaaagcag | 1620 |
| gccctcgaaa | ccgtgcagcg | cctcctccca | gtgctgtgcc | aggcacatgg | cctcacaccc | 1680 |
| gagcaagtgg | tggctatcgc | cagccacgac | ggagggaagc | aggctctgga | gaccgtgcag | 1740 |
| aggctgctgc | ctgtcctgtg | ccaggcccac | gggcttactc | cagagcaggt | cgtcgccatc | 1800 |
| gccagtcatg | atgggggaa | gcaggccctt | gagacagtcc | agcggctgct | gccagtcctt | 1860 |
| tgccaggctc | acggcttgac | tcccgagcag | gtcgtggcca | ttgcctcaaa | cattggggc | 1920 |
| aaacaggccc | tggagacagt | gcaggccctg | ctgcccgtgt | tgtgtcaggc | ccacggcttg | 1980 |
| acacccagc | aggtggtcgc | cattgcctct | aatggcggcg | ggagaccgc | cttggagagc | 2040 |
| attgttgccc | agtatctcg | ccctgatccg | gcgttggcg | cgttgaccaa | cgaccacctc | 2100 |
| gtcgccttgg | cctgcctcgg | cgggcgtcct | gcgctggatg | cagtgaaaaa | gggattgggg | 2160 |

| | |
|---|---:|
| gatcctatca gccgttccca gctggtgaag tccgagctgg aggagaagaa atccgagttg | 2220 |
| aggcacaagc tgaagtacgt gccccacgag tacatcgagc tgatcgagat cgcccggaac | 2280 |
| agcacccagg accgtatcct ggagatgaag gtgatggagt tcttcatgaa ggtgtacggc | 2340 |
| tacaggggca agcacctggg cggctccagg aagcccgacg cgccatctac accgtgggc | 2400 |
| tcccccatcg actacggcgt gatcgtggac accaaggcct actccggcgg ctacaacctg | 2460 |
| cccatcggcc aggccgacga atgcagagg tacgtggagg agaaccagac caggaacaag | 2520 |
| cacatcaacc ccaacgagtg gtggaaggtg taccctcca gcgtgaccga gttcaagttc | 2580 |
| ctgttcgtgt ccggccactt caagggcaac tacaaggccc agctgaccag gctgaaccac | 2640 |
| atcaccaact gcaacggcgc cgtgctgtcc gtggaggagc tcctgatcgg cggcgagatg | 2700 |
| atcaaggccg gcaccctgac cctggaggag gtgaggagga gttcaacaa cggcgagatc | 2760 |
| aacttcgcgg ccgactgata a | 2781 |

<210> SEQ ID NO 4
<211> LENGTH: 2778
<212> TYPE: DNA
<213> ORGANISM: artificial sequence
<220> FEATURE:
<223> OTHER INFORMATION: PD1T3R

<400> SEQUENCE: 4

| | |
|---|---:|
| atgggcgatc ctaaaaagaa acgtaaggtc atcgatatcg ccgatctacg cacgctcggc | 60 |
| tacagccagc agcaacagga gaagatcaaa ccgaaggttc gttcgacagt ggcgcagcac | 120 |
| cacgaggcac tggtcggcca cgggtttaca cacgcgcaca tcgttgcgtt aagccaacac | 180 |
| ccggcagcgt tagggaccgt cgctgtcaag tatcaggaca tgatcgcagc gttgccagag | 240 |
| gcgacacacg aagcgatcgt tggcgtcggc aaacagtggt ccggcgcacg cgctctggag | 300 |
| gccttgctca cggtggcggg agagttgaga ggtccaccgt tacagttgga cacaggccaa | 360 |
| cttctcaaga ttgcaaaacg tggcggcgtg accgcagtgg aggcagtgca tgcatggcgc | 420 |
| aatgcactga cgggtgcccc gctcaacttg accccgagc aagtcgtcgc aatcgccagc | 480 |
| catgatggag ggaagcaagc cctcgaaacc gtgcagcggt tgcttcctgt gctctgccag | 540 |
| gcccacggcc ttacccctca gcaggtggtg gccatcgcaa gtaacggagg aggaaagcaa | 600 |
| gccttggaga cagtgcagcg cctgttgccc gtgctgtgcc aggcacacgg cctcacacca | 660 |
| gagcaggtcg tggccattgc ctcccatgac ggggggaaac aggctctgga gaccgtccag | 720 |
| aggctgctgc ccgtcctctg tcaagctcac ggcctgactc cccaacaagt ggtcgccatc | 780 |
| gcctctaatg gcggcgggaa gcaggcactg gaaacagtgc agagactgct ccctgtgctt | 840 |
| tgccaagctc atgggttgac ccccaacag gtcgtcgcta ttgcctcaaa cggggggggc | 900 |
| aagcaggccc ttgagactgt gcagaggctg ttgccagtgc tgtgtcaggc tcacgggctc | 960 |
| actccacaac aggtggtcgc aattgccagc aacggcggcg gaaagcaagc tcttgaaacc | 1020 |
| gtgcaacgcc tcctgcccgt gctctgtcag gctcatggcc tgacaccaca acaagtcgtg | 1080 |
| gccatcgcca gtaataatgg cgggaaacag gctcttgaga ccgtccagag gctgctccca | 1140 |
| gtgctctgcc aggcacacgg gctgaccccc gagcaggtgg tggctatcgc cagcaatatt | 1200 |
| gggggcaagc aggccctgga aacagtccag gccctgctgc cagtgctttg ccaggctcac | 1260 |
| gggctcactc cccagcaggt cgtggcaatc gcctccaacg gcggagggaa gcaggctctg | 1320 |
| gagaccgtgc agagactgct gccgtcttg tgccaggccc acggactcac acctgaacag | 1380 |
| gtcgtcgcca ttgcctctca cgatgggggc aaacaagccc tggagacagt gcagcggctg | 1440 |

```
ttgcctgtgt tgtgccaagc ccacggcttg actcctcaac aagtggtcgc catcgcctca    1500
aatggcggcg gaaaacaagc tctggagaca gtgcagaggt tgctgcccgt cctctgccaa    1560
gcccacggcc tgactcccca acaggtcgtc gccattgcca gcaacaacgg aggaaagcag    1620
gctctcgaaa ctgtgcagcg gctgcttcct gtgctgtgtc aggctcatgg gctgacccc    1680 gagcaagtgg tggctattgc ctctaatgga ggcaagcaag cccttgagac agtccagagg    1740
ctgttgccag tgctgtgcca ggcccacggg ctcacacccc agcaggtggt cgccatcgcc    1800
agtaacaacg ggggcaaaca ggcattggaa accgtccagc gcctgcttcc agtgctctgc    1860
caggcacacg gactgacacc cgaacaggtg gtggccattg catcccatga tgggggcaag    1920
caggccctgg agaccgtgca gagactcctg ccagtgttgt gccaagctca cggcctcacc    1980
cctcagcaag tcgtggccat cgcctcaaac gggggggggcc ggcctgcact ggagagcatt    2040 gttgccagt tatctcgccc tgatccggcg ttggccgcgt tgaccaacga ccacctcgtc    2100
gccttggcct gcctcggcgg gcgtcctgcg ctggatgcag tgaaaaaggg attgggggat    2160
cctatcagcc gttcccagct ggtgaagtcc gagctggagg agaagaaatc cgagttgagg    2220
cacaagctga agtacgtgcc ccacgagtac atcgagctga tcgagatcgc ccggaacagc    2280
acccaggacc gtatcctgga gatgaaggtg atggagttct tcatgaaggt gtacggctac    2340
aggggcaagc acctgggcgg ctccaggaag cccgacggcg ccatctacac cgtgggctcc    2400
cccatcgact acggcgtgat cgtggacacc aaggcctact ccggcggcta caacctgccc    2460
atcggccagg ccgacgaaat gcagaggtac gtggaggaga accagaccag gaacaagcac    2520
atcaacccca cgagtggtg gaaggtgtac ccctccagcg tgaccgagtt caagttcctg    2580
ttcgtgtccg gccacttcaa gggcaactac aaggcccagc tgaccaggct gaaccacatc    2640
accaactgca acggcgccgt gctgtccgtg gaggagctcc tgatcggcgg cgagatgatc    2700
aaggccggca ccctgacccct ggaggaggtg aggaggaagt tcaacaacgg cgagatcaac    2760
ttcgcggccg actgataa                                                 2778

<210> SEQ ID NO 5
<211> LENGTH: 49
<212> TYPE: DNA
<213> ORGANISM: artificial sequence
<220> FEATURE:
<223> OTHER INFORMATION: PD1-T3

<400> SEQUENCE: 5
tacctctgtg gggccatctc cctggccccc aaggcgcaga tcaaagaga               49

<210> SEQ ID NO 6
<211> LENGTH: 60
<212> TYPE: DNA
<213> ORGANISM: artificial sequence
<220> FEATURE:
<223> OTHER INFORMATION: 2A-element

<400> SEQUENCE: 6
tccggtgagg gcagaggaag tcttctaaca tgcggtgacg tggaggagaa tccgggcccc    60

<210> SEQ ID NO 7
<211> LENGTH: 1989
<212> TYPE: DNA
<213> ORGANISM: artificial sequence
<220> FEATURE:
<223> OTHER INFORMATION: apoptosis CAR
```

<400> SEQUENCE: 7

```
gctttgcctg tcactgcctt gctgcttcca cttgctctgt tgttgcacgc cgcaagaccc      60
gaggtcaagc tccaggaaag cggaccaggg ctggtggccc ctagtcagtc attgagcgtc     120
acttgcaccg tcagcggcgt gtctctgccc gattacggcg tgagctggat cagacagccc     180
ccaaggaagg gactggagtg gctgggcgtc atctggggga gcgagactac ctactacaac     240
agcgccctga gagcaggct gaccatcatt aaggacaact ccaagtccca ggtctttctg     300
aaaatgaaca gcctgcagac tgatgacact gccatctact actgcgccaa gcattactac     360
tacgggggca gctacgctat ggactactgg gggcagggga cctctgtcac agtgtcaagt     420
ggcggaggag gcagtggcgg aggggggaagt ggggcggcg gcagcgacat ccagatgacc     480
cagacaacat ccagcctctc cgcctctctg ggcacagag tgacaatcag ctgccgggcc     540
agtcaggaca tcagcaagta tctcaattgg taccagcaga accagacgg gacagtgaaa     600
ttgctgatct accacacatc caggctgcac tcaggagtcc ccagcaggtt ttccggctcc     660
ggctccggga cagattacag tctgaccatt tccaacctgg agcaggagga tattgccaca     720
tactttgcc agcaaggcaa cactctgccc tataccttcg gcggaggcac aaaactggag     780
attactcggt cggatcccga gcccaaatct cctgacaaaa ctcacacatg cccaccgtgc     840
ccagcacctc ccgtggccgg cccgtcagtg ttcctcttcc ccccaaaacc caaggacacc     900
ctcatgatcg cccggacccc tgaggtcaca tgcgtggtgg tggacgtgag ccacgaggac     960
cctgaggtca agttcaactg gtacgtggac ggcgtggagg tgcataatgc caagacaaag    1020
ccgcgggagg agcagtacaa cagcacgtac cgtgtggtca gcgtcctcac cgtcctgcac    1080
caggactggc tgaatggcaa ggagtacaag tgcaaggtgt ccaacaaagc cctcccagcc    1140
cccatcgaga aaaccatctc caaagccaaa gggcagcccc gagaaccaca ggtgtacacc    1200
ctgcccccat cccgggatga gctgaccaag aaccaggtca gcctgacctg cctggtcaaa    1260
ggcttctatc ccagcgacat cgccgtggag tgggagagca atgggcaacc ggagaacaac    1320
tacaagacca cgcctcccgt gctggactcc gacggctcct tcttcctcta cagcaagctc    1380
accgtggaca agagcaggtg gcagcagggg aacgtgttct catgctccgt gatgcatgag    1440
gccctgcaca atcactatac ccagaaatct ctgagtctga gcccaggcaa gaaggatatt    1500
ttgggggtggc tttgccttct tcttttgcca attccactaa ttgtttgggt gaagagaaag    1560
gaagtacaga aaacatgcag aaagcacaga aaggaaaacc aaggttctca tgaatctcca    1620
accttaaatc ctgaaacagt ggcaataaat ttatctgatg ttgacttgag taaatatatc    1680
accactattg ctggagtcat gacactaagt caagttaaag gctttgttcg aaagaatggt    1740
gtcaatgaag ccaaaataga tgagatcaag aatgacaatg tccaagacac agcagaacag    1800
aaagttcaac tgcttcgtaa ttggcatcaa cttcatggaa agaaagaagc gtatgacaca    1860
ttgattgcag atctcaaaaa agccaatctt tgtactcttg cagagaaaat tcagactatc    1920
atcctcaagg acattactag tgactcagaa aattcaaact tcagaaatga aatccagagc    1980
ttggtcgaa                                                            1989
```

<210> SEQ ID NO 8
<211> LENGTH: 276
<212> TYPE: DNA
<213> ORGANISM: artificial sequence
<220> FEATURE:
<223> OTHER INFORMATION: BGH polyA

<400> SEQUENCE: 8

```
tctagagggc cgtttaaac ccgctgatca gcctcgactg tgccttctag ttgccagcca        60
tctgttgttt gccctcccc cgtgccttcc ttgaccctgg aaggtgccac tcccactgtc       120
ctttcctaat aaaatgagga aattgcatcg cattgtctga gtaggtgtca ttctattctg       180
gggggtgggg tggggcagga cagcaagggg gaggattggg aagacaatag caggcatgct       240
ggggatgcgg tgggctctat gactagtggc gaattc                                276
```

```
<210> SEQ ID NO 9
<211> LENGTH: 1000
<212> TYPE: DNA
<213> ORGANISM: artificial sequence
<220> FEATURE:
<223> OTHER INFORMATION: Lck left homology

<400> SEQUENCE: 9
gggatagggg gtgcctctgt gtgtgtgtgt gagagtgtgt gtgtgtaggg tgtgtatatg        60
tatagggtgt gtgtgagtgt gtgtgtgtga gagagtgtgt gtgtggcaga atagactgcg       120
gaggtggatt tcatcttgat atgaaaggtc tggaatgcat ggtacattaa actttgagga       180
cagcgctttc caagcactct gaggagcagc cctagagaag gaggagctgc agggactccg       240
ggggcttcaa agtgagggcc ccactctgct tcaggcaaaa caggcacaca tttatcactt       300
tatctatgga gttctgcttg atttcatcag acaaaaaatt tccactgcta aaacaggcaa       360
ataaacaaaa aaaagttat ggccaacaga gtcactggag ggttttctgc tggggagaag        420
caagcccgtg tttgaaggaa ccctgtgaga tgactgtggg ctgtgtgagg ggaacagcgg       480
gggcttgatg gtggacttcg ggagcagaag cctctttctc agcctcctca gctagacagg       540
ggaattataa taggaggtgt ggcgtgcaca cctctccagt aggggagggt ctgataagtc       600
aggtctctcc caggcttggg aaagtgtgtg tcatctctag gaggtggtcc tcccaacaca       660
gggtactggc agagggagag ggaggggggca gaggcaggaa gtgggtaact agactaacaa       720
aggtgcctgt ggcggtttgc ccatcccagg tgggagggtg gggctagggc tcaggggccg       780
tgtgtgaatt tacttgtagc ctgagggctc agagggagca ccggtttgga gctgggaccc       840 cctatttag cttttctgtg gctggtgaat ggggatccca ggatctcaca atctcaggta        900
cttttggaac tttccagggc aaggccccat tatatctgat gttgggggag cagatcttgg       960 gggagccct tcagccccct cttccattcc ctcagggacc                              1000
```

```
<210> SEQ ID NO 10
<211> LENGTH: 219
<212> TYPE: PRT
<213> ORGANISM: artificial sequence
<220> FEATURE:
<223> OTHER INFORMATION: Interleukin-12 subunit alpha

<400> SEQUENCE: 10

Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80
```

```
Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215

<210> SEQ ID NO 11
<211> LENGTH: 328
<212> TYPE: PRT
<213> ORGANISM: artificial sequence
<220> FEATURE:
<223> OTHER INFORMATION: Interleukin-12 subunit beta

<400> SEQUENCE: 11

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
        50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220
```

```
Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
            245                 250                 255

Glu Tyr Pro Asp Thr Trp Ser Thr Pro His Ser Tyr Phe Ser Leu Thr
        260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
        290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325
```

```
<210> SEQ ID NO 12
<211> LENGTH: 1000
<212> TYPE: DNA
<213> ORGANISM: artificial sequence
<220> FEATURE:
<223> OTHER INFORMATION: lck right homology

<400> SEQUENCE: 12
ggctgtggct gcagctcaca cccggaagat gactggatgg aaaacatcga tgtgtgtgag        60
aactgccatt atcccatagt cccactggat ggcaagggca cggtaagagg cgagacaggg       120
gccttggtga gggagttggg tagagaatgc aacccaggag aaagaaatga ccagcactac       180
aggcccttga agaatagag tggccctctc ccctgaaata cagaaaggaa agaggcccca       240
gagaggggaa gggaatctcc taagatcaca cagaaagtag ttggtaaact cagggataac       300
atctaaccag gctggagagg ctgagagcag agcaggggga aggggggcca gggtctgacc       360
caatcttctg ctttctgacc ccaccctcat ccccactcc acagctgctc atccgaaatg       420
gctctgaggt gcgggaccca ctggttacct acgaaggctc caatccgccg gcttccccac       480
tgcaaggtga ccccaggcag cagggcctga agacaaggc ctgcggatcc ctggctgttg       540
gcttccacct ctccccacc tactttctcc ccggtcttgc cttccttgtc ccccaccctg       600
taactccagg cttcctgccg atcccagctc ggttctccct gatgcccctt gtctttacag       660
acaacctggt tatcgctctg cacagctatg agccctctca cgacggagat ctgggctttg       720
agaaggggga acagctccgc atcctggagc agtgagtccc tctccacctt gctctggcgg       780
agtccgtgag ggagcggcga tctccgcgac ccgcagccct cctgcggccc ttgaccagct       840
cggggtggcc gcccttggga caaaattcga ggctcagtat tgctgagcca gggttggggg       900
aggctggctt aaggggtgga ggggtctttg agggagggtc tcaggtcgac ggctgagcga       960
gccacactga cccacctccg tggcgcagga gcggcgagtg                            1000

<210> SEQ ID NO 13
<211> LENGTH: 1992
<212> TYPE: DNA
<213> ORGANISM: artificial sequence
<220> FEATURE:
<223> OTHER INFORMATION: apoptosis CAR

<400> SEQUENCE: 13
atggctttgc ctgtcactgc cttgctgctt ccacttgctc tgttgttgca cgccgcaaga        60
cccgaggtca agctccagga aagcggacca gggctggtgg cccctagtca gtcattgagc       120
```

| | | | | |
|---|---|---|---|---|
| gtcacttgca | ccgtcagcgg | cgtgtctctg | cccgattacg | gcgtgagctg gatcagacag | 180 |
| ccccaagga | agggactgga | gtggctgggc | gtcatctggg | ggagcgagac tacctactac | 240 |
| aacagcgccc | tgaagagcag | gctgaccatc | attaaggaca | actccaagtc ccaggtcttt | 300 |
| ctgaaaatga | acagcctgca | gactgatgac | actgccatct | actactgcgc caagcattac | 360 |
| tactacgggg | gcagctacgc | tatggactac | tggggggcagg | ggacctctgt cacagtgtca | 420 |
| agtggcggag | gaggcagtgg | cggaggggga | agtgggggcg | gcggcagcga catccagatg | 480 |
| acccagacaa | catccagcct | ctccgcctct | ctgggcgaca | gagtgacaat cagctgccgg | 540 |
| gccagtcagg | acatcagcaa | gtatctcaat | tggtaccagc | agaaaccaga cgggacagtg | 600 |
| aaattgctga | tctaccacac | atccaggctg | cactcaggag | tccccagcag gttttccggc | 660 |
| tccggctccg | ggacagatta | cagtctgacc | atttccaacc | tggagcagga ggatattgcc | 720 |
| acatactttt | gccagcaagg | caacactctg | ccctatacct | tcggcggagg cacaaaactg | 780 |
| gagattactc | ggtcggatcc | cgagcccaaa | tctcctgaca | aaactcacac atgcccaccg | 840 |
| tgcccagcac | ctcccgtggc | cggcccgtca | gtgttcctct | tccccccaaa acccaaggac | 900 |
| accctcatga | tctcccggac | ccctgaggtc | acatgcgtgg | tggtggacgt gagccacgag | 960 |
| gaccctgagg | tcaagttcaa | ctggtacgtg | gacggcgtgg | aggtgcataa tgccaagaca | 1020 |
| aagccgcggg | aggagcagta | caacagcacg | taccgtgtgg | tcagcgtcct caccgtcctg | 1080 |
| caccaggact | ggctgaatgg | caaggagtac | aagtgcaagg | tgtccaacaa agccctccca | 1140 |
| gcccccatcg | agaaaaccat | ctccaaagcc | aaagggcagc | cccgagaacc acaggtgtac | 1200 |
| accctgcccc | catcccggga | tgagctgacc | aagaaccagg | tcagcctgac ctgcctggtc | 1260 |
| aaaggcttct | atcccagcga | catcgccgtg | gagtgggaga | gcaatgggca accggagaac | 1320 |
| aactacaaga | ccacgcctcc | cgtgctggac | tccgacggct | ccttcttcct ctacagcaag | 1380 |
| ctcaccgtgg | acaagagcag | gtggcagcag | gggaacgtgt | tctcatgctc cgtgatgcat | 1440 |
| gaggccctgc | acaatcacta | tacccagaaa | tctctgagtc | tgagcccagg caagaaggat | 1500 |
| attttggggt | ggctttgcct | tcttcttttg | ccaattccac | taattgtttg ggtgaagaga | 1560 |
| aaggaagtac | agaaaacatg | cagaaagcac | agaaggaaa | accaaggttc tcatgaatct | 1620 |
| ccaaccttaa | atcctgaaac | agtggcaata | aatttatctg | atgttgactt gagtaaatat | 1680 |
| atcaccacta | ttgctggagt | catgacacta | agtcaagtta | aaggctttgt tcgaaagaat | 1740 |
| ggtgtcaatg | aagccaaaat | agatgagatc | aagaatgaca | atgtccaaga cacagcagaa | 1800 |
| cagaaagttc | aactgcttcg | taattggcat | caacttcatg | gaaagaaaga agcgtatgac | 1860 |
| acattgattg | cagatctcaa | aaaagccaat | ctttgtactc | ttgcagagaa aattcagact | 1920 |
| atcatcctca | aggacattac | tagtgactca | gaaaattcaa | acttcagaaa tgaaatccag | 1980 |
| agcttggtcg | aa | | | | 1992 |

<210> SEQ ID NO 14
<211> LENGTH: 1000
<212> TYPE: DNA
<213> ORGANISM: artificial sequence
<220> FEATURE:
<223> OTHER INFORMATION: Lck left homology

<400> SEQUENCE: 14

| | | | | |
|---|---|---|---|---|
| ctcataacaa | ttctatgagg | taggaacagt | tatttactct | attttccaaa taaggaaact | 60 |
| gggctcgccc | aaggttccac | aactaacatg | tgtgtattat | tgagcattta atttacacca | 120 |

```
gggaagcagg ttgtggtggt gtgcacctgt tgtccagcta tttaggaggc tgaggtgaaa      180
ggatcacttg aacggaggag ttcaaatttg caatgtgcta tgattgtgcc tgtgaacagc      240
tgctgcactc cagcctgggc aacatagtga gatcccttat ctaaaacatt ttttttaagt     300
aaataatcag gtgggcacgg tggctcacgc ctgtaatcca gcactttggg aggctgaggc      360
gggcggatca cctgaggtca ggagttcaag accagcctga ccaacatgga gaaacccgtc      420
tctactaaaa atacaaaatt agcttggcgt ggtggtgcat gcctgtaatc ccagctactc      480
gagaagctga ggcaggagaa ttgtttgaac ctgggaggtg gaggttgcgg tgagccgaga      540
tcgcaccatt gcactccagc ctgggcaaca agagtgaaat tgcatctcaa aaaaaagaa      600 aaggaaataa tctataccag gcactccaag tggtgtgact gatattcaac aagtacctct      660
agtgtgacct taccattgat gaagaccaag attcttttgg attggtgctc acactgtgcc      720
agttaaatat tccgaacatt acccttgcct gtgggcttcc agtgcctgac cttgatgtcc      780
tttcacccat caacccgtag ggatgaccaa cccggaggtg attcagaacc tggagcgagg      840
ctaccgcatg gtgcgccctg acaactgtcc agaggagctg taccaactca tgaggctgtg      900
ctggaaggag cgcccagagg accggccac ctttgactac ctgcgcagtg tgctggagga      960
cttcttcacg gccacagagg gccagtacca gcctcagcct                           1000

<210> SEQ ID NO 15
<211> LENGTH: 1000
<212> TYPE: DNA
<213> ORGANISM: artificial sequence
<220> FEATURE:
<223> OTHER INFORMATION: lck right homology

<400> SEQUENCE: 15
gaggccttga gaggccctgg ggttctcccc ctttctctcc agcctgactt ggggagatgg       60
agttcttgtg ccatagtcac atggcctatg cacatatgga ctctgcacat gaatcccacc      120
cacatgtgac acatatgcac cttgtgtctg tacacgtgtc ctgtagttgc gtggactctg      180
cacatgtctt gtacatgtgt agcctgtgca tgtatgtctt ggacactgta caaggtaccc      240
ctttctggct ctcccatttc ctgagaccac agagagaggg gagaagcctg ggattgacag      300
aagcttctgc ccacctactt ttctttcctc agatcatcca gaagttcctc aagggccagg      360
actttatcta atacctctgt gtgctcctcc ttggtgcctg gcctggcaca catcaggagt      420
tcaataaatg tctgttgatg actgttgtac atctctttgc tgtccactct ttgtgggtgg      480
gcagtggggg ttaagaaaat ggtaattagg tcaccctgag ttggggtgaa agatgggatg      540
agtggatgtc tggaggctct gcagacccct tcaaatggga cagtgctcct cacccctccc      600
caaaggattc agggtgactc ctacctggaa tcccttaggg aatgggtgcg tcaaaggacc      660
ttcctcccca ttataaaagg gcaacagcat ttttactga ttcaagggct atatttgacc      720
tcagattttg ttttttttaag gctagtcaaa tgaagcggcg ggaatggagg aggaacaaat      780
aaatctgtaa ctatcctcag attttttttt tttttgaga ctgggtctca cttttttcatc      840 caggctggag tgcagtcgca tgatcacggc tcactgtagc ctcaacctct ccagctcaaa      900
tgctcctcct gtctcagcct cccgagtacc tgggactact tcttgaggc caggaattca      960 agaacagagt aagatcctgg tctccaaaaa aagttttaaa                           1000

<210> SEQ ID NO 16
<211> LENGTH: 936
<212> TYPE: PRT
<213> ORGANISM: artificial sequence
```

<220> FEATURE:
<223> OTHER INFORMATION: TALEN TRAC

<400> SEQUENCE: 16

Met Gly Asp Pro Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Glu Lys Ile Lys Pro Lys Val Arg Ser Thr Val
35                  40                  45

Ala Gln His His Glu Ala Leu Val Gly His Gly Phe Thr His Ala His
50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Gly Gly Lys
                165                 170                 175

Gln Ala Leu Glu Thr Val Gln Arg Leu Leu Pro Val Leu Cys Gln Ala
            180                 185                 190

His Gly Leu Thr Pro Gln Gln Val Val Ala Ile Ala Ser Asn Asn Gly
        195                 200                 205

Gly Lys Gln Ala Leu Glu Thr Val Gln Arg Leu Leu Pro Val Leu Cys
210                 215                 220

Gln Ala His Gly Leu Thr Pro Gln Gln Val Val Ala Ile Ala Ser Asn
225                 230                 235                 240

Gly Gly Gly Lys Gln Ala Leu Glu Thr Val Gln Arg Leu Leu Pro Val
                245                 250                 255

Leu Cys Gln Ala His Gly Leu Thr Pro Glu Gln Val Val Ala Ile Ala
            260                 265                 270

Ser His Asp Gly Gly Lys Gln Ala Leu Glu Thr Val Gln Arg Leu Leu
        275                 280                 285

Pro Val Leu Cys Gln Ala His Gly Leu Thr Pro Glu Gln Val Val Ala
290                 295                 300

Ile Ala Ser His Asp Gly Gly Lys Gln Ala Leu Glu Thr Val Gln Arg
305                 310                 315                 320

Leu Leu Pro Val Leu Cys Gln Ala His Gly Leu Thr Pro Glu Gln Val
                325                 330                 335

Val Ala Ile Ala Ser His Asp Gly Gly Lys Gln Ala Leu Glu Thr Val
            340                 345                 350

Gln Arg Leu Leu Pro Val Leu Cys Gln Ala His Gly Leu Thr Pro Glu
        355                 360                 365

Gln Val Val Ala Ile Ala Ser Asn Ile Gly Gly Lys Gln Ala Leu Glu
370                 375                 380

Thr Val Gln Ala Leu Leu Pro Val Leu Cys Gln Ala His Gly Leu Thr
385                 390                 395                 400

```
Pro Glu Gln Val Val Ala Ile Ala Ser His Asp Gly Lys Gln Ala
            405                 410                 415

Leu Glu Thr Val Gln Arg Leu Leu Pro Val Leu Cys Gln Ala His Gly
            420                 425                 430

Leu Thr Pro Glu Gln Val Val Ala Ile Ala Ser Asn Ile Gly Gly Lys
            435                 440                 445

Gln Ala Leu Glu Thr Val Gln Ala Leu Leu Pro Val Leu Cys Gln Ala
        450                 455                 460

His Gly Leu Thr Pro Gln Gln Val Val Ala Ile Ala Ser Asn Asn Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Glu Gln Val Val Ala Ile Ala Ser Asn
                500                 505                 510

Ile Gly Gly Lys Gln Ala Leu Glu Thr Val Gln Ala Leu Leu Pro Val
            515                 520                 525

Leu Cys Gln Ala His Gly Leu Thr Pro Gln Gln Val Val Ala Ile Ala
        530                 535                 540

Ser Asn Gly Gly Gly Lys Gln Ala Leu Glu Thr Val Gln Arg Leu Leu
545                 550                 555                 560

Pro Val Leu Cys Gln Ala His Gly Leu Thr Pro Glu Gln Val Val Ala
                565                 570                 575

Ile Ala Ser Asn Ile Gly Gly Lys Gln Ala Leu Glu Thr Val Gln Ala
            580                 585                 590

Leu Leu Pro Val Leu Cys Gln Ala His Gly Leu Thr Pro Gln Gln Val
            595                 600                 605

Val Ala Ile Ala Ser Asn Gly Gly Gly Lys Gln Ala Leu Glu Thr Val
        610                 615                 620

Gln Arg Leu Leu Pro Val Leu Cys Gln Ala His Gly Leu Thr Pro Glu
625                 630                 635                 640

Gln Val Val Ala Ile Ala Ser His Asp Gly Lys Gln Ala Leu Glu
                645                 650                 655

Thr Val Gln Arg Leu Leu Pro Val Leu Cys Gln Ala His Gly Leu Thr
            660                 665                 670

Pro Gln Gln Val Val Ala Ile Ala Ser Asn Gly Gly Gly Arg Pro Ala
            675                 680                 685

Leu Glu Ser Ile Val Ala Gln Leu Ser Arg Pro Asp Pro Ala Leu Ala
        690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
            755                 760                 765

Ala Arg Asn Ser Thr Gln Asp Arg Ile Leu Glu Met Lys Val Met Glu
        770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815
```

-continued

Gly Val Ile Val Asp Thr Lys Ala Tyr Ser Gly Gly Tyr Asn Leu Pro
                820                 825                 830

Ile Gly Gln Ala Asp Glu Met Gln Arg Tyr Val Glu Gly Asn Gln Thr
                835                 840                 845

Arg Asn Lys His Ile Asn Pro Asn Glu Trp Trp Lys Val Tyr Pro Ser
                850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
                900                 905                 910

Lys Ala Gly Thr Leu Thr Leu Glu Glu Val Arg Arg Lys Phe Asn Asn
                915                 920                 925

Gly Glu Ile Asn Phe Ala Ala Asp
                930                 935

<210> SEQ ID NO 17
<211> LENGTH: 942
<212> TYPE: PRT
<213> ORGANISM: artificial sequence
<220> FEATURE:
<223> OTHER INFORMATION: TALEN TRAC

<400> SEQUENCE: 17

Met Gly Asp Pro Lys Lys Lys Arg Lys Val Ile Asp Lys Glu Thr Ala
1                   5                   10                  15

Ala Ala Lys Phe Glu Arg Gln His Met Asp Ser Ile Asp Ile Ala Asp
                20                  25                  30

Leu Arg Thr Leu Gly Tyr Ser Gln Gln Gln Gln Glu Lys Ile Lys Pro
                35                  40                  45

Lys Val Arg Ser Thr Val Ala Gln His His Glu Ala Leu Val Gly His
                50                  55                  60

Gly Phe Thr His Ala His Ile Val Ala Leu Ser Gln His Pro Ala Ala
65                  70                  75                  80

Leu Gly Thr Val Ala Val Lys Tyr Gln Asp Met Ile Ala Ala Leu Pro
                85                  90                  95

Glu Ala Thr His Glu Ala Ile Val Gly Val Gly Lys Gln Trp Ser Gly
                100                 105                 110

Ala Arg Ala Leu Glu Ala Leu Leu Thr Val Ala Gly Glu Leu Arg Gly
                115                 120                 125

Pro Pro Leu Gln Leu Asp Thr Gly Gln Leu Leu Lys Ile Ala Lys Arg
                130                 135                 140

Gly Gly Val Thr Ala Val Glu Ala Val His Ala Trp Arg Asn Ala Leu
145                 150                 155                 160

Thr Gly Ala Pro Leu Asn Leu Thr Pro Glu Gln Val Val Ala Ile Ala
                165                 170                 175

Ser His Asp Gly Gly Lys Gln Ala Leu Glu Thr Val Gln Arg Leu Leu
                180                 185                 190

Pro Val Leu Cys Gln Ala His Gly Leu Thr Pro Gln Gln Val Val Ala
                195                 200                 205

Ile Ala Ser Asn Gly Gly Gly Lys Gln Ala Leu Glu Thr Val Gln Arg
                210                 215                 220

Leu Leu Pro Val Leu Cys Gln Ala His Gly Leu Thr Pro Glu Gln Val
225                 230                 235                 240

-continued

```
Val Ala Ile Ala Ser His Asp Gly Gly Lys Gln Ala Leu Glu Thr Val
            245                 250                 255
Gln Arg Leu Leu Pro Val Leu Cys Gln Ala His Gly Leu Thr Pro Glu
        260                 265                 270
Gln Val Val Ala Ile Ala Ser Asn Ile Gly Gly Lys Gln Ala Leu Glu
    275                 280                 285
Thr Val Gln Ala Leu Leu Pro Val Leu Cys Gln Ala His Gly Leu Thr
290                 295                 300
Pro Gln Gln Val Val Ala Ile Ala Ser Asn Asn Gly Gly Lys Gln Ala
305                 310                 315                 320
Leu Glu Thr Val Gln Arg Leu Leu Pro Val Leu Cys Gln Ala His Gly
            325                 330                 335
Leu Thr Pro Glu Gln Val Val Ala Ile Ala Ser His Asp Gly Gly Lys
        340                 345                 350
Gln Ala Leu Glu Thr Val Gln Arg Leu Leu Pro Val Leu Cys Gln Ala
    355                 360                 365
His Gly Leu Thr Pro Gln Gln Val Val Ala Ile Ala Ser Asn Gly Gly
370                 375                 380
Gly Lys Gln Ala Leu Glu Thr Val Gln Arg Leu Leu Pro Val Leu Cys
385                 390                 395                 400
Gln Ala His Gly Leu Thr Pro Gln Gln Val Val Ala Ile Ala Ser Asn
            405                 410                 415
Asn Gly Gly Lys Gln Ala Leu Glu Thr Val Gln Arg Leu Leu Pro Val
        420                 425                 430
Leu Cys Gln Ala His Gly Leu Thr Pro Gln Gln Val Val Ala Ile Ala
    435                 440                 445
Ser Asn Asn Gly Gly Lys Gln Ala Leu Glu Thr Val Gln Arg Leu Leu
450                 455                 460
Pro Val Leu Cys Gln Ala His Gly Leu Thr Pro Gln Gln Val Val Ala
465                 470                 475                 480
Ile Ala Ser Asn Gly Gly Gly Lys Gln Ala Leu Glu Thr Val Gln Arg
            485                 490                 495
Leu Leu Pro Val Leu Cys Gln Ala His Gly Leu Thr Pro Glu Gln Val
        500                 505                 510
Val Ala Ile Ala Ser Asn Ile Gly Gly Lys Gln Ala Leu Glu Thr Val
    515                 520                 525
Gln Ala Leu Leu Pro Val Leu Cys Gln Ala His Gly Leu Thr Pro Glu
530                 535                 540
Gln Val Val Ala Ile Ala Ser His Asp Gly Gly Lys Gln Ala Leu Glu
545                 550                 555                 560
Thr Val Gln Arg Leu Leu Pro Val Leu Cys Gln Ala His Gly Leu Thr
            565                 570                 575
Pro Glu Gln Val Val Ala Ile Ala Ser Asn Ile Gly Gly Lys Gln Ala
        580                 585                 590
Leu Glu Thr Val Gln Ala Leu Leu Pro Val Leu Cys Gln Ala His Gly
    595                 600                 605
Leu Thr Pro Glu Gln Val Val Ala Ile Ala Ser His Asp Gly Gly Lys
610                 615                 620
Gln Ala Leu Glu Thr Val Gln Arg Leu Leu Pro Val Leu Cys Gln Ala
625                 630                 635                 640
His Gly Leu Thr Pro Gln Gln Val Val Ala Ile Ala Ser Asn Asn Gly
            645                 650                 655
Gly Lys Gln Ala Leu Glu Thr Val Gln Arg Leu Leu Pro Val Leu Cys
```

-continued

```
                660             665             670
Gln Ala His Gly Leu Thr Pro Gln Gln Val Val Ala Ile Ala Ser Asn
            675                 680                 685
Gly Gly Gly Arg Pro Ala Leu Glu Ser Ile Val Ala Gln Leu Ser Arg
        690                 695                 700
Pro Asp Pro Ala Leu Ala Ala Leu Thr Asn Asp His Leu Val Ala Leu
705                 710                 715                 720
Ala Cys Leu Gly Gly Arg Pro Ala Leu Asp Ala Val Lys Lys Gly Leu
                725                 730                 735
Gly Asp Pro Ile Ser Arg Ser Gln Leu Val Lys Ser Glu Leu Glu Glu
            740                 745                 750
Lys Lys Ser Glu Leu Arg His Lys Leu Lys Tyr Val Pro His Glu Tyr
        755                 760                 765
Ile Glu Leu Ile Glu Ile Ala Arg Asn Ser Thr Gln Asp Arg Ile Leu
    770                 775                 780
Glu Met Lys Val Met Glu Phe Phe Met Lys Val Tyr Gly Tyr Arg Gly
785                 790                 795                 800
Lys His Leu Gly Gly Ser Arg Lys Pro Asp Gly Ala Ile Tyr Thr Val
                805                 810                 815
Gly Ser Pro Ile Asp Tyr Gly Val Ile Val Asp Thr Lys Ala Tyr Ser
            820                 825                 830
Gly Gly Tyr Asn Leu Pro Ile Gly Gln Ala Asp Glu Met Gln Arg Tyr
        835                 840                 845
Val Glu Glu Asn Gln Thr Arg Asn Lys His Ile Asn Pro Asn Glu Trp
    850                 855                 860
Trp Lys Val Tyr Pro Ser Ser Val Thr Glu Phe Lys Phe Leu Phe Val
865                 870                 875                 880
Ser Gly His Phe Lys Gly Asn Tyr Lys Ala Gln Leu Thr Arg Leu Asn
                885                 890                 895
His Ile Thr Asn Cys Asn Gly Ala Val Leu Ser Val Glu Glu Leu Leu
            900                 905                 910
Ile Gly Gly Glu Met Ile Lys Ala Gly Thr Leu Thr Leu Glu Glu Val
        915                 920                 925
Arg Arg Lys Phe Asn Asn Gly Glu Ile Asn Phe Ala Ala Asp
    930                 935                 940

<210> SEQ ID NO 18
<211> LENGTH: 913
<212> TYPE: PRT
<213> ORGANISM: artificial sequence
<220> FEATURE:
<223> OTHER INFORMATION: TALEN CD25

<400> SEQUENCE: 18

Met Gly Asp Pro Lys Lys Lys Arg Lys Val Ile Asp Tyr Pro Tyr Asp
1               5                   10                  15
Val Pro Asp Tyr Ala Ile Asp Ile Ala Asp Leu Arg Thr Leu Gly Tyr
            20                  25                  30
Ser Gln Gln Gln Gln Glu Lys Ile Lys Pro Lys Val Arg Ser Thr Val
        35                  40                  45
Ala Gln His His Glu Ala Leu Val Gly His Gly Phe Thr His Ala His
    50                  55                  60
Ile Val Ala Leu Ser Gln His Pro Ala Ala Leu Gly Thr Val Ala Val
65                  70                  75                  80
Lys Tyr Gln Asp Met Ile Ala Ala Leu Pro Glu Ala Thr His Glu Ala
```

```
               85                  90                  95
Ile Val Gly Val Gly Lys Gln Trp Ser Gly Arg Ala Leu Glu Ala
            100                 105                 110
Leu Leu Thr Val Ala Gly Glu Leu Arg Gly Pro Leu Gln Leu Asp
            115                 120                 125
Thr Gly Gln Leu Leu Lys Ile Ala Lys Arg Gly Val Thr Ala Val
            130                 135                 140
Glu Ala Val His Ala Trp Arg Asn Ala Leu Thr Gly Ala Pro Leu Asn
145                 150                 155                 160
Leu Thr Pro Gln Gln Val Val Ala Ile Ala Ser Asn Gly Gly Lys
            165                 170                 175
Gln Ala Leu Glu Thr Val Gln Arg Leu Leu Pro Val Leu Cys Gln Ala
            180                 185                 190
His Gly Leu Thr Pro Gln Gln Val Val Ala Ile Ala Ser Asn Gly Gly
            195                 200                 205
Gly Lys Gln Ala Leu Glu Thr Val Gln Arg Leu Leu Pro Val Leu Cys
            210                 215                 220
Gln Ala His Gly Leu Thr Pro Gln Gln Val Val Ala Ile Ala Ser Asn
225                 230                 235                 240
Gly Gly Gly Lys Gln Ala Leu Glu Thr Val Gln Arg Leu Leu Pro Val
            245                 250                 255
Leu Cys Gln Ala His Gly Leu Thr Pro Glu Gln Val Val Ala Ile Ala
            260                 265                 270
Ser His Asp Gly Gly Lys Gln Ala Leu Glu Thr Val Gln Arg Leu Leu
            275                 280                 285
Pro Val Leu Cys Gln Ala His Gly Leu Thr Pro Gln Gln Val Val Ala
            290                 295                 300
Ile Ala Ser Asn Gly Gly Gly Lys Gln Ala Leu Glu Thr Val Gln Arg
305                 310                 315                 320
Leu Leu Pro Val Leu Cys Gln Ala His Gly Leu Thr Pro Gln Gln Val
            325                 330                 335
Val Ala Ile Ala Ser Asn Gly Gly Gly Lys Gln Ala Leu Glu Thr Val
            340                 345                 350
Gln Arg Leu Leu Pro Val Leu Cys Gln Ala His Gly Leu Thr Pro Gln
            355                 360                 365
Gln Val Val Ala Ile Ala Ser Asn Gly Gly Gly Lys Gln Ala Leu Glu
            370                 375                 380
Thr Val Gln Arg Leu Leu Pro Val Leu Cys Gln Ala His Gly Leu Thr
385                 390                 395                 400
Pro Gln Gln Val Val Ala Ile Ala Ser Asn Gly Gly Gly Lys Gln Ala
            405                 410                 415
Leu Glu Thr Val Gln Arg Leu Leu Pro Val Leu Cys Gln Ala His Gly
            420                 425                 430
Leu Thr Pro Gln Gln Val Val Ala Ile Ala Ser Asn Asn Gly Gly Lys
            435                 440                 445
Gln Ala Leu Glu Thr Val Gln Arg Leu Leu Pro Val Leu Cys Gln Ala
            450                 455                 460
His Gly Leu Thr Pro Gln Gln Val Val Ala Ile Ala Ser Asn Asn Gly
465                 470                 475                 480
Gly Lys Gln Ala Leu Glu Thr Val Gln Arg Leu Leu Pro Val Leu Cys
            485                 490                 495
Gln Ala His Gly Leu Thr Pro Gln Gln Val Val Ala Ile Ala Ser Asn
            500                 505                 510
```

```
Gly Gly Gly Lys Gln Ala Leu Glu Thr Val Gln Arg Leu Leu Pro Val
        515                 520                 525

Leu Cys Gln Ala His Gly Leu Thr Pro Gln Gln Val Val Ala Ile Ala
        530                 535                 540

Ser Asn Gly Gly Gly Lys Gln Ala Leu Glu Thr Val Gln Arg Leu Leu
545                 550                 555                 560

Pro Val Leu Cys Gln Ala His Gly Leu Thr Pro Gln Gln Val Val Ala
                565                 570                 575

Ile Ala Ser Asn Gly Gly Gly Lys Gln Ala Leu Glu Thr Val Gln Arg
                580                 585                 590

Leu Leu Pro Val Leu Cys Gln Ala His Gly Leu Thr Pro Gln Gln Val
        595                 600                 605

Val Ala Ile Ala Ser Asn Gly Gly Gly Lys Gln Ala Leu Glu Thr Val
        610                 615                 620

Gln Arg Leu Leu Pro Val Leu Cys Gln Ala His Gly Leu Thr Pro Glu
625                 630                 635                 640

Gln Val Val Ala Ile Ala Ser His Asp Gly Gly Lys Gln Ala Leu Glu
                645                 650                 655

Thr Val Gln Arg Leu Leu Pro Val Leu Cys Gln Ala His Gly Leu Thr
                660                 665                 670

Pro Gln Gln Val Val Ala Ile Ala Ser Asn Gly Gly Gly Arg Pro Ala
        675                 680                 685

Leu Glu Ser Ile Val Ala Gln Leu Ser Arg Pro Asp Pro Ser Gly Ser
        690                 695                 700

Gly Ser Gly Gly Asp Pro Ile Ser Arg Ser Gln Leu Val Lys Ser Glu
705                 710                 715                 720

Leu Glu Glu Lys Lys Ser Glu Leu Arg His Lys Leu Lys Tyr Val Pro
                725                 730                 735

His Glu Tyr Ile Glu Leu Ile Glu Ile Ala Arg Asn Ser Thr Gln Asp
                740                 745                 750

Arg Ile Leu Glu Met Lys Val Met Glu Phe Phe Met Lys Val Tyr Gly
        755                 760                 765

Tyr Arg Gly Lys His Leu Gly Gly Ser Arg Lys Pro Asp Gly Ala Ile
        770                 775                 780

Tyr Thr Val Gly Ser Pro Ile Asp Tyr Gly Val Ile Val Asp Thr Lys
785                 790                 795                 800

Ala Tyr Ser Gly Gly Tyr Asn Leu Pro Ile Gly Gln Ala Asp Glu Met
                805                 810                 815

Gln Arg Tyr Val Glu Glu Asn Gln Thr Arg Asn Lys His Ile Asn Pro
                820                 825                 830

Asn Glu Trp Trp Lys Val Tyr Pro Ser Ser Val Thr Glu Phe Lys Phe
        835                 840                 845

Leu Phe Val Ser Gly His Phe Lys Gly Asn Tyr Lys Ala Gln Leu Thr
        850                 855                 860

Arg Leu Asn His Ile Thr Asn Cys Asn Gly Ala Val Leu Ser Val Glu
865                 870                 875                 880

Glu Leu Leu Ile Gly Gly Glu Met Ile Lys Ala Gly Thr Leu Thr Leu
                885                 890                 895

Glu Glu Val Arg Arg Lys Phe Asn Asn Gly Glu Ile Asn Phe Ala Ala
                900                 905                 910

Asp
```

```
<210> SEQ ID NO 19
<211> LENGTH: 913
<212> TYPE: PRT
<213> ORGANISM: artificial sequence
<220> FEATURE:
<223> OTHER INFORMATION: TALEN CD25

<400> SEQUENCE: 19

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Glu Gln Val Val Ala Ile Ala Ser Asn Ile Gly Gly Lys
                165                 170                 175

Gln Ala Leu Glu Thr Val Gln Ala Leu Leu Pro Val Leu Cys Gln Ala
            180                 185                 190

His Gly Leu Thr Pro Glu Gln Val Val Ala Ile Ala Ser His Asp Gly
        195                 200                 205

Gly Lys Gln Ala Leu Glu Thr Val Gln Arg Leu Leu Pro Val Leu Cys
    210                 215                 220

Gln Ala His Gly Leu Thr Pro Glu Gln Val Val Ala Ile Ala Ser Asn
225                 230                 235                 240

Ile Gly Gly Lys Gln Ala Leu Glu Thr Val Gln Ala Leu Leu Pro Val
                245                 250                 255

Leu Cys Gln Ala His Gly Leu Thr Pro Gln Gln Val Val Ala Ile Ala
            260                 265                 270

Ser Asn Asn Gly Gly Lys Gln Ala Leu Glu Thr Val Gln Arg Leu Leu
        275                 280                 285

Pro Val Leu Cys Gln Ala His Gly Leu Thr Pro Gln Gln Val Val Ala
    290                 295                 300

Ile Ala Ser Asn Asn Gly Gly Lys Gln Ala Leu Glu Thr Val Gln Arg
305                 310                 315                 320

Leu Leu Pro Val Leu Cys Gln Ala His Gly Leu Thr Pro Glu Gln Val
                325                 330                 335

Val Ala Ile Ala Ser Asn Ile Gly Gly Lys Gln Ala Leu Glu Thr Val
            340                 345                 350

Gln Ala Leu Leu Pro Val Leu Cys Gln Ala His Gly Leu Thr Pro Gln
        355                 360                 365

Gln Val Val Ala Ile Ala Ser Asn Asn Gly Gly Lys Gln Ala Leu Glu
```

```
              370                 375                 380
Thr Val Gln Arg Leu Leu Pro Val Leu Cys Gln Ala His Gly Leu Thr
385                 390                 395                 400

Pro Gln Gln Val Val Ala Ile Ala Ser Asn Asn Gly Gly Lys Gln Ala
                405                 410                 415

Leu Glu Thr Val Gln Arg Leu Leu Pro Val Leu Cys Gln Ala His Gly
                420                 425                 430

Leu Thr Pro Glu Gln Val Val Ala Ile Ala Ser Asn Ile Gly Gly Lys
                435                 440                 445

Gln Ala Leu Glu Thr Val Gln Ala Leu Leu Pro Val Leu Cys Gln Ala
            450                 455                 460

His Gly Leu Thr Pro Glu Gln Val Val Ala Ile Ala Ser Asn Ile Gly
465                 470                 475                 480

Gly Lys Gln Ala Leu Glu Thr Val Gln Ala Leu Leu Pro Val Leu Cys
                485                 490                 495

Gln Ala His Gly Leu Thr Pro Gln Gln Val Val Ala Ile Ala Ser Asn
                500                 505                 510

Asn Gly Gly Lys Gln Ala Leu Glu Thr Val Gln Arg Leu Leu Pro Val
                515                 520                 525

Leu Cys Gln Ala His Gly Leu Thr Pro Glu Gln Val Val Ala Ile Ala
            530                 535                 540

Ser Asn Ile Gly Gly Lys Gln Ala Leu Glu Thr Val Gln Ala Leu Leu
545                 550                 555                 560

Pro Val Leu Cys Gln Ala His Gly Leu Thr Pro Gln Gln Val Val Ala
                565                 570                 575

Ile Ala Ser Asn Asn Gly Gly Lys Gln Ala Leu Glu Thr Val Gln Arg
                580                 585                 590

Leu Leu Pro Val Leu Cys Gln Ala His Gly Leu Thr Pro Gln Gln Val
                595                 600                 605

Val Ala Ile Ala Ser Asn Gly Gly Lys Gln Ala Leu Glu Thr Val
            610                 615                 620

Gln Arg Leu Leu Pro Val Leu Cys Gln Ala His Gly Leu Thr Pro Glu
625                 630                 635                 640

Gln Val Val Ala Ile Ala Ser Asn Ile Gly Gly Lys Gln Ala Leu Glu
                645                 650                 655

Thr Val Gln Ala Leu Leu Pro Val Leu Cys Gln Ala His Gly Leu Thr
                660                 665                 670

Pro Gln Gln Val Val Ala Ile Ala Ser Asn Gly Gly Gly Arg Pro Ala
                675                 680                 685

Leu Glu Ser Ile Val Ala Gln Leu Ser Arg Pro Asp Pro Ser Gly Ser
            690                 695                 700

Gly Ser Gly Gly Asp Pro Ile Ser Arg Ser Gln Leu Val Lys Ser Glu
705                 710                 715                 720

Leu Glu Glu Lys Lys Ser Glu Leu Arg His Lys Leu Lys Tyr Val Pro
                725                 730                 735

His Glu Tyr Ile Glu Leu Ile Glu Ile Ala Arg Asn Ser Thr Gln Asp
                740                 745                 750

Arg Ile Leu Glu Met Lys Val Met Glu Phe Phe Met Lys Val Tyr Gly
                755                 760                 765

Tyr Arg Gly Lys His Leu Gly Gly Ser Arg Lys Pro Asp Gly Ala Ile
            770                 775                 780

Tyr Thr Val Gly Ser Pro Ile Asp Tyr Gly Val Ile Val Asp Thr Lys
785                 790                 795                 800
```

```
Ala Tyr Ser Gly Gly Tyr Asn Leu Pro Ile Gly Gln Ala Asp Glu Met
            805                 810                 815

Gln Arg Tyr Val Glu Asn Gln Thr Arg Asn Lys His Ile Asn Pro
        820                 825                 830

Asn Glu Trp Trp Lys Val Tyr Pro Ser Ser Val Thr Glu Phe Lys Phe
        835                 840                 845

Leu Phe Val Ser Gly His Phe Lys Gly Asn Tyr Lys Ala Gln Leu Thr
850                 855                 860

Arg Leu Asn His Ile Thr Asn Cys Asn Gly Ala Val Leu Ser Val Glu
865                 870                 875                 880

Glu Leu Leu Ile Gly Gly Glu Met Ile Lys Ala Gly Thr Leu Thr Leu
                885                 890                 895

Glu Glu Val Arg Arg Lys Phe Asn Asn Gly Glu Ile Asn Phe Ala Ala
                900                 905                 910

Asp

<210> SEQ ID NO 20
<211> LENGTH: 936
<212> TYPE: PRT
<213> ORGANISM: artificial sequence
<220> FEATURE:
<223> OTHER INFORMATION: TALEN PD1

<400> SEQUENCE: 20

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Glu Gln Val Val Ala Ile Ala Ser Lys Leu Gly Gly Lys
                165                 170                 175

Gln Ala Leu Glu Thr Val Gln Ala Leu Leu Pro Val Leu Cys Gln Ala
            180                 185                 190

His Gly Leu Thr Pro Glu Gln Val Val Ala Ile Ala Ser His Asp Gly
        195                 200                 205

Gly Lys Gln Ala Leu Glu Thr Val Gln Arg Leu Leu Pro Val Leu Cys
    210                 215                 220

Gln Ala His Gly Leu Thr Pro Glu Gln Val Val Ala Ile Ala Ser His
225                 230                 235                 240
```

```
Asp Gly Gly Lys Gln Ala Leu Glu Thr Val Gln Arg Leu Leu Pro Val
            245                 250                 255

Leu Cys Gln Ala His Gly Leu Thr Pro Gln Gln Val Val Ala Ile Ala
            260                 265                 270

Ser Asn Gly Gly Lys Gln Ala Leu Glu Thr Val Gln Arg Leu Leu
            275                 280                 285

Pro Val Leu Cys Gln Ala His Gly Leu Thr Pro Glu Gln Val Val Ala
            290                 295                 300

Ile Ala Ser His Asp Gly Gly Lys Gln Ala Leu Glu Thr Val Gln Arg
305                 310                 315                 320

Leu Leu Pro Val Leu Cys Gln Ala His Gly Leu Thr Pro Gln Gln Val
                325                 330                 335

Val Ala Ile Ala Ser Asn Gly Gly Lys Gln Ala Leu Glu Thr Val
            340                 345                 350

Gln Arg Leu Leu Pro Val Leu Cys Gln Ala His Gly Leu Thr Pro Gln
            355                 360                 365

Gln Val Val Ala Ile Ala Ser Tyr Lys Gly Gly Lys Gln Ala Leu Glu
            370                 375                 380

Thr Val Gln Arg Leu Leu Pro Val Leu Cys Gln Ala His Gly Leu Thr
385                 390                 395                 400

Pro Gln Gln Val Val Ala Ile Ala Ser Asn Gly Gly Lys Gln Ala
            405                 410                 415

Leu Glu Thr Val Gln Arg Leu Leu Pro Val Leu Cys Gln Ala His Gly
            420                 425                 430

Leu Thr Pro Gln Gln Val Val Ala Ile Ala Ser Asn Asn Gly Gly Lys
            435                 440                 445

Gln Ala Leu Glu Thr Val Gln Arg Leu Leu Pro Val Leu Cys Gln Ala
450                 455                 460

His Gly Leu Thr Pro Gln Gln Val Val Ala Ile Ala Ser Asn Asn Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Gln Gln Val Val Ala Ile Ala Ser Asn
            500                 505                 510

Asn Gly Gly Lys Gln Ala Leu Glu Thr Val Gln Arg Leu Leu Pro Val
            515                 520                 525

Leu Cys Gln Ala His Gly Leu Thr Pro Gln Gln Val Val Ala Ile Ala
            530                 535                 540

Ser Asn Asn Gly Gly Lys Gln Ala Leu Glu Thr Val Gln Arg Leu Leu
545                 550                 555                 560

Pro Val Leu Cys Gln Ala His Gly Leu Thr Pro Glu Gln Val Val Ala
                565                 570                 575

Ile Ala Ser His Asp Gly Gly Lys Gln Ala Leu Glu Thr Val Gln Arg
            580                 585                 590

Leu Leu Pro Val Leu Cys Gln Ala His Gly Leu Thr Pro Glu Gln Val
            595                 600                 605

Val Ala Ile Ala Ser His Asp Gly Gly Lys Gln Ala Leu Glu Thr Val
            610                 615                 620

Gln Arg Leu Leu Pro Val Leu Cys Gln Ala His Gly Leu Thr Pro Glu
625                 630                 635                 640

Gln Val Val Ala Ile Ala Ser Asn Ile Gly Gly Lys Gln Ala Leu Glu
            645                 650                 655

Thr Val Gln Ala Leu Leu Pro Val Leu Cys Gln Ala His Gly Leu Thr
```

```
                  660               665               670
Pro Gln Gln Val Val Ala Ile Ala Ser Asn Gly Gly Gly Arg Pro Ala
            675                 680                 685
Leu Glu Ser Ile Val Ala Gln Leu Ser Arg Pro Asp Pro Ala Leu Ala
        690                 695                 700
Ala Leu Thr Asn Asp His Leu Val Ala Leu Ala Cys Leu Gly Gly Arg
705                 710                 715                 720
Pro Ala Leu Asp Ala Val Lys Lys Gly Leu Gly Asp Pro Ile Ser Arg
                725                 730                 735
Ser Gln Leu Val Lys Ser Glu Leu Glu Glu Lys Lys Ser Glu Leu Arg
            740                 745                 750
His Lys Leu Lys Tyr Val Pro His Glu Tyr Ile Glu Leu Ile Glu Ile
        755                 760                 765
Ala Arg Asn Ser Thr Gln Asp Arg Ile Leu Glu Met Lys Val Met Glu
    770                 775                 780
Phe Phe Met Lys Val Tyr Gly Tyr Arg Gly Lys His Leu Gly Gly Ser
785                 790                 795                 800
Arg Lys Pro Asp Gly Ala Ile Tyr Thr Val Gly Ser Pro Ile Asp Tyr
                805                 810                 815
Gly Val Ile Val Asp Thr Lys Ala Tyr Ser Gly Gly Tyr Asn Leu Pro
            820                 825                 830
Ile Gly Gln Ala Asp Glu Met Gln Arg Tyr Val Glu Glu Asn Gln Thr
        835                 840                 845
Arg Asn Lys His Ile Asn Pro Asn Glu Trp Trp Lys Val Tyr Pro Ser
    850                 855                 860
Ser Val Thr Glu Phe Lys Phe Leu Phe Val Ser Gly His Phe Lys Gly
865                 870                 875                 880
Asn Tyr Lys Ala Gln Leu Thr Arg Leu Asn His Ile Thr Asn Cys Asn
                885                 890                 895
Gly Ala Val Leu Ser Val Glu Glu Leu Leu Ile Gly Gly Glu Met Ile
            900                 905                 910
Lys Ala Gly Thr Leu Thr Leu Glu Glu Val Arg Arg Lys Phe Asn Asn
        915                 920                 925
Gly Glu Ile Asn Phe Ala Ala Asp
    930                 935

<210> SEQ ID NO 21
<211> LENGTH: 941
<212> TYPE: PRT
<213> ORGANISM: artificial sequence
<220> FEATURE:
<223> OTHER INFORMATION: TALEN PD1

<400> SEQUENCE: 21

Met Gly Asp Pro Lys Lys Lys Arg Lys Val Ile Asp Lys Glu Thr Ala
1               5                   10                  15
Ala Ala Lys Phe Glu Arg Gln His Met Asp Ser Ile Asp Ile Ala Asp
                20                  25                  30
Leu Arg Thr Leu Gly Tyr Ser Gln Gln Gln Gln Glu Lys Ile Lys Pro
            35                  40                  45
Lys Val Arg Ser Thr Val Ala Gln His His Glu Ala Leu Val Gly His
        50                  55                  60
Gly Phe Thr His Ala His Ile Val Ala Leu Ser Gln His Pro Ala Ala
65                  70                  75                  80
Leu Gly Thr Val Ala Val Lys Tyr Gln Asp Met Ile Ala Ala Leu Pro
```

-continued

```
                85                  90                  95
Glu Ala Thr His Glu Ala Ile Val Gly Val Gly Lys Gln Trp Ser Gly
            100                 105                 110
Ala Arg Ala Leu Glu Ala Leu Leu Thr Val Ala Gly Glu Leu Arg Gly
            115                 120                 125
Pro Pro Leu Gln Leu Asp Thr Gly Gln Leu Leu Lys Ile Ala Lys Arg
            130                 135                 140
Gly Gly Val Thr Ala Val Glu Ala Val His Ala Trp Arg Asn Ala Leu
145                 150                 155                 160
Thr Gly Ala Pro Leu Asn Leu Thr Pro Glu Gln Val Val Ala Ile Ala
            165                 170                 175
Ser His Asp Gly Gly Lys Gln Ala Leu Glu Thr Val Gln Arg Leu Leu
            180                 185                 190
Pro Val Leu Cys Gln Ala His Gly Leu Thr Pro Gln Gln Val Val Ala
            195                 200                 205
Ile Ala Ser Asn Gly Gly Gly Lys Gln Ala Leu Glu Thr Val Gln Arg
            210                 215                 220
Leu Leu Pro Val Leu Cys Gln Ala His Gly Leu Thr Pro Glu Gln Val
225                 230                 235                 240
Val Ala Ile Ala Ser His Asp Gly Gly Lys Gln Ala Leu Glu Thr Val
            245                 250                 255
Gln Arg Leu Leu Pro Val Leu Cys Gln Ala His Gly Leu Thr Pro Gln
            260                 265                 270
Gln Val Val Ala Ile Ala Ser Asn Gly Gly Gly Lys Gln Ala Leu Glu
            275                 280                 285
Thr Val Gln Arg Leu Leu Pro Val Leu Cys Gln Ala His Gly Leu Thr
            290                 295                 300
Pro Gln Gln Val Val Ala Ile Ala Ser Asn Gly Gly Gly Lys Gln Ala
305                 310                 315                 320
Leu Glu Thr Val Gln Arg Leu Leu Pro Val Leu Cys Gln Ala His Gly
            325                 330                 335
Leu Thr Pro Gln Gln Val Val Ala Ile Ala Ser Asn Gly Gly Gly Lys
            340                 345                 350
Gln Ala Leu Glu Thr Val Gln Arg Leu Leu Pro Val Leu Cys Gln Ala
            355                 360                 365
His Gly Leu Thr Pro Gln Gln Val Val Ala Ile Ala Ser Asn Asn Gly
            370                 375                 380
Gly Lys Gln Ala Leu Glu Thr Val Gln Arg Leu Leu Pro Val Leu Cys
385                 390                 395                 400
Gln Ala His Gly Leu Thr Pro Glu Gln Val Val Ala Ile Ala Ser Asn
            405                 410                 415
Ile Gly Gly Lys Gln Ala Leu Glu Thr Val Gln Ala Leu Leu Pro Val
            420                 425                 430
Leu Cys Gln Ala His Gly Leu Thr Pro Gln Gln Val Val Ala Ile Ala
            435                 440                 445
Ser Asn Gly Gly Gly Lys Gln Ala Leu Glu Thr Val Gln Arg Leu Leu
            450                 455                 460
Pro Val Leu Cys Gln Ala His Gly Leu Thr Pro Glu Gln Val Val Ala
465                 470                 475                 480
Ile Ala Ser His Asp Gly Gly Lys Gln Ala Leu Glu Thr Val Gln Arg
            485                 490                 495
Leu Leu Pro Val Leu Cys Gln Ala His Gly Leu Thr Pro Gln Gln Val
            500                 505                 510
```

```
Val Ala Ile Ala Ser Asn Gly Gly Lys Gln Ala Leu Glu Thr Val
            515                 520                 525
Gln Arg Leu Leu Pro Val Leu Cys Gln Ala His Gly Leu Thr Pro Gln
530                 535                 540
Gln Val Val Ala Ile Ala Ser Asn Asn Gly Gly Lys Gln Ala Leu Glu
545                 550                 555                 560
Thr Val Gln Arg Leu Leu Pro Val Leu Cys Gln Ala His Gly Leu Thr
                565                 570                 575
Pro Glu Gln Val Val Ala Ile Ala Ser Asn Gly Gly Lys Gln Ala Leu
                580                 585                 590
Glu Thr Val Gln Arg Leu Leu Pro Val Leu Cys Gln Ala His Gly Leu
            595                 600                 605
Thr Pro Gln Gln Val Val Ala Ile Ala Ser Asn Asn Gly Gly Lys Gln
            610                 615                 620
Ala Leu Glu Thr Val Gln Arg Leu Leu Pro Val Leu Cys Gln Ala His
625                 630                 635                 640
Gly Leu Thr Pro Glu Gln Val Val Ala Ile Ala Ser His Asp Gly Gly
                645                 650                 655
Lys Gln Ala Leu Glu Thr Val Gln Arg Leu Leu Pro Val Leu Cys Gln
                660                 665                 670
Ala His Gly Leu Thr Pro Gln Gln Val Val Ala Ile Ala Ser Asn Gly
            675                 680                 685
Gly Gly Arg Pro Ala Leu Glu Ser Ile Val Ala Gln Leu Ser Arg Pro
690                 695                 700
Asp Pro Ala Leu Ala Ala Leu Thr Asn Asp His Leu Val Ala Leu Ala
705                 710                 715                 720
Cys Leu Gly Gly Arg Pro Ala Leu Asp Ala Val Lys Lys Gly Leu Gly
                725                 730                 735
Asp Pro Ile Ser Arg Ser Gln Leu Val Lys Ser Glu Leu Glu Glu Lys
                740                 745                 750
Lys Ser Glu Leu Arg His Lys Leu Lys Tyr Val Pro His Glu Tyr Ile
            755                 760                 765
Glu Leu Ile Glu Ile Ala Arg Asn Ser Thr Gln Asp Arg Ile Leu Glu
            770                 775                 780
Met Lys Val Met Glu Phe Phe Met Lys Val Tyr Gly Tyr Arg Gly Lys
785                 790                 795                 800
His Leu Gly Gly Ser Arg Lys Pro Asp Gly Ala Ile Tyr Thr Val Gly
                805                 810                 815
Ser Pro Ile Asp Tyr Gly Val Ile Val Asp Thr Lys Ala Tyr Ser Gly
                820                 825                 830
Gly Tyr Asn Leu Pro Ile Gly Gln Ala Asp Glu Met Gln Arg Tyr Val
            835                 840                 845
Glu Glu Asn Gln Thr Arg Asn Lys His Ile Asn Pro Asn Glu Trp Trp
850                 855                 860
Lys Val Tyr Pro Ser Ser Val Thr Glu Phe Lys Phe Leu Phe Val Ser
865                 870                 875                 880
Gly His Phe Lys Gly Asn Tyr Lys Ala Gln Leu Thr Arg Leu Asn His
                885                 890                 895
Ile Thr Asn Cys Asn Gly Ala Val Leu Ser Val Glu Glu Leu Leu Ile
                900                 905                 910
Gly Gly Glu Met Ile Lys Ala Gly Thr Leu Thr Leu Glu Glu Val Arg
            915                 920                 925
```

```
Arg Lys Phe Asn Asn Gly Glu Ile Asn Phe Ala Ala Asp
    930             935             940
```

<210> SEQ ID NO 22
<211> LENGTH: 2814
<212> TYPE: DNA
<213> ORGANISM: artificial sequence
<220> FEATURE:
<223> OTHER INFORMATION: TALEN TRAC pCLS11370

<400> SEQUENCE: 22

```
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa cacccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480
ttgacccccc agcaggtggt ggccatcgcc agcaatggcg gtggcaagca ggcgctggag   540
acggtccagc ggctgttgcc ggtgctgtgc caggcccacg gcttgacccc ccagcaggtg   600
gtggccatcg ccagcaataa tggtggcaag caggcgctgg agacggtcca gcggctgttg   660
ccggtgctgt gccaggccca cggcttgacc cccagcagg tggtggccat cgccagcaat   720
ggcggtggca gcaggcgct ggagacggtc cagcggctgt tgccggtgct gtgccaggcc   780
cacggcttga ccccggagca ggtggtggcc atcgccagcc acgatggcgg caagcaggcg   840
ctggagacgg tccagcggct gttgccggtg ctgtgccagg cccacggctt gaccccggag   900
caggtggtgg ccatcgccag ccacgatggc ggcaagcagg cgctggagac ggtccagcgg   960
ctgttgccgg tgctgtgcca ggcccacggc ttgaccccgg agcaggtggt ggccatcgcc  1020
agccacgatg cggcaagca ggcgctggag acggtccagc ggctgttgcc ggtgctgtgc  1080
caggcccacg gcttgacccc ggagcaggtg gtggccatcg ccagcaatat tggtggcaag  1140
caggcgctgg agacggtgca ggcgctgttg ccggtgctgt gccaggccca cggcttgacc  1200
ccggagcagg tggtggccat cgccagccac gatggcggca agcaggcgct ggagacggtc  1260
cagcggctgt tgccggtgct gtgccaggcc cacggcttga ccccggagca ggtggtggcc  1320
atcgccagca atattggtgg caagcaggcg ctggagacgg tgcaggcgct gttgccggtg  1380
ctgtgccagg cccacggctt gaccccccag caggtggtgg ccatcgccag caataatggt  1440
ggcaagcagg cgctggagac ggtccagcgg ctgttgccgg tgctgtgcca ggcccacggc  1500
ttgaccccgg agcaggtggt ggccatcgcc agcaatattg gtggcaagca ggcgctggag  1560
acggtgcagg cgctgttgcc ggtgctgtgc caggcccacg gcttgacccc ccagcaggtg  1620
gtggccatcg ccagcaatgg cggtggcaag caggcgctgg agacggtcca gcggctgttg  1680
ccggtgctgt gccaggccca cggcttgacc ccggagcagg tggtggccat cgccagcaat  1740
attggtggca agcaggcgct ggagacggtg caggcgctgt tgccggtgct gtgccaggcc  1800
cacggcttga ccccccagca ggtggtggcc atcgccagca atgcggtgg caagcaggcg  1860
ctggagacgg tccagcggct gttgccggtg ctgtgccagg cccacggctt gaccccggag  1920
caggtggtgg ccatcgccag ccacgatggc ggcaagcagg cgctggagac ggtccagcgg  1980
```

```
ctgttgccgg tgctgtgcca ggcccacggc ttgacccctc agcaggtggt ggccatcgcc      2040
agcaatggcg gcggcaggcc ggcgctggag agcattgttg cccagttatc tcgccctgat      2100
ccggcgttgg ccgcgttgac caacgaccac ctcgtcgcct tggcctgcct cggcgggcgt      2160
cctgcgctat atgcagtgaa aaagggattg ggggatccta tcagccgttc ccagctggtg      2220
aagtccgagc tggaggagaa gaaatccgag ttgaggcaca agctgaagta cgtgccccac      2280
gagtacatcg agctgatcga gatcgcccgg aacagcaccc aggaccgtat cctggagatg      2340
aaggtgatgg agttcttcat gaaggtgtac ggctacaggg gcaagcacct gggcggctcc      2400
aggaagcccg acggcgccat ctacaccgtg gctcccccca tcgactacgg cgtgatcgtg      2460
gacaccaagg cctactccgg cggctacaac ctgcccatcg gccaggccga cgaaatgcag      2520
aggtacgtgg aggagaacca gaccaggaac aagcacatca ccccaacga gtggtggaag      2580 gtgtaccct ccagcgtgac cgagttcaag ttcctgttcg tgtccggcca cttcaagggc       2640
aactacaagg cccagctgac caggctgaac cacatcacca actgcaacgg cgccgtgctg      2700
tccgtggagg agctcctgat cggcggcgag atgatcaagg ccggcaccct gaccctggag      2760
gaggtgagga ggaagttcaa caacggcgag atcaacttcg cggccgactg ataa           2814
```

<210> SEQ ID NO 23
<211> LENGTH: 2832
<212> TYPE: DNA
<213> ORGANISM: artificial sequence
<220> FEATURE:
<223> OTHER INFORMATION: TALEN TRAC pCLS11369

<400> SEQUENCE: 23

```
atgggcgatc ctaaaaagaa acgtaaggtc atcgataagg agaccgccgc tgccaagttc       60
gagagacagc acatggacag catcgatatc gccgatctac gcacgctcgg ctacagccag      120
cagcaacagg agaagatcaa accgaaggtt cgttcgacag tggcgcagca ccacgaggca      180
ctggtcggcc acgggtttac acacgcgcac atcgttgcgt taagccaaca cccggcagcg      240
ttagggaccg tcgctgtcaa gtatcaggac atgatcgcag cgttgccaga ggcgacacac      300
gaagcgatct tggcgtcgg caaacagtgg tccggcgcac gcgctctgga ggccttgctc       360
acggtggcgg gagagttgag aggtccaccg ttacagttgg acacaggcca acttctcaag      420
attgcaaaac gtgcggcgt gaccgcagtg gaggcagtgc atgcatgcg caatgcactg       480 acgggtgccc cgctcaactt gacccggag caggtggtgg ccatcgccag ccacgatggc       540
ggcaagcagg cgctggagac ggtccagcgg ctgttgccgg tgctgtgcca ggcccacggc      600 ttgaccccc agcaggtggt ggccatcgcc agcaatggcg gtggcaagca ggcgctggag      660
acggtccagc ggctgttgcc ggtgctgtgc caggcccacg gcttgacccc ggagcaggtg      720
gtggccatcg ccagccacga tggcggcaag caggcgctga gacggtcca gcggctgttg       780 ccggtgctgt gccaggccca cggcttgacc ccggagcagg tggtggccat cgccagcaat      840
attggtggca agcaggcgct ggagacggtg caggcgctgt gccggtgct gtgccaggcc       900 cacggcttga ccccccagca ggtggtggcc atcgccagca ataatggtgg caagcaggcg      960
ctggagacgt ccagcggct gttgccggtg ctgtgccagg cccacggctt gaccccggag      1020
caggtggtgg ccatcgccag ccacgatggc ggcaagcagg cgctggagac ggtccagcgg      1080
ctgttgccgg tgctgtgcca ggcccacggc ttgacccccc agcaggtggt ggccatcgcc      1140
agcaatggcg gtggcaagca ggcgctggag acggtccagc ggctgttgcc ggtgctgtgc      1200
caggcccacg gcttgacccc ccagcaggtg gtggccatcg ccagcaataa tggtggcaag      1260
```

```
caggcgctgg agacggtcca gcggctgttg ccggtgctgt gccaggccca cggcttgacc    1320
ccccagcagg tggtggccat cgccagcaat aatggtggca agcaggcgct ggagacggtc    1380
cagcggctgt tgccggtgct gtgccaggcc acggcttga ccccccagca ggtggtggcc    1440
atcgccagca atggcggtgg caagcaggcg ctggagacgg tccagcggct gttgccggtg    1500
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc cggagcagg tggtggccat cgccagccac    1860
gatggcggca agcaggcgct ggagacggtc agcggctgt tgccggtgct gtgccaggcc    1920
cacggcttga ccccccagca ggtggtggcc atcgccagca ataatggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag    2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg    2640
tccggccact tcaagggcaa ctacaaggcc agctgacca ggctgaacca catcaccaac    2700
tgcaacggcg ccgtgctgtc cgtggaggag ctcctgatcg gcggcgagat gatcaaggcc    2760 ggcacccctga ccctggagga ggtgaggagg aagttcaaca cggcgagat caacttcgcg    2820 gccgactgat aa                                                        2832

<210> SEQ ID NO 24
<211> LENGTH: 2745
<212> TYPE: DNA
<213> ORGANISM: artificial sequence
<220> FEATURE:
<223> OTHER INFORMATION: TALEN CD25 pCLS30480

<400> SEQUENCE: 24
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa cacccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
```

```
gtgaccgcag tggaggcagt gcatgcatgg cgcaatgcac tgacgggtgc cccgctcaac    480
ttgaccccc  agcaggtggt ggccatcgcc agcaataatg gtggcaagca ggcgctggag    540
acggtccagc ggctgttgcc ggtgctgtgc caggcccacg gcttgacccc ccagcaggtg    600
gtggccatcg ccagcaatgg cggtggcaag caggcgctgg agacggtcca gcggctgttg    660
ccggtgctgt gccaggccca cggcttgacc ccccagcagg tggtggccat cgccagcaat    720
ggcggtggca agcaggcgct ggagacggtc agcggctgt  tgccggtgct gtgccaggcc    780
cacggcttga ccccggagca ggtggtggcc atcgccagcc acgatggcgg caagcaggcg    840
ctggagacgg tccagcggct gttgccggtg ctgtgccagg cccacggctt gacccccag    900
caggtggtgg ccatcgccag caatggcggt ggcaagcagg cgctggagac ggtccagcgg    960
ctgttgccgg tgctgtgcca ggcccacggc ttgaccccc  agcaggtggt ggccatcgcc   1020
agcaatggcg gtggcaagca ggcgctggag acggtccagc ggctgttgcc ggtgctgtgc   1080
caggcccacg gcttgacccc ccagcaggtg gtggccatcg ccagcaatgg cggtggcaag   1140
caggcgctgg agacggtcca gcggctgttg ccggtgctgt gccaggccca cggcttgacc   1200
ccccagcagg tggtggccat cgccagcaat ggcggtggca agcaggcgct ggagacggtc   1260
cagcggctgt tgccggtgct gtgccaggcc cacggcttga ccccccagca ggtggtggcc   1320
atcgccagca ataatggtgg caagcaggcg ctggagacgg tccagcggct gttgccggtg   1380
ctgtgccagg cccacggctt gacccccag  caggtggtgg ccatcgccag caataatggt   1440
ggcaagcagg cgctggagac ggtccagcgg ctgttgccgg tgctgtgcca ggcccacggc   1500
ttgaccccc  agcaggtggt ggccatcgcc agcaatggcg gtggcaagca ggcgctggag   1560
acggtccagc ggctgttgcc ggtgctgtgc caggcccacg gcttgacccc ccagcaggtg   1620
gtggccatcg ccagcaatgg cggtggcaag caggcgctgg agacggtcca gcggctgttg   1680
ccggtgctgt gccaggccca cggcttgacc ccccagcagg tggtggccat cgccagcaat   1740
ggcggtggca agcaggcgct ggagacggtc agcggctgt  tgccggtgct gtgccaggcc   1800
cacggcttga ccccccagca ggtggtggcc atcgccagca atggcggtgg caagcaggcg   1860
ctggagacgg tccagcggct gttgccggtg ctgtgccagg cccacggctt gaccccggag   1920
caggtggtgg ccatcgccag ccacgatggc ggcaagcagg cgctggagac ggtccagcgg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccgagtggca gcggaagtgg cggggatcct atcagccgtt cccagctggt gaagtccgag   2160
ctggaggaga agaaatccga gttgaggcac aagctgaagt acgtgcccca cgagtacatc   2220
gagctgatcg agatcgcccg gaacagcacc caggaccgta tcctggagat gaaggtgatg   2280
gagttcttca tgaaggtgta cggctacagg ggcaagcacc tgggcggctc caggaagccc   2340
gacggcgcca tctacaccgt gggctccccc atcgactacg gcgtgatcgt ggacaccaag   2400
gcctactccg gcggctacaa cctgcccatc ggccaggccg acgaaatgca gaggtacgtg   2460
gaggagaacc agaccaggaa caagcacatc aaccccaacg agtggtggaa ggtgtacccc   2520
tccagcgtga ccgagttcaa gttcctgttc gtgtccggcc acttcaaggg caactacaag   2580
gcccagctga ccaggctgaa ccacatcacc aactgcaacg gcgccgtgct gtccgtggag   2640
gagctcctga tcggcggcga gatgatcaag gccggcaccc tgaccctgga ggaggtgagg   2700
aggaagttca acaacggcga gatcaacttc gcggccgact gataa                   2745
```

<210> SEQ ID NO 25
<211> LENGTH: 2745
<212> TYPE: DNA
<213> ORGANISM: artificial sequence
<220> FEATURE:
<223> OTHER INFORMATION: TALEN CD25 pCLS30479

<400> SEQUENCE: 25

| | |
|---|---|
| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa caccccggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca agattgcaaa acgtggcggc | 420 |
| gtgaccgcag tggaggcagt gcatgcatgg cgcaatgcac tgacgggtgc cccgctcaac | 480 |
| ttgacccccgg agcaggtggt ggccatcgcc agcaatattg gtggcaagca ggcgctggag | 540 |
| acggtgcagg cgctgttgcc ggtgctgtgc caggcccacg gcttgacccc ggagcaggtg | 600 |
| gtggccatcg ccagccacga tgcggcaag caggcgctgg agacggtcca gcggctgttg | 660 |
| ccggtgctgt gccaggccca cggcttgacc ccggagcagg tggtggccat cgccagcaat | 720 |
| attggtggca agcaggcgct ggagacggtg caggcgctgt tgccggtgct gtgccaggcc | 780 |
| cacggcttga ccccccagca ggtggtggcc atcgccagca ataatggtgg caagcaggcg | 840 |
| ctggagacgg tccagcggct gttgccggtg ctgtgccagg cccacggctt gaccccccag | 900 |
| caggtggtgg ccatcgccag caataatggt ggcaagcagg cgctggagac ggtccagcgg | 960 |
| ctgttgccgg tgctgtgcca ggcccacggc ttgaccccgg agcaggtggt ggccatcgcc | 1020 |
| agcaatattg gtggcaagca ggcgctggag acggtgcagg cgctgttgcc ggtgctgtgc | 1080 |
| caggcccacg gcttgacccc ccagcaggtg gtggccatcg ccagcaataa tggtggcaag | 1140 |
| caggcgctgg agacggtcca gcggctgttg ccggtgctgt gccaggccca cggcttgacc | 1200 |
| ccccagcagg tggtggccat cgccagcaat aatggtggca agcaggcgct ggagacggtc | 1260 |
| cagcggctgt tgccggtgct gtgccaggcc cacggcttga ccccggagca ggtggtggcc | 1320 |
| atcgccagca atattggtgg caagcaggcg ctggagacgg tgcaggcgct gttgccggtg | 1380 |
| ctgtgccagg cccacggctt gaccccggag caggtggtgg ccatcgccag caatattggt | 1440 |
| ggcaagcagg cgctggagac ggtgcaggcg ctgttgccgg tgctgtgcca ggcccacggc | 1500 |
| ttgaccccccc agcaggtggt ggccatcgcc agcaataatg gtggcaagca ggcgctggag | 1560 |
| acggtccagc ggctgttgcc ggtgctgtgc caggcccacg gcttgacccc ggagcaggtg | 1620 |
| gtggccatcg ccagcaatat tggtggcaag caggcgctgg agacggtgca ggcgctgttg | 1680 |
| ccggtgctgt gccaggccca cggcttgacc ccccagcagg tggtggccat cgccagcaat | 1740 |
| aatggtggca agcaggcgct ggagacggtc agcggctgt tgccggtgct gtgccaggcc | 1800 |
| cacggcttga ccccccagca ggtggtggcc atcgccagca atggcggtgg caagcaggcg | 1860 |
| ctggagacgg tccagcggct gttgccggtg ctgtgccagg cccacggctt gaccccggag | 1920 |
| caggtggtgg ccatcgccag caatattggt ggcaagcagg cgctggagac ggtgcaggcg | 1980 |
| ctgttgccgg tgctgtgcca ggcccacggc ttgaccccctc agcaggtggt ggccatcgcc | 2040 |
| agcaatggcg gcggcaggcc ggcgctggag agcattgttg cccagttatc tcgccctgat | 2100 |

| | |
|---|---:|
| ccgagtggca gcggaagtgg cggggatcct atcagccgtt cccagctggt gaagtccgag | 2160 |
| ctggaggaga agaaatccga gttgaggcac aagctgaagt acgtgcccca cgagtacatc | 2220 |
| gagctgatcg agatcgcccg gaacagcacc caggaccgta tcctggagat gaaggtgatg | 2280 |
| gagttcttca tgaaggtgta cggctacagg ggcaagcacc tgggcggctc caggaagccc | 2340 |
| gacggcgcca tctacaccgt gggctccccc atcgactacg gcgtgatcgt ggacaccaag | 2400 |
| gcctactccg gcggctacaa cctgcccatc ggccaggccg acgaaatgca gaggtacgtg | 2460 |
| gaggagaacc agaccaggaa caagcacatc aaccccaacg agtggtggaa ggtgtacccc | 2520 |
| tccagcgtga ccgagttcaa gttcctgttc gtgtccggcc acttcaaggg caactacaag | 2580 |
| gcccagctga ccaggctgaa ccacatcacc aactgcaacg gcgccgtgct gtccgtggag | 2640 |
| gagctcctga tcggcggcga gatgatcaag gccggcaccc tgaccctgga ggaggtgagg | 2700 |
| aggaagttca acaacggcga gatcaacttc gcggccgact gataa | 2745 |

<210> SEQ ID NO 26
<211> LENGTH: 2814
<212> TYPE: DNA
<213> ORGANISM: artificial sequence
<220> FEATURE:
<223> OTHER INFORMATION: TALEN PD1 pCLS28959

<400> SEQUENCE: 26

| | |
|---|---:|
| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa caccccggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca agattgcaaa acgtggcggc | 420 |
| gtgaccgcag tggaggcagt gcatgcatgg cgcaatgcac tgacgggtgc cccgctcaac | 480 |
| ttgacccccg agcaagtggt ggctatcgct tccaagctgg ggggaaagca ggccctggag | 540 |
| accgtccagg cccttctccc agtgctttgc caggctcacg gactgacccc tgaacaggtg | 600 |
| gtggcaattg cctcacacga cggggggcaag caggcactgg agactgtcca gcggctgctg | 660 |
| cctgtcctct gccaggccca cggactcact cctgagcagg tcgtggccat tgccagccac | 720 |
| gatgggggca acaggctct ggagaccgtg cagcgcctcc tcccagtgct gtgccaggct | 780 |
| catgggctga ccccacagca ggtcgtcgcc attgccagta acggcggggg gaagcaggcc | 840 |
| ctcgaaacag tgcagaggct gctgccccgtc ttgtgccaag cacacggcct gacacccgag | 900 |
| caggtggtgg ccatcgcctc tcatgacggc ggcaagcagg cccttgagac agtgcagaga | 960 |
| ctgttgcccg tgttgtgtca ggcccacggg ttgacacccc agcaggtggt cgccatcgcc | 1020 |
| agcaatggcg ggggaaagca ggcccttgag accgtgcagc ggttgcttcc agtgttgtgc | 1080 |
| caggcacacg gactgacccc tcaacaggtg gtcgcaatcg ccagctacaa gggcggaaag | 1140 |
| caggctctgg agacagtgca gcgcctcctg ccgtgctgt gtcaggctca cggactgaca | 1200 |
| ccacagcagg tggtcgccat cgccagtaac gggggcggca agcaggcttt ggagaccgtc | 1260 |
| cagagactcc tccccgtcct ttgccaggcc cacgggttga cacctcagca ggtcgtcgcc | 1320 |
| attgcctcca acaacggggg caagcaggcc ctcgaaactg tgcagaggct gctgcctgtg | 1380 |
| ctgtgccagg ctcatgggct gacaccccag caggtggtgg ccattgcctc taacaacggc | 1440 |

```
ggcaaacagg cactggagac cgtgcaaagg ctgctgcccg tcctctgcca agcccacggg    1500
ctcactccac agcaggtcgt ggccatcgcc tcaaacaatg gcgggaagca ggccctggag    1560
actgtgcaaa ggctgctccc tgtgctctgc caggcacacg gactgacccc tcagcaggtg    1620
gtggcaatcg cttccaacaa cggggggaaag caggccctcg aaaccgtgca gcgcctcctc    1680
ccagtgctgt gccaggcaca tggcctcaca cccgagcaag tggtggctat cgccagccac    1740
gacggaggga agcaggctct ggagaccgtg cagaggctgc tgcctgtcct gtgccaggcc    1800
cacgggctta ctccagagca ggtcgtcgcc atcgccagtc atgatggggg aagcaggcc    1860 cttgagacag tccagcggct gctgccagtc ctttgccagg ctcacggctt gactcccgag    1920
caggtcgtgg ccattgcctc aaacattggg ggcaaacagg ccctggagac agtgcaggcc    1980
ctgctgcccg tgttgtgtca ggcccacggc ttgacacccc agcaggtggt cgccattgcc    2040
tctaatggcg gcgggagacc cgccttggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatga gttcttcat gaaggtgtac ggctacaggg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg gccaggccga cgaaatgcag    2520
aggtacgtgg aggagaacca gaccaggaac aagcacatca ccccaacga gtggtggaag    2580 gtgtaccccc tccagcgtga ccgagttcaag ttcctgttcg tgtccggcca cttcaagggc    2640
aactacaagg cccagctgac caggctgaac cacatcacca ctgcaacgg cgccgtgctg    2700 tccgtggagg agctcctgat cggcggcgag atgatcaagg ccggcaccct gacctggag    2760 gaggtgagga ggaagttcaa caacggcgag atcaacttcg cggccgactg ataa    2814
```

<210> SEQ ID NO 27
<211> LENGTH: 2829
<212> TYPE: DNA
<213> ORGANISM: artificial sequence
<220> FEATURE:
<223> OTHER INFORMATION: TALEN PD1 pCLS18792

<400> SEQUENCE: 27

```
atgggcgatc ctaaaaagaa acgtaaggtc atcgataagg agaccgccgc tgccaagttc    60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccc tcgctgtcaa gtatcaggac atgatcgcag cgttgccaga ggcgacacac    300
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccgag caagtcgtcg caatcgccag ccatgatgga    540
gggaagcaag ccctcgaaac cgtgcagcgg ttgcttcctg tgctctgcca ggcccacggc    600 cttaccccctc agcaggtggt ggccatcgca agtaacggag gaggaaagca agccttggag    660
```

-continued

```
acagtgcagc gcctgttgcc cgtgctgtgc caggcacacg gcctcacacc agagcaggtc    720
gtggccattg cctcccatga cggggggaaa caggctctgg agaccgtcca gaggctgctg    780
cccgtcctct gtcaagctca cggcctgact ccccaacaag tggtcgccat cgcctctaat    840
ggcggcggga agcaggcact ggaaacagtg cagagactgc tccctgtgct ttgccaagct    900
catgggttga ccccccaaca ggtcgtcgct attgcctcaa acggggggg caagcaggcc    960
cttgagactg tgcagaggct gttgccagtg ctgtgtcagg ctcacgggct cactccacaa   1020
caggtggtcg caattgccag caacggcggc ggaaagcaag ctcttgaaac cgtgcaacgc   1080
ctcctgcccg tgctctgtca ggctcatggc ctgacaccac aacaagtcgt ggccatcgcc   1140
agtaataatg gcgggaaaca ggctcttgag accgtccaga ggctgctccc agtgctctgc   1200
caggcacacg gctgacccc cgagcaggtg gtggctatcg ccagcaatat tgggggcaag   1260
caggccctgg aaacagtcca ggccctgctg ccagtgcttt gccaggctca cgggctcact   1320
ccccagcagg tcgtggcaat cgcctccaac ggcggaggga agcaggctct ggagaccgtg   1380
cagagactgc tgcccgtctt gtgccaggcc acggactca cacctgaaca ggtcgtcgcc   1440
attgcctctc acgatggggg caaacaagcc ctggagacag tgcagcggct gttgcctgtg   1500
ttgtgccaag cccacggctt gactcctcaa caagtggtcg ccatcgcctc aaatggcggc   1560
ggaaaacaag ctctggagac agtgcagagg ttgctgcccg tcctctgcca agcccacggc   1620
ctgactcccc aacaggtcgt cgccattgcc agcaacaacg gaggaaagca ggctctcgaa   1680
actgtgcagc ggctgcttcc tgtgctgtgt caggctcatg ggctgacccc cgagcaagtg   1740
gtggctattg cctctaatgg aggcaagcaa gcccttgaga cagtccagag gctgttgcca   1800
gtgctgtgcc aggcccacgg gctcacaccc cagcaggtgg tcgccatcgc cagtaacaac   1860
gggggcaaac aggcattgga aaccgtccag cgcctgcttc cagtgctctg ccaggcacac   1920
ggactgacac ccgaacaggt ggtggccatt gcatcccatg atggggcaa gcaggccctg   1980
gagaccgtgc agagactcct gccagtgttg tgccaagctc acggcctcac ccctcagcaa   2040
gtcgtggcca tcgcctcaaa cgggggggc cggcctgcac tggagagcat tgttgcccag   2100
ttatctcgcc ctgatccggc gttggccgcg ttgaccaacg accacctcgt cgccttggcc   2160
tgcctcggcg ggcgtcctgc gctggatgca gtgaaaaagg gattggggga tcctatcagc   2220
cgttcccagc tggtgaagtc cgagctggag gagaagaaat ccgagttgag gcacaagctg   2280
aagtacgtgc cccacgagta catcgagctg atcgagatcg cccggaacag cacccaggac   2340
cgtatcctgg agatgaaggt gatggagttc ttcatgaagg tgtacggcta caggggcaag   2400
cacctgggcg gctccaggaa gcccgacggc gccatctaca ccgtgggctc ccccatcgac   2460
tacgcgtga tcgtggacac caaggcctac tccggcggct acaacctgcc catcggccag   2520
gccgacgaaa tgcagaggta cgtggaggag aaccagacca ggaacaagca catcaaccc   2580
aacgagtggt ggaaggtgta cccctccagc gtgaccgagt tcaagttcct gttcgtgtcc   2640
ggccacttca agggcaacta caaggcccag ctgaccaggc tgaaccacat caccaactgc   2700
aacggcgccg tgctgtccgt ggaggagctc ctgatcggcg gcgagatgat caaggccggc   2760
accctgaccc tggaggaggt gaggaggaag ttcaacaacg gcgagatcaa cttcgcggcc   2820
gactgataa                                                          2829
```

<210> SEQ ID NO 28
<211> LENGTH: 49
<212> TYPE: DNA
<213> ORGANISM: artificial sequence

```
<220> FEATURE:
<223> OTHER INFORMATION: TALEN target TRAC

<400> SEQUENCE: 28
ttgtcccaca gatatccaga accctgaccc tgccgtgtac cagctgaga          49

<210> SEQ ID NO 29
<211> LENGTH: 45
<212> TYPE: DNA
<213> ORGANISM: artificial sequence
<220> FEATURE:
<223> OTHER INFORMATION: TALEN target CD25

<400> SEQUENCE: 29
tacaggagga agagtagaag aacaatctag aaaaccaaaa gaaca              45

<210> SEQ ID NO 30
<211> LENGTH: 49
<212> TYPE: DNA
<213> ORGANISM: artificial sequence
<220> FEATURE:
<223> OTHER INFORMATION: TALEN target PD1

<400> SEQUENCE: 30
tacctctgtg gggccatctc cctggccccc aaggcgcaga tcaaagaga          49

<210> SEQ ID NO 31
<211> LENGTH: 2897
<212> TYPE: DNA
<213> ORGANISM: artificial sequence
<220> FEATURE:
<223> OTHER INFORMATION: Matrice TRAC locus_CubiCAR CD22 pCLS30056

<400> SEQUENCE: 31
ttgctgggcc ttttccccat gcctgccttt actctgccag agttatattg ctggggtttt    60
gaagaagatc ctattaaata aaagaataag cagtattatt aagtagccct gcatttcagg   120
tttccttgag tggcaggcca ggcctggccg tgaacgttca ctgaaatcat ggcctcttgg   180
ccaagattga tagcttgtgc ctgtccctga gtcccagtcc atcacgagca gctggttttct  240 aagatgctat ttcccgtata aagcatgaga ccgtgacttg ccagccccac agagcccgc   300 ccttgtccat cactggcatc tggactccag cctgggttgg ggcaaagagg gaaatgagat   360
catgtcctaa ccctgatcct cttgtcccac agatatccag taccctacg acgtgcccga   420 ctacgcctcc ggtgagggca gaggaagtct tctaacatgc ggtgacgtgg aggagaatcc   480
gggccccgga tccgctctgc ccgtcaccgc tctgctgctg ccactggcac tgctgctgca   540
cgctgctagg cccggagggg gaggcagctg ccctacagc aaccccagcc tgtgcagcgg    600
aggcggcggc agcggcggag ggggtagcca ggtgcagctg cagcagagcg ccctggcct   660 ggtgaagcca agccagacac tgtccctgac ctgcgccatc agcggcgatt ccgtgagctc   720
caactccgcc gcctggaatt ggatcaggca gtcccccttct cggggcctgg agtggctggg   780
aaggacatac tatcggtcta agtggtacaa cgattatgcc gtgtctgtga agagcagaat   840
cacaatcaac cctgacacct ccaagaatca gttctctctg cagctgaata gcgtgacacc   900
agaggacacc gccgtgtact attgcgccag ggaggtgacc ggcgacctgg aggatgcctt   960
tgacatctgg ggccagggca atggtgac cgtgagctcc ggaggcggcg gatctggcgg  1020
aggaggaagt gggggcggcg ggagtgatat ccagatgaca cagtcccccat cctctctgag  1080 cgcctccgtg ggcgacagag tgacaatcac ctgtaggggcc tcccagacca tctggtctta  1140
```

| | | | | | |
|---|---|---|---|---|---|
| cctgaactgg | tatcagcaga | ggcccggcaa | ggcccctaat | ctgctgatct | acgcagcaag | 1200 |
| ctccctgcag | agcggagtgc | catccagatt | ctctggcagg | ggctccggca | cagacttcac | 1260 |
| cctgaccatc | tctagcctgc | aggccgagga | cttcgccacc | tactattgcc | agcagtctta | 1320 |
| tagcatcccc | cagacatttg | gccagggcac | caagctggag | atcaagtcgg | atcccggaag | 1380 |
| cggaggggga | ggcagctgcc | cctacagcaa | ccccagcctg | tgcagcggag | cggcggcag | 1440 |
| cgagctgccc | acccagggca | ccttctccaa | cgtgtccacc | aacgtgagcc | cagccaagcc | 1500 |
| caccaccacc | gcctgtcctt | attccaatcc | ttccctgtgt | gctcccacca | aaccccgc | 1560 |
| tccaaggccc | cctaccccg | caccaactat | tgcctcccag | ccactctcac | tgcggcctga | 1620 |
| ggcctgtcgg | cccgctgctg | gaggcgcagt | gcatacaagg | ggcctcgatt | tcgcctgcga | 1680 |
| tatttacatc | tgggcacccc | tcgccggcac | ctgcggggtg | cttctcctct | ccctggtgat | 1740 |
| taccctgtat | tgcagacggg | gccggaagaa | gctcctctac | atttttaagc | agcctttcat | 1800 |
| gcggccagtg | cagacaaccc | aagaggagga | tgggtgttcc | tgcagattcc | ctgaggaaga | 1860 |
| ggaaggcggg | tgcgagctga | gagtgaagtt | ctccaggagc | gcagatgccc | cgcctatca | 1920 |
| acagggccag | aaccagctct | acaacgagct | taacctcggg | aggcgcgaag | aatacgacgt | 1980 |
| gttggataag | agaaggggc | gggaccccga | gatggggaga | aagccccgga | ggaagaaccc | 2040 |
| tcaggagggc | ctgtacaacg | agctgcagaa | ggataagatg | gccgaggcct | actcagagat | 2100 |
| cgggatgaag | ggggagcggc | gccgcggaa | ggggcacgat | gggctctacc | aggggctgag | 2160 |
| cacagccaca | aaggacacat | acgacgcctt | gcacatgcag | gcccttccac | cccgggaata | 2220 |
| gtctagaggg | cccgtttaaa | cccgctgatc | agcctcgact | gtgccttcta | gttgccagcc | 2280 |
| atctgttgtt | tgcccctccc | ccgtgccttc | cttgaccctg | gaaggtgcca | ctcccactgt | 2340 |
| cctttcctaa | taaatgagg | aaattgcatc | gcattgtctg | agtaggtgtc | attctattct | 2400 |
| gggggtggg | gtgggcagg | acagcaaggg | ggaggattgg | gaagacaata | gcaggcatgc | 2460 |
| tggggatgcg | gtgggctcta | tgactagtgg | cgaattcccg | tgtaccagct | gagagactct | 2520 |
| aaatccagtg | acaagtctgt | ctgcctattc | accgattttg | attctcaaac | aaatgtgtca | 2580 |
| caaagtaagg | attctgatgt | gtatatcaca | gacaaaactg | tgctagacat | gaggtctatg | 2640 |
| gacttcaaga | gcaacagtgc | tgtggcctgg | agcaacaaat | ctgactttgc | atgtgcaaac | 2700 |
| gccttcaaca | acagcattat | tccagaagac | accttcttcc | ccagcccagg | taagggcagc | 2760 |
| tttggtgcct | tcgcaggctg | tttccttgct | tcaggaatgg | ccaggttctg | cccagagctc | 2820 |
| tggtcaatga | tgtctaaaac | tcctctgatt | ggtggtctcg | gccttatcca | ttgccaccaa | 2880 |
| aaccctcttt | ttactaa | | | | | 2897 |

<210> SEQ ID NO 32
<211> LENGTH: 2688
<212> TYPE: DNA
<213> ORGANISM: artificial sequence
<220> FEATURE:
<223> OTHER INFORMATION: Matrice CD25 locus_IL15_2A_sIL15Ra pCLS30519

<400> SEQUENCE: 32

| | | | | | |
|---|---|---|---|---|---|
| gtttattatt | cctgttccac | agctattgtc | tgccatataa | aaacttaggc | caggcacagt | 60 |
| ggctcacacc | tgtaatccca | gcactttgga | aggccgaggc | aggcagatca | caaggtcagg | 120 |
| agttcgagac | cagcctggcc | aacatagcaa | aaccccatct | ctactaaaaa | tacaaaaatt | 180 |
| agccaggcat | ggtggcgtgt | gcactggttt | agagtgagga | ccacttttt | ttggtgccgt | 240 |
| gttacacata | tgaccgtgac | tttgttacac | cactacagga | ggaagagtag | aagaacaatc | 300 |

```
ggttctggcg tgaaacagac tttgaatttt gaccttctca agttggcggg agacgtggag    360
tccaacccag ggcccggtac cgggtccgcc accatggact ggacctggat tctgttcctc    420
gtggctgctg ctacaagagt gcacagcggc attcatgtct tcattttggg ctgtttcagt    480
gcagggcttc ctaaaacaga agccaactgg gtgaatgtaa taagtgattt gaaaaaaatt    540
gaagatctta ttcaatctat gcatattgat gctactttat atacggaaag tgatgttcac    600
cccagttgca aagtaacagc aatgaagtgc tttctcttgg agttacaagt tatttcactt    660
gagtccggag atgcaagtat tcatgataca gtagaaaatc tgatcatcct agcaaacaac    720
agtttgtctt ctaatgggaa tgtaacagaa tctggatgca agaatgtgag ggaactggag    780
gaaaaaaata ttaaagaatt tttgcagagt tttgtacata ttgtccaaat gttcatcaac    840
acttctggaa gcggagctac taacttcagc ctgctgaagc aggctggaga cgtggaggag    900
aaccctggac ctgggaccgg ctctgcaacc atggattgga cgtggatcct gtttctcgtg    960
gcagctgcca aagagttca cagtatcacg tgccctcccc ccatgtccgt ggaacacgca   1020
gacatctggg tcaagagcta cagcttgtac tccagggagc ggtacatttg taactctggt   1080
ttcaagcgta aagccggcac gtccagcctg acggagtgcg tgttgaacaa ggccacgaat   1140
gtcgcccact ggacaacccc cagtctcaaa tgcattagag accctgccct ggttcaccaa   1200
aggccagcgc caccctccac agtaacgacg gcagggtgga ccccacagcc agagagcctc   1260
tcccttctg gaaaagagcc cgcagcttca tctcccagct caaacaacac agcggccaca   1320
acagcagcta ttgtcccggg ctcccagctg atgccttcaa aatcaccttc cacaggaacc   1380
acagagataa gcagtcatga gtcctcccac ggcaccccct ctcagacaac agccaagaac   1440
tgggaactca cagcatccgc ctcccaccag ccgccaggtg tgtatccaca gggccacagc   1500
gacaccactg agggcagagg cagcctgctg acctgcggcg acgtcgagga aaccccgggg   1560
cccatggggg caggtgccac cggccgcgcc atggacgggc gcgcctgct gctgttgctg   1620
cttctggggg tgtcccttgg aggtgccaag gaggcatgcc ccacaggcct gtacacacac   1680
agcggtgagt gctgcaaagc ctgcaacctg ggcgagggtg tggcccagcc ttgtggagcc   1740
aaccagaccg tgtgtgagcc ctgcctggac agcgtgacgt tctccgacgt ggtgagcgcg   1800
accgagccgt gcaagccgtg caccgagtgc gtgggctcc agagcatgtc ggcgccgtgc   1860
gtggaggcca tgacgccgt gtgccgctgc gcctacggct actaccagga tgagacgact   1920
gggcgctgcg aggcgtgccg cgtgtgcgag gcgggctcgg gcctcgtgtt ctcctgccag   1980
gacaagcaga acaccgtgtg cgaggagtgc cccgacggca cgtattccga cgaggccaac   2040
cacgtggacc cgtgcctgcc ctgcaccgtg tgcgaggaca ccgagcgcca gctccgcgag   2100
tgcacacgct gggccgacgc cgagtgcgag gagatccctg gccgttggat tacacggtcc   2160
acaccccag agggctcgga cagcacagcc cccagcaccc aggagcctga ggcacctcca   2220
gaacaagacc tcatagccag cacggtggca ggtgtggtga ccacagtgat gggcagctcc   2280
cagcccgtgg tgacccgagg caccaccgac aacctcatcc ctgtctattg ctccatcctg   2340
gctgctgtgg ttgtgggtct tgtggcctac atagccttca gaggtgaaa aaccaaaaga   2400
acaagaattt cttggtaaga agccgggaac agacaacaga agtcatgaag cccaagtgaa   2460
atcaaaggtg ctaaatggtc gcccaggaga catccgttgt gcttgcctgc gttttggaag   2520
ctctgaagtc acatcacagg acacggggca gtggcaacct tgtctctatg ccagctcagt   2580
cccatcagag agcgagcgct acccacttct aaatagcaat ttcgccgttg aagaggaagg   2640
```
gcaaaaccac tagaactctc catcttattt tcatgtatat gtgttcat         2688

<210> SEQ ID NO 33
<211> LENGTH: 2964
<212> TYPE: DNA
<213> ORGANISM: artificial sequence
<220> FEATURE:
<223> OTHER INFORMATION: Matrice PD1 locus_IL15_2A_sIL15Ra pCLS30513

<400> SEQUENCE: 33

| | |
|---|---|
| gactccccag acaggccctg gaaccccccc accttctccc cagccctgct cgtggtgacc | 60 |
| gaagggggaca cgccaccctt cacctgcagc ttctccaaca catcggagag cttcgtgcta | 120 |
| aactggtacc gcatgagccc cagcaaccag acggacaagc tggccgcctt ccccgaggac | 180 |
| cgcagccagc ccggccagga ctgccgcttc cgtgtcacac aactgcccaa cgggcgtgac | 240 |
| ttccacatga gcgtggtcag ggcccggcgc aatgacagcg gcacctacct ctgtggggcc | 300 |
| ggttctggcg tgaaacagac tttgaatttt gaccttctca gttggcggg agacgtggag | 360 |
| tccaacccag ggcccggtac cgggtccgcc accatggact ggacctggat tctgttcctc | 420 |
| gtggctgctg ctacaagagt gcacagcggc attcatgtct tcattttggg ctgtttcagt | 480 |
| gcagggcttc ctaaaacaga agccaactgg gtgaatgtaa taagtgattt gaaaaaaatt | 540 |
| gaagatctta ttcaatctat gcatattgat gctactttat atacggaaag tgatgttcac | 600 |
| cccagttgca aagtaacagc aatgaagtgc tttctcttgg agttacaagt tatttcacttt | 660 |
| gagtccggag atgcaagtat tcatgataca gtagaaaatc tgatcatcct agcaaacaac | 720 |
| agtttgtctt ctaatgggaa tgtaacagaa tctggatgca aagaatgtga ggaactggag | 780 |
| gaaaaaaata ttaaagaatt tttgcagagt tttgtacata ttgtccaaat gttcatcaac | 840 |
| acttctggaa gcgagctac taacttcagc ctgctgaagc aggctggaga cgtggaggag | 900 |
| aaccctggac ctgggaccgg ctctgcaacc atggattgga cgtggatcct gtttctcgtg | 960 |
| gcagctgcca caagagttca cagtatcacg tgccctcccc ccatgtccgt ggaacacgca | 1020 |
| gacatctggg tcaagagcta cagcttgtac tccagggagc ggtacatttg taactctggt | 1080 |
| ttcaagcgta aagccggcac gtccagcctg acggagtgcg tgttgaacaa ggccacgaat | 1140 |
| gtcgcccact ggacaacccc cagtctcaaa tgcattagag accctgccct ggttcaccaa | 1200 |
| aggccagcgc caccctccac agtaacgacg gcagggtga ccccacagcc agagagcctc | 1260 |
| tccccttctg gaaaagagcc cgcagcttca tctcccagct caaacaacac agcggccaca | 1320 |
| acagcagcta ttgtcccggg ctcccagctg atgccttcaa aatcaccttc cacaggaacc | 1380 |
| acagagataa gcagtcatga gtcctcccac ggcaccccct ctcagacaac agccaagaac | 1440 |
| tgggaactca cagcatccgc ctcccaccag ccgccaggtg tgtatccaca gggcacagc | 1500 |
| gacaccactg agggcagagg cagcctgctg acctgcggcg acgtcgagga aaccccggg | 1560 |
| cccatggggg caggtgccac cggccgcgcc atggacgggc cgcgcctgct gctgttgctg | 1620 |
| cttctggggg tgtcccttgg aggtgccaag gaggcatgcc ccacaggcct gtacacacac | 1680 |
| agcggtgagt gctgcaaagc ctgcaacctg ggcgagggtg tggcccagcc ttgtggagcc | 1740 |
| aaccagaccg tgtgtgagcc ctgcctggac agcgtgacgt tctccgacgt ggtgagcgcg | 1800 |
| accgagccgt gcaagccgtg caccgagtgc gtggggctcc agagcatgtc ggcgccgtgc | 1860 |
| gtggaggcca tgacgccgt gtgccgctgc gcctacggct actaccagga tgagacgact | 1920 |
| gggcgctgcg aggcgtgccg cgtgtgcgag gcgggctcgg gcctcgtgtt ctcctgccag | 1980 |
| gacaagcaga acaccgtgtg cgaggagtgc cccgacggca cgtattccga cgaggccaac | 2040 |

```
cacgtggacc cgtgcctgcc ctgcaccgtg tgcgaggaca ccgagcgcca gctccgcgag    2100
tgcacacgct gggccgacgc cgagtgcgag gagatccctg ccgttggat  tacacggtcc    2160 acaccccag  agggctcgga cagcacagcc cccagcaccc aggagcctga ggcacctcca    2220
gaacaagacc tcatagccag cacggtggca ggtgtggtga ccacagtgat gggcagctcc    2280
cagcccgtgg tgacccgagg caccaccgac aacctcatcc ctgtctattg ctccatcctg    2340
gctgctgtgg ttgtgggtct tgtggcctac atagccttca gaggtgatc  tagagggccc    2400 gtttaaaccc gctgatcagc ctcgactgtg ccttctagtt gccagccatc tgttgtttgc    2460
ccctcccccg tgccttcctt gaccctggaa ggtgccactc ccactgtcct ttcctaataa    2520
aatgaggaaa ttgcatcgca ttgtctgagt aggtgtcatt ctattctggg gggtggggtg    2580
gggcaggaca gcaaggggga ggattgggaa gacaatagca ggcatgctgg ggatgcggtg    2640
ggctctatga ctagtggcga attcggcgca gatcaaagag agcctgcggg cagagctcag    2700
ggtgacaggt gcggcctcgg aggccccggg gcagggg tga gctgagccgg tcctggggtg    2760 ggtgtccct  cctgcacagg atcaggagct ccagggtcgt agggcaggga ccccccagct    2820
ccagtccagg gctctgtcct gcacctgggg aatggtgacc ggcatctctg tcctctagct    2880
ctggaagcac cccagcccct ctagtctgcc ctcacccctg accctgaccc tccaccctga    2940
ccccgtccta accctgacc  tttg                                          2964
```

<210> SEQ ID NO 34
<211> LENGTH: 3363
<212> TYPE: DNA
<213> ORGANISM: artificial sequence
<220> FEATURE:
<223> OTHER INFORMATION: Matrice CD25 locus_IL12a_2A_IL12b pCLS30520

<400> SEQUENCE: 34

```
gtttattatt cctgttccac agctattgtc tgccatataa aaactaggc  caggcacagt      60 ggctcacacc tgtaatccca gcactttgga aggccgaggc aggcagatca caaggtcagg     120
agttcgagac cagcctggcc aacatagcaa aaccccatct ctactaaaaa tacaaaaatt     180
agccaggcat ggtggcgtgt gcactggttt agagtgagga ccacatttttt ttggtgccgt    240 gttacacata tgaccgtgac tttgttacac cactacagga ggaagagtag aagaacaatc    300
ggttctggcg tgaaacagac tttgaatttt gaccttctca agttggcggg agacgtggag    360
tccaacccag ggcccatgtg gcccctgg   tcagcctccc agccaccgcc ctcacctgcc   420
gcggccacag gtctgcatcc agcggctcgc cctgtgtccc tgcagtgccg gctcagcatg    480
tgtccagcgc gcagcctcct ccttgtggct accctggtcc tcctggacca cctcagtttg    540
gccagaaacc tccccgtggc cactccgac  ccaggaatgt tcccatgcct tcaccactcc    600
caaaacctgc tgagggccgt cagcaacatg ctccagaagg ccagacaaac tctagaattt    660
tacccttgca cttctgaaga gattgatcat gaagatatca caaagataa aaccagcaca    720 gtggaggcct gtttaccatt ggaattaacc aagaatgaga gttgcctaaa ttccagagag    780
acctctttca taactaatgg gagttgcctg gcctccagaa agacctcttt tatgatggcc    840
ctgtgcctta gtagtattta tgaagacttg aagatgtacc aggtggagtt caagaccatg    900
aatgcaaagc ttctgatgga tcctaagagg cagatctttc tagatcaaaa catgctggca    960
gttattgatg agctgatgca ggccctgaat ttcaacagtg agactgtgcc acaaaaatcc    1020
tcccttgaag aaccggattt ttataaaact aaaatcaagc tctgcatact tcttcatgct    1080
```

```
ttcagaattc gggcagtgac tattgataga gtgatgagct atctgaatgc ttccggaagc    1140
ggagctacta acttcagcct gctgaagcag gctggagacg tggaggagaa ccctggacct    1200
atgtgtcacc agcagttggt catctcttgg ttttccctgg tttttctggc atctcccctc    1260
gtggccatat gggaactgaa gaaagatgtt tatgtcgtag aattggattg gtatccggat    1320
gcccctggag aaatggtggt cctcacctgt gacacccctg aagaagatgg tatcacctgg    1380
accttggacc agagcagtga ggtcttaggc tctggcaaaa ccctgaccat ccaagtcaaa    1440
gagtttggag atgctggcca gtacacctgt cacaaaggag gcgaggttct aagccattcg    1500
ctcctgctgc ttcacaaaaa ggaagatgga atttggtcca ctgatatttt aaaggaccag    1560
aaagaaccca aaaataagac ctttctaaga tgcgaggcca agaattattc tggacgtttc    1620
acctgctggt ggctgacgac aatcagtact gatttgacat tcagtgtcaa agcagcaga    1680 ggctcttctg accccaagg ggtgacgtgc ggagctgcta cactctctgc agagagagtc    1740
agaggggaca caaggagta tgagtactca gtggagtgcc aggaggacag tgcctgccca    1800
gctgctgagg agagtctgcc cattgaggtc atggtggatg ccgttcacaa gctcaagtat    1860
gaaaactaca ccagcagctt cttcatcagg gacatcatca aacctgaccc acccaagaac    1920
ttgcagctga agccattaaa gaattctcgg caggtggagg tcagctggga gtaccctgac    1980
acctggagta ctccacattc ctacttctcc ctgacattct gcgttcaggt ccagggcaag    2040
agcaagagag aaaagaaaga tagagtcttc acggacaaga cctcagccac ggtcatctgc    2100
cgcaaaaatg ccagcattag cgtgcgggcc caggaccgct actatagctc atcttggagc    2160
gaatgggcat ctgtgccctg cagtgagggc agaggcagcc tgctgacctg cggcgacgtc    2220
gaggagaacc ccgggcccat gggggcaggt gccaccggcc gcgccatgga cgggccgcgc    2280
ctgctgctgt tgctgcttct gggggtgtcc cttggaggtg ccaaggaggc atgccccaca    2340
ggcctgtaca cacacagcgg tgagtgctgc aaagcctgca acctgggcga gggtgtggcc    2400
cagccttgtg gagccaacca gaccgtgtgt gagccctgcc tggacagcgt gacgttctcc    2460
gacgtggtga gcgcgaccga gccgtgcaag ccgtgcaccg agtgcgtggg gctccagagc    2520 atgtcgcgc cgtgcgtgga ggccgatgac gccgtgtgcc gctgcgccta cggctactac    2580
caggatgaga cgactgggcg ctgcgaggcg tgccgcgtgt gcgaggcggg ctcgggcctc    2640
gtgttctcct gccaggacaa gcagaacacc gtgtgcgagg agtgccccga cggcacgtat    2700
tccgacgagg ccaaccacgt ggacccgtgc ctgccctgca ccgtgtgcga ggacaccgag    2760
cgccagctcc gcgagtgcac acgctgggcc gacgccgagt gcgaggagat ccctggccgt    2820
tggattacac ggtccacacc cccagagggc tcggacagca cagcccccag cacccaggag    2880
cctgaggcac ctccagaaca agacctcata gccagcacgg tggcaggtgt ggtgaccaca    2940
gtgatgggca gctcccagcc cgtggtgacc cgaggcacca ccgacaacct catccctgtc    3000
tattgctcca tcctggctgc tgtggttgtg ggtcttgtgg cctacatagc cttcaagagg    3060
tgaaaaacca aagaacaag aatttcttgg taagaagccg gaacagaca acagaagtca    3120 tgaagcccaa gtgaaatcaa aggtgctaaa tggtcgccca ggagacatcc gttgtgcttg    3180
cctgcgtttt ggaagctctg aagtcacatc acaggacacg gggcagtggc aaccttgtct    3240
ctatgccagc tcagtcccat cagagagcga gcgctaccca cttctaaata gcaatttcgc    3300
cgttgaagag aagggcaaa accactagaa ctctccatct tatttcatg tatatgtgtt    3360 cat                                                                 3363
```

```
<210> SEQ ID NO 35
<211> LENGTH: 3639
<212> TYPE: DNA
<213> ORGANISM: artificial sequence
<220> FEATURE:
<223> OTHER INFORMATION: Matrice PD1 locus_IL12a_2A_IL12b pCLS30511

<400> SEQUENCE: 35
gactccccag acaggccctg aaccccccc accttctccc cagccctgct cgtggtgacc      60 gaagggaca acgccaccttt cacctgcagc ttctccaaca catcggagag cttcgtgcta    120
aactggtacc gcatgagccc cagcaaccag acggacaagc tggccgcctt ccccgaggac    180
cgcagccagc ccggccagga ctgccgcttc cgtgtcacac aactgcccaa cgggcgtgac    240
ttccacatga gcgtggtcag ggcccggcgc aatgacagcg cacctacct ctgtggggcc     300 ggttctggcg tgaaacagac tttgaatttt gaccttctca gttggcggg agacgtggag     360 tccaacccag ggcccatgtg gcccctggg tcagcctccc agccaccgcc ctcacctgcc     420
gcggccacag gtctgcatcc agcggctcgc cctgtgtccc tgcagtgccg gctcagcatg    480
tgtccagcgc gcagcctcct ccttgtggct accctggtcc tcctggacca cctcagtttg    540
gccagaaacc tccccgtggc cactccagac ccaggaatgt tcccatgcct tcaccactcc    600
caaaacctgc tgagggccgt cagcaacatg ctccagaagg ccagacaaac tctagaattt    660 taccccttgca cttctgaaga gattgatcat aagagatatca caaaagataa aaccagcaca    720
gtggaggcct gtttaccatt ggaattaacc aagaatgaga gttgcctaaa ttccagagag    780
acctctttca taactaatgg gagttgcctg gcctccagaa agacctcttt tatgatggcc    840
ctgtgcctta gtagtattta tgaagacttg aagatgtacc aggtggagtt caagaccatg    900
aatgcaaagc ttctgatgga tcctaagagg cagatctttc tagatcaaaa catgctggca    960
gttattgatg agctgatgca ggccctgaat ttcaacagtg agactgtgcc acaaaaatcc   1020
tcccttgaag aaccggattt ttataaaact aaaatcaagc tctgcatact tcttcatgct   1080
ttcagaattc gggcagtgac tattgataga gtgatgagct atctgaatgc ttccggaagc   1140
ggagctacta acttcagcct gctgaagcag gctggagacg tggaggagaa ccctggacct   1200
atgtgtcacc agcagttggt catctcttgg ttttccctgg tttttctggc atctcccctc   1260
gtggccatat gggaactgaa gaaagatgtt tatgtcgtag aattggattg gtatccggat   1320
gcccctggag aaatggtggt cctcacctgt gacacccctg aagaagatgg tatcacctgg   1380
accttggacc agagcagtga ggtcttaggc tctggcaaaa ccctgaccat ccaagtcaaa   1440
gagtttggag atgctggcca gtacacctgt cacaaaggag cgaggttct aagccattcg    1500 ctcctgctgc ttcacaaaaa ggaagatgga atttggtcca ctgatatttt aaaggaccag   1560
aaagaaccca aaaataagac ctttctaaga tgcgaggcca gaattattc tggacgtttc   1620 acctgctggt ggctgacgac aatcagtact gatttgacat tcagtgtcaa aagcagcaga   1680
ggctcttctg acccccaagg ggtgacgtgc ggagctgcta cactctctgc agagagagtc   1740
agaggggaca acaaggagta tgagtactca gtggagtgcc aggaggacag tgcctgccca   1800
gctgctgagg agagtctgcc cattgaggtc atggtggatg ccgttcacaa gctcaagtat   1860
gaaaactaca ccagcagctt cttcatcagg gacatcatca acctgaccc acccaagaac   1920 ttgcagctga agccattaaa gaattctcgg caggtggagg tcagctggga gtaccctgac   1980
acctggagta ctccacattc ctacttctcc ctgacattct gcgttcaggt ccagggcaag   2040
agcaagagag aaaagaaaga tagagtcttc acggacaaga cctcagccac ggtcatctgc   2100
```

| | | | | | |
|---|---|---|---|---|---|
| cgcaaaaatg | ccagcattag | cgtgcgggcc | caggaccgct | actatagctc | atcttggagc | 2160 |
| gaatgggcat | ctgtgccctg | cagtgagggc | agaggcagcc | tgctgacctg | cggcgacgtc | 2220 |
| gaggagaacc | ccgggcccat | ggggcaggt | gccaccggcc | gcgccatgga | cgggccgcgc | 2280 |
| ctgctgctgt | tgctgcttct | gggggtgtcc | cttggaggtg | ccaaggaggc | atgccccaca | 2340 |
| ggcctgtaca | cacacagcgg | tgagtgctgc | aaagcctgca | acctgggcga | gggtgtggcc | 2400 |
| cagccttgtg | gagccaacca | gaccgtgtgt | gagccctgcc | tggacagcgt | gacgttctcc | 2460 |
| gacgtggtga | gcgcgaccga | gccgtgcaag | ccgtgcaccg | agtgcgtggg | gctccagagc | 2520 |
| atgtcggcgc | cgtgcgtgga | ggccgatgac | gccgtgtgcc | gctgcgccta | cggctactac | 2580 |
| caggatgaga | cgactgggcg | ctgcgaggcg | tgccgcgtgt | gcgaggcggg | ctcgggcctc | 2640 |
| gtgttctcct | gccaggacaa | gcagaacacc | gtgtgcgagg | agtgcccga | cggcacgtat | 2700 |
| tccgacgagg | ccaaccacgt | ggacccgtgc | ctgccctgca | ccgtgtgcga | ggacaccgag | 2760 |
| cgccagctcc | gcgagtgcac | acgctgggcc | gacgccgagt | gcgaggagat | ccctggccgt | 2820 |
| tggattacac | ggtccacacc | cccagagggc | tcggacagca | cagcccccag | cacccaggag | 2880 |
| cctgaggcac | ctccagaaca | agacctcata | gccagcacgg | tggcaggtgt | ggtgaccaca | 2940 |
| gtgatgggca | gctcccagcc | cgtggtgacc | cgaggcacca | ccgacaacct | catccctgtc | 3000 |
| tattgctcca | tcctggctgc | tgtggttgtg | ggtcttgtgg | cctacatagc | cttcaagagg | 3060 |
| tgatctagag | ggcccgttta | aacccgctga | tcagcctcga | ctgtgccttc | tagttgccag | 3120 |
| ccatctgttg | tttgccctc | ccccgtgcct | tccttgaccc | tggaaggtgc | cactcccact | 3180 |
| gtcctttcct | aataaaatga | ggaaattgca | tcgcattgtc | tgagtaggtg | tcattctatt | 3240 |
| ctggggggtg | gggtggggca | ggacagcaag | ggggaggatt | gggaagacaa | tagcaggcat | 3300 |
| gctggggatg | cggtgggctc | tatgactagt | ggcgaattcg | cgcagatca | aagagagcct | 3360 |
| gcgggcagag | ctcagggtga | caggtgcggc | ctcggaggcc | ccggggcagg | ggtgagctga | 3420 |
| gccggtcctg | gggtgggtgt | cccctcctgc | acaggatcag | gagctccagg | gtcgtagggc | 3480 |
| agggaccccc | cagctccagt | ccagggctct | gtcctgcacc | tggggaatgg | tgaccggcat | 3540 |
| ctctgtcctc | tagctctgga | agcaccccag | cccctctagt | ctgccctcac | ccctgaccct | 3600 |
| gaccctccac | cctgaccccg | tcctaacccc | tgacctttg | | | 3639 |

<210> SEQ ID NO 36
<211> LENGTH: 3017
<212> TYPE: DNA
<213> ORGANISM: artificial sequence
<220> FEATURE:
<223> OTHER INFORMATION: Inserted matrice TRAC locus_CubiCAR CD22 (60
      nucleotides upstream and downstream)

<400> SEQUENCE: 36

| | | | | | |
|---|---|---|---|---|---|
| atgagatcat | gtcctaaccc | tgatcctctt | gtcccacaga | tatccagaac | cctgaccctg | 60 |
| ttgctgggcc | tttttcccat | gcctgccttt | actctgccag | agttatattg | ctggggtttt | 120 |
| gaagaagatc | ctattaaata | aaagaataag | cagtattatt | aagtagccct | gcatttcagg | 180 |
| tttccttgag | tggcaggcca | ggcctggccg | tgaacgttca | ctgaaatcat | ggcctcttgg | 240 |
| ccaagattga | tagcttgtgc | ctgtccctga | gtccagtcc | atcacgagca | gctggtttct | 300 |
| aagatgctat | ttcccgtata | aagcatgaga | ccgtgacttg | ccagccccac | agagccccgc | 360 |
| ccttgtccat | cactggcatc | tggactccag | cctgggttgg | ggcaaagagg | gaaatgagat | 420 |
| catgtcctaa | ccctgatcct | cttgtcccac | agatatccag | taccctacg | acgtgcccga | 480 |

```
ctacgcctcc ggtgagggca gaggaagtct tctaacatgc ggtgacgtgg aggagaatcc     540
gggcccggga tccgctctgc ccgtcaccgc tctgctgctg ccactggcac tgctgctgca     600
cgctgctagg cccggagggg gaggcagctg ccctacagc aacccagcc tgtgcagcgg       660
aggcggcggc agcggcggag ggggtagcca ggtgcagctg cagcagagcg ccctggcct      720
ggtgaagcca agccagacac tgtccctgac ctgcgccatc agcggcgatt ccgtgagctc     780
caactccgcc gcctggaatt ggatcaggca gtccccttct cggggcctgg agtggctggg     840
aaggacatac tatcggtcta agtggtacaa cgattatgcc gtgtctgtga agagcagaat    900
cacaatcaac cctgacacct ccaagaatca gttctctctg cagctgaata gcgtgacacc    960
agaggacacc gccgtgtact attgcgccag ggaggtgacc ggcgacctgg aggatgcctt   1020
tgacatctgg ggccagggca aatggtgac cgtgagctcc ggaggcggcg gatcggcgg     1080
aggaggaagt ggggcggcg ggagtgatat ccagatgaca cagtccccat cctctctgag    1140
cgcctccgtg ggcgacagag tgacaatcac ctgtagggcc tcccagacca tctggtctta   1200
cctgaactgg tatcagcaga ggcccggcaa ggccctaat ctgctgatct acgcagcaag    1260
ctccctgcag agcggagtgc catccagatt ctctggcagg ggctccggca cagacttcac   1320
cctgaccatc tctagcctgc aggccgagga cttcgccacc tactattgcc agcagtctta   1380
tagcatcccc cagacatttg ccagggcac caagctggag atcaagtcgg atcccggaag    1440
cggagggga ggcagctgcc cctacagcaa ccccagcctg tgcagcggag cggcggcag     1500
cgagctgccc acccagggca ccttctccaa cgtgtccacc aacgtgagcc agccaagcc     1560
caccaccacc gcctgtcctt attccaatcc ttccctgtgt gctcccacca caaccccgc    1620
tccaaggccc cctaccccg caccaactat gcctcccag ccactctcac tgcggcctga    1680
ggcctgtcgg cccgctgctg gaggcgcagt gcatacaagg ggcctcgatt cgcctgcga    1740
tatttacatc tgggcacccc tcgccggcac ctgcggggtg cttctcctct ccctggtgat   1800
taccctgtat tgcagacggg gccggaagaa gctcctctac attttaagc agcctttcat    1860
gcggccagtg cagacaaccc aagaggagga tgggtgttcc tgcagattcc ctgaggaaga   1920
ggaaggcggg tgcgagctga gagtgaagtt ctccaggagc gcagatgccc ccgcctatca   1980
acagggccag aaccagctct acaacgagct taacctcggg aggcgcgaag aatacgacgt   2040
gttggataag agaaggggc gggaccccga gatgggagga aagccccgga ggaagaaccc   2100
tcaggagggc ctgtacaacg agctgcagaa ggataagatg gccgaggcct actcagagat   2160
cgggatgaag ggggagcggc gccgcggaa ggggcacgat gggctctacc aggggctgag   2220
cacagccaca aaggacacat cgacgccttt gcacatgcag gcccttccac cccgggaata   2280
gtctagaggg cccgtttaaa cccgctgatc agcctcgact gtgccttcta gttgccagcc   2340
atctgttgtt tgcccctccc ccgtgccttc cttgaccctg gaaggtgcca ctcccactgt   2400
cctttcctaa taaaatgagg aaattgcatc gcattgtctg agtaggtgtc attctattct   2460
ggggggtggg gtggggcagg acagcaaggg ggaggattgg gaagacaata gcaggcatgc   2520
tggggatgcg gtgggctcta tgactagtgg cgaattcccg tgtaccagct gagagactct   2580
aaatccagtg acaagtctgt ctgcctattc accgattttg attctcaaac aaatgtgtca   2640
caaagtaagg attctgatgt gtatatcaca gacaaaactg tgctagacat gaggtctatg   2700
gacttcaaga gcaacagtgc tgtggcctgg agcaacaaat ctgactttgc atgtgcaaac   2760
gccttcaaca acagcattat tccagaagac accttcttcc ccagcccagg taagggcagc   2820
tttggtgcct tcgcaggctg tttccttgct tcaggaatgg ccaggttctg cccagagctc   2880
```

```
tggtcaatga tgtctaaaac tcctctgatt ggtggtctcg gccttatcca ttgccaccaa    2940
aaccctcttt ttactaagaa acagtgagcc ttgttctggc agtccagaga atgacacggg    3000
aaaaaagcag atgaaga                                                  3017

<210> SEQ ID NO 37
<211> LENGTH: 2808
<212> TYPE: DNA
<213> ORGANISM: artificial sequence
<220> FEATURE:
<223> OTHER INFORMATION: Inserted matrice CD25 locus_IL15_2A_sIL15Ra (60
      nucleotides upstream and downstream)

<400> SEQUENCE: 37
agtgctggct agaaaccaag tgctttactg catgcacatc atttagcaca gttagttgct      60
gtttattatt cctgttccac agctattgtc tgccatataa aaacttaggc caggcacagt     120
ggctcacacc tgtaatccca gcactttgga aggccgaggc aggcagatca caaggtcagg     180
agttcgagac cagcctggcc aacatagcaa accccatctc tactaaaaaa tacaaaaatt     240
agccaggcat ggtggcgtgt gcactggttt agagtgagga ccacattttt ttggtgccgt     300
gttacacata tgaccgtgac tttgttacac cactacagga ggaagagtag aagaacaatc     360
ggttctggcg tgaaacagac tttgaatttt gaccttctca gttggcggg agacgtggag      420 tccaacccag ggcccggtac cgggtccgcc accatggact ggacctggat tctgttcctc     480
gtggctgctg ctacaagagt gcacagcggc attcatgtct tcattttggg ctgtttcagt     540
gcagggcttc ctaaaacaga agccaactgg gtgaatgtaa taagtgattt gaaaaaaatt     600
gaagatctta ttcaatctat gcatattgat gctactttat atacggaaag tgatgttcac     660
cccagttgca aagtaacagc aatgaagtgc tttctcttgg agttacaagt tatttcactt     720
gagtccggag atgcaagtat tcatgataca gtagaaaatc tgatcatcct agcaaacaac     780
agtttgtctt ctaatgggaa tgtaacagaa tctggatgca agaatgtga ggaactggag      840 gaaaaaaata ttaagaaatt tttgcagagt tttgtacata ttgtccaaat gttcatcaac     900
acttctggaa gcggagctac taacttcagc ctgctgaagc aggctggaga cgtggaggag     960
aaccctggac ctgggaccgg ctctgcaacc atggattgga cgtggatcct gtttctcgtg    1020
gcagctgcca aagagttca gtatcacg tgccctcccc ccatgtccgt ggaacacgca       1080
gacatctggg tcaagagcta cagcttgtac tccagggagc ggtacatttg taactctggt    1140
ttcaagcgta aagccggcac gtccagcctg acggagtgcg tgttgaacaa ggccacgaat    1200
gtcgcccact ggacaacccc cagtctcaaa tgcattagag accctgccct ggttcaccaa    1260
aggccagcgc caccctccac agtaacgacg gcagggtga ccccacagcc agagagcctc     1320
tccccttctg gaaaagagcc cgcagcttca tctcccagct caaacaacac agcggccaca    1380
acagcagcta ttgtcccggg ctcccagctg atgccttcaa aatcaccttc cacaggaacc    1440
acagagataa gcagtcatga gtcctcccac ggcaccccct ctcagacaac agccaagaac    1500
tgggaactca cagcatccgc ctcccaccag ccgccaggtg tgtatccaca gggccacagc    1560
gacaccactg agggcagagg cagcctgctg acctgcggcg acgtcgagga accccggg     1620 cccatggggg caggtgccac cggccgcgcc atggacgggc gcgcctgct gctgttgctg    1680 cttctggggg tgtcccttgg aggtgccaag gaggcatgcc ccacaggcct gtacacacac    1740
agcggtgagt gctgcaaagc ctgcaacctg ggcgagggtg tggcccagcc ttgtggagcc    1800
aaccagaccg tgtgtgagcc ctgcctggac agcgtgacgt tctccgacgt ggtgagcgcg    1860
```

```
accgagccgt gcaagccgtg caccgagtgc gtggggctcc agagcatgtc ggcgccgtgc    1920
gtggaggccg atgacgccgt gtgccgctgc gcctacggct actaccagga tgagacgact    1980
gggcgctgcg aggcgtgccg cgtgtgcgag gcgggctcgg gcctcgtgtt ctcctgccag    2040
gacaagcaga acaccgtgtg cgaggagtgc cccgacggca cgtattccga cgaggccaac    2100
cacgtggacc cgtgcctgcc ctgcaccgtg tgcgaggaca ccgagcgcca gctccgcgag    2160
tgcacacgct gggccgacgc cgagtgcgag gagatccctg ccgttggat acacggtcc      2220 acacccccag agggctcgga cagcacagcc cccagcaccc aggagcctga ggcacctcca    2280
gaacaagacc tcatagccag cacggtggca ggtgtggtga ccacagtgat gggcagctcc    2340
cagcccgtgg tgacccgagg caccaccgac aacctcatcc ctgtctattg ctccatcctg    2400
gctgctgtgg ttgtgggtct tgtggcctac atagccttca gaggtgaaa aaccaaaaga    2460 acaagaattt cttggtaaga agccgggaac agacaacaga agtcatgaag cccaagtgaa    2520
atcaaaggtg ctaaatggtc gcccaggaga catccgttgt gcttgcctgc gttttggaag    2580
ctctgaagtc acatcacagg acacggggca gtggcaacct tgtctctatg ccagctcagt    2640
cccatcagag agcgagcgct acccacttct aaatagcaat ttcgccgttg aagaggaagg    2700
gcaaaaccac tagaactctc catcttattt tcatgtatat gtgttcatta aagcatgaat    2760
ggtatggaac tctctccacc ctatatgtag tataaagaaa agtaggtt               2808

<210> SEQ ID NO 38
<211> LENGTH: 3084
<212> TYPE: DNA
<213> ORGANISM: artificial sequence
<220> FEATURE:
<223> OTHER INFORMATION: Inserted matrice PD1 locus_IL15_2A_sIL15Ra (60
      nucleotides upstream and downstream)

<400> SEQUENCE: 38
ggtggccggg gaggctttgt ggggccaccc agcccttcc tcacctctct ccatctctca       60
gactccccag acaggccctg aaccccccc accttctccc cagccctgct cgtggtgacc      120 gaagggggaca cgccaccctt cacctgcagc ttctccaaca tcggagag cttcgtgcta     180 aactggtacc gcatgagccc cagcaaccag acggacaagc tggccgcctt ccccgaggac    240
cgcagccagc ccgccagga ctgccgcttc cgtgtcacac aactgcccaa cgggcgtgac     300
ttccacatga gcgtggtcag ggcccggcgc aatgacagcg gcacctacct ctgtggggcc    360
ggttctggcg tgaaacagac tttgaattt gaccttctca gttggcggg agacgtggag      420 tccaacccag ggcccggtac cgggtccgcc accatggact ggacctggat tctgttcctc    480
gtggctgctg ctacaagagt gcacagcggc attcatgtct tcattttggg ctgtttcagt    540
gcagggcttc ctaaaacaga agccaactgg gtgaatgtaa taagtgattt gaaaaaaatt   600
gaagatctta ttcaatctat gcatattgat gctactttat atacggaaag tgatgttcac    660
cccagttgca aagtaacagc aatgaagtgc tttctcttgg agttacaagt tatttcactt   720
gagtccggag atgcaagtat tcatgataca gtagaaaatc tgatcatcct agcaaacaac    780 agttgtctt ctaatgggaa tgtaacagaa tctggatgca agaatgtga ggaactggag       840 gaaaaaaata ttaagaatt tttgcagagt tttgtacata ttgtccaaat gttcatcaac     900
acttctggaa gcggagctac taacttcagc ctgctgaagc aggctggaga cgtggaggag    960
aaccctggac ctgggaccgg ctctgcaacc atggattgga cgtggatcct gtttctcgtg   1020
gcagctgcca aagagttca gtatcacg tgccctcccc ccatgtccgt ggaacacgca     1080
```

```
gacatctggg tcaagagcta cagcttgtac tccagggagc ggtacatttg taactctggt    1140
ttcaagcgta aagccggcac gtccagcctg acggagtgcg tgttgaacaa ggccacgaat    1200
gtcgcccact ggacaacccc cagtctcaaa tgcattagag accctgccct ggttcaccaa    1260
aggccagcgc caccctccac agtaacgacg gcaggggtga ccccacagcc agagagcctc    1320
tccccttctg gaaaagagcc cgcagcttca tctcccagct caaacaacac agcggccaca    1380
acagcagcta ttgtcccggg ctcccagctg atgccttcaa aatcaccttc cacaggaacc    1440
acagagataa gcagtcatga gtcctcccac ggcacccccct ctcagacaac agccaagaac    1500
tgggaactca cagcatccgc ctcccaccag ccgccaggtg tgtatccaca gggccacagc    1560
gacaccactg agggcagagg cagcctgctg acctgcggcg acgtcgagga aacccgggg    1620 cccatggggg caggtccac cggccgcgcc atggacgggc cgcgcctgct gctgttgctg    1680
cttctggggg tgtcccttgg aggtgccaag gaggcatgcc ccacaggcct gtacacacac    1740
agcggtgagt gctgcaaagc ctgcaacctg ggcgagggtg tggcccagcc ttgtggagcc    1800
aaccagaccg tgtgtgagcc ctgcctggac agcgtgacgt tctccgacgt ggtgagcgcg    1860
accgagccgt gcaagccgtg caccgagtgc gtggggctcc agagcatgtc ggcgccgtgc    1920
gtggaggccg atgacgccgt gtgccgctgc gcctacggct actaccagga tgagacgact    1980
gggcgctgcg aggcgtgccg cgtgtgcgag gcgggctcgg gcctcgtgtt ctccgccag    2040 gacaagcaga acaccgtgtg cgaggagtgc cccgacggca cgtattccga cgaggccaac    2100
cacgtggacc cgtgcctgcc ctgcaccgtg tgcgaggaca ccgagcgcca gctccgcgag    2160
tgcacacgct gggccgacgc cgagtgcgag gagatccctg gccgttggat tacacggtcc    2220 acaccccag agggctcgga cagcacagcc cccagcaccc aggagcctga ggcacctcca    2280
gaacaagacc tcatagccag cacggtggca ggtgtggtga ccacagtgat gggcagctcc    2340
cagcccgtgg tgacccgagg caccaccgac aacctcatcc ctgtctattg ctccatcctg    2400
gctgctgtgg ttgtgggtct tgtggcctac atagccttca gaggtgatc tagagggccc    2460 gtttaaaccc gctgatcagc ctcgactgtg ccttctagtt gccagccatc tgttgtttgc    2520 ccctccccg tgccttcctt gaccctggaa ggtgccactc ccactgtcct ttcctaataa    2580
aatgaggaaa ttgcatcgca ttgtctgagt aggtgtcatt ctattctggg gggtggggtg    2640
gggcaggaca gcaaggggga ggattgggaa gacaatagca ggcatgctgg ggatgcggtg    2700
ggctctatga ctagtggcga attcggcgca gatcaaagag agcctgcggg cagagctcag    2760
ggtgacaggt gcggcctcgg aggccccggg gcaggggtga gctgagccgg tcctggggtg    2820
ggtgtcccct cctgcacagg atcaggagct ccagggtcgt agggcaggga ccccccagct    2880
ccagtccagg gctctgtcct gcacctgggg aatggtgacc ggcatctctg tcctctagct    2940
ctggaagcac cccagcccct ctagtctgcc ctcaccctg accctgaccc tccaccctga    3000
ccccgtccta accctgacc tttgtgcccct tccagagaga agggcagaag tgcccacagc    3060
ccaccccagc ccctcaccca ggcc                                          3084
```

<210> SEQ ID NO 39
<211> LENGTH: 3475
<212> TYPE: DNA
<213> ORGANISM: artificial sequence
<220> FEATURE:
<223> OTHER INFORMATION: Inserted matrice CD25 locus_IL12a_2A_IL12b (60 nucleotides upstream and downstream)

<400> SEQUENCE: 39

```
agtgctggct agaaaccaag tgctttactg catgcacatc atttagcaca gttagttgct      60
gtttattatt cctgttccac agctattgtc tgccatataa aaacttaggc caggcacagt     120
ggctcacacc tgtaatccca gcactttgga aggccgaggc aggcagatca caaggtcagg     180
agttcgagac cagcctggcc aacatagcaa accccatct ctactaaaaa tacaaaaatt      240
agccaggcat ggtggcgtgt gcactggttt agagtgagga ccacattttt ttggtgccgt     300
gttacacata tgaccgtgac tttgttacac cactacagga ggaagagtag aagaacaatc     360
ggttctggcg tgaaacagac tttgaatttt gaccttctca agttggcggg agacgtggag     420
tccaacccag ggcccatgtg gcccctggg tcagcctccc agccaccgcc ctcacctgcc      480
gcggccacag gtctgcatcc agcggctcgc cctgtgtccc tgcagtgccg gctcagcatg     540
tgtccagcgc gcagcctcct ccttgtggct accctggtcc tcctggacca cctcagtttg     600
gccagaaacc tccccgtggc cactccagac ccaggaatgt tcccatgcct tcaccactcc     660
caaaacctgc tgagggccgt cagcaacatg ctccagaagg ccagacaaac tctagaattt     720
taccccttgca cttctgaaga gattgatcat gaagatatca caaaagataa aaccagcaca     780
gtggaggcct gtttaccatt ggaattaacc aagaatgaga gttgcctaaa ttccagagag     840
acctctttca taactaatgg gagttgcctg gcctccagaa agacctcttt tatgatggcc     900
ctgtgcctta gtagtattta tgaagacttg aagatgtacc aggtggagtt caagaccatg     960
aatgcaaagc ttctgatgga tcctaagagg cagatctttc tagatcaaaa catgctggca    1020
gttattgatg agctgatgca ggccctgaat ttcaacagtg agactgtgcc acaaaaatcc    1080
tcccttgaag aaccggattt ttataaaact aaaatcaagc tctgcatact tcttcatgct    1140
ttcagaattc gggcagtgac tattgataga gtgatgagct atctgaatgc ttccggaagc    1200
ggagctacta acttcagcct gctgaagcag gctggagacg tggaggagaa ccctggacct    1260
atgtgtcacc agcagttggt catctcttgg ttttccctgg tttttctggc atctcccctc    1320
gtggccatat gggaactgaa gaaagatgtt tatgtcgtag aattggattg gtatccggat    1380
gcccctggag aaatggtggt cctcacctgt gacaccccctg aagaagatgg tatcacctgg    1440
accttggacc agagcagtga ggtcttaggc tctggcaaaa ccctgaccat ccaagtcaaa    1500
gagtttggag atgctggcca gtacacctgt cacaaaggag cgaggttct aagccattcg     1560
ctcctgctgc ttcacaaaaa ggaagatgga atttggtcca ctgatatttt aaaggaccag    1620
aaagaaccca aaaataagac cttttctaaga tgcgaggcca agaattattc tggacgtttc    1680
acctgctggt ggctgacgac aatcagtact gatttgacat tcagtgtcaa aagcagcaga    1740
ggctcttctg accccaagg ggtgacgtgc ggagctgcta cactctctgc agagagagtc     1800
agaggggaca caaggagta tgagtactca gtggagtgcc aggaggacag tgcctgccca    1860
gctgctgagg agagtctgcc cattgaggtc atggtggatg ccgttcacaa gctcaagtat    1920
gaaaactaca ccagcagctt cttcatcagg gacatcatca aacctgaccc acccaagaac    1980
ttgcagctga agccattaaa gaattctcgg caggtggagg tcagctggga gtaccctgac    2040
acctggagta ctccacattc ctacttctcc ctgacattct gcgttcaggt ccagggcaag    2100
agcaagagag aaaagaaaga tagagtcttc acggacaaga cctcagccac ggtcatctgc    2160
cgcaaaaatg ccagcattag cgtgcgggcc caggaccgct actatagctc atcttggagc    2220
gaatgggcat ctgtgccctg cagtgagggc agaggcagcc tgctgacctg cggcgacgtc    2280
gaggagaacc ccgggcccat gggggcaggt gccaccggcc gcgccatgga cgggccgcgc    2340
```

```
ctgctgctgt tgctgcttct gggggtgtcc cttggaggtg ccaaggaggc atgccccaca      2400
ggcctgtaca cacacagcgg tgagtgctgc aaagcctgca acctgggcga gggtgtggcc      2460
cagccttgtg gagccaacca gaccgtgtgt gagccctgcc tggacagcgt gacgttctcc      2520
gacgtggtga gcgcgaccga gccgtgcaag ccgtgcaccg agtgcgtggg gctccagagc      2580
atgtcggcgc cgtgcgtgga ggccgatgac gccgtgtgcc gctgcgccta cggctactac      2640
caggatgaga cgactgggcg ctgcgaggcg tgccgcgtgt gcgaggcggg ctcgggcctc      2700
gtgttctcct gccaggacaa gcagaacacc gtgtgcgagg agtgccccga cggcacgtat      2760
tccgacgagg ccaaccacgt ggacccgtgc ctgccctgca ccgtgtgcga ggacaccgag      2820
cgccagctcc gcgagtgcac acgctgggcc gacgccgagt gcgaggagat ccctggccgt      2880
tggattacac ggtccacacc cccagagggc tcggacagca cagcccccag cacccaggag      2940
cctgaggcac ctccagaaca agacctcata gccagcacgg tggcaggtgt ggtgaccaca      3000
gtgatgggca gctcccagcc cgtggtgacc cgaggcacca ccgacaacct catccctgtc      3060
tattgctcca tcctggctgc tgtggttgtg ggtcttgtgg cctacatagc cttcaagagg      3120
tgaaaaacca aaagaacaag aatttcttgg taagaagccg ggaacagaca acagaagtca      3180
tgaagcccaa gtgaaatcaa aggtgctaaa tggtcgccca ggagacatcc gttgtgcttg      3240
cctgcgtttt ggaagctctg aagtcacatc acaggacacg gggcagtggc aaccttgtct      3300
ctatgccagc tcagtcccat cagagagcga gcgctaccca cttctaaata gcaatttcgc      3360
cgttgaagag gaagggcaaa accactagaa ctctccatct tatttttcatg tatatgtgtt     3420 catgaatggt atggaactct ctccacccta tatgtagtat aaagaaaagt aggtt           3475
```

<210> SEQ ID NO 40
<211> LENGTH: 3759
<212> TYPE: DNA
<213> ORGANISM: artificial sequence
<220> FEATURE:
<223> OTHER INFORMATION: Inserted matrice  PD1 locus_IL12a_2A_IL12b (60
      nucleotides upstream and downstream)

<400> SEQUENCE: 40

```
ggtggccggg gaggctttgt ggggccaccc agccccttcc tcacctctct ccatctctca        60
gactccccag acaggccctg gaaccccccc accttctccc cagccctgct cgtggtgacc       120
gaaggggaca cgccacctt cacctgcagc ttctccaaca catcggagag cttcgtgcta        180
aactggtacc gcatgagccc cagcaaccag acggacaagc tggccgcctt ccccgaggac       240
cgcagccagc ccggccagga ctgccgcttc cgtgtcacac aactgcccaa cgggcgtgac       300
ttccacatga cgtggtcag ggcccggcgc aatgacagcg cacctacct ctgtggggcc        360 ggttctggcg tgaaacagac tttgaatttt gaccttctca gttggcggg agacgtggag       420 tccaacccag ggcccatgtg gcccctggg tcagcctccc agccaccgcc ctcacctgcc       480
gcggccacag gtctgcatcc agcggctcgc cctgtgtccc tgcagtgccg gctcagcatg      540
tgtccagcgc gcagcctcct ccttgtggct acctggtcc tctggaccct ctcagtttg       600 gccagaaacc tccccgtggc cactccagac ccaggaatgt tcccatgcct tcaccactcc      660
caaaacctgc tgagggccgt cagcaacatg ctccagaagg ccagacaaac tctagaattt      720
tacccttgca cttctgaaga gattgatcat gaagatatca caaagataa aaccagcaca       780 gtggaggcct gtttaccatt ggaattaacc aagaatgaga gttgcctaaa ttccagagag      840
acctctttca taactaatgg gagttgcctg gcctccagaa agacctcttt tatgatggcc      900
```

```
ctgtgcctta gtagtattta tgaagacttg aagatgtacc aggtggagtt caagaccatg    960
aatgcaaagc ttctgatgga tcctaagagg cagatctttc tagatcaaaa catgctggca   1020
gttattgatg agctgatgca ggccctgaat tcaacagtg agactgtgcc acaaaaatcc   1080
tcccttgaag aaccggattt ttataaaact aaaatcaagc tctgcatact tcttcatgct   1140
ttcagaattc gggcagtgac tattgataga gtgatgagct atctgaatgc ttccggaagc   1200
ggagctacta acttcagcct gctgaagcag gctggagacg tggaggagaa ccctggacct   1260
atgtgtcacc agcagttggt catctcttgg tttttccctgg tttttctggc atctcccctc   1320
gtggccatat gggaactgaa gaaagatgtt tatgtcgtag aattggattg gtatccggat   1380
gcccctggag aaatggtggt cctcacctgt gacacccctg aagaagatgg tatcacctgg   1440
accttggacc agagcagtga ggtcttaggc tctggcaaaa ccctgaccat ccaagtcaaa   1500
gagtttggag atgctggcca gtacacctgt cacaaaggag gcgaggttct aagccattcg   1560
ctcctgctgc ttcacaaaaa ggaagatgga atttggtcca ctgatatttt aaaggaccag   1620
aaagaaccca aaataagac cttttctaaga tgcgaggcca agaattattc tggacgtttc   1680
acctgctggt ggctgacgac aatcagtact gatttgacat tcagtgtcaa aagcagcaga   1740
ggctcttctg acccccaagg ggtgacgtgc ggagctgcta cactctctgc agagagagtc   1800
agagggaca acaaggagta tgagtactca gtggagtgcc aggaggacag tgcctgccca   1860
gctgctgagg agagtctgcc cattgaggtc atggtggatg ccgttcacaa gctcaagtat   1920
gaaaactaca ccagcagctt cttcatcagg gacatcatca aacctgaccc acccaagaac   1980
ttgcagctga agccattaaa gaattctcgg caggtggagg tcagctggga gtaccctgac   2040
acctggagta ctccacattc ctacttctcc ctgacattct gcgttcaggt ccagggcaag   2100
agcaagagag aaaagaaaga tagagtcttc acggacaaga cctcagccac ggtcatctgc   2160
cgcaaaaatg ccagcattag cgtgcgggcc caggaccgct actatagctc atcttggagc   2220
gaatgggcat ctgtgccctg cagtgagggc agaggcagcc tgctgacctg cggcgacgtc   2280
gaggagaacc ccgggcccat gggggcaggt gccaccggcc gcgccatgga cgggccgcgc   2340
ctgctgctgt tgctgcttct gggggtgtcc cttggaggtg ccaaggaggc atgccccaca   2400
ggcctgtaca cacacagcgg tgagtgctgc aaagcctgca acctgggcga gggtgtggcc   2460
cagccttgtg gagccaacca gaccgtgtgt gagccctgcc tggacagcgt gacgttctcc   2520
gacgtggtga gcgcgaccga gccgtgcaag ccgtgcaccg agtgcgtggg gctccagagc   2580
atgtcggcgc cgtgcgtgga ggccgatgac gccgtgtgcc gctgcgccta cggctactac   2640
caggatgaga cgactgggcg ctgcgaggcg tgccgcgtgt gcgaggcggg ctcgggcctc   2700
gtgttctcct gccaggacaa gcagaacacc gtgtgcgagg agtgccccga cggcacgtat   2760
tccgacgagg ccaaccacgt ggacccgtgc ctgccctgca ccgtgtgcga ggacaccgag   2820
cgccagctcc gcgagtgcac acgctgggcc gacgccgagt gcgaggagat ccctggccgt   2880
tggattacac ggtccacacc cccagagggc tcggacagca cagcccccag cacccaggag   2940
cctgaggcac ctccagaaca agacctcata gccagcacgg tggcaggtgt ggtgaccaca   3000
gtgatgggca gctcccagcc cgtggtgacc cgaggcacca ccgacaacct catccctgtc   3060
tattgctcca tcctggctgc tgtggttgtg ggtcttgtgg cctacatagc cttcaagagg   3120
tgatctagag ggcccgttta aacccgctga tcagcctcga ctgtgccttc tagttgccag   3180
ccatctgttg tttgccccctc ccccgtgcct tccttgaccc tggaaggtgc cactcccact   3240
gtcctttcct aataaaatga ggaaattgca tcgcattgtc tgagtaggtg tcattctatt   3300
```

```
ctgggggtg gggtgggca ggacagcaag ggggaggatt gggaagacaa tagcaggcat   3360 gctgggatg cggtgggctc tatgactagt ggcgaattcg gcgcagatca aagagagcct   3420
gcgggcagag ctcagggtga caggtgcggc ctcggaggcc ccggggcagg ggtgagctga   3480
gccggtcctg gggtgggtgt cccctcctgc acaggatcag gagctccagg gtcgtagggc   3540
agggaccccc cagctccagt ccagggctct gtcctgcacc tggggaatgg tgaccggcat   3600
ctctgtcctc tagctctgga agcacccag cccctctagt ctgccctcac ccctgaccct   3660
gaccctccac cctgaccccg tcctaaccc tgacctttgt gcccttccag agagaagggc   3720
agaagtgccc acagcccacc ccagcccctc acccaggcc                         3759
```

<210> SEQ ID NO 41
<211> LENGTH: 60
<212> TYPE: DNA
<213> ORGANISM: artificial sequence
<220> FEATURE:
<223> OTHER INFORMATION: upstream TRAC locus polynucleotide sequence

<400> SEQUENCE: 41

```
atgagatcat gtcctaaccc tgatcctctt gtcccacaga tatccagaac cctgaccctg   60
```

<210> SEQ ID NO 42
<211> LENGTH: 60
<212> TYPE: DNA
<213> ORGANISM: artificial sequence
<220> FEATURE:
<223> OTHER INFORMATION: downstream TRAC locus polynucleotide sequence

<400> SEQUENCE: 42

```
gaaacagtga gccttgttct ggcagtccag agaatgacac gggaaaaaag cagatgaaga   60
```

<210> SEQ ID NO 43
<211> LENGTH: 60
<212> TYPE: DNA
<213> ORGANISM: artificial sequence
<220> FEATURE:
<223> OTHER INFORMATION: upstream CD25 locus polynucleotide sequence

<400> SEQUENCE: 43

```
agtgctggct agaaaccaag tgctttactg catgcacatc atttagcaca gttagttgct   60
```

<210> SEQ ID NO 44
<211> LENGTH: 52
<212> TYPE: DNA
<213> ORGANISM: artificial sequence
<220> FEATURE:
<223> OTHER INFORMATION: downstream CD25 locus polynucleotide sequence

<400> SEQUENCE: 44

```
gaatggtatg gaactctctc caccctatat gtagtataaa gaaaagtagg tt            52
```

<210> SEQ ID NO 45
<211> LENGTH: 60
<212> TYPE: DNA
<213> ORGANISM: artificial sequence
<220> FEATURE:
<223> OTHER INFORMATION: upstream PD1 locus polynucleotide sequence

<400> SEQUENCE: 45

```
ggtggccggg gaggctttgt ggggccaccc agcccttcc tcacctctct ccatctctca    60
```

<210> SEQ ID NO 46

```
<211> LENGTH: 60
<212> TYPE: DNA
<213> ORGANISM: artificial sequence
<220> FEATURE:
<223> OTHER INFORMATION: downstream PD1 locus polynucleotide sequence

<400> SEQUENCE: 46
tgcccttcca gagagaaggg cagaagtgcc cacagcccac cccagcccct cacccaggcc    60

<210> SEQ ID NO 47
<211> LENGTH: 759
<212> TYPE: DNA
<213> ORGANISM: artificial sequence
<220> FEATURE:
<223> OTHER INFORMATION: IL-12a polynucleotide

<400> SEQUENCE: 47
atgtggcccc ctgggtcagc ctcccagcca ccgccctcac ctgccgcggc cacaggtctg    60
catccagcgg ctcgccctgt gtccctgcag tgccggctca gcatgtgtcc agcgcgcagc   120
ctcctccttg tggctaccct ggtcctcctg gaccacctca gtttggccag aaacctcccc   180
gtggccactc cagacccagg aatgttccca tgccttcacc actcccaaaa cctgctgagg   240
gccgtcagca acatgctcca gaaggccaga caaactctag aattttaccc ttgcacttct   300
gaagagattg atcatgaaga tatcacaaaa gataaaacca gcacagtgga ggcctgttta   360
ccattggaat taaccaagaa tgagagttgc ctaaattcca gagagacctc tttcataact   420
aatgggagtt gcctggcctc agaaagacc tcttttatga tggccctgtg ccttagtagt   480
atttatgaag acttgaagat gtaccaggtg gagttcaaga ccatgaatgc aaagcttctg   540
atggatccta gaggcagat cttttctagat caaaacatgc tggcagttat tgatgagctg   600
atgcaggccc tgaatttcaa cagtgagact gtgccacaaa aatcctccct tgaagaaccg   660 gattttttata aaactaaaat caagctctgc atacttcttc atgctttcag aattcgggca   720
gtgactattg atagagtgat gagctatctg aatgcttcc                           759

<210> SEQ ID NO 48
<211> LENGTH: 984
<212> TYPE: DNA
<213> ORGANISM: artificial sequence
<220> FEATURE:
<223> OTHER INFORMATION: IL12b polynucleotide

<400> SEQUENCE: 48
atgtgtcacc agcagttggt catctcttgg tttccctgg tttttctggc atctccctc     60 gtggccatat gggaactgaa gaaagatgtt tatgtcgtag aattggattg gtatccggat   120
gcccctggag aaatggtggt cctcacctgt gacacccctg aagaagatgg tatcacctgg   180
accttggacc agagcagtga ggtcttaggc tctggcaaaa ccctgaccat ccaagtcaaa   240
gagtttggag atgctggcca gtacacctgt cacaaaggag cgaggttct aagccattcg   300 ctcctgctgc ttcacaaaaa ggaagatgga atttggtcca ctgatatttt aaaggaccag   360
aaagaaccca aaaataagac ctttctaaga tgcgaggcca gaattattc tggacgtttc   420 acctgctggt ggctgacgac aatcagtact gatttgacat tcagtgtcaa agcagcaga   480 ggctcttctg accccaaggg ggtgacgtgc ggagctgcta cactctctgc agagagagtc   540
agaggggaca caaggagta tgagtactca gtggagtgcc aggaggacag tgcctgccca   600
gctgctgagg agagtctgcc cattgaggtc atgtggatg ccgttcacaa gctcaagtat   660
gaaaactaca ccagcagctt cttcatcagg gacatcatca aacctgaccc acccaagaac   720
```

```
ttgcagctga agccattaaa gaattctcgg caggtggagg tcagctggga gtaccctgac    780
acctggagta ctccacattc ctacttctcc ctgacattct gcgttcaggt ccagggcaag    840
agcaagagag aaaagaaaga tagagtcttc acggacaaga cctcagccac ggtcatctgc    900
cgcaaaaatg ccagcattag cgtgcgggcc caggaccgct actatagctc atcttggagc    960
gaatgggcat ctgtgccctg cagt                                           984

<210> SEQ ID NO 49
<211> LENGTH: 399
<212> TYPE: DNA
<213> ORGANISM: artificial sequence
<220> FEATURE:
<223> OTHER INFORMATION: IL15 polynucleotide

<400> SEQUENCE: 49
ggcattcatg tcttcatttt gggctgtttc agtgcagggc ttcctaaaac agaagccaac     60
tgggtgaatg taataagtga tttgaaaaaa attgaagatc ttattcaatc tatgcatatt    120
gatgctactt tatatacgga aagtgatgtt caccccagtt gcaaagtaac agcaatgaag    180
tgctttctct tggagttaca agttatttca cttgagtccg gagatgcaag tattcatgat    240
acagtagaaa atctgatcat cctagcaaac aacagtttgt cttctaatgg gaatgtaaca    300
gaatctggat gcaaagaatg tgaggaactg gaggaaaaaa atattaaaga atttttgcag    360
agttttgtac atattgtcca aatgttcatc aacacttct                           399

<210> SEQ ID NO 50
<211> LENGTH: 525
<212> TYPE: DNA
<213> ORGANISM: artificial sequence
<220> FEATURE:
<223> OTHER INFORMATION: sIL15ra polynucleotide

<400> SEQUENCE: 50
atcacgtgcc ctcccccat gtccgtggaa cacgcagaca tctgggtcaa gagctacagc      60
ttgtactcca gggagcggta catttgtaac tctggtttca gcgtaaaagc cggcacgtcc    120
agcctgacgg agtgcgtgtt gaacaaggcc acgaatgtcg cccactggac aaccccccagt   180 ctcaaatgca ttagagaccc tgccctggtt caccaaaggc cagcgccacc ctccacagta    240
acgacggcag gggtgacccc acagccagag agcctctccc cttctggaaa agagcccgca    300
gcttcatctc ccagctcaaa caacacagcg ccacaacag cagctattgt cccgggctcc     360
cagctgatgc cttcaaaatc accttccaca ggaaccacag agataagcag tcatgagtcc    420
tcccacggca ccccctctca gacaacagcc aagaactggg aactcacagc atccgcctcc    480
caccagccgc caggtgtgta tccacagggc cacagcgaca ccact                    525

<210> SEQ ID NO 51
<211> LENGTH: 1818
<212> TYPE: DNA
<213> ORGANISM: artificial sequence
<220> FEATURE:
<223> OTHER INFORMATION: soluble GP130 polynucleotide

<400> SEQUENCE: 51
atgctgacac tgcagacttg gctggtgcag gcactgtttta ttttctgac tactgaatca     60 actggcgaac tgctggaccc ttgtggctac atcagccctg agtccccagt ggtgcagctg    120
cacagcaact tcaccgccgt gtgcgtgctg aaggagaagt gtatggacta ctttcacgtg    180
```

```
aacgccaatt atatcgtgtg aaaaccaac cacttcacaa tccccaagga gcagtacacc    240
atcatcaata ggacagccag ctccgtgacc tttacagaca tcgcctccct gaacatccag    300
ctgacctgca atatcctgac attcggccag ctggagcaga acgtgtatgg catcaccatc    360
atctctggcc tgcccctga gaagcctaag aacctgagct gcatcgtgaa tgagggcaag    420
aagatgcggt gtgagtggga cggcggcaga gagacacacc tggagacaaa cttcaccctg    480
aagtccgagt gggccacaca caagtttgcc gactgcaagg ccaagcgcga taccccaaca    540
tcctgtaccg tggattactc tacagtgtat tttgtgaaca tcgaagtgtg ggtggaggcc    600
gagaatgccc tggcaaggt gacctccgac cacatcaact tcgatcccgt gtacaaggtg     660
aagcctaacc caccccacaa tctgagcgtg atcaattccg aggagctgtc tagcatcctg    720
aagctgacct ggacaaaccc atctatcaag agcgtgatca tcctgaagta caatatccag    780
tatcggacca aggacgcctc cacatggagc cagatccctc agaggatac cgccagcaca     840 agatcctctt tcaccgtgca ggacctgaag cccttcacag agtacgtgtt tcggatcaga    900
tgtatgaagg aggacggcaa gggctactgg agcgattggt ccgaggaggc cagcggcatc    960
acctatgagg acaggccttc taaggccccc agcttctggt acaagatcga tccatcccac    1020
acccagggct atcgcacagt gcagctggtg tggaaaaccc tgccccttt cgaggccaac     1080 ggcaagatcc tggactacga ggtgaccctg acacggtgga agtcccacct gcagaactat    1140
accgtgaatg ccaccaagct gacagtgaac ctgacaaatg atcggtacct ggccaccctg    1200
acagtgagaa acctggtggg caagtctgac gccgccgtgc tgaccatccc tgcctgcgat    1260
ttccaggcca cacacccagt gatggacctg aaggcctttc ccaaggataa tatgctgtgg    1320
gtggagtgga ccacacctag agagtccgtg aagaagtaca tcctggagtg gtgcgtgctg    1380
tctgacaagg ccccatgtat caccgactgg cagcaggagg atggcaccgt gcacaggaca    1440
tatctgcgcg gcaacctggc cgagtctaag tgttacctga tcaccgtgac acccgtgtat    1500
gcagacggac caggctctcc tgagagcatc aaggcctacc tgaagcaggc accaccaagc    1560
aagggaccaa ccgtgcggac aaagaaggtc ggcaagaatg aggccgtgct ggagtgggac    1620
cagctgcctg tggatgtgca gaacggcttc atcaggaatt acaccatctt ttatcgcaca    1680
atcatcggca acgagacagc cgtgaatgtg gacagctccc acaccgagta tactctgtct    1740
agcctgacct ccgatacact gtacatggtg aggatggccg cctatacaga cgagggcggc    1800
aaggatggcc ccgagttt                                                   1818

<210> SEQ ID NO 52
<211> LENGTH: 72
<212> TYPE: DNA
<213> ORGANISM: artificial sequence
<220> FEATURE:
<223> OTHER INFORMATION: IgE signal sequence

<400> SEQUENCE: 52
ggtaccgggt ccgccaccat ggactggacc tggattctgt tcctcgtggc tgctgctaca     60
agagtgcaca gc                                                         72

<210> SEQ ID NO 53
<211> LENGTH: 75
<212> TYPE: DNA
<213> ORGANISM: artificial sequence
<220> FEATURE:
<223> OTHER INFORMATION: F2A

<400> SEQUENCE: 53
```

```
ggttctggcg tgaaacagac tttgaatttt gaccttctca agttggcggg agacgtggag    60
tccaacccag ggccc                                                     75
```

<210> SEQ ID NO 54
<211> LENGTH: 66
<212> TYPE: DNA
<213> ORGANISM: artificial sequence
<220> FEATURE:
<223> OTHER INFORMATION: P2A

<400> SEQUENCE: 54

```
ggaagcggag ctactaactt cagcctgctg aagcaggctg agacgtgga ggagaaccct    60 ggacct                                                               66
```

<210> SEQ ID NO 55
<211> LENGTH: 54
<212> TYPE: DNA
<213> ORGANISM: artificial sequence
<220> FEATURE:
<223> OTHER INFORMATION: T2A

<400> SEQUENCE: 55

```
gagggcagag gcagcctgct gacctgcggc gacgtcgagg agaaccccgg gccc          54
```

<210> SEQ ID NO 56
<211> LENGTH: 825
<212> TYPE: DNA
<213> ORGANISM: artificial sequence
<220> FEATURE:
<223> OTHER INFORMATION: LNGFR

<400> SEQUENCE: 56

```
atggggggcag gtgccaccgg ccgcgccatg gacgggccgc gcctgctgct gttgctgctt    60 ctggggtgt cccttggagg tgccaaggag gcatgcccca caggcctgta cacacacagc   120
ggtgagtgct gcaaagcctg caacctgggc gagggtgtgg cccagccttg tggagccaac   180
cagaccgtgt gtgagccctg cctggacagc gtgacgttct ccgacgtggt gagcgcgacc   240
gagccgtgca agccgtgcac cgagtgcgtg gggctccaga gcatgtcggc gccgtgcgtg   300
gaggccgatg acgccgtgtg ccgctgcgcc tacggctact accaggatga gacgactggg   360
cgctgcgagg cgtgccgcgt gtgcgaggcg ggctcgggcc tcgtgttctc ctgccaggac   420
aagcagaaca ccgtgtgcga ggagtgcccc gacggcacgt attccgacga ggccaaccac   480
gtggacccgt gcctgccctg caccgtgtgc gaggacaccg agcgcagct ccgcgagtgc   540 acacgctggg ccgacgccga gtgcgaggag atccctggcc gttggattac acggtccaca   600
cccccagagg gctcggacag cacagccccc agcacccagg agcctgaggc acctccagaa   660
caagacctca tagccagcac ggtggcaggt gtggtgacca cagtgatggg cagctcccag   720
cccgtggtga cccgaggcac caccgacaac ctcatccctg tctattgctc catcctggct   780
gctgtggttg tgggtcttgt ggcctacata gccttcaaga ggtga                    825
```

<210> SEQ ID NO 57
<211> LENGTH: 253
<212> TYPE: PRT
<213> ORGANISM: artificial sequence
<220> FEATURE:
<223> OTHER INFORMATION: IL-12a polypeptide

<400> SEQUENCE: 57

Met Trp Pro Pro Gly Ser Ala Ser Gln Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
        35                  40                  45

Leu Leu Asp His Leu Ser Leu Ala Arg Asn Leu Pro Val Ala Thr Pro
50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250

<210> SEQ ID NO 58
<211> LENGTH: 328
<212> TYPE: PRT
<213> ORGANISM: artificial sequence
<220> FEATURE:
<223> OTHER INFORMATION: IL12b polypeptide

<400> SEQUENCE: 58

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
        50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

```
Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 59
<211> LENGTH: 133
<212> TYPE: PRT
<213> ORGANISM: artificial sequence
<220> FEATURE:
<223> OTHER INFORMATION: IL15 polypeptide

<400> SEQUENCE: 59

Gly Ile His Val Phe Ile Leu Gly Cys Phe Ser Ala Gly Leu Pro Lys
1               5                   10                  15

Thr Glu Ala Asn Trp Val Asn Val Ile Ser Asp Leu Lys Lys Ile Glu
            20                  25                  30

Asp Leu Ile Gln Ser Met His Ile Asp Ala Thr Leu Tyr Thr Glu Ser
        35                  40                  45

Asp Val His Pro Ser Cys Lys Val Thr Ala Met Lys Cys Phe Leu Leu
    50                  55                  60

Glu Leu Gln Val Ile Ser Leu Glu Ser Gly Asp Ala Ser Ile His Asp
65                  70                  75                  80

Thr Val Glu Asn Leu Ile Ile Leu Ala Asn Asn Ser Leu Ser Ser Asn
                85                  90                  95

Gly Asn Val Thr Glu Ser Gly Cys Lys Glu Cys Glu Glu Leu Glu Glu
            100                 105                 110

Lys Asn Ile Lys Glu Phe Leu Gln Ser Phe Val His Ile Val Gln Met
        115                 120                 125

Phe Ile Asn Thr Ser
    130
```

```
<210> SEQ ID NO 60
<211> LENGTH: 175
<212> TYPE: PRT
<213> ORGANISM: artificial sequence
<220> FEATURE:
<223> OTHER INFORMATION: sIL15ra polypeptide

<400> SEQUENCE: 60

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr
                165                 170                 175

<210> SEQ ID NO 61
<211> LENGTH: 606
<212> TYPE: PRT
<213> ORGANISM: artificial sequence
<220> FEATURE:
<223> OTHER INFORMATION: soluble gp130

<400> SEQUENCE: 61

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140
```

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
            165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
            195                 200                 205

Ser Asp His Ile Asn Phe Asp Pro Val Tyr Lys Val Lys Pro Asn Pro
210                 215                 220

Pro His Asn Leu Ser Val Ile Asn Ser Glu Leu Ser Ser Ile Leu
225                 230                 235                 240

Lys Leu Thr Trp Thr Asn Pro Ser Ile Lys Ser Val Ile Ile Leu Lys
            245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
            275                 280                 285

Leu Lys Pro Phe Thr Glu Tyr Val Phe Arg Ile Arg Cys Met Lys Glu
            290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
            325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
            355                 360                 365

Thr Leu Thr Arg Trp Lys Ser His Leu Gln Asn Tyr Thr Val Asn Ala
            370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
            405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
            435                 440                 445

Ser Val Lys Lys Tyr Ile Leu Glu Trp Cys Val Leu Ser Asp Lys Ala
            450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
            485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
            515                 520                 525

Lys Val Gly Lys Asn Glu Ala Val Leu Glu Trp Asp Gln Leu Pro Val
            530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
        565                 570                 575

Tyr Thr Leu Ser Ser Leu Thr Ser Asp Thr Leu Tyr Met Val Arg Met
        580                 585                 590

Ala Ala Tyr Thr Asp Glu Gly Gly Lys Asp Gly Pro Glu Phe
        595                 600                 605

<210> SEQ ID NO 62
<211> LENGTH: 836
<212> TYPE: PRT
<213> ORGANISM: artificial sequence
<220> FEATURE:
<223> OTHER INFORMATION: soluble gp130 fused to a Fc

<400> SEQUENCE: 62

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

-continued

```
Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Arg Ser
        595                 600                 605

Cys Asp Lys Thr His Thr Cys Pro Pro Cys Pro Ala Pro Glu Ala Glu
    610                 615                 620

Gly Gly Pro Ser Val Phe Leu Phe Pro Pro Lys Pro Lys Asp Thr Leu
625                 630                 635                 640

Met Ile Ser Arg Thr Pro Glu Val Thr Cys Val Val Val Asp Val Ser
                645                 650                 655

His Glu Asp Pro Glu Val Lys Phe Asn Trp Tyr Val Asp Gly Val Glu
            660                 665                 670

Val His Asn Ala Lys Thr Lys Pro Arg Glu Glu Gln Tyr Asn Ser Thr
        675                 680                 685

Tyr Arg Val Val Ser Val Leu Thr Val Leu His Gln Asp Trp Leu Asn
    690                 695                 700

Gly Lys Glu Tyr Lys Cys Lys Val Ser Asn Lys Ala Leu Pro Ala Pro
705                 710                 715                 720

Ile Glu Lys Thr Ile Ser Lys Ala Lys Gly Gln Pro Arg Glu Pro Gln
                725                 730                 735

Val Tyr Thr Leu Pro Pro Ser Arg Glu Glu Met Thr Lys Asn Gln Val
```

```
                 740                745                 750
Ser Leu Thr Cys Leu Val Lys Gly Phe Tyr Pro Ser Asp Ile Ala Val
            755                 760                 765

Glu Trp Glu Ser Asn Gly Gln Pro Glu Asn Asn Tyr Lys Thr Thr Pro
        770                 775                 780

Pro Val Leu Asp Ser Asp Gly Ser Phe Phe Leu Tyr Ser Lys Leu Thr
785                 790                 795                 800

Val Asp Lys Ser Arg Trp Gln Gln Gly Asn Val Phe Ser Cys Ser Val
            805                 810                 815

Met His Glu Ala Leu His Asn His Tyr Thr Gln Lys Ser Leu Ser Leu
        820                 825                 830

Ser Pro Gly Lys
        835

<210> SEQ ID NO 63
<211> LENGTH: 7711
<212> TYPE: DNA
<213> ORGANISM: artificial sequence
<220> FEATURE:
<223> OTHER INFORMATION: Matrice TRAC locus_CubiCAR CD22 pCLS30056 full
      sequence

<400> SEQUENCE: 63
gtggcacttt tcggggaaat gtgcgcggaa cccctatttg tttattttc taaatacatt      60 caaatatgta tccgctcatg agacaataac cctgataaat gcttcaataa tattgaaaaa    120
ggaagagtat gagtattcaa catttccgtg tcgcccttat tcccttttt gcggcatttt     180 gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcactttaa agttctgcta tgtggcgcgg     360
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca caacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtggttctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc cttttttgata   1080 atctcatgac caaaatccct aacgtgagt tttcgttcca ctgagcgtca gaccccgtag    1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt    1260
ttccgaaggt aactggcttc agcagagcgc agataccaaa tactgttctt ctagtgtagc    1320
cgtagttagg ccaccacttc aagaactctg tagcaccgcc tacatacctc gctctgctaa    1380
tcctgttacc agtggctgct gccagtggcg ataagtcgtg tcttaccggg ttggactcaa   1440
```

```
gacgatagtt accggataag gcgcagcggt cgggctgaac ggggggttcg tgcacacagc    1500
ccagcttgga gcgaacgacc tacaccgaac tgagatacct acagcgtgag ctatgagaaa    1560
gcgccacgct tcccgaaggg agaaaggcgg acaggtatcc ggtaagcggc agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740 tatgaaaaa cgccagcaac gcggccttt tacggttcct ggccttttgc tggccttttg    1800
ctcacatggt ctttcctgcg ttatccctg attctgtgga taaccgtatt accgcctttg    1860
agtgagctga taccgctcgc cgcagccgaa cgaccgagcg cagcgagtca gtgagcgagg    1920
aagcggagag cgcccaatac gcaaaccgcc tctccccgcg cgttggccga ttcattaatg    1980
cagctggcac gacaggtttc ccgactgaaa agcgggcagt gagcgcaacg caattaatgt    2040
gagttagctc actcattagg cacccccaggc tttacacttt atgcttccgg ctcgtatgtt    2100
gtgtggaatt gtgagcggat aacaatttca caggaaac agctatgacc atgattacgc    2160
caagcgcgtc aattaaccct cactaaaggg aacaaaagct gttaattaat tgctgggcct    2220
ttttcccatg cctgccttta ctctgccaga gttatattgc tggggttttg aagaagatcc    2280
tattaaataa aagaataagc agtattatta agtagccctg catttcaggt ttccttgagt    2340
ggcaggccag gcctggccgt gaacgttcac tgaaatcatg gcctcttggc caagattgat    2400
agcttgtgcc tgtccctgag tcccagtcca tcacgagcag ctggtttcta agatgctatt    2460
tcccgtataa agcatgagac cgtgacttgc cagccccaca gagccccgcc cttgtccatc    2520
actggcatct ggactccagc ctgggttggg gcaaagaggg aaatgagatc atgtcctaac    2580
cctgatcctc ttgtcccaca gatatccagt accctacga cgtgcccgac tacgcctccg    2640
gtgagggcag aggaagtctt ctaacatgcg gtgacgtgga ggagaatccg ggccccggat    2700
ccgctctgcc cgtcaccgct ctgctgctgc cactggcact gctgctgcac gctgctaggc    2760
ccggaggggg aggcagctgc ccctacagca accccagcct gtgcagcgga ggcggcggca    2820
gcggcggagg gggtagccag gtgcagctgc agcagagcgg ccctggcctg gtgaagccaa    2880
gccagacact gtccctgacc tgcgccatca gcggcgattc cgtgagctcc aactccgccg    2940
cctggaattg gatcaggcag tccccttctc ggggcctgga gtggctggga aggacatact    3000
atcggtctaa gtggtacaac gattatgccg tgtctgtgaa gagcagaatc acaatcaacc    3060
ctgacacctc caagaatcag ttctctctgc agctgaatag cgtgacacca gaggacaccg    3120
ccgtgtacta ttgcgccagg gaggtgaccg gcgacctgga ggatgccttt gacatctggg    3180
gccagggcac aatggtgacc gtgagctccg gaggcggcgg atctggcgga ggaggaagtg    3240
ggggcggcgg gagtgatatc cagatgacac agtccccatc ctctctgagc gcctccgtgg    3300
gcgacagagt gacaatcacc tgtagggcct cccagaccat ctggtcttac ctgaactggt    3360
atcagcagag gcccggcaag gcccctaatc tgctgatcta cgcagcaagc tccctgcaga    3420
gcggagtgcc atccagattc tctggcaggg gctccggcac agacttcacc ctgaccatct    3480
ctagcctgca ggccgaggac ttcgccacct actattgcca gcagtcttat agcatccccc    3540
agacatttgg ccagggcacc aagctggaga tcaagtcgga tccgaagcg gaggggggag    3600 gcagctgccc ctacagcaac cccagcctgt gcagcggagg cggcggcagc gagctgccca    3660
cccagggcac cttctccaac gtgtccacca acgtgagccc agccaagccc accaccaccg    3720 cctgtccctta ttccaatcct tccctgtgtg ctcccaccac aacccccgct ccaaggcccc    3780 ctaccccgc accaactatt gcctcccagc cactctcact gcggcctgag gcctgtcggc    3840
```

```
ccgctgctgg aggcgcagtg catacaaggg gcctcgattt cgcctgcgat atttacatct   3900
gggcacccct cgccggcacc tgcgggtgc ttctcctctc cctggtgatt accctgtatt   3960
gcagacgggg ccggaagaag ctcctctaca tttttaagca gcctttcatg cggccagtgc   4020
agacaaccca agaggaggat gggtgttcct gcagattccc tgaggaagag aaggcgggt   4080 gcgagctgag agtgaagttc tccaggagcg cagatgcccc cgcctatcaa cagggccaga   4140
accagctcta caacgagctt aacctcggga ggcgcgaaga atacgacgtg ttggataaga   4200
gaagggggcg ggaccccgag atgggaggaa agccccggag gaagaaccct caggagggcc   4260
tgtacaacga gctgcagaag gataagatgg ccgaggccta ctcagagatc gggatgaagg   4320
gggagcggcg ccgcgggaag gggcacgatg gctctacca ggggctgagc acagccacaa   4380
aggacacata cgacgccttg cacatgcagg ccctccacc ccgggaatag tctagagggc   4440
ccgtttaaac ccgctgatca gcctcgactg tgccttctag ttgccagcca tctgttgttt   4500 gccctcccc cgtgccttcc ttgacccggg aaggtgccac tcccactgtc ctttcctaat   4560
aaaatgagga aattgcatcg cattgtctga gtaggtgtca ttctattctg ggggtgggg   4620 tgggcagga cagcaagggg gaggattggg aagacaatag caggcatgct ggggatgcgg   4680
tgggctctat gactagtggc gaattcccgt gtaccagctg agagactcta aatccagtga   4740
caagtctgtc tgcctattca ccgattttga ttctcaaaca aatgtgtcac aaagtaagga   4800
ttctgatgtg tatatcacag acaaaactgt gctagacatg aggtctatgg acttcaagag   4860
caacagtgct gtggcctgga gcaacaaatc tgactttgca tgtgcaaacg ccttcaacaa   4920
cagcattatt ccagaagaca ccttcttccc cagcccaggt aagggcagct tggtgccttc   4980
cgcaggctgt ttccttgctt caggaatggc caggttctgc ccagagctct ggtcaatgat   5040
gtctaaaact cctctgattg gtggtctcgg cctatccat tgccaccaaa ccctcttttt   5100
tactaagcga tcgctccggt gcccgtcagt gggcagagcg cacatcgccc acagtcccg   5160 agaagttggg gggaggggtc ggcaattgaa cgggtgccta gagaaggtgg cgcggggtaa   5220
actgggaaag tgatgtcgtg tactggctcc gcctttttcc cgagggtggg ggagaaccgt   5280
atataagtgc agtagtcgcc gtgaacgttc tttttcgcaa cgggtttgcc gccagaacac   5340
agctgaagct tcgaggggct cgcatctctc cttcacgcgc ccgccgccct acctgaggcc   5400
gccatccacg ccggttgagt cgcgttctgc cgcctcccgc ctgtggtgcc tcctgaactg   5460
cgtccgccgt ctaggtaagt ttaaagctca ggtcgagacc gggcctttgt ccggcgctcc   5520
cttggagcct acctagactc agccggctct ccacgctttg cctgaccctg cttgctcaac   5580
tctacgtctt tgtttcgttt tctgttctgc gccgttacag atccaagctg taccggcgc   5640 ctacctgaga tcaccggcgc caccatggct tcttaccctg acaccagca tgcttctgcc   5700 tttgaccagg ctgccagatc caggggccac tccaacagga gaactgcct aagacccaga   5760 agacagcagg aagccactga ggtgaggcct gagcagaaga tgccaaccct gctgagggtg   5820
tacattgatg gacctcatgg catgggcaag accaccacca ctcaactgct ggtggcactg   5880
ggctccaggg atgacattgt gtatgtgcct gagccaatga cctactggag agtgctagga   5940
gcctctgaga ccattgccaa catctacacc acccagcaca gctggaccc gggagaaatc   6000 tctgctggag atgctgctgt ggtgatgacc tctgcccaga tcacaatggg aatgccctat   6060
gctgtgactg atgctgttct ggctcctcac attggaggag aggctggctc ttctcatgcc   6120
cctccacctg ccctgaccct gatctttgac agacacccca ttgcagccct gctgtgctac   6180
```

| | |
|---|---|
| ccagcagcaa ggtacctcat gggctccatg accccacagg ctgtgctggc ttttgtggcc | 6240 |
| ctgatccctc caaccctccc tggcaccaac attgttctgg gagcactgcc tgaagacaga | 6300 |
| cacattgaca ggctggcaaa gaggcagaga cctggagaga gactggacct ggccatgctg | 6360 |
| gctgcaatca aagggtgta tggactgctg gcaaacactg tgagatacct ccagtgtgga | 6420 |
| ggctcttgga gagaggactg gggacagctc tctggaacag cagtgccccc tcaaggagct | 6480 |
| gagcccagt ccaatgctgg tccaagaccc cacattgggg cacccctgtt caccctgttc | 6540 |
| agagcccctg agctgctggc tcccaatgga gacctgtaca atgtgtttgc ctgggctctg | 6600 |
| gatgttctag ccaagaggct gaggtccatg catgtgttca tcctggacta tgaccagtcc | 6660 |
| cctgctggat gcagagatgc tctgctgcaa ctaacctctg gcatggtgca gacccatgtg | 6720 |
| accaccctg gcagcatccc caccatctgt gacctagcca gaacctttgc cagggagatg | 6780 |
| ggagaggcca actaaggcgc gccactcgag cgctagctgg ccagacatga aagatacat | 6840 |
| tgatgagttt ggacaaacca caactagaat gcagtgaaaa aaatgcttta tttgtgaaat | 6900 |
| ttgtgatgct attgctttat ttgtaaccat tataagctgc aataaacaag ttaacaacaa | 6960 |
| caattgcatt cattttatgt ttcaggttca gggggaggtg tgggaggttt tttaaagcaa | 7020 |
| gtaaaacctc tacaaatgtg gtatggaagg cgcgcccaat tcgccctata gtgagtcgta | 7080 |
| ttacgtcgcg ctcactggcc gtcgttttac aacgtcgtga ctgggaaaac cctggcgtta | 7140 |
| cccaacttaa tcgccttgca gcacatcccc ctttcgccag ctggcgtaat agcgaagagg | 7200 |
| cccgcaccga aacgcccttc caacagttg cgcagcctga atggcgaatg ggagcgccct | 7260 |
| gtagcggcgc attaagcgcg gcgggtgtgg tggttacgcg cagcgtgacc gctacacttg | 7320 |
| ccagcgccct agcgcccgct cctttcgctt tcttcccttc ctttctcgcc acgttcgccg | 7380 |
| gctttccccg tcaagctcta aatcgggggc tccctttagg gttccgattt agtgctttac | 7440 |
| ggcacctcga cccaaaaaaa cttgattagg gtgatggttg cctgtagtg gccatagcc | 7500 |
| ctgatagacg gtttttcgcc ctttgacgtt ggagtccacg ttctttaata gtggactctt | 7560 |
| gttccaaact ggaacaacac tcaaccctat ctcggtctat tcttttgatt tataagggat | 7620 |
| tttgccgatt tcggcctatt ggttaaaaaa tgagctgatt taacaaaaat ttaacgcgaa | 7680 |
| ttttaacaaa atattaacgc ttacaattta g | 7711 |

<210> SEQ ID NO 64
<211> LENGTH: 7502
<212> TYPE: DNA
<213> ORGANISM: artificial sequence
<220> FEATURE:
<223> OTHER INFORMATION: Matrice CD25 locus_IL15_2A_sIL15Ra pCLS30519
      full sequence

<400> SEQUENCE: 64

| | |
|---|---|
| gtttattatt cctgttccac agctattgtc tgccatataa aaacttaggc caggcacagt | 60 |
| ggctcacacc tgtaatccca gcactttgga aggccgaggc aggcagatca caaggtcagg | 120 |
| agttcgagac cagcctggcc aacatagcaa aaccccatct ctactaaaaa tacaaaaatt | 180 |
| agccaggcat ggtggcgtgt gcactggttt agagtgagga ccacattttt ttggtgccgt | 240 |
| gttacacata tgaccgtgac tttgttacac cactacagga ggaagagtag aagaacaatc | 300 |
| ggttctggcg tgaaacagac tttgaatttt gaccttctca agttggcggg agacgtggag | 360 |
| tccaacccag ggcccggtac cgggtccgcc accatggact ggacctggat tctgttcctc | 420 |
| gtggctgctg ctacaagagt gcacagcggc attcatgtct tcattttggg ctgtttcagt | 480 |

```
gcagggcttc ctaaaacaga agccaactgg gtgaatgtaa taagtgattt gaaaaaaatt      540
gaagatctta ttcaatctat gcatattgat gctactttat atacggaaag tgatgttcac      600
cccagttgca aagtaacagc aatgaagtgc tttctcttgg agttacaagt tatttcactt      660
gagtccggag atgcaagtat tcatgataca gtagaaaatc tgatcatcct agcaaacaac      720
agtttgtctt ctaatgggaa tgtaacagaa tctggatgca agaatgtgga ggaactggag      780
gaaaaaaata ttaaagaatt tttgcagagt tttgtacata ttgtccaaat gttcatcaac      840
acttctggaa gcggagctac taacttcagc ctgctgaagc aggctggaga cgtggaggag      900
aaccctggac ctgggaccgg ctctgcaacc atggattgga cgtggatcct gtttctcgtg      960
gcagctgcca aagagttca cagtatcacg tgccctcccc ccatgtccgt ggaacacgca      1020
gacatctggg tcaagagcta cagcttgtac tccagggagc ggtacatttg taactctggt      1080
ttcaagcgta aagccggcac gtccagcctg acggagtgcg tgttgaacaa ggccacgaat      1140
gtcgcccact ggacaacccc cagtctcaaa tgcattagag accctgccct ggttcaccaa      1200
aggccagcgc caccctccac agtaacgacg gcaggggtga ccccacagcc agagagcctc      1260
tccccttctg gaaaagagcc cgcagcttca tctcccagct caaacaacac agcggccaca      1320
acagcagcta ttgtcccggg ctcccagctg atgccttcaa aatcaccttc cacaggaacc      1380
acagagataa gcagtcatga gtcctcccac ggcacccccc tcagacaaca gccaagaac      1440 tgggaactca cagcatccgc ctcccaccag ccgccaggtg tgtatccaca gggccacagc      1500
gacaccactg agggcagagg cagcctgctg acctgcggcg acgtcgagga aaccccggg      1560 cccatggggg caggtgccac cggccgcgcc atggacgggc cgcgcctgct gctgttgctg      1620
cttctggggg tgtcccttgg aggtgccaag gaggcatgcc ccacaggcct gtacacacac      1680
agcggtgagt gctgcaaagc ctgcaacctg ggcgagggtg tggcccagcc ttgtggagcc      1740
aaccagaccg tgtgtgagcc ctgcctggac agcgtgacgt tctccgacgt ggtgagcgcg      1800
accgagccgt gcaagccgtg caccgagtgc gtggggctcc agagcatgtc ggcgccgtgc      1860
gtggaggccg atgacgccgt gtgccgctgc gcctacggct actaccagga tgagacgact      1920
gggcgctgcg aggcgtgccg cgtgtgcgag gcgggctcgg gcctcgtgtt ctcctgccag      1980
gacaagcaga acaccgtgtg cgaggagtgc cccgacggca cgtattccga cgaggccaac      2040
cacgtggacc cgtgcctgcc ctgcaccgtg tgcgaggaca ccgagcgcca gctccgcgag      2100
tgcacacgct gggccgacgc cgagtgcgag gagatccctg gccgttggat tacacggtcc      2160 acaccccag agggctcgga cagcacagcc cccagcaccc aggagcctga ggcacctcca      2220
gaacaagacc tcatagccag cacggtggca ggtgtggtga ccacagtgat gggcagctcc      2280
cagcccgtgg tgacccgagg caccaccgac aacctcatcc ctgtctattg ctccatcctg      2340
gctgctgtgg ttgtgggtct tgtggcctac atagccttca agaggtgaaa aaccaaaga      2400 acaagaattt cttggtaaga agccgggaac agacaacaga agtcatgaag cccaagtgaa      2460
atcaaaggtg ctaaatggtc gcccaggaga catccgttgt gcttgcctgc gttttggaag      2520
ctctgaagtc acatcacagg acacggggca gtggcaacct tgtctctatg ccagctcagt      2580
cccatcagag agcgagcgct acccacttct aaatagcaat ttcgccgttg aagaggaagg      2640
gcaaaaccac tagaactctc catcttatttt tcatgtatat gtgttcatgc gatcgctccg      2700
gtgcccgtca gtgggcagag cgcacatcgc ccacagtccc cgagaagttg ggggagggg      2760 tcggcaattg aacgggtgcc tagagaaggt ggcgcggggt aaactgggaa agtgatgtcg      2820
tgtactggct ccgccttttt cccgagggtg ggggagaacc gtatataagt gcagtagtcg      2880
```

```
ccgtgaacgt tcttttccgc aacgggtttg ccgccagaac acagctgaag cttcgagggg    2940
ctcgcatctc tccttcacgc gcccgccgcc ctacctgagg ccgccatcca cgccggttga    3000
gtcgcgttct gccgcctccc gcctgtggtg cctcctgaac tgcgtccgcc gtctaggtaa    3060
gtttaaagct caggtcgaga ccgggccttt gtccggcgct cccttggagc ctacctagac    3120
tcagccggct ctccacgctt tgcctgaccc tgcttgctca actctacgtc tttgtttcgt    3180
tttctgttct gcgccgttac agatccaagc tgtgaccggc gcctacctga gatcaccggc    3240
gccaccatgg cttcttaccc tggacaccag catgcttctg cctttgacca ggctgccaga    3300
tccaggggcc actccaacag gagaactgcc ctaagaccca gaagacagca ggaagccact    3360
gaggtgaggc ctgagcagaa gatgccaacc ctgctgaggg tgtacattga tggacctcat    3420
ggcatgggca agaccaccac cactcaactg ctggtggcac tgggctccag ggatgacatt    3480
gtgtatgtgc ctgagccaat gacctactgg agagtgctag gagcctctga gaccattgcc    3540
aacatctaca ccacccagca caggctggac caggagaaaa tctctgctgg agatgctgct    3600
gtggtgatga cctctgccca gatcacaatg ggaatgccct atgctgtgac tgatgctgtt    3660
ctggctcctc acattggagg agaggctggc tcttctcatg cccctccacc tgccctgacc    3720
ctgatctttg acagacaccc cattgcagcc ctgctgtgct acccagcagc aaggtacctc    3780
atgggctcca tgaccccaca ggctgtgctg gcttttgtgg ccctgatccc tccaaccctc    3840
cctggcacca acattgttct gggagcactg cctgaagaca gacacattga caggctggca    3900
aagaggcaga gacctggaga gagactggac ctggccatgc tggctgcaat cagaagggtg    3960
tatggactgc tggcaaacac tgtgagatac ctccagtgtg gaggctcttg gagagaggac    4020
tggggacagc tctctggaac agcagtgccc cctcaaggag ctgagcccca gtccaatgct    4080
ggtccaagac cccacattgg ggacaccctg ttcaccctgt tcagagcccc tgagctgctg    4140
gctcccaatg gagacctgta caatgtgttt gcctgggctc tggatgttct agccaagagg    4200
ctgaggtcca tgcatgtgtt catcctggac tatgaccagt ccctgctgg atgcagagat    4260
gctctgctgc aactaacctc tggcatggtg cagacccatg tgaccacccc tggcagcatc    4320
cccaccatct gtgacctagc cagaaccttt gccagggaga tgggagaggc caactaaggc    4380
gcgccactcg agcgctagct ggccagacat gataagatac attgatgagt ttggacaaac    4440
cacaactaga atgcagtgaa aaaaatgctt tatttgtgaa atttgtgatg ctattgcttt    4500
atttgtaacc attataagct gcaataaaca agttaacaac aacaattgca ttcattttat    4560
gtttcaggtt caggggagg tgtgggaggt tttttaaagc aagtaaaacc tctacaaatg    4620
tggtatggaa ggcgcgccca attcgcccta tagtgagtcg tattacgtcg cgctcactgg    4680
ccgtcgtttt acaacgtcgt gactgggaaa accctggcgt tacccaactt aatcgccttg    4740
cagcacatcc cctttcgcc agctggcgta atagcgaaga ggcccgcacc gaaacgccct    4800
tcccaacagt tgcgcagcct gaatggcgaa tgggagcgcc ctgtagcggc gcattaagcg    4860
cggcgggtgt ggtggttacg cgcagcgtga ccgctacact tgccagcgcc ctagcgcccg    4920
ctcctttcgc tttcttccct tcctttctcg ccacgttcgc cggctttccc cgtcaagctc    4980
taaatcgggg gctccctta gggttccgat ttagtgcttt acggcacctc gaccccaaaa    5040
aacttgatta gggtgatggt tggcctgtag tgggccatag ccctgataga cggttttttcg    5100
ccctttgacg ttggagtcca cgttctttaa tagtggactc ttgttccaaa ctggaacaac    5160
actcaaccct atctcggtct attcttttga tttataaggg attttgccga tttcggccta    5220
```

```
ttggttaaaa aatgagctga tttaacaaaa atttaacgcg aattttaaca aaatattaac    5280
gcttacaatt taggtggcac ttttcgggga aatgtgcgcg gaacccctat ttgtttattt    5340
ttctaaatac attcaaatat gtatccgctc atgagacaat aaccctgata aatgcttcaa    5400
taatattgaa aaaggaagag tatgagtatt caacatttcc gtgtcgccct tattcccttt    5460
tttgcggcat tttgccttcc tgttttttgct cacccagaaa cgctggtgaa agtaaaagat    5520
gctgaagatc agttgggtgc acgagtgggt tacatcgaac tggatctcaa cagcggtaag    5580
atccttgaga gttttcgccc cgaagaacgt tttccaatga tgagcacttt taaagttctg    5640
ctatgtggcg cggtattatc ccgtattgac gccgggcaag agcaactcgg tcgccgcata    5700
cactattctc agaatgactt ggttgagtac tcaccagtca cagaaaagca tcttacggat    5760
ggcatgacag taagagaatt atgcagtgct gccataacca tgagtgataa cactgcggcc    5820
aacttacttc tgacaacgat cggaggaccg aaggagctaa ccgcttttttt gcacaacatg    5880
ggggatcatg taactcgcct tgatcgttgg gaaccggagc tgaatgaagc cataccaaac    5940
gacgagcgtg acaccacgat gcctgtagca atggcaacaa cgttgcgcaa actattaact    6000
ggcgaactac ttactctagc ttcccggcaa caattaatag actggatgga gcggataaaa    6060
gttgcaggac cacttctgcg ctcggccctt ccggctggct ggtttattgc tgataaatct    6120
ggagccggtg agcgtggttc tcgcggtatc attgcagcac tggggccaga tggtaagccc    6180
tcccgtatcg tagttatcta cacgacgggg agtcaggcaa ctatggatga acgaaataga    6240
cagatcgctg agataggtgc ctcactgatt aagcattggt aactgtcaga ccaagtttac    6300
tcatatatac tttagattga tttaaaactt catttttaat ttaaaaggat ctaggtgaag    6360
atcctttttg ataatctcat gaccaaaatc ccttaacgtg agttttcgtt ccactgagcg    6420
tcagaccccg tagaaaagat caaaggatct tcttgagatc ctttttttct gcgcgtaatc    6480
tgctgcttgc aaacaaaaaa accaccgcta ccagcggtgg tttgtttgcc ggatcaagag    6540
ctaccaactc tttttccgaa ggtaactggc ttcagcagag cgcagatacc aaatactgtt    6600
cttctagtgt agccgtagtt aggccaccac ttcaagaact ctgtagcacc gcctacatac    6660
ctcgctctgc taatcctgtt accagtggct gctgccagtg gcgataagtc gtgtcttacc    6720
gggttggact caagacgata gttaccggat aaggcgcagc ggtcgggctg aacggggggt    6780
tcgtgcacac agcccagctt ggagcgaacg acctacaccg aactgagata cctacagcgt    6840
gagctatgag aaagcgccac gcttcccgaa gggagaaagg cggacaggta tccggtaagc    6900
ggcagggtcg gaacaggaga gcgcacgagg gagcttccag ggggaaacgc ctggtatctt    6960
tatagtcctg tcgggtttcg ccacctctga cttgagcgtc gatttttgtg atgctcgtca    7020
ggggggcgga gcctatggaa aaacgccagc aacgcggcct ttttacggtt cctggccttt    7080
tgctggcctt ttgctcacat ggtctttcct gcgttatccc ctgattctgt ggataaccgt    7140
attaccgcct ttgagtgagc tgataccgct cgccgcagcc gaacgaccga gcgcagcgag    7200
tcagtgagcg aggaagcgga gagcgcccaa tacgcaaacc gcctctcccc gcgcgttggc    7260
cgattcatta atgcagctgg cacgacaggt ttcccgactg gaaagcgggc agtgagcgca    7320
acgcaattaa tgtgagttag ctcactcatt aggcaccccca ggctttacac tttatgcttc    7380
cggctcgtat gttgtgtgga attgtgagcg gataacaatt tcacacagga aacagctatg    7440
accatgatta cgccaagcgc gtcaattaac cctcactaaa gggaacaaaa gctgttaatt    7500
aa                                                                   7502
```

<210> SEQ ID NO 65
<211> LENGTH: 7778
<212> TYPE: DNA
<213> ORGANISM: artificial sequence
<220> FEATURE:
<223> OTHER INFORMATION: Matrice PD1 locus_IL15_2A_sIL15Ra pCLS30513 full sequence

<400> SEQUENCE: 65

```
gactccccag acaggccctg aaccccccc accttctccc cagccctgct cgtggtgacc      60
gaagggggaca acgccacctt cacctgcagc ttctccaaca catcggagag cttcgtgcta     120
aactggtacc gcatgagccc cagcaaccag acggacaagc tggccgcctt ccccgaggac     180
cgcagccagc ccggccagga ctgccgcttc cgtgtcacac aactgcccaa cgggcgtgac     240
ttccacatga gcgtggtcag ggcccggcgc aatgacagcg gcacctacct ctgtggggcc     300
ggttctggcg tgaaacagac tttgaatttt gaccttctca agttggcggg agacgtggag     360
tccaacccag gcccggtac cgggtccgcc accatggact ggacctggat tctgttcctc     420
gtggctgctg ctacaagagt gcacagcggc attcatgtct tcattttggg ctgtttcagt     480
gcagggcttc ctaaaacaga agccaactgg gtgaatgtaa taagtgattt gaaaaaaatt     540
gaagatctta ttcaatctat gcatattgat gctactttat atacggaaag tgatgttcac     600
cccagttgca aagtaacagc aatgaagtgc tttctcttgg agttacaagt tatttcactt     660
gagtccggag atgcaagtat tcatgataca gtagaaaatc tgatcatcct agcaaacaac     720
agtttgtctt ctaatgggaa tgtaacagaa tctggatgca aagaatgtga ggaactggag     780
gaaaaaaata ttaagaatt tttgcagagt tttgtacata ttgtccaaat gttcatcaac     840
acttctggaa gcggagctac taacttcagc ctgctgaagc aggctggaga cgtggaggag     900
aaccctggac ctgggaccgg ctctgcaacc atggattgga cgtggatcct gtttctcgtg     960
gcagctgcca caagagttca gtatcacg tgccctcccc ccatgtccgt ggaacacgca    1020
gacatctggg tcaagagcta cagccttgtac tccagggagc ggtacatttg taactctggt    1080
ttcaagcgta aagccggcac gtccagcctg acggagtgcg tgttgaacaa ggccacgaat    1140
gtcgcccact ggacaacccc cagtctcaaa tgcattagag accctgccct ggttcaccaa    1200
aggccagcgc accctccac agtaacgacg gcaggggtga ccccacagcc agagagcctc    1260
tccccttctg aaaagagcc cgcagcttca tctcccagct caacaacac agcggccaca    1320
acagcagcta ttgtcccggg ctcccagctg atgccttcaa aatcaccttc cacaggaacc    1380
acagagataa gcagtcatga gtcctcccac ggcacccct ctcagacaac agccaagaac    1440
tgggaactca cagcatccgc ctcccaccag ccgccaggtg tgtatccaca gggccacagc    1500
gacaccactg agggcagagg cagcctgctg acctgcggcg acgtcgagga gaaccccggg    1560
cccatggggg gcaggtgccac cggccgcgcc atggacgggc cgcgcctgct gctgttgctg    1620
cttctggggg tgtccttgg aggtgccaag gaggcatgcc ccacaggcct gtacacacac    1680
agcggtgagt gctgcaaagc ctgcaacctg ggcgagggtg tggcccagcc ttgtggagcc    1740
aaccagaccg tgtgtgagcc ctgcctggac agcgtgacgt tctccgacgt ggtgagcgcg    1800
accgagccgt gcaagccgtg caccgagtgc gtggggctcc agagcatgtc ggcgccgtgc    1860
gtggaggccg atgacgccgt gtgccgctgc gcctacggct actaccagga tgagacgact    1920
gggcgctgcg aggcgtgccg cgtgtgcgag cgggctcgg gcctcgtgtt ctcctgccag    1980
gacaagcaga acaccgtgtg cgaggagtgc cccgacggca cgtattccga cgaggccaac    2040
cacgtggacc cgtgcctgcc ctgcaccgtg tgcgaggaca ccgagcgcca gctccgcgag    2100
```

```
tgcacacgct gggccgacgc cgagtgcgag gagatccctg gccgttggat tacacggtcc    2160 acaccccag  agggctcgga cagcacagcc cccagcaccc aggagcctga ggcacctcca    2220
gaacaagacc tcatagccag cacggtggca ggtgtggtga ccacagtgat gggcagctcc    2280
cagcccgtgg tgacccgagg caccaccgac aacctcatcc ctgtctattg ctccatcctg    2340
gctgctgtgg ttgtgggtct tgtggcctac atagccttca agaggtgatc tagagggccc    2400
gtttaaaccc gctgatcagc ctcgactgtg ccttctagtt gccagccatc tgttgtttgc    2460
ccctcccccg tgccttcctt gaccctggaa ggtgccactc ccactgtcct ttcctaataa    2520
aatgaggaaa ttgcatcgca ttgtctgagt aggtgtcatt ctattctggg gggtggggtg    2580
gggcaggaca gcaaggggga ggattgggaa gacaatagca ggcatgctgg ggatgcggtg    2640
ggctctatga ctagtggcga attcggcgca gatcaaagag agcctgcggg cagagctcag    2700
ggtgacaggt gcggcctcgg aggccccggg gcaggggtga gctgagccgg tcctggggtg    2760
ggtgtcccct cctgcacagg atcaggagct ccagggtcgt agggcaggga cccccccagct   2820 ccagtccagg gctctgtcct gcacctgggg aatggtgacc ggcatctctg tcctctagct    2880
ctggaagcac cccagcccct ctagtctgcc ctcaccctg  acctgaccc tccaccctga    2940 ccccgtccta acccctgacc tttggcgatc gctccggtgc ccgtcagtgg gcagagcgca    3000
catcgcccac agtccccgag aagttggggg gaggggtcgg caattgaacg ggtgcctaga    3060
gaaggtggcg cggggtaaac tgggaaagtg atgtcgtgta ctggctccgc ctttttcccg    3120
agggtggggg agaaccgtat ataagtgcag tagtcgccgt gaacgttctt tttcgcaacg    3180
ggtttgccgc cagaacacag ctgaagcttc gaggggctcg catctctcct tcacgcgccc    3240
gccgccctac ctgaggccgc catccacgcc ggttgagtcg cgttctgccg cctcccgcct    3300
gtggtgcctc ctgaactgcg tccgccgtct aggtaagttt aaagctcagg tcgagaccgg    3360
gcctttgtcc ggcgctccct tggagcctac ctagactcag ccggctctcc acgctttgcc    3420
tgaccctgct tgctcaactc tacgtctttg tttcgttttc tgttctgcgc cgttacagat    3480
ccaagctgtg accggcgcct acctgagatc accggcgcca ccatggcttc ttaccctgga    3540
caccagcatg cttctgcctt tgaccaggct gccagatcca ggggccactc caacaggaga    3600
actgccctaa gacccagaag acagcaggaa gccactgagg tgaggcctga gcagaagatg    3660
ccaaccctgc tgagggtgta cattgatgga cctcatggca tgggcaagac caccaccact    3720
caactgctgg tggcactggg ctccagggat gacattgtgt atgtgcctga gccaatgacc    3780
tactggagag tgctaggagc ctctgagacc attgccaaca tctacaccac ccagcacagg    3840
ctggaccagg gagaaatctc tgctggagat gctgctgtgg tgatgacctc tgcccagatc    3900
acaatgggaa tgcccatgc tgtgactgat gctgttctgg ctcctcacat ggaggagag    3960 gctggctctt tcatgcccc tccacctgcc ctgaccctga tctttgacag acaccccatt    4020
gcagccctgc tgtgctaccc agcagcaagg tacctcatgg gctccatgac cccacaggct    4080
gtgctggctt ttgtggccct gatccctcca accctccctg gcaccaacat tgttctggga    4140
gcactgcctg aagacagaca cattgacagg ctggcaaaga ggcagagacc tggagagaga    4200
ctggaccctg ccatgctggc tgcaatcaga agggtgtatg gactgctggc aaacactgtg    4260
agatacctcc agtgtggagg ctcttggaga gaggactggg gacagctctc tggaacagca    4320
gtgccccctc aaggagctga gcccagtcc  aatgctggtc caagaccccca cattgggac    4380 accctgttca ccctgttcag agcccctgag ctgctggctc caatggaga  cctgtacaat    4440
```

```
gtgtttgcct gggctctgga tgttctagcc aagaggctga ggtccatgca tgtgttcatc      4500
ctggactatg accagtcccc tgctggatgc agagatgctc tgctgcaact aacctctggc      4560
atggtgcaga cccatgtgac caccctggc agcatccca ccatctgtga cctagccaga        4620
acctttgcca gggagatggg agaggccaac taaggcgcgc cactcgagcg ctagctggcc      4680
agacatgata agatacattg atgagtttgg acaaaccaca actagaatgc agtgaaaaaa      4740
atgctttatt tgtgaaattt gtgatgctat tgctttattt gtaaccatta taagctgcaa      4800
taaacaagtt aacaacaaca attgcattca ttttatgttt caggttcagg gggaggtgtg      4860
ggaggttttt taaagcaagt aaaacctcta caaatgtggt atggaaggcg cgcccaattc      4920
gccctatagt gagtcgtatt acgtcgcgct cactggccgt cgttttacaa cgtcgtgact      4980
gggaaaaccc tggcgttacc caacttaatc gccttgcagc acatcccct ttcgccagct       5040 ggcgtaatag cgaagaggcc cgcaccgaaa cgccttccc aacagttgcg cagcctgaat       5100
ggcgaatggg agcgcctgt agcggcgcat taagcgcggc gggtgtggtg gttacgcgca      5160
gcgtgaccgc tacacttgcc agcgccctag cgcccgctcc tttcgctttc ttcccttcct      5220
ttctcgccac gttcgccggc tttccccgtc aagctctaaa tcgggggctc cctttagggt      5280
tccgatttag tgctttacgg cacctcgacc ccaaaaaact tgattagggt gatggttggc      5340
ctgtagtggg ccatagccct gatagacggt ttttcgccct ttgacgttgg agtccacgtt      5400
ctttaatagt ggactcttgt tccaaactgg aacaacactc aaccctatct cggtctattc      5460
ttttgattta agggatttt gccgatttc ggcctattgg ttaaaaatg agctgattta         5520 acaaaattt aacgcgaatt ttaacaaaat attaacgctt acaatttagg tggcactttt       5580
cggggaaatg tgcgcggaac ccctatttgt ttatttttct aaatacattc aaatatgtat      5640
ccgctcatga caataaacc ctgataaatg cttcaataat attgaaaaag gaagagtatg       5700
agtattcaac atttccgtgt cgcccttatt ccctttttg cggcattttg ccttcctgtt       5760
tttgctcacc cagaaacgct ggtgaaagta aaagatgctg aagatcagtt gggtgcacga      5820
gtgggttaca tcgaactgga tctcaacagc ggtaagatcc ttgagagttt cgccccgaa       5880 gaacgttttc caatgatgag cacttttaaa gttctgctat gtggcgcggt attatcccgt      5940
attgacgccg ggcaagagca actcggtcgc cgcatacact attctcagaa tgacttggtt      6000
gagtactcac cagtcacaga aaagcatctt acggatggca tgacagtaag agaattatgc      6060
agtgctgcca taaccatgag tgataacact gcggccaact tacttctgac aacgatcgga      6120
ggaccgaagg agctaaccgc ttttttgcac aacatggggg atcatgtaac tcgccttgat      6180
cgttgggaac cggagctgaa tgaagccata ccaaacgacg agcgtgacac cacgatgcct      6240
gtagcaatgg caacaacgtt gcgcaaacta ttaactggcg aactacttac tctagcttcc      6300
cggcaacaat taatagactg gatggaggcg gataaagttg caggaccact tctgcgctcg      6360
gcccttccgg ctggctggtt tattgctgat aaatctggag ccggtgagcg tggttctcgc      6420
ggtatcattg cagcactggg gccagatggt aagccctccc gtatcgtagt tatctacacg      6480
acggggagtc aggcaactat ggatgaacga atagacaga tcgctgagat aggtgcctca      6540
ctgattaagc attggtaact gtcagaccaa gtttactcat atatacttta gattgattta      6600
aaacttcatt tttaatttaa aaggatctag gtgaagatcc ttttgataa tctcatgacc       6660 aaaatccctt aacgtgagtt ttcgttccac tgagcgtcag accccgtaga aaagatcaaa      6720
ggatcttctt gagatccttt ttttctgcgc gtaatctgct gcttgcaaac aaaaaaacca      6780
ccgctaccag cggtggtttg tttgccggat caagagctac caactctttt tccgaaggta      6840
```

```
actggcttca gcagagcgca gataccaaat actgttcttc tagtgtagcc gtagttaggc    6900
caccacttca agaactctgt agcaccgcct acatacctcg ctctgctaat cctgttacca    6960
gtggctgctg ccagtggcga taagtcgtgt cttaccgggt tggactcaag acgatagtta    7020
ccggataagg cgcagcggtc gggctgaacg ggggggttcgt gcacacagcc cagcttggag    7080
cgaacgacct acaccgaact gagatacccta cagcgtgagc tatgagaaag cgccacgctt    7140
cccgaaggga gaaggcgga caggtatccg gtaagcggca gggtcggaac aggagagcgc    7200
acgagggagc ttccagggg aaacgcctgg tatctttata gtcctgtcgg gtttcgccac    7260
ctctgacttg agcgtcgatt tttgtgatgc tcgtcagggg ggcggagcct atggaaaaac    7320
gccagcaacg cggcctttt acggttcctg gccttttgct ggcctttgc tcacatggtc    7380 tttcctgcgt tatccctga ttctgtggat aaccgtatta ccgcctttga gtgagctgat    7440
accgctcgcc gcagccgaac gaccgagcgc agcgagtcag tgagcgagga agcggagagc    7500
gcccaatacg caaaccgcct ctccccgcgc gttggccgat tcattaatgc agctggcacg    7560 acaggttttcc cgactggaaa gcgggcagtg agcgcaacgc aattaatgtg agttagctca    7620
ctcattaggc accccaggct ttacacttta tgcttccggc tcgtatgttg tgtggaattg    7680
tgagcggata acaatttcac acaggaaaca gctatgacca tgattacgcc aagcgcgtca    7740
attaaccctc actaaaggga acaaaagctg ttaattaa    7778
```

<210> SEQ ID NO 66
<211> LENGTH: 8177
<212> TYPE: DNA
<213> ORGANISM: artificial sequence
<220> FEATURE:
<223> OTHER INFORMATION: Matrice CD25 locus_IL12a_2A_IL12b pCLS30520
    full sequence

<400> SEQUENCE: 66

```
gtttattatt cctgttccac agctattgtc tgccatataa aaacttaggc caggcacagt      60
ggctcacacc tgtaatccca gcactttgga aggccgaggc aggcagatca caaggtcagg     120
agttcgagac cagcctggcc aacatagcaa aaccccatct ctactaaaaa tacaaaaatt     180
agccaggcat ggtggcgtgt gcactggttt agagtgagga ccacattttt ttggtgccgt     240
gttacacata tgaccgtgac tttgttacac cactacagga ggaagagtag aagaacaatc     300
ggttctggcg tgaaacagac tttgaatttt gaccttctca agttggcggg agacgtggag     360
tccaacccag ggcccatgtg gccccctggg tcagcctccc agccaccgcc ctcacctgcc     420
gcggccacag gtctgcatcc agcggctcgc cctgtgtccc tgcagtgccg gctcagcatg     480
tgtccagcgc gcagcctcct ccttgtggct accctggtcc tcctggacca cctcagtttg     540
gccagaaacc tccccgtggc cactccagac ccaggaatgt tcccatgcct tcaccactcc     600
caaaacctgc tgagggccgt cagcaacatg ctccagaagg ccagacaaac tctagaattt     660 taccccttgca cttctgaaga gattgatcat gaagatatca caaagataa aaccagcaca     720 gtggaggcct gtttaccatt ggaattaacc aagaatgaga gttgcctaaa ttccagagag     780
acctctttca taactaatgg gagttgcctg gcctccagaa agacctcttt tatgatggcc     840
ctgtgcctta gtagtattta tgaagacttg aagatgtacc aggtggagtt caagaccatg     900
aatgcaaagc ttctgatgga tcctaagagg cagatctttc tagatcaaaa catgctggca     960
gttattgatg agctgatgca ggccctgaat ttcaacagtg agactgtgcc acaaaaatcc    1020
tcccttgaag aaccggattt ttataaaact aaaatcaagc tctgcatact tcttcatgct    1080
```

```
ttcagaattc gggcagtgac tattgataga gtgatgagct atctgaatgc ttccggaagc    1140
ggagctacta acttcagcct gctgaagcag gctggagacg tggaggagaa ccctggacct    1200
atgtgtcacc agcagttggt catctcttgg tttttcctgg tttttctggc atctcccctc    1260
gtggccatat gggaactgaa gaaagatgtt tatgtcgtag aattggattg gtatccggat    1320
gcccctggag aaatggtggt cctcacctgt gacacccctg aagaagatgg tatcacctgg    1380
accttggacc agagcagtga ggtcttaggc tctggcaaaa ccctgaccat ccaagtcaaa    1440
gagtttggag atgctggcca gtacacctgt cacaaggag gcgaggttct aagccattcg    1500
ctcctgctgc ttcacaaaaa ggaagatgga atttggtcca ctgatatttt aaaggaccag    1560
aaagaaccca aaaataagac ctttctaaga tgcgaggcca gaattattc tggacgtttc    1620 acctgctggt ggctgacgac aatcagtact gatttgacat tcagtgtcaa aagcagcaga    1680
ggctcttctg accccaagg ggtgacgtgc ggagctgcta cactctctgc agagagagtc    1740
agaggggaca caaggagta tgagtactca gtgagtgcc aggaggacag tgcctgccca    1800
gctgctgagg agagtctgcc cattgaggtc atggtggatg ccgttcacaa gctcaagtat    1860
gaaaactaca ccagcagctt cttcatcagg acatcatca aacctgaccc acccaagaac    1920
ttgcagctga agccattaaa gaattctcgg caggtggagg tcagctggga gtaccctgac    1980
acctggagta ctccacattc ctacttctcc ctgacattct gcgttcaggt ccagggcaag    2040
agcaagagag aaaagaaaga tagagtcttc acggacaaga cctcagccac ggtcatctgc    2100
cgcaaaaatg ccagcattag cgtgcgggcc caggaccgct actatagctc atcttggagc    2160
gaatgggcat ctgtgccctg cagtgagggc agaggcagcc tgctgacctg cggcgacgtc    2220
gaggagaacc ccgggcccat gggggcaggt gccaccggcc gcgccatgga cgggccgcgc    2280
ctgctgctgt tgctgcttct gggggtgtcc cttggaggtg ccaaggaggc atgccccaca    2340
ggcctgtaca cacacagcgg tgagtgctgc aaagcctgca acctgggcga gggtgtggcc    2400
cagccttgtg gagccaacca gaccgtgtgt gagccctgcc tggacagcgt gacgttctcc    2460
gacgtggtga gcgcgaccga gccgtgcaag ccgtgcaccg agtgcgtggg gctccagagc    2520
atgtcggcgc cgtgcgtgga ggccgatgac gccgtgtgcc gctgcgccta cggctactac    2580
caggatgaga cgactgggcg ctgcgaggcg tgccgcgtgt gcgaggcggg ctcgggcctc    2640
gtgttctcct gccaggacaa gcagaacacc gtgtgcgagg agtgccccga cggcacgtat    2700
tccgacgagg ccaaccacgt ggacccgtgc ctgccctgca ccgtgtgcga ggacaccgag    2760
cgccagctcc gcgagtgcac acgctgggcc gacgccgagt gcgaggagat ccctggccgt    2820
tggattacac ggtccacacc cccagagggc tcggacagca cagccccag cacccaggag    2880 cctgaggcac ctcagaaaca agacctcata gccagcacgt ggcaggtgt ggtgaccaca    2940 gtgatgggca gctcccagcc cgtggtgacc cgaggcacca ccgacaacct catccctgtc    3000
tattgctcca tcctgctgc tgtggttgtg ggtcttgtgg cctacatagc cttcaagagg    3060
tgaaaaacca aaagaacaag aatttcttgg taagaagccg ggaacagaca acagaagtca    3120
tgaagcccaa gtgaaatcaa aggtgctaaa tggtcgccca ggagacatcc gttgtgcttg    3180
cctgcgtttt ggaagctctg aagtcacatc acaggacacg gggcagtggc aaccttgtct    3240
ctatgccagc tcagtcccat cagagagcga gcgctaccca cttctaaata gcaatttcgc    3300
cgttgaagag gaagggcaaa accactagaa ctctccatct tatttcatg tatatgtgtt    3360 catgcgatcg ctccggtgcc cgtcagtggg cagagcgcac atcgcccaca gtccccgaga    3420
```

```
agttgggggg agggtcggc aattgaacgg gtgcctagag aaggtggcgc ggggtaaact    3480
gggaaagtga tgtcgtgtac tggctccgcc ttttcccga gggtggggga gaaccgtata    3540
taagtgcagt agtcgccgtg aacgttcttt ttcgcaacgg gtttgccgcc agaacacagc    3600
tgaagcttcg aggggctcgc atctctcctt cacgcgcccg ccgccctacc tgaggccgcc    3660
atccacgccg gttgagtcgc gttctgccgc ctcccgcctg tggtgcctcc tgaactgcgt    3720
ccgccgtcta ggtaagttta aagctcaggt cgagaccggg cctttgtccg gcgctccctt    3780
ggagcctacc tagactcagc cggctctcca cgctttgcct gaccctgctt gctcaactct    3840
acgtctttgt ttcgttttct gttctgcgcc gttacagatc caagctgtga ccggcgccta    3900
cctgagatca ccggcgccac catggcttct taccctggac accagcatgc ttctgccttt    3960
gaccaggctg ccagatccag gggccactcc aacaggagaa ctgccctaag acccagaaga    4020
cagcaggaag ccactgaggt gaggcctgag cagaagatgc caaccctgct gagggtgtac    4080
attgatggac ctcatggcat gggcaagacc accaccactc aactgctggt ggcactgggc    4140
tccagggatg acattgtgta tgtgcctgag ccaatgacct actggagagt gctaggagcc    4200
tctgagacca ttgccaacat ctacaccacc cagcacaggc tggaccaggg agaaatctct    4260
gctggagatg ctgctgtggt gatgacctct gcccagatca caatgggaat gccctatgct    4320
gtgactgatg ctgttctggc tcctcacatt ggaggagagg ctggctcttc tcatgcccct    4380
ccacctgccc tgaccctgat cttggacaga cacccccattg cagccctgct gtgctaccca    4440
gcagcaaggt acctcatggg ctccatgacc ccacaggctg tgctggcttt tgtggccctg    4500
atccctccaa ccctccctgg caccaacatt gttctgggag cactgcctga agacagacac    4560
attgacaggc tggcaaagag gcagagacct ggagagagac tggacctggc catgctggct    4620
gcaatcagaa gggtgtatgg actgctggca aacactgtga atacctcca gtgtggaggc    4680
tcttggagag aggactgggg acagctctct ggaacagcag tgccccctca aggagctgag    4740
ccccagtcca atgctggtcc aagacccac attggggaca ccctgttcac cctgttcaga    4800
gcccctgagc tgctggctcc caatggagac ctgtacaatg tgtttgcctg ggctctggat    4860
gttctagcca agaggctgag gtccatgcat gtgttcatcc tggactatga ccagtcccct    4920
gctggatgca gagatgctct gctgcaacta acctctggca tggtgcagac ccatgtgacc    4980
accccctggca gcatccccac catctgtgac ctagccagaa cctttgccag ggagatggga    5040
gaggccaact aaggcgcgcc actcgagcgc tagctggcca gacatgataa gatacattga    5100
tgagtttgga caaaccacaa ctagaatgca gtgaaaaaaa tgctttattt gtgaaatttg    5160
tgatgctatt gctttatttg taaccattat aagctgcaat aaacaagtta acaacaacaa    5220
ttgcattcat tttatgtttc aggttcaggg ggaggtgtgg gaggttttt aaagcaagta    5280
aaacctctac aaatgtggta tggaaggcgc gcccaattcg ccctatagtg agtcgtatta    5340
cgtcgcgctc actggccgtc gttttacaac gtcgtgactg ggaaaaccct ggcgttaccc    5400
aacttaatcg ccttgcagca catccccctt tcgccagctg gcgtaatagc gaagaggccc    5460
gcaccgaaac gccttcccca acagttgcgc agcctgaatg gcgaatggga gcgccctgta    5520
gcggcgcatt aagcgcggcg ggtgtggtgg ttacgcgcag cgtgaccgct acacttgcca    5580
gcgccctagc gcccgctcct ttcgctttct tcccttcctt tctcgccacg ttcgccggct    5640
ttccccgtca agctctaaat cggggggctcc ctttagggtt ccgatttagt gctttacggc    5700
acctcgaccc caaaaaactt gattagggtg atggttggcc tgtagtgggc catagccctg    5760
atagacggtt tttcgccctt tgacgttgga gtccacgttc tttaatagtg gactcttgtt    5820
```

```
ccaaactgga acaacactca accctatctc ggtctattct tttgatttat aagggatttt    5880
gccgatttcg gcctattggt taaaaaatga gctgatttaa caaaaattta acgcgaattt    5940
taacaaaata ttaacgctta caatttaggt ggcacttttc ggggaaatgt gcgcggaacc    6000
cctatttgtt tattttttcta aatacattca aatatgtatc cgctcatgag acaataaccc   6060
tgataaatgc ttcaataata ttgaaaaagg aagagtatga gtattcaaca tttccgtgtc    6120
gcccttattc ccttttttgc ggcattttgc cttcctgttt ttgctcaccc agaaacgctg    6180
gtgaaagtaa aagatgctga agatcagttg ggtgcacgag tgggttacat cgaactggat    6240
ctcaacagcg gtaagatcct tgagagtttt cgccccgaag aacgttttcc aatgatgagc    6300
acttttaaag ttctgctatg tggcgcggta ttatcccgta ttgacgccgg caagagcaa     6360
ctcggtcgcc gcatacacta ttctcagaat gacttggttg agtactcacc agtcacagaa    6420
aagcatctta cggatggcat gacagtaaga gaattatgca gtgctgccat aaccatgagt    6480
gataacactg cggccaactt acttctgaca acgatcggag gaccgaagga gctaaccgct    6540
tttttgcaca acatggggga tcatgtaact cgccttgatc gttgggaacc ggagctgaat    6600
gaagccatac caaacgacga gcgtgacacc acgatgcctg tagcaatggc aacaacgttg    6660
cgcaaactat taactggcga actacttact ctagcttccc ggcaacaatt aatagactgg    6720
atggaggcgg ataaagttgc aggaccactt ctgcgctcgg cccttccggc tggctggttt    6780
attgctgata atctggagcc ggtgagcgt ggttctcgcg gtatcattgc agcactgggg     6840
ccagatggta gccctcccg tatcgtagtt atctacacga cggggagtca ggcaactatg     6900
gatgaacgaa atagacagat cgctgagata ggtgcctcac tgattaagca ttggtaactg    6960
tcagaccaag tttactcata tatactttag attgatttaa aacttcattt ttaatttaaa    7020
aggatctagg tgaagatcct ttttgataat ctcatgacca aaatccctta acgtgagttt    7080
tcgttccact gagcgtcaga ccccgtagaa aagatcaaag gatcttcttg agatcctttt    7140
tttctgcgcg taatctgctg cttgcaaaca aaaaaaccac cgctaccagc ggtggtttgt    7200
ttgccggatc aagagctacc aactctttt ccgaaggtaa ctggcttcag cagagcgcag     7260
ataccaaata ctgttcttct agtgtagccg tagttaggcc accacttcaa gaactctgta    7320
gcaccgccta catacctcgc tctgctaatc ctgttaccag tggctgctgc cagtggcgat    7380
aagtcgtgtc ttaccgggtt ggactcaaga cgatagttac cggataaggc gcagcggtcg    7440
ggctgaacgg ggggttcgtg cacacagccc agcttggagc gaacgaccta caccgaactg    7500
agatacctac agcgtgagct atgagaaagc gccacgcttc ccgaagggag aaaggcggac    7560
aggtatccgg taagcggcag ggtcggaaca ggagagcgca cgagggagct tccaggggga    7620
aacgcctggt atctttatag tcctgtcggg tttcgccacc tctgacttga gcgtcgattt    7680
ttgtgatgct cgtcaggggg gcggagccta tggaaaaacg ccagcaacgc ggcctttta    7740
cggttcctgg ccttttgctg gccttttgct cacatggtct ttcctgcgtt atcccctgat    7800
tctgtggata accgtattac cgcctttgag tgagctgata ccgctcgccg cagccgaacg    7860
accgagcgca gcgagtcagt gagcgaggaa gcggagagcg cccaatacgc aaaccgcctc    7920
tccccgcgcg ttggccgatt cattaatgca gctggcacga caggtttccc gactggaaag    7980
cgggcagtga gcgcaacgca attaatgtga gttagctcac tcattaggca ccccaggctt    8040
tacactttat gcttccggct cgtatgttgt gtggaattgt gagcggataa caatttcaca    8100
caggaaacag ctatgaccat gattacgcca agcgcgtcaa ttaaccctca ctaaagggaa    8160
```
caaaagctgt taattaa                                                        8177

<210> SEQ ID NO 67
<211> LENGTH: 6349
<212> TYPE: DNA
<213> ORGANISM: artificial sequence
<220> FEATURE:
<223> OTHER INFORMATION: Matrice PD1 locus_IL12a_2A_IL12b pCLS30511 full
      sequence

<400> SEQUENCE: 67

| | | | | | |
|---|---|---|---|---|---|
| tcgcgcgttt | cggtgatgac | ggtgaaaacc | tctgacacat | gcagctcccg gagacggtca | 60 |
| cagcttgtct | gtaagcggat | gccgggagca | gacaagcccg | tcagggcgcg tcagcgggtg | 120 |
| ttggcgggtg | tcggggctgg | cttaactatg | cggcatcaga | gcagattgta ctgagagtgc | 180 |
| accatatgcg | gtgtgaaata | ccgcacagat | gcgtaaggag | aaaataccgc atcaggcgcc | 240 |
| attcgccatt | caggctgcgc | aactgttggg | aagggcgatc | ggtgcgggcc tcttcgctat | 300 |
| tacgccagct | ggcgaaaggg | ggatgtgctg | caaggcgatt | aagttgggta acgccagggt | 360 |
| tttcccagtc | acgacgttgt | aaaacgacgg | ccagtgaatt | cgagctcggt acctcgcgaa | 420 |
| tgcatctaga | tgactcccca | gacaggccct | ggaaccccc | caccttctcc ccagccctgc | 480 |
| tcgtggtgac | cgaaggggac | aacgccacct | tcacctgcag | cttctccaac acatcggaga | 540 |
| gcttcgtgct | aaactggtac | cgcatgagcc | cagcaacca | gacggacaag ctggccgcct | 600 |
| tccccgagga | ccgcagccag | cccggccagg | actgccgctt | ccgtgtcaca caactgccca | 660 |
| acgggcgtga | cttccacatg | agcgtggtca | gggcccggcg | caatgacagc ggcacctacc | 720 |
| tctgtggggc | cggttctggc | gtgaaacaga | ctttgaattt | tgaccttctc aagttggcgg | 780 |
| gagacgtgga | gtccaaccca | gggcccatgt | ggcccctgg | gtcagcctcc agccaccgc | 840 |
| cctcacctgc | cgcggccaca | ggtctgcatc | cagcggctcg | ccctgtgtcc ctgcagtgcc | 900 |
| ggctcagcat | gtgtccagcg | cgcagcctcc | tccttgtggc | tacccctgtc ctcctggacc | 960 |
| acctcagttt | ggccagaaac | ctccccgtgg | ccactccaga | cccaggaatg ttcccatgcc | 1020 |
| ttcaccactc | ccaaaacctg | ctgagggccg | tcagcaacat | gctccagaag gccagacaaa | 1080 |
| ctctagaatt | ttaccttgc | acttctgaag | agattgatca | tgaagatatc acaaaagata | 1140 |
| aaaccagcac | agtggaggcc | tgtttaccat | tggaattaac | caagaatgag agttgcctaa | 1200 |
| attccagaga | gacctctttc | ataactaatg | ggagttgcct | ggcctccaga aagacctctt | 1260 |
| ttatgatggc | cctgtgcctt | agtagtattt | atgaagactt | gaagatgtac caggtggagt | 1320 |
| tcaagaccat | gaatgcaaag | cttctgatgg | atcctaagag | gcagatcttt ctagatcaaa | 1380 |
| acatgctggc | agttattgat | gagctgatgc | aggccctgaa | tttcaacagt gagactgtgc | 1440 |
| cacaaaaatc | ctcccttgaa | gaaccggatt | tttataaaac | taaaatcaag ctctgcatac | 1500 |
| ttcttcatgc | tttcagaatt | cgggcagtga | ctattgatag | agtgatgagc tatctgaatg | 1560 |
| cttccggaag | cggagctact | aacttcagcc | tgctgaagca | ggctggagac gtggaggaga | 1620 |
| accctggacc | tatgtgtcac | cagcagttgg | tcatctcttg | gttttccctg gttttttctgg | 1680 |
| catctcccct | cgtggccata | tgggaactga | agaaagatgt | ttatgtcgta gaattggatt | 1740 |
| ggtatccgga | tgcccctgga | gaaatggtgg | tcctcacctg | tgacacccct gaagaagatg | 1800 |
| gtatcacctg | gaccttggac | cagagcagtg | aggtcttagg | ctctggcaaa accctgacca | 1860 |
| tccaagtcaa | agagtttgga | gatgctggcc | agtacacctg | tcacaaagga ggcgaggttc | 1920 |
| taagccattc | gctcctgctg | cttcacaaaa | aggaagatgg | aatttggtcc actgatattt | 1980 |

```
taaaggacca gaaagaaccc aaaaataaga cctttctaag atgcgaggcc aagaattatt    2040
ctggacgttt cacctgctgg tggctgacga caatcagtac tgatttgaca ttcagtgtca    2100
aaagcagcag aggctcttct gacccccaag gggtgacgtg cggagctgct acactctctg    2160
cagagagagt cagaggggac aacaaggagt atgagtactc agtggagtgc caggaggaca    2220
gtgcctgccc agctgctgag gagagtctgc ccattgaggt catggtggat gccgttcaca    2280
agctcaagta tgaaaactac accagcagct tcttcatcag ggacatcatc aaacctgacc    2340
cacccaagaa cttgcagctg aagccattaa agaattctcg gcaggtggag gtcagctggg    2400
agtaccctga cacctggagt actccacatt cctacttctc cctgacattc tgcgttcagg    2460
tccagggcaa gagcaagaga gaaaagaaag atagagtctt cacggacaag acctcagcca    2520
cggtcatctg ccgcaaaaat gccagcatta gcgtgcgggc ccaggaccgc tactatagct    2580
catcttggag cgaatgggca tctgtgccct gcagtgaggg cagaggcagc ctgctgacct    2640
gcggcgacgt cgaggagaac cccgggccca tgggggcagg tgccaccggc cgcgccatgg    2700
acgggccgcg cctgctgctg ttgctgcttc tgggggtgtc ccttggaggt gccaaggagg    2760
catgccccac aggcctgtac acacacagcg gtgagtgctg caaagcctgc aacctgggcg    2820
agggtgtggc ccagccttgt ggagccaacc agaccgtgtg tgagccctgc ctggacagcg    2880
tgacgttctc cgacgtggtg agcgcgaccg agccgtgcaa gccgtgcacc gagtgcgtgg    2940
ggctccagag catgtcggcg ccgtgcgtgg aggccgatga cgccgtgtgc cgctgcgcct    3000
acggctacta ccaggatgag acgactgggc gctgcgaggc gtgccgcgtg tgcgaggcgg    3060
gctcgggcct cgtgttctcc tgccaggaca gcagaacac cgtgtgcgag gagtgccccg    3120
acggcacgta ttccgacgag gccaaccacg tggaccgtg cctgccctgc accgtgtgcg    3180
aggacaccga gcgccagctc cgcgagtgca cacgctgggc cgacgccgag tgcgaggaga    3240
tccctggccg ttggattaca cggtccacac ccccagaggg ctcggacagc acagccccca    3300
gcacccagga gcctgaggca cctccagaac aagaccccat agccagcacg gtggcaggtg    3360
tggtgaccac agtgatgggc agctcccagc ccgtggtgac ccgaggcacc accgacaacc    3420
tcatccctgt ctattgctcc atcctggctg ctgtggttgt gggtcttgtg cctacatag    3480
ccttcaagag gtgatctaga gggcccgttt aaacccgctg atcagcctcg actgtgcctt    3540
ctagttgcca gccatctgtt gtttgcccct ccccgtgcc ttccttgacc ctggaaggtg    3600
ccactcccac tgtccttttcc taataaaatg aggaaattgc atcgcattgt ctgagtaggt    3660
gtcattctat tctgggggt ggggtgggc aggacagcaa gggggaggat tgggaagaca    3720
atagcaggca tgctggggat gcggtgggct ctatgactag tggcgaattc ggcgcagatc    3780
aaagagagcc tgcgggcaga gctcagggtg acaggtgcgg cctcggaggc cccggggcag    3840
gggtgagctg agccggtcct ggggtgggtg tcccctcctg cacaggatca ggagctccag    3900
ggtcgtaggg cagggacccc ccagctccag tccaggctc tgtcctgcac ctggggaatg    3960
gtgaccggca tctctgtcct ctagctctgg aagcacccca gcccctctag tctgccctca    4020
cccctgaccc tgaccctcca ccctgacccc gtcctaaccc ctgacctttg atcggatccc    4080
gggcccgtcg actgcagagg cctgcatgca agcttggcgt aatcatggtc atagctgttt    4140
cctgtgtgaa attgttatcc gctcacaatt ccacacaaca tacgagccgg aagcataaag    4200
tgtaaagcct ggggtgccta atgagtgagc taactcacat taattgcgtt gcgctcactg    4260
cccgctttcc agtcgggaaa cctgtcgtgc cagctgcatt aatgaatcgg ccaacgcgcg    4320
ggagaggcg gtttgcgtat tgggcgctct tccgcttcct cgctcactga ctcgctgcgc    4380
```

```
tcggtcgttc ggctgcggcg agcggtatca gctcactcaa aggcggtaat acggttatcc    4440
acagaatcag gggataacgc aggaaagaac atgtgagcaa aaggccagca aaaggccagg    4500
aaccgtaaaa aggccgcgtt gctggcgttt ttccataggc tccgcccccc tgacgagcat    4560
cacaaaaatc gacgctcaag tcagaggtgg cgaaacccga caggactata agataccag    4620
gcgtttcccc ctggaagctc cctcgtgcgc tctcctgttc cgaccctgcc gcttaccgga    4680
tacctgtccg cctttctccc ttcgggaagc gtggcgcttt ctcatagctc acgctgtagg    4740
tatctcagtt cggtgtaggt cgttcgctcc aagctgggct gtgtgcacga acccccgtt    4800
cagcccgacc gctgcgcctt atccggtaac tatcgtcttg agtccaaccc ggtaagacac    4860
gacttatcgc cactggcagc agccactggt aacaggatta gcagagcgag gtatgtaggc    4920
ggtgctacag agttcttgaa gtggtggcct aactacggct acactagaag aacagtattt    4980
ggtatctgcg ctctgctgaa gccagttacc ttcggaaaaa gagttggtag ctcttgatcc    5040
ggcaaacaaa ccaccgctgg tagcggtggt ttttttgttt gcaagcagca gattacgcgc    5100
agaaaaaaag gatctcaaga agatcctttg atcttttcta cggggtctga cgctcagtgg    5160
aacgaaaact cacgttaagg gattttggtc atgagattat caaaaaggat cttcacctag    5220
atccttttaa attaaaaatg aagttttaaa tcaatctaaa gtatatatga gtaaacttgg    5280
tctgacagtt accaatgctt aatcagtgag gcacctatct cagcgatctg tctatttcgt    5340
tcatccatag ttgcctgact ccccgtcgtg tagataacta cgatacggga gggcttacca    5400
tctggcccca gtgctgcaat gataccgcga gacccacgct caccggctcc agatttatca    5460
gcaataaacc agccagccgg aagggccgag cgcagaagtg gtcctgcaac tttatccgcc    5520
tccatccagt ctattaattg ttgccgggaa gctagagtaa gtagttcgcc agttaatagt    5580
ttgcgcaacg ttgttgccat tgctacaggc atcgtggtgt cacgctcgtc gtttggtatg    5640
gcttcattca gctccggttc ccaacgatca aggcgagtta catgatcccc catgttgtgc    5700
aaaaaagcgg ttagctcctt cggtcctccg atcgttgtca gaagtaagtt ggccgcagtg    5760
ttatcactca tggttatggc agcactgcat aattctctta ctgtcatgcc atccgtaaga    5820
tgcttttctg tgactggtga gtactcaacc aagtcattct gagaatagtg tatgcggcga    5880
ccgagttgct cttgcccggc gtcaatacgg gataataccg cgccacatag cagaacttta    5940
aaagtgctca tcattggaaa acgttcttcg ggcgaaaac tctcaaggat cttaccgctg    6000
ttgagatcca gttcgatgta acccactcgt gcacccaact gatcttcagc atcttttact    6060
ttcaccagcg tttctgggtg agcaaaaaca ggaaggcaaa atgccgcaaa aaagggaata    6120
agggcgacac ggaaatgttg aatactcata ctcttccttt ttcaatatta ttgaagcatt    6180
tatcagggtt attgtctcat gagcggatac atatttgaat gtatttagaa aaataaacaa    6240
ataggggttc cgcgcacatt tccccgaaaa gtgccacctg acgtctaaga aaccattatt    6300
atcatgacat taacctataa aaataggcgt atcacgaggc cctttcgtc              6349
```

<210> SEQ ID NO 68
<211> LENGTH: 14
<212> TYPE: PRT
<213> ORGANISM: Human immunodeficiency virus type 1
<220> FEATURE:
<221> NAME/KEY: MISC_FEATURE
<222> LOCATION: (5)..(5)
<223> OTHER INFORMATION: Xaa is Ile or Val
<220> FEATURE:
<221> NAME/KEY: MISC_FEATURE
<222> LOCATION: (13)..(13)

```
<223> OTHER INFORMATION: Xaa is Lys, Arg, or Gln

<400> SEQUENCE: 68

Leu Gln Ala Arg Xaa Leu Ala Val Glu Arg Tyr Leu Xaa Asp
1               5                   10

<210> SEQ ID NO 69
<211> LENGTH: 14
<212> TYPE: PRT
<213> ORGANISM: Human immunodeficiency virus type 2
<220> FEATURE:
<221> NAME/KEY: MISC_FEATURE
<222> LOCATION: (13)..(13)
<223> OTHER INFORMATION: Xaa is Lys, Ala, or Gln
<220> FEATURE:
<221> NAME/KEY: MISC_FEATURE
<222> LOCATION: (14)..(14)
<223> OTHER INFORMATION: Xaa is Asp or His

<400> SEQUENCE: 69

Leu Gln Ala Arg Val Thr Ala Ile Glu Lys Tyr Leu Xaa Xaa
1               5                   10

<210> SEQ ID NO 70
<211> LENGTH: 14
<212> TYPE: PRT
<213> ORGANISM: Simian immunodeficiency virus

<400> SEQUENCE: 70

Leu Gln Ala Arg Leu Leu Ala Val Glu Arg Tyr Leu Lys Asp
1               5                   10

<210> SEQ ID NO 71
<211> LENGTH: 14
<212> TYPE: PRT
<213> ORGANISM: Moloney murine leukemia virus

<400> SEQUENCE: 71

Leu Gln Asn Arg Arg Gly Leu Asp Leu Leu Phe Leu Lys Glu
1               5                   10

<210> SEQ ID NO 72
<211> LENGTH: 14
<212> TYPE: PRT
<213> ORGANISM: Human T-cell lymphotropic virus

<400> SEQUENCE: 72

Ala Gln Asn Arg Arg Gly Leu Asp Leu Leu Phe Trp Glu Gln
1               5                   10

<210> SEQ ID NO 73
<211> LENGTH: 14
<212> TYPE: PRT
<213> ORGANISM: Mason-Pfizer monkey virus

<400> SEQUENCE: 73

Leu Gln Asn Arg Arg Gly Leu Asp Leu Leu Thr Ala Glu Gln
1               5                   10

<210> SEQ ID NO 74
<211> LENGTH: 14
<212> TYPE: PRT
<213> ORGANISM: Homo sapiens

<400> SEQUENCE: 74

Leu Gln Asn Arg Arg Ala Leu Asp Leu Leu Thr Ala Glu Arg
```

```
<210> SEQ ID NO 75
<211> LENGTH: 14
<212> TYPE: PRT
<213> ORGANISM: Homo sapiens

<400> SEQUENCE: 75

Leu Gln Asn Arg Arg Gly Leu Asp Met Leu Thr Ala Ala Gln
1               5                   10

<210> SEQ ID NO 76
<211> LENGTH: 14
<212> TYPE: PRT
<213> ORGANISM: Human endogenous retrovirus K

<400> SEQUENCE: 76

Leu Ala Asn Gln Ile Asn Asp Leu Arg Gln Thr Val Ile Trp
1               5                   10

<210> SEQ ID NO 77
<211> LENGTH: 14
<212> TYPE: PRT
<213> ORGANISM: Feline leukemia virus

<400> SEQUENCE: 77

Leu Gln Asn Arg Arg Gly Leu Asp Ile Leu Phe Leu Gln Glu
1               5                   10

<210> SEQ ID NO 78
<211> LENGTH: 9
<212> TYPE: PRT
<213> ORGANISM: Human immunodeficiency virus type 1

<400> SEQUENCE: 78

Gly Ala Leu Phe Leu Gly Phe Leu Gly
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide

<400> SEQUENCE: 79

Ala Gly Phe Gly Leu Leu Leu Gly Phe
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic peptide

<400> SEQUENCE: 80

Ala Gly Leu Phe Leu Gly Phe Leu Gly
1               5
```

The invention claimed is:

1. A population of engineered primary human NK or T cells, comprising an exogenous coding sequence encoding an interleukin selected from IL-15, IL-12, or IL-2 inserted into an endogenous gene such that said interleukin is under transcriptional control of an endogenous gene promoter locus, while disrupting the coding sequence of the endogenous gene,
wherein the endogenous gene encodes PD1;
wherein said primary human NK or T cells further comprise an exogenous coding sequence encoding a chimeric antigen receptor (CAR) or a recombinant TCR; and
wherein said primary human NK or T cells secrete a level of the interleukin sufficient to enhance the antitumor activity of the cells.

2. The population of engineered primary human T cells according to claim 1, wherein said interleukin is IL-2.

3. The population of engineered primary human T cells according to claim 1, wherein said interleukin is IL-12.

4. The population of engineered primary human T cells according to claim 1, wherein said interleukin is IL-15.

5. The population of engineered primary human NK or T cells according to claim 1, wherein more than 50% of said cells are TCR negative T-cells and/or more than 50% of said cells are CAR positive cells.

6. The population of engineered primary human NK or T cells according to claim 1, wherein the CAR is an antiCD22 CAR.

7. The population of engineered primary human NK or T cells according to claim 2, wherein the CAR is an antiCD22 CAR.

8. The population of engineered primary human NK or T cells according to claim 3, wherein the CAR is an antiCD22 CAR.

9. The population of engineered primary human NK or T cells according to claim 1, wherein the CAR is an antiCD22 CAR.

10. The population of engineered primary human NK or T cells according to claim 1, wherein the CAR is inserted at the TRAC locus using TALENS having the sequence of SEQ ID NO:16 and 17.

11. The population of engineered primary human NK or T cells according to claim 2, wherein the CAR is inserted at the TRAC locus using TALENS having the sequence of SEQ ID NO:16 and 17.

12. The population of engineered primary human NK or T cells according to claim 3, wherein the CAR is inserted at the TRAC locus using TALENS having the sequence of SEQ ID NO:16 and 17.

13. The population of engineered primary human NK or T cells according to claim 4, wherein the CAR is inserted at the TRAC locus using TALENS having the sequence of SEQ ID NO:16 and 17.

14. The population of engineered primary human NK or T cells according to claim 7, wherein the CAR is inserted at the TRAC locus using TALENS having the sequence of SEQ ID NO:16 and 17.

15. The population of engineered primary human NK or T cells according to claim 8, wherein the CAR is inserted at the TRAC locus using TALENS having the sequence of SEQ ID NO:16 and 17.

16. The population of engineered primary human NK or T cells according to claim 9, wherein the CAR is inserted at the TRAC locus using TALENS having the sequence of SEQ ID NO:16 and 17.

17. The population of engineered primary human NK or T cells according to claim 7, wherein the exogenous coding sequence encoding an interleukin is inserted into the middle of the PD1 open reading frame using TALENS having the sequence of SEQ ID NO:20 and 21.

18. The population of engineered primary human NK or T cells according to claim 8, wherein the exogenous coding sequence encoding an interleukin is inserted into the middle of the PD1 open reading frame using TALENS having the sequence of SEQ ID NO:20 and 21.

19. The population of engineered primary human NK or T cells according to claim 9, wherein the exogenous coding sequence encoding an interleukin is inserted into the middle of the PD1 open reading frame using TALENS having the sequence of SEQ ID NO:20 and 21.

* * * * *

UNITED STATES PATENT AND TRADEMARK OFFICE
CERTIFICATE OF CORRECTION

| | | |
|---|---|---|
| PATENT NO. | : 11,873,511 B2 | Page 1 of 1 |
| APPLICATION NO. | : 16/340222 | |
| DATED | : January 16, 2024 | |
| INVENTOR(S) | : Brian Busser et al. | |

It is certified that error appears in the above-identified patent and that said Letters Patent is hereby corrected as shown below:

In the Claims

Column 273: Line 36, Claim 9, replace "according to claim 1" with "according to claim 4"

Signed and Sealed this
Fourteenth Day of May, 2024

Katherine Kelly Vidal
*Director of the United States Patent and Trademark Office*